(12) United States Patent
Fukutomi et al.

(10) Patent No.: US 7,375,115 B2
(45) Date of Patent: May 20, 2008

(54) 4-(2-FUROYL) AMINOPIPERIDINES, INTERMEDIATES IN SYNTHESIZING THE SAME, PROCESS FOR PRODUCING THE SAME AND MEDICINAL USE OF THE SAME

(75) Inventors: Ryuuta Fukutomi, Iruma-gun (JP); Hitoshi Inoue, Iruma-gun (JP); Koji Kawamura, Iruma-gun (JP); Takuya Kishimoto, Iruma-gun (JP); Masashi Suzuki, Iruma-gun (JP); Rie Shibayama, Iruma-gun (JP); Kazuko Kojima, Iruma-gun (JP); Kouichirou Hagihara, Iruma-gun (JP)

(73) Assignees: Kyorin Pharmaceutical Co., Ltd., Tokyo (JP); Nisshin Pharma Inc., Tokyo (JP)

( * ) Notice: Subject to any disclaimer, the term of this patent is extended or adjusted under 35 U.S.C. 154(b) by 399 days.

(21) Appl. No.: 10/492,065

(22) PCT Filed: Oct. 8, 2002

(86) PCT No.: PCT/JP02/10449

§ 371 (c)(1),
(2), (4) Date: Oct. 20, 2004

(87) PCT Pub. No.: WO03/035645

PCT Pub. Date: May 1, 2003

(65) Prior Publication Data

US 2005/0085508 A1    Apr. 21, 2005

(30) Foreign Application Priority Data

Oct. 9, 2001    (JP)    ............... 2001-311828

(51) Int. Cl.
*A01N 43/40* (2006.01)
*C07D 401/00* (2006.01)

(52) U.S. Cl. .................... 514/318; 546/207
(58) Field of Classification Search ............... 548/400; 514/318
See application file for complete search history.

(56) References Cited

U.S. PATENT DOCUMENTS 4,560,684 A * 12/1985 Sugasawa et al. .......... 514/221
4,791,112 A * 12/1988 Bagley et al. ............. 514/237.2
4,912,109 A * 3/1990 Bagley et al. .......... 514/255.05

FOREIGN PATENT DOCUMENTS

| EP | 0 160 422 | 11/1985 |
| EP | 0 277 794 | 8/1988 |
| JP | 63-264460 | 11/1988 |
| WO | WO 94/27967 | 12/1994 |

OTHER PUBLICATIONS

Martin et al. "The Effects of Morphine- and Nalorphine- Like Drugs in the Nondependent and Morphine-Dependent Chronic Spinal Dog." The Journal of Pharmacology and Experimental Therapeutics. vol. 197, No. 3, pp. 517-532, 1976.

(Continued)

*Primary Examiner*—Kamal A. Saeed
*Assistant Examiner*—Robert Havlin
(74) *Attorney, Agent, or Firm*—Ohlandt, Greeley, Ruggiero & Perle, L.L.P.

(57) ABSTRACT

There are provided novel 4(2-furoyl)aminopiperidines represented by the general formula (I), their synthetic intermediates, processes for their preparation and medicaments containing them.

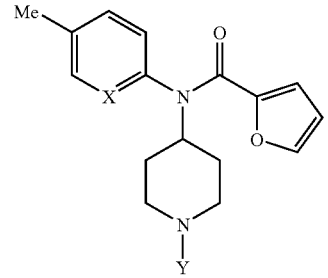

(I)

In the above formula, X is OH or N, and Y is a group of the following general formula (II), formula (II-a) or formula (III):

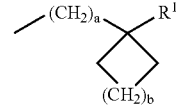

(II)

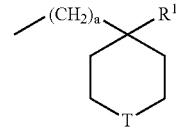

(II-a)

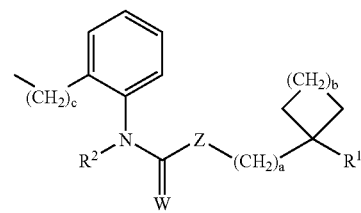

(III)

wherein
a, b and c are each an integer of 0-6;
Z is $CH_2$ or NH;
W is O or S;
T is O or N—$R^{15}$ wherein $R^{15}$ is H, a C1-C6 alkyl group, a benzyl group or a phenethyl group; and
$R^1$ is H, a C1-C6 alkoxycarbonyl group, a benzyloxycarbonyl group, or the like.

The 4-(2-furoyl)aminopiperidine derivatives according to this invention possess opioid μ antagonistic activity and are useful for the treatment or prevention of side effects which are caused by μ receptors agonist and which are selected from constipation, nausea/emesis or itch, or for the treatment or prevention of idiopathic constipation, postoperative ileus, paralytic ileus, irritable bowel syndrome or chronic pruritus.

10 Claims, No Drawings

OTHER PUBLICATIONS

Konturek et al. "Influence of methionine-enkephalin and morphine on myoelectric activity of small bowel." Am. J. Physiol. 238: G-384-389, 1980.

Orwoll et al. "β-Endorphin and Adrenocorticotropin in Extrapituitary Sites: Gastrointestinal Tract." Endocrinology, vol. 107, No. 2, 438-442, 1980.

"Enkephalins and Endorphins Stress and the Immune System." Ed. by Plotnikoff et al., Plenum Press, New York, pp. 35-45, 1986.

Simonin et al. "The Human δ-Opioid Receptor: Genomic Organization, cDNA Cloning, Functional Expression, and distribution in Human Brain." Molecular Pharmacology. 46:1015-1021, 1994.

Wang et al. "Human μ opiate receptor cDNA and genomic clones, pharmacologic characterization and chromosomal assignment." FEBS Letters 338, pp. 217-222, 1994.

Simonin et al. "k-Opioid receptor in humans: cDNA and genomic cloning, chromosomal assignment, functional expression, pharmacology, and expression pattern in the central nervous system." Proc. Natl. Acad. Sci. USA, 92: 7006-7010, 1995.

Yamaguchi et al. "Itch-Associated Response and Antinociception Induced by Intracisternal Endomorphins in Mice." Jpn. J. Pharmacol. 78: 337-343, 1998.

* cited by examiner

4-(2-FUROYL) AMINOPIPERIDINES, INTERMEDIATES IN SYNTHESIZING THE SAME, PROCESS FOR PRODUCING THE SAME AND MEDICINAL USE OF THE SAME

FIELD OF THE INVENTION

This invention relates to novel 4-(2-furoyl)aminopiperidines and processes for preparing them, intermediates for synthesizing them and processes for preparing them, and their in vivo metabolites, as well as to medicaments containing them, more specifically, their use as opioid μ antagonists.

DISCUSSION OF THE BACKGROUND ART

Opioid receptors are the receptors to which drugs having morphine-like action specifically bind, and they are found in the central nervous system or intestinal nervous system. Opioid receptors are known to include the three types of μ, δ and κ, where the primary structure of each receptor has been elucidated by cDNA cloning (Wang J-B, FEBS Lett, 338: 217-222, 1994, Simonin F, Mol Pharmacol, 46: 1015-1021, 1994, Simonin F, Proc Natl Acad Sci USA, 92: 7006-7010, 1995). Pharmacological activities of these opioid receptors differ, depending on the types of receptors (Martin W R, J Pharmacol Exp Ther. 197: 517-532, 1976). The μ receptors are involved in analgesia, respiratory depression, euphoria, psychosomatic dependence, tolerance, enterokinesis depression, bradycardia, constipation, miosis, etc. On the other hand, the δ receptors are involved in analgesia, psychosomatic dependence, emotional reaction, etc. The κ receptors are involved in analgesia, sedation, euphoria, diuresis, aversion, miosis, etc.

Morphine is a representative μ receptor agonist (Wood P L, Neuropharmacology, 20: 1215-1220, 1981) and it has been used for those patients with carcinomatous pain or postoperative pain as a potent analgesic. However, morphine exerts analgesic activity, while it causes side effects such as constipation, nausea/emesis, drowsiness, hallucination/obfuscation, respiratory depression, xerostomia/mouth dryness, perspiration, itch, dysuria, unsteadiness/dizziness, and myoclonus. Of these side effects, constipation, nausea/emesis may frequently appear, and itch is also very frequently observed in intrathecal or epidual administration (Guidelines for Alleviation of Carcinomatous Pain, Ed. by the Alleviation Medical Society of Japan, "the Committee for Drafting Guidelines for Alleviation Carcinomatous Pain", Department of Publication of Medical Books, SINKO-SYUPPAN KOUEKI Co., Ltd., 68-78, 2000).

Opioid peptide is a generic name for the peptide group having morphine-like action and binding to opioid receptors, and the opioid peptides found in the central nervous system and peripheral tissues (intestine, adrenal gland, etc.) are referred to as "endogenous opioid peptides." β-Endorphin, enkephalin and dynorphin are known as endogenous opioid peptides. Of these peptides, β-endorphin and enkephalin have affinity to μ receptors (Opioid Peptides, Ed. by Hiroo IMURA, CHYUGAI IGAKU Co., Ltd., 240-250, 1985). It has also been reported that production and release of these endogenous opioid peptides are stimulated under various stress environments (in Enkephalins and Endoephins, Ed. by Plotnikoff N P, Plenum, 1986). This has pointed out that endogenous opioid peptides may be a pathogenic cause of idiopathic constipation, postoperative ileus, paralytic ileus, irritable bowel syndrome, chronic pruritus, etc. (Orwoll E S, Endocrinology, 107: 438-442, 1980, Konturek S J, Am J Physiol, 238: G384-G389, 1980, Yamaguchi T, Jpn J Pharmacol, 78: 337-343, 1998).

It is, therefore, believed that the μ receptor antagonists are effective against side effects which are caused by the μ receptor agonists, such as constipation, nausea/emesis, and itch, or diseases such as idiopathic constipation, postoperative ileus, paralytic ileus, irritable bowel syndrome and chronic pruritus.

According to Japanese Patent Kokai No. 264460/1988 (JP-A-63264460), a drug having the action of reversing respiratory depression, one of side effects of morphine, that is, an opioid μ receptor antagonist has been identified as the compound of the formula (XI), which is an analogous compound originated from fentanyl, an opioid μ receptor agonist.

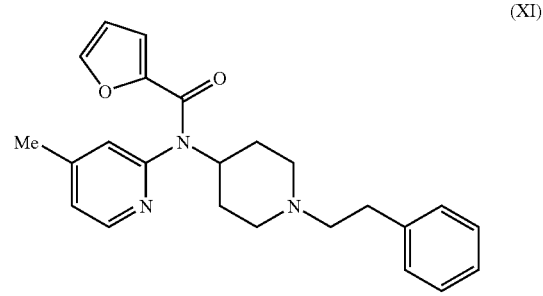

(XI)

However, the opioid μ receptor antagonistic activity of this drug is weak and insufficient as a therapeutic agent for imperfect enterokinesis such as constipation and irritable bowel syndrome. Therefore, there has been a need for more potent opioid μ receptor antagonists.

SUMMARY OF THE INVENTION

Provided are novel 4-(2-furoyl)aminopiperadine compounds represented by the general formula (I):

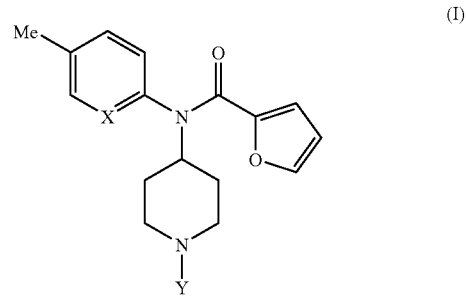

(I)

wherein
X is CH or N; and
Y is a group of the general formula (II):

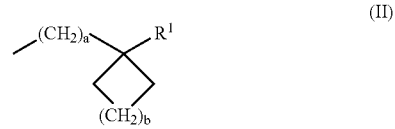

(II)

or a group of the general formula (II-a)

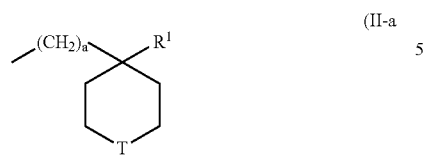

(II-a)

or a group of the general formula (III):

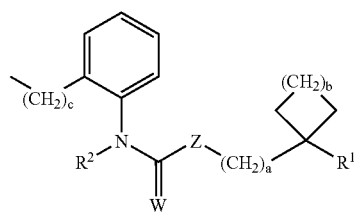

(III)

wherein a, b and c are each an integer of 0-6;

Z is $CH_2$ or NH;

W is O or S;

T is O or N—$R^{15}$ wherein R is H, a C1-C6 alkyl group, a benzyl group or a phenethyl group;

$R^1$ is H, a C1-C6 alkoxycarbonyl group, a benzyloxycarbonyl group, a carboxy group, a 2-phenyl-1,3-dioxan-5-yl group, a 2,2-dimethyl-1,3-dioxan-5-yl group, or a group of the general formula (IV):

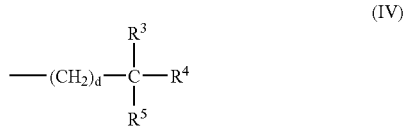

(IV)

wherein d is an integer of 0-6; and $R^3$, $R^4$, and $R^5$ may be the same or different and are each independently H, —$(CH_2)_eR^6$ or —$(CH_2)_fCONR^7R^8$ wherein e and f are each an integer of 0-6; $R^6$ is a hydroxy group, a C1-C6 alkanoyloxy group, a benzoyloxy group, a 2-furoyloxy group, a 01-0-6 alkoxy C1-C6 alkoxy group, a C1-C6 alkoxycarbonylphenoxy group, a carboxyphenoxy group, a dicarboxyphenoxy group, a di C1-C6alkoxy-carbonylphenoxy group, a dihydroxy C1-C6alkylphenoxy group, an amino group, a C1-C6alkoxycarbonylamino group, a C1-C6alkylsulfonamido group, benzenesulfonamido group, a p-toluenesulfonamido group, a p-halobenzenesulfonamido group, a carboxy group, a C1-C6alkoxycarbonyl group, a carbohydroxamic group, a carbohydroxamic acid C1-C6alkyl ester group, a cyano group, a 1H-tetrazol-5-yl group, a 11(C1-C6 alkyl)1H-tetrazolylgroup, a 2-(C1-C6alkyl)-2H-tetrazol-5-yl group, a $N^2$-hydroxycarbamidoyl group, a $N^1$-(C1-C6 alkoxy-carbonyl)-$N^2$-hydroxycarbamidoyl group, a 2H-5-thioxo-1,2,4-oxadiazol-3-yl group, a 2H-5-oxo-1,2,4-oxadiazol-3-yl group, a guanidino group, a di C1-C6alkoxycarbonyl-guanidino group or a morpholinocarbonyl group; and $R^7$ and $R^8$ may be the same or different and are each independently H, a C1-C6 alkyl group, a C1-C6 alkanoyloxy C1-C6 alkyl group, a hydroxy C1-C6 alkyl group, a bis(C1-C6alkanoyloxy C1-C6alkyl)methyl group, a bis(hydroxy C1-C6 alkyl)methyl group, a tris(C1-C6 alkanoyloxy C1-C6 alkyl)methyl group, a tris(hydroxy C1-C6 alkyl)-methyl group, a carboxy C1-C6alkyl group, a C1-C6 alkoxycarbonyl C1-C6 alkyl group, a N,N-bis(C1-C6alkanoyloxy C1-C6 alkyl)carbamoyl C1-C6 alkyl group, a N,N-bis(carboxy C1-C6 alkyl) carbamoyl C1-C6alkyl group, a C1-C6alkylsulfonyl group, a carboxyphenyl group or a pyrazinyl group; and $R^2$ is H or a group of the above general formula (IV), or a pharmaceutically acceptable salt thereof.

Also provided are synthetic intermediates thereof, processes for their preparation and medicaments containing them.

DISCLOSURE OF THE INVENTION

The present inventors conducted thorough investigations to solve the above problems and, as a result, have found that compounds of the general formula (I) or pharmaceutically acceptable salts thereof as described below possess potent opioid μ receptor antagonistic activity. The present compounds correspond to compounds of the formula (XI) wherein the 4-methylpyridin-2-yl group has been structurally converted to a 5-methylpyridin-2-yl group or a p-tolyl group and a cycloalkyl group is bound to the piperidine group at the 1-position thereof via a suitable spacer moiety and the compounds of the formula (XI) are analogous to fentanyl as disclosed in Japan Kokai 284460/1988.

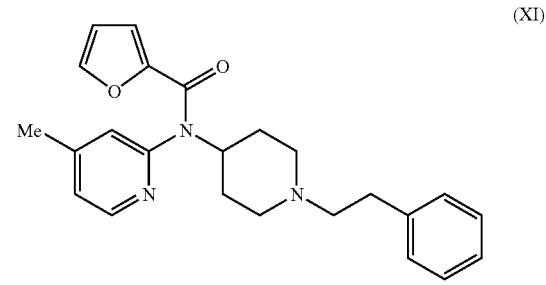

(XI)

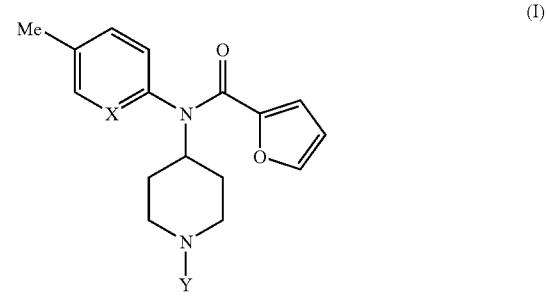

(I)

wherein

X is CH or N; and

Y is a group of the general formula (II):

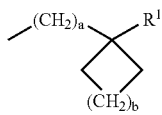

or a group of the general formula (II-a):

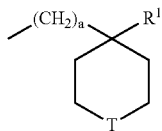

or a group of the general formula (III):

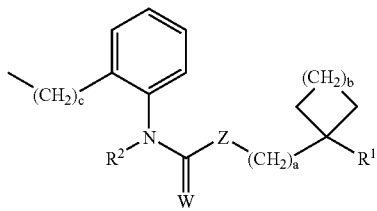

wherein
a, b and c are each an integer of 0-6;
Z is $CH_2$ or NH;
W is O or S;
T is O or N—$R^{15}$ wherein $R^{15}$ is H, a C1-C6 alkyl group, a benzyl group or a phenethyl group;
$R^1$ is H, a C1-C6 alkoxycarbonyl group, a benzyloxycarbonyl group, a carboxy group, a 2-phenyl-1,3-dioxan-5-yl group, a 2,2-dimethyl-1,3-dioxan-5-yl group, or a group of the general formula (IV):

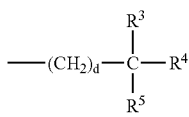

wherein
d is an integer of 0-6; and
$R^3$, $R^4$, and $R^5$ may be the same or different and are each independently H, —$(CH_2)_eR^6$ or —$(CH_2)_fCONR^7R^8$ wherein e and f are each an integer of 0-6; $R^6$ is a hydroxy group, a C1-C6 alkanoyloxy group, a benzoyloxy group, a 2-furoyloxy group, a C1-C6 alkoxy C1-C6 alkoxy group, a C1-C6 alkoxycarbonylphenoxy group, a carboxyphenoxy group, a dicarboxyphenoxy group, a di C1-C6 alkoxycarbonylphenoxy group, a dihydroxy C1-C6 alkylphenoxy group, an amino group, a C1-C6 alkoxycarbonylamino group, a C1-C6 alkyl sulfonamido group, a benzenesulfonamido group, a p-toluenesulfonamido group, a p-halobenzenesulfonamido group, a carboxy group, a C1-C6 alkoxycarbonyl group, a carbohydroxamic acid group, a carbohydroxamic acid C1-C6 alkyl ester group, a cyano group, a 1H-tetrazol-5-yl group, a 1-(C1-C6 alkyl)-1H-tetrazol-5-yl group, a 2-(C1-C6 alkyl)-2H-tetrazol-5-yl group, a $N^2$-hydroxycarbamidoyl group, a $N^1$-(C1-C6 alkoxycarbonyl)-$N^2$-hydroxycarbamidoyl group, a 2H-5-thioxo-1,2,4-oxadiazol-3-yl group, a 2H-5-oxo-1,2,4-oxadiazol-3-yl group, a guanidino group, a di C1-C6 alkoxycarbonylguanidino group or a morpholinocarbonyl group; and
$R^7$ and $R^8$ may be the same or different and are each independently is H, a C1-C6 alkyl group, a C1-C6 alkanoyloxy C1-C6 alkyl group, a hydroxy C1-C6 alkyl group, a bis(C1-C6 alkanoyloxy C1-C6 alkyl)methyl group, a bis(hydroxy C1-C6 alkyl)methyl group, a tris (C1-C6 alkanoyloxy C6 alkyl)methyl group, a tris(hydroxy C1-C6 alkyl)methyl group, a carboxy C1-C6 alkyl group, a C1-C6 alkoxycarbonyl C1-C6 alkyl group, a N,N-bis(C1-C6 alkanoyloxy C1-C6 alkyl)carbamoyl C1-C6 alkyl group, a N,N-bis(carboxy C1-C6 alkyl) carbamoyl C1-C6 alkyl group, a C1-C6 alkylsulfonyl group, a carboxyphenyl group or a pyrazinyl group; and
$R^2$ is H or a group of the above general formula (IV).

Moreover, it has also been found that the group of the present compounds possess peripheral selectivity and are medicaments with less activity to the central nervous system and high selectivity to digestive tracts. Therefore, the 4-(2-furoyl)aminopiperidines according to this invention are believed to be effective against side effects which are caused by the μ receptor agonists such as constipation, nausea/emesis, and itch or diseases such as idiopathic constipation, postoperative ileus, paralytic ileus, irritable bowel syndrome and chronic pruritus.

In the compounds represented by the general formula (I), the substituent Y bears a group selected from a cycloalkyl group, a piperidyl group or a tetrahydropyranyl group, as shown in the general formulae (II), (II-a) and (III). In the general formulae (II) and (III), b is an integer of 0-6, so that specific examples of the cycloalkyl group may include cyclopropyl, cyclobutyl, cyclopentyl, cyclohexyl, cycloheptyl, cyclooctyl and cyclononyl groups.

The cycloalkyl group, the piperidyl group or the tetrahydropyranyl group is bound to the piperidyl group of the compound represented by the general formula (I) via the structure as shown by the general formulae (II), (II-a) and (III). The cycloalkyl group, the piperidyl group or the tetrahydropyranyl group bears a substituent as defined by $R^1$.

Specific examples of $R^1$ may include hydrogen, a carboxy group, a carboxymethyl group, a 3-carboxypropyl group, a 3,3-bis(carboxy)propyl group, a N,N-bis(carboxymethyl) carbamoylmethyl group, a N-(carboxymethyl)carbamoylmethyl group, a N-(2-carboxyethyl)carbamoylmethyl group, a N,N-bis[N,N-bis(carboxymethyl)carbamoylmethyl]carbamoylmethyl, a methoxycarbonyl group, a methoxycarbonylmethyl group, a 3-methoxycarbonylpropyl group, a 3,3-bis (methoxycarbonyl)propyl group, a 3,3,3-tris (ethoxycarbonyl)propyl group, a N,N-bis (ethoxycarbonylmethyl)carbamoylmethyl group, a N-(ethoxycarbonylmethyl)carbamoylmethyl group, a N-(2-ethoxycarbonylethyl)carbamoylmethyl group, a N-(3-ethoxycarbonylpropyl)carbamoylmethyl group, a N,N-bis [N,N-bis(ethoxycarboxymethyl)carbamoylmethyl] carbamoylmethyl group, a 2-hydroxyethyl group, a 3-hydroxypropyl group, a 3,3-bis(hydroxymethyl)propyl group, a 5-hydroxy-3,3-bis(hydroxymethyl)pentyl group, a 1,3-dihydroxy-2-propyl group, a 6-carboxy-3,3-bis(hydroxymethyl)hexyl group, a 6-methoxycarbonyl-3,3-bis(hydroxymethyl)hexyl group, a tris(hydroxymethyl)methylcarbamoylmethyl group, a N,N-bis[tris(hydroxymethyl)methylcarbamoylmethyl]carbamoylmethyl group, a 3-acetoxypropyl group, a 3,3-bis(acetoxymethyl)propyl group, a 3,3-bis(methoxymethoxymethyl)propyl group, a 5-acetoxy-3,3-bis(acetoxymethyl)pentyl group, a 2-phenyl-1,3-dioxan-5-yl group, a 2,2-dimethyl-1,3-dioxan-5-yl group, a 6-methoxycarbonyl-3,3-bis(benzoyloxymethyl)hexyl group, a 2-(2-furoyloxy)ethyl group, a tris(acetoxymethyl)methylcarbamoylmethyl group, a carbamoylmethyl group, a cyanomethyl group, a 2-cyanoethyl group, a 2-(tetrazolyl)ethyl group, an acetohydroxamic acid group, a N-(t-butoxy)carbamoylmethyl group, a 2-aminoethyl group, a 2-(t-butoxycarboxamido)ethyl group, a 2-(methanesulfonamido)ethyl group, a 2-(p-chlorobenzenesulfonamido)ethyl group, a 2-(2-methoxycarbonylphenoxy)ethyl group, a 2-(2-carboxyphenoxy)ethyl group, a 2-(3,5-dicarboxyphenoxy)ethyl group, a 2-(3,5-dimethoxycarbonylphenoxy)ethyl group, a 2-(3,5-dihydroxymethylphenoxy)ethyl group, a 2-(1-methyl-1H-tetrazol-5-yl)ethyl group, a 2-(2-methyl-2H-tetrazol-5-yl) ethyl group, a 2-($N^1$-methoxycarbonyl-$N^2$-hydroxycarbamidoyl)ethyl group, a 2-(1,2-dimethoxycarbonylguanidino)ethyl group, a methanesulfonylcarbamoylmethyl group, a carboxyphenylcarbamoylmethyl group, a pyrazinylcarbamoyl methyl group, etc.

Specific examples of —$(CH_2)_a$— in the group of the general formula (II) may include a single bond, a methylene group, an ethylene group, a trimethylene group, a tetramethylene group, a pentamethylene group, a hexamethylene group, etc.

Specific examples of the group of the general formula (II-a) may include a 2-[4-(2-hydroxyethyl)tetrahydropyran-4-yl]ethyl group, a 2-[1-benzyl-4-(2-hydroxyethyl)piperidin-4-yl]ethyl group, etc.

Specific examples of the group of the general formula (III) may include a 2-(cyclohexylacetamido)benzyl group, a 2-[2-(cyclohexylacetamido)phenyl]ethyl group, a 2-[2-[N-(cyclohexylacetyl)carboxymethylamino]phenyl]ethyl group, a 2-[2-[N-(cyclohexylacetyl)-tert-butoxycarbonylmethylamino]phenyl]ethyl group, a 3-[2-(cyclohexylacetamido)phenyl]propyl group, a 3-[2-(3-cyclohexylpropionamido)phenyl]propyl group, a 3-[2-[N-(3-cyclohexylpropionyl)carboxymethylamino]phenyl]propyl group, a 3-[2-[N-(3-cyclohexylpropionyl)-tert-butoxycarboxymethylamino]phenyl]propyl group, a 3-[2-[N-(3-cyclohexylpropionyl)-3-carboxypropylamino]phenyl]propyl group, a 2-[2-(3-cyclohexylureido)phenyl]ethyl group, a 2-[2-[N-(N-cyclohexylcarbamoyl)carboxymethylamino]phenyl]ethyl group, a 2-[2-[N-(N-cyclohexylcarbamoyl)ethoxycarbonylmethylamino]phenyl]ethyl group, a 3-[2-(4-cyclohexylbutyramido)phenyl]propyl group, a 2-[2-[N-[1-(carboxymethyl)cyclohexylacetyl]carbonylmethylamino]phenyl]ethyl group, a 2-[2-[N-[1-(carboxymethyl)cyclohexylacetyl]ethoxycarbonylmethylamino]phenyl]ethyl group, a 2-[2-[1-(carboxymethyl)cyclohexylacetamido]phenyl]ethyl group, a 2-[2-[1-(methoxycarboxymethyl)cyclohexylacetamido]phenyl]ethyl group, a 3-[2-(3-cyclohexylureido)phenyl]propyl group, a 3-[2-[N-(3-cyclohexylthioureido)phenyl]propyl group, etc.

A compound of this invention represented by the general formula (X):

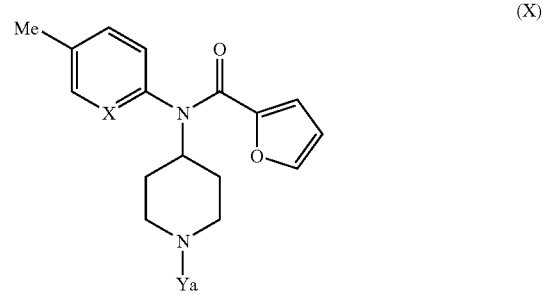

wherein
X is CH or N; and
$Y_a$ is a group of the general formula (VI):

or a group of the general formula (VI-a):

or a group of the general formula (VII):

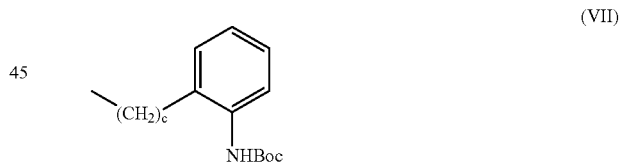

or a group of the general formula (VIII):

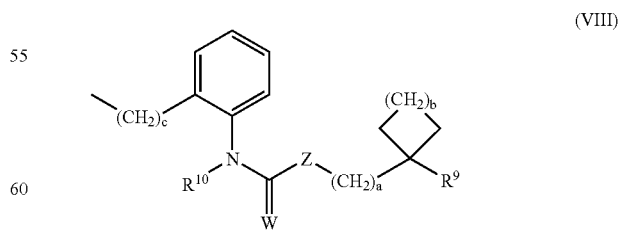

wherein
a, b and c are each an integer of 0-6;
Z is $CH_2$ or NH;
W is O or S;

T is O or N—R$^{15}$ wherein R$^{15}$ is H, a C1-C6 alkyl group, a benzyl group or a phenethyl group;

R$^9$ is H, a C1-C6 alkoxycarbonyl group, a benzyloxycarbonyl group, a carboxy group, a 2-phenyl-1,3-dioxan-5-yl group, a 2,2-dimethyl-1,3-dioxan-5-yl group or a group of the general formula (IX):

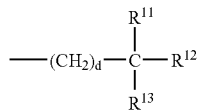

(IX)

wherein d is an integer of 0-6; and R$^{11}$, R$^{12}$, and R$^{13}$ may be the same or different and are each independently H or —(CH$_2$)$_e$R$^{14}$ wherein e is 0-6; R$^{14}$ is a C1-C6 alkanoyloxy group, a benzoyloxy group, a 2-furoyloxy group, a C1-C6 alkoxy C1-C6 alkoxy group, a C1-C6 alkoxycarbonylphenoxy group, a di C1-C6 alkoxycarbonylphenoxy group, a dihydroxy C1-C6 alkylphenoxy group, a carboxy group, a C1-C6 alkoxycarbonyl group, a C1-C6 alkoxycarbonylamino group, a benzyloxycarbonyl group, a cyano group or a C1-C6 alkylsulfonamido group; and R$^{10}$ is H or a group of the general formula (IX), may be prepared, for example, by reacting a compound represented by the general formula (V):

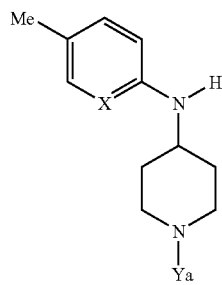

(V)

wherein X and Ya are the same as those defined in the general formula (X), with 2-furancarboxylic acid or its reactive derivative such as 2-furoyl chloride.

The reaction is carried out in an organic solvent such as dichloromethane, chloroform, diethyl ether or tetrahydrofuran at a temperature of from ice cooling temperature to reflux temperature.

When the reaction with 2-furoyl chloride is carried out in the presence of a base, specific examples of the base may include triethylamine and the like.

Specific examples of the compound represented by the general formula (X) may include:

N-[1-(cyclohexylmethyl)piperidin-4-yl]-N-(5-methylpyridin-2-yl)-2-furancarboxamide,
N-[1-(2-cyclohexylethyl)piperidin-4-yl]-N-(5-methylpyridin-2-yl)-2-furancarboxamide,
N-[1-(3-cyclohexylpropyl)piperidin-4-yl]-N-(5-methylpyridin-2-yl)-2-furancarboxamide,
N-[1-(4-cyclohexylbutyl)piperidin-4-yl]-N-(5-methylpyridin-2-yl)-2-furancarboxamide,
N-[1-(2-cyclohexyloctylethyl)piperidin-4-yl]-N-(5-methylpyridin2-yl)2furancarboxamide,
N-[1-(3-cyclohexylpropyl)piperidin-4-yl]-N-(p-tolyl)-2-furancarboxamide,
N-(1-cyclohexylpiperidin-4-yl)-N-(5-methylpyridin-2-yl)-2-furancarboxamide,
N-[1-[3-[2—(cyclohexylacetamido)phenyl]prOpyl]piperidin4-yl]-N-(5-methylpyridin-2-yl)-2-furancarboxamide,
N-[1-[2-[2-(cyclohexylacetamido)phenyl]ethyl]piperidin-4-yl]-N-(5-methylpyridin-2-yl)-2-furancarboxamide,
methyl [1-[2-[4-[N-(5-methylpyridin-2-yl)-2-furancarboxamido]piperidinlyl]ethyl]cyclohexyl]acetate,
methyl [1-[2-[4-[N-(5-methylpyridin-2-yl)-2-furancarboxamido]piperidin-1-yl]ethyl]cyclopentyl]acetate,
methyl [1-[2-[4 -[N-(5-methylpyridin-2-yl)-2-furancarboxamido]piperidin-1-yl]ethyl]cyclohexanecarboxylate,
[1-[2-[4-[N-(5-methylpyridin-2-yl)-2-furancarboxamido]piperidin-1-yl]ethyl]cyclohexanecarboxylic acid,
methyl 4-[1-[2-[4-[N-(5-methylpyridin-2-yl)-2-furancarboxamido]piperidin-1yl]ethyl]cyclohexyl]butyrate,
triethyl 3-[1-[1-[4-[N(5-methylpyridin-2-yl)-2furancarboxamido]piperidin-1-yl]ethyl]cyclohexyl]-1,1,1-propanetricarboxylate,
dimethyl 3-[1-[2-[4-[N-(p-tolyl)-2furancarboxamido]piperidin-1-yl]ethyl]cyclohexyl]-1,1-propanedicarboxylate,
methyl [1-[2-[4-[N-(p-tolyl)-2-furancarboxamido]piperidin-1-yl]ethyl]cyclohexyl]acetate,
propyl 3-[1-[2-[4 -[N-(5methylpyridin-2yl)-2-furancarboxamido]piperidin-1-yl]methyl]cyclohexyl]acetate,
2-[1-[1-[2-[4-[N-(5-methylpyridin-2yl)2-furancarboxamido]-piperidinl-yl]ethyl]cyclohexyl]ethyl]1,3-diacetoxypropane,
N-[1-[2-1-[4-(methoxymethoxy)-3-(rnethoxymethoxy)butyl]cyclohexyl]ethyl]piperidin4-yl]-N-(5methylpyridin-2-yl)-2-furancarboxamide,
2-(acetoxymethyl)-2-[2-[1-[2-[4-[N-(5methylpyridin2-yl)-2-furancarboxamido]piperidin-1-yl]ethyl]cyclohexyl]ethyl]-1,4-diacetoxybutane,
N-[1-[2-[1-(2-phenyl-1,3-dioxan-5-yl)cyclohexyl]ethyl]piperidin-4-yl]-N-(5-methylpyridin-2-yl)-2-furancarboxamide,
N-[1-[1-[1-(2,2-dimethyl-1,3-dioxan-5-yl)cyclohexyl]ethyl]-piperidin4yl]-N-(p-tolyl)2-furancarboxamide,
methyl 5,5bis(benzoyloxymethyl)-7-[1-[2-[4-[N-(5methylpyridin-2-yl)-2-furancarboxamido]piperidin-1-yl]ethyl]cyclohexyl]heptanoate,
methyl 5,5-bis(benzoyloxymethyl)-7-[1-[2-[4-[N-(p-tolyl)-2-furancarboxamido]piperidin-1-yl]ethyl]cyclohexyl] heptanoate,
2-[1-[1-[2-[4-[N-(p-tolyl)-2-furancarboxamido]piperidin-1-yl]ethyl]cyclohexyl]ethyl]-1,3diacetoxypropane,
2-[2-[1-[2-[4 [N-(5methylpiperidin-2-yl)2-furancarboxamido]piperidin1-yl]ethyl]cyclohexyl]ethyl 2-furancarboxylate
N-[1-[2-[1-(2-cyanoethyl)cyclohexyl]ethyl]piperidin4yl]-N-(5-methylpyridin2-yl)-2furancarboxamide,
tert-butyl [2-[1-[2-[4-[N-(5-methylpyridin-2-yl)-2-furancarboxamido]piperidin-1-yl]ethyl]cyclohexyl]ethyl]carbamate,
N -[1-[1-[1(2methanesulfonamidoethyl)cyclohexyl]ethyl] piperidin-4-yl]-N-(5-methylpyridin-2-yl)-2-furancarboxamide,
N-[1-[2-(cyclohexylacetamido)benzyl]piperidin-4-yl]-N-(5-methylpyridin-2-yl)-2-furancarboxamide,
N-[1-[2-[2-(cyclohexylacetamido)phenyl]ethyl]piperidin-4-yl]-N-(p-tolyl)-2-furancarboxamide, N-[1-[3-[2-(3-cyclohexylpropionamido)phenyl]propyl]piperidin-4-yl]-N-(p-tolyl)-2-furancarboxamide, tertbutyl [2-[3-[4-[N-(5methylpyridin2yl)-2furancarboxamido]piperidin-1-yl]propyl]phenyl]carbamate, tert-butyl [2-[3-[4-[N-(ptolyl)-2furancarboxamidO]piperidin-1-yl]propyl]phenyl]carbamate, N-[1-[2-[1-(2-cyanoethyl)cyclohexyl]ethyl]piperidin-4-yl]-N-(p-tolyl)-2-furancarboxamide, 2-(acetoxymethyl)-1-[1-[1-[2-[4-[N-(p-tolyl)2furancarboxamido]piperidin-1-yl]ethyl]cyclohexyl]ethyl]-1,4-diacetoxybutane, tert-butyl 2-[1-[2-[4-[N-(p-tolyl)-2-furancarboxamido]piperidin-1-yl]ethyl]cyclohexyl]ethylcarbamate, dimethyl 5-[2-[1-[4-[N-(p-tolyl)-2-furancarboxamido]piperidin-1-yl]ethyl]cyclohexyl]ethoxy]isophthalate, methyl 2-[2-[1-[2-[4-[N-(p-tolyl)-2-furancarboxamido]piperidin-1-yl]ethyl]cyclohexyl]ethoxy]benzoate, 2-[1-[2-[4-[N-(ptolyl)-2furancarboxamido]piperidinl-yl]ethyl]cyclohexyl]ethyl 2-furancarboxylate methyl 4-[1-[2-[4-[N-(p-tolyl)-2-furancarboxamido]piperidin-1-yl]ethyl]cyclohexyl]butyrate, triethyl 3-[1-[2-[4-[N-(p-tolyl)-2furancarboxamidol]piperidin-1-yl]ethyl]cyclohexyl]-1,1,1-propanetricarboxylate, etc.

A compound of the following general formula (XII):

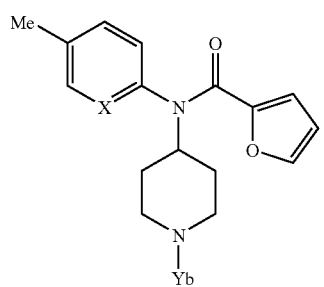

(XII)

wherein

X is CH or N; and

Yb is a group of the general formula (II):

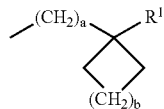

wherein b is an integer of 0-6; and

R$^1$ is a carboxy group or a group of the general formula (IV):

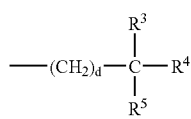

wherein d is an integer of 0-6; R$^3$ is H or —(CH$_2$)$_e$COOH; R$^4$ and R$^5$ may be the same or different and are each independently H or —(CH$_2$)$_e$R$^6$ wherein e is an integer of 0-6; R$^6$ is a carboxy group, a hydroxy group, or a carboxyphenoxy group, which is included within the compounds of this invention represented by the general formula (I), may be prepared by hydrolysis of the corresponding methyl ester, ethyl ester, etc. with a base (e.g., lithium hydroxide, sodium hydroxide, potassium hydroxide or potassium carbonate) or by debenzylation of the corresponding benzyl ester in the presence of a catalyst (e.g., palladium-carbon) under hydrogen atmosphere.

The reaction is carried out in water or an organic solvent such as methanol, ethanol, 1,4-dioxane, acetic acid, or ethyl acetate at a temperature of from room temperature to reflux temperature.

Specific examples of the compound represented by the general formula (XII) may include:

[1-[2-[4-[N-(5-methylpyridin-2-yl)-2-furancarboxamido]piperidin-1-yl]ethyl]cyclohexyl]acetic acid,

[1-[2-[4-[N-(5-methylpyridin-2-yl)-2-furancarboxamido]piperidin-1-yl]ethyl]cyclopentyl]acetic acid, 4-[1-[2-[4-[N-(5-methylpyridin-2-yl)-2-furancarboxamido]piperidin-1-yl]ethyl]cyclohexyl]butyric acid, 3-[1-[2-[4-[N-(5-methylpyridin-2-yl)-2-furancarboxamido]piperidin-1-yl]ethyl]cyclohexyl]-1,1-propanedicarboxylic acid, 3-[1-[2-[4-[N-(p-tolyl)-2-furancarboxamido]piperidin-1-yl]ethyl]cyclohexyl]-1,1-propanedicarboxylic acid,

[1-[2-[4-[N-(p-tolyl)-2-furancarboxamido]piperidin-1-yl]ethyl]cyclohexyl]acetic acid, 5,5-bis(hydroxymethyl)-7-[1-[2-[4-[N-(5-methylpyridin-2-yl)-2-furancarboxamido]piperidin-1-yl]ethyl]cyclohexyl]heptanoic acid, 5,5-bis(hydroxymethyl)-7-[1-[2-[4-[N-(p-tolyl)-2-furancarboxamido]piperidin-1-yl]ethyl]cyclohexyl]heptanoic acid, 5-[2-[1-[2-[4-[N-(p-tolyl)-2-furancarboxamido]piperidin-1-yl]ethyl]cyclohexyl]ethoxy]isophthalic acid, 2-[2-[1-[2-[4-[N-(p-tolyl)-2-furancarboxamido]piperidin-1-yl]ethyl]cyclohexyl]ethoxy]benzoic acid, 4-[1-[2-[4-[N-(p-tolyl)-2-furancarboxamido]piperidin-1-yl]ethyl]cyclohexyl]butyric acid, etc.

Moreover, the compound represented by the general formula (XII) may be activated with a carboxy group activating agent, and then, reacted with an amino acid ester or amino alcohol acetic acid ester, or alternatively reacted with an amino acid ester or amino alcohol acetic acid ester in the presence of a condensing agent to prepare the corresponding amino acid ester derivative or amino alcohol acetic acid ester derivative. Further, this amino acid ester derivative or amino alcohol acetic acid ester derivative may be hydrolyzed with an acid or base to prepare the corresponding amino acid derivative or amino alcohol derivative. The compounds thus prepared are also included within the compounds of this invention represented by the general formula (I).

Specific examples of the carboxy group activating agent may include oxalyl chloride, thionyl chloride, etc. Specific examples of the condensing agent may include dicyclohexylcarbodiimide, 1-ethyl-3-(3-dimethylaminoprpoyl)carbodiimide hydrochloride, benzotriazol-1-yloxytris(dimethylamino)phosphonium hexafluorophosphate, benzotriazol-1-yloxytrispyrrolidinophosphonium hexafluorophosphate, O-(7-azabenzotriazol-1-yl)-1,1,3,3-tetramethyluronium hexafluorophosphate, 2-bromo-1-ethylpyrydinium tetrafluoroborate, 2-fluoro-1-ethylpyridinium tetrafluoroborate, etc.

Specific examples of the amino acid ester may include ethyl aminoacetate, ethyl 3-aminopropionate, ethyl 4-aminobutyrate, diethyl iminodiacetate, tris(acetoxymethyl)aminomethane, etc. The bases to be used for hydrolysis may include lithium hydroxide, sodium hydroxide, potassium hydroxide, potassium carbonate, etc. and the acids may include hydrochloric acid, trifluoroacetic acid, etc.

Specific examples of the amino acid ester derivative, amino alcohol acetic acid ester derivative, amino acid derivative and amino alcohol derivative thus prepared may include:

N-[1-[2-[1-[N-[tris(hydroxymethyl)methyl]carbamoylmethyl]cyclohexyl]ethyl]piperidin-4-yl]-N-(5-methylpyridin-2-yl)-2-furancarboxyamide, 2-acetoxymethyl-2-[1-[2-[4-[N-(5-methylpyridin-2-yl)-2-furancarboxamido]piperidin-1-yl]ethyl]cyclohexyl]acetamido-1,3-diacetoxypropane, diethyl 2-[1-[2-[4-[N-(5-methylpyridin-2-yl)-2-furancarboxamido]piperidin-1-yl]ethyl]cyclohexyl]acetyliminodiacetate, 2-[1-[2-[4-[N-(5-methylpyridin-2-yl)-2-furancarboxamido]piperidin-1-yl]ethyl]cyclohexyl]acetyliminodiacetic acid, ethyl 4-[2-[1-[2-[4-[N-(5-methylpyridin-2-yl)-2-furancarboxamido]piperidin-1-yl]ethyl]cyclohexyl]acetamido]butyrate, ethyl [2-[1-[2-[4-[N-(5-methylpyridin-2-yl)-2-furancarboxamido]piperidin-1-yl]ethyl]cyclohexyl]acetamido]acetate,

[2-[1-[2-[4-[N-(5-methylpyridin-2-yl)-2-furancarboxamido]piperidin-1-yl]ethyl]cyclohexyl]acetamido]acetic acid, ethyl 3-2-[1-[2-[4-[N-(5-methylpyridin-2-yl)-2-furancarboxamido]piperidin-1-yl]ethyl]cyclohexyl]acetamido]propionate, 3-[2-[1-[2-[4-[N-(5-methylpyridin-2-yl)-2-furancarboxamido]piperidin-1-yl]ethyl]cyclohexyl]acetamido]propionic acid, ethyl 4-[2-[1-[2-[4-[N-(5-methylpyridin-2-yl)-2-furancarboxamido]piperidin-1-yl]ethyl]cyclopentyl]acetamido]butyrate, N-[1-[2-[1-[N,N-bis[N-tris(acetoxymethyl)methyl]carbamoylmethyl]carbamoylmethyl]cyclohexyl]ethyl]piperidin-4-yl]-N-(5-methylpyridin-2-yl)-2-furancarboxyamide, N-[1-[2-[1-[N,N-bis[N-tris(hydroxymethyl)carbamoylmethyl]carbamoylmethyl]cyclohexyl]ethyl]piperidin-4-yl]-N-(5-methylpyridin-2-yl)-2-furancarboxyamide,

[2-[1-[2-[4-[N-(p-tolyl)-2-furancarboxamido]piperidin-1-yl]ethyl]cyclohexyl]acetamido]acetic acid, 4-[2-[1-[2-[4-[N-(p-tolyl)-2-furancarboxamido]piperidin-1-yl]ethyl]cyclohexyl]acetamido]butyric acid, 2-[1-[2-[4-[N-(p-tolyl)-2-furancarboxamido]piperidin-1-yl]ethyl]cyclohexyl]acetyliminodiacetic acid, tetraethyl 2-[1-[2-[4-[N-(p-tolyl)-2-furancarboxamido]piperidin-1-yl]ethyl]cyclohexyl]acetylimino-N,N-bis(acetyliminodiacetate), 2-[1-[2-[4-[N-(p-tolyl)-2-furancarboxamido]piperidin-1-yl]ethyl]cyclohexyl]acetylimino-N,N-bis(acetyliminodiacetic acid), etc.

The carboxamide derivative may be prepared by reacting a compound represented by the general formula (XII) with ammonia, an ammonium salt, an amine, an amine salt, a sulfonamide, etc., in the presence of a condensing agent. Specific examples of the amine may include morpholine, 2-methoxycarbonylaniline, pyrazinylamine, etc. Specific examples of the sulfonamide may include methanesulfonamide and the like. Of these derivatives, the ester derivative may be hydrolyzed with an acid or base to prepare the corresponding carboxylic acid. These carboxamide derivatives are also included within the compounds of this invention represented by the general formula (I).

Specific examples of the condensing agent may include dicyclohexylcarbodiimide, 1-ethyl-3-(3-dimethylamino-prpoyl)carbodiimide hydrochloride, benzotriazol-1-yloxytris(dimethylamino)phosphonium hexafluorophosphate, benzotriazol-1-yloxytrispyrrolidinophosphonium hexafluorophosphate, O-(7-azabenzotriazol-1-yl)-1,1,3,3-tetramethyluronium hexafluorophosphate, 2-bromo-1-ethylpyrydimium tetrafluoroborate, 2-fluoro-1-ethylpyridimium tetrafluoroborate, etc.

The reaction is carried out in an organic solvent such as dichloromethane, chloroform, tetrahydrofuran or N,N-dimethylformamide at a temperature of from room temperature to reflux temperature.

The bases to be used for hydrolysis may include lithium hydroxide, sodium hydroxide, potassium hydroxide, potassium carbonate, etc., and the acids may include hydrochloric acid, trifluoroacetic acid, etc.

Specific examples of the carboxamide derivative may include:

N-[1-[2-[1-(carbamoylmethyl)cyclohexyl]ethyl]piperidin-4-yl]-N-(5-methylpyridin-2-yl)-2-furancarboxamide, N-[1-[2-[1-(1-methanesulfonylcarbamoylmethyl)cyclohexyl]ethyl]piperidin-4-yl]-N-(p-tolyl)-2-furancarboxamide, N-[1-[2-[1-(1,1-dimethylcarbamoylmethyl)cyclohexyl]ethyl]piperidin-4-yl]-N-(p-tolyl)-2-furancaroxamide, N-[1-[2-[1-(2-morpholin-4-yl-2-oxoethyl)cyclohexyl]ethyl]piperidin-4-yl]-N-(p-tolyl)-2-furancarboxamide, 2-[2-[1-[2-[4-[N-(p-tolyl)-2-furancarboxamido]piperidin-1-yl]ethyl]cyclohexyl]acetylamino]benzoic acid, N-[1-[2-[1-[1-(pyrazin-2-yl)carbamoylmethyl]cyclohexyl]ethyl]piperidin-4-yl]-N-(p-tolyl)-2-furancarboxamide, N-[1-[2-[1-(1,1-dimethylcarbamoylmethyl)cyclohexyl]ethyl]piperidin-4-yl]-N-(5-methylpiperidin-2-yl)-2-furancarboxamide, N-[1-[2-[1-(2-morpholin-4-yl-2-oxoethyl)cyclohexyl]ethyl]piperidin-4-yl]-N-(5-methylpiperidin-2-yl)-2-furancarboxamide, 2-[2-[1-[2-[4-[N-(5-methylpyridin-2-yl)-2-furancarboxamido]piperidin-1-yl]ethyl]cyclohexyl]acetylamino]benzoic acid, N-[1-[2-[1-(carbamoylmethyl)cyclohexyl]ethyl]piperidin-4-yl]-N-(p-tolyl)-2-furancarboxamide, etc.

The carboxamide derivative may be further converted to a nitrile derivative in the presence of a sulfonyl chloride (e.g., methanesulfonyl chloride or benzenesulfonyl chloride) and triethylamine. The nitrile derivatives are also included within the compounds of this invention represented by the general formula (I).

The reaction is carried out in an organic solvent such as dichloromethane, chloroform, tetrahydrofuran or N,N-dimethylformamide at a temperature of from room temperature to reflux temperature.

Specific examples of the nitrile derivative may include N-[1-[2-[1-(cyanomethyl)cyclohexyl]ethyl]piperidin-4-yl]-N-(5-methylpyridin-2-yl)-2-furancarboxamide, N-[1-[2-[1-(cyanomethyl)cyclohexyl]ethyl]piperidin-4-yl]-N-(p-tolyl)-2-furancarboxamide, etc.

The nitrile derivative may further be converted to a tetrazole derivative by reacting it with trimethylsilyl azide. The tetrazole derivatives are also encompassed by the compounds of this invention represented by the general formula (I).

The reaction is carried out in an organic solvent such as benzene, toluene, xylene, tetrahydrofuran or 1,4-dioxane at a temperature of from ice cooling temperature to reflux temperature.

The tetrazole derivative may be converted to another tetrazole derivative by reacting it with trimethylsilyl diazomethane. The latter tetrazole derivatives are also included within the compounds of this invention represented by the general formula (I).

The reaction is carried out in an organic solvent such as benzene, toluene, xylene, tetrahydrofuran or 1,4-dioxane at a temperature of from ice cooling temperature to reflux temperature.

Specific examples of the tetrazole derivative may include:
N-[1-[2-[1-(2-tetrazolylethyl)cyclohexyl]ethyl]piperidin-4-yl]-N-(5-methylpyridin-2-yl)-2-furancarboxamide,
N-[1-[2-[1-(2-tetrazolylethyl)cyclohexyl]ethyl]piperidin-4-yl]-N-(p-tolyl)-2-furancarboxamide,
N-[1-[2-[1-[2-(2-methyl-2H-tetrazol-5-yl)ethyl]cyclohexyl]ethyl]piperidin-4-yl]-N-(5-methylpyridin-2-yl)-2-furancarboxamide,
N-[1-[2-[1-[2-(1-methyl-1H-tetrazol-5-yl)ethyl]cyclohexyl]ethyl]piperidin-4-yl]-N-(5-methylpyridin-2-yl)-2-furancarboxamide, etc.

The nitrile drivative may, for example, be further converted to a hydroxycarbamidoyl derivative by reacting it with hydroxylamine in the presence of a base such as sodium hydrogencarbonate or potassium carbonate. The hydroxycarbamidoyl derivatives are also included within the compounds of this invention represented by the general formula (I).

The reaction is carried out in an organic solvent such as benzene, toluene, xylene, tetrahydrofuran or 1,4-dioxane at a temperature of from ice cooling temperature to reflux temperature.

Specific examples of the hydroxycarbamoyl derivative may include N-[1-[2-[1-[2-($N^2$-hydroxycarbamidoyl)ethyl]cyclohexyl]ethyl]piperidin-4-yl]-N-(p-tolyl)-2-furancarboxamide and the like.

The hydroxycarbamidoyl derivative may, for example, be converted to a thiooxooxadiazole derivative by reacting it with 1,1-thiocarbonyldiimidazole. The thiooxooxadiazole derivatives are also included within the compounds of this invention represented by the general formula (I).

The reaction is carried out in an organic solvent such as acetonitrile, benzene, toluene, xylene, tetrahydrofuran or 1,4-dioxane at a temperature of from ice cooling temperature to reflux temperature.

Specific examples of the thiooxooxadiazole derivative may include N-[1-[2-[1-[2-(2H-5-thioxo-1,2,4-oxadiazol-3-yl)ethyl]cyclohexyl]ethyl]piperidin-4-yl]-N-(p-tolyl)-2-furancarboxamide and the like.

The hydroxycarbamidoyl derivatives may, for example, be converted to a hydroxymethoxycarbonylcarbamidoyl derivative by reacting it with methyl chloroformate in the presence of a base such as pyridine. The hydroxymethoxycarbonylcarbamidoyl derivatives are also included within the compounds of this invention represented by the general formula (I).

The reaction is carried out in an organic solvent such as N,N-dimethylformamide, acetonitrile, benzene, toluene, xylene, tetrahydrofuran or 1,4-dioxane at a temperature of from ice cooling temperature to reflux temperature.

Specific examples of the hydroxymethoxycarbamidoyl derivative may include methyl 1-[1-hydroxyimino-3-[1-[2-[4-[N-(p-tolyl)-2-furancarboxamido]piperidin-1-yl]ethyl]cyclohexyl]propyl]carbamate and the like.

The hydroxymethoxycarbonylcarbamidoyl derivative may, foe example, be converted to an oxooxadiazole derivative by reacting it with a base such as 1,8-diazabicyclo[5.4.0]-7-undecene. The oxooxadiazole derivatives are also included within the compounds of this invention represented by the general formula (I).

The reaction is carried out in an organic solvent such as acetonitrile, benzene, toluene, xylene, tetrahydrofuran, or 1,4-dioxane at a temperature of from ice cooling temperature to reflux temperature.

Specific examples of the oxooxadiazole derivative may include N-[1-[2-[1-[2-(2H-oxo-1,2,4-oxadiazol-3-yl)ethyl]piperidin-4-yl]-N-(p-tolyl)-2-furancarboxamide and the like.

The hydroxamic acid derivative may be prepared by reacting a compound represented by the general formula (XII) with hydroxylamine hydrochloride, O-(tert-butyl)hydroxylamine hydrochloride or the like. The butyl group may be deprotected by acid (e.g., hydrochloric acid or trifluoroacetic acid). The hydroxamic acid derivatives are also included within the compounds of this invention represented by the general formula (I).

Specific examples of the hydroxamic acid derivative may include:
tert-butyl [1-[2-[4-[N-(5-methylpyridin-2-yl)-2-furancarboxamido]piperidin-1-yl]ethyl]cyclohexyl]-acetohydroxamate,
[1-[2-[4-[N-(5-methylpyridin-2-yl)-2-furancarboxamido]piperidin-1-yl]ethyl]cyclohexyl]acetohydroxamic acid,
tert-butyl [1-[2-[4-[N-(p-tolyl)-2-furancarboxamido]piperidin-1-yl]ethyl]cyclohexyl]acetohydroxamate,
[1-[2-[4-[N-(p-tolyl)-2-furancarboxamido]piperidin-1-yl]ethyl]cyclohexyl]acetohydroxamic acid, etc.

A compound represented by the general formula (XIII):

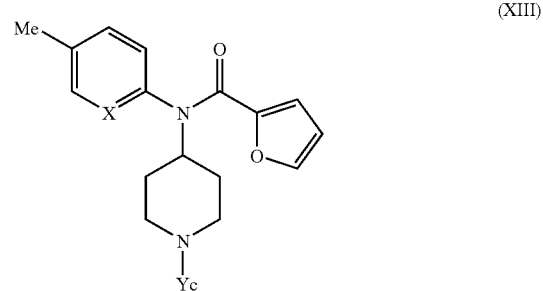

(XIII)

wherein

X is CH or N; and

Yc is a group of the general formula (II):

(II)

or a group of the general formula (II-a):

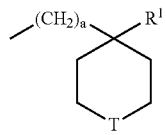

wherein a and b are each an integer of 0-6;
T is O or N—$R^{15}$ wherein $R^{15}$ is H, a C1-C6 alkyl group, a benzyl group or a phenethyl group;
$R^1$ is a group of the general formula (IV):

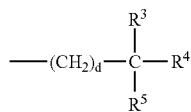

wherein d is an integer of 0-6; $R^3$ is —$(CH_2)_e$OH wherein e is an integer of 0-6; $R^4$ and $R^5$ may be the same or different and are each independently H or —$(CH_2)_e R^6$ wherein $R^6$ is a carboxy group, a hydroxy group or a dihydroxy C1-C6 alkylphenoxy group, which is included within the compounds of this invention represented by the general formula (I), may be prepared by hydrolysis of the corresponding acetic acid ester form, benzoyl ester form or 2-furoyl ester form with a base (e.g., lithium hydroxide, sodium hydroxide, potassium hydroxide or potassium carbonate), or alternatively by hydrolysis of the corresponding acetal form (e.g., the 2-phenyl-1,3-dioxane-5-yl form, 2,2-dimethyl-1,3-dioxan-5-yl form or methoxymethyl form) with an acid (e.g., hydrochloric acid or p-toluenesulfonic acid), or hydrolysis of the corresponding silyl ether derivative with an acid (e.g., hydrochloric acid or p-toluenesulfonic acid) or by treatment the derivative with a fluorinating agent (e.g., tetra-n-butylammonium fluoride).

The hydrolysis reaction is carried out in water or an organic solvent such as methanol, ethanol or 2-propanol at a temperature of from ice cooling temperature to reflux temperature. The treatment with the fluorinating agent is carried out in an organic solvent such as dichloromethane, chloroform, diethyl ether or tetrahydrofuran at a temperature of from ice cooling temperature to reflux temperature.

Specific examples of the compound represented by the general formula (XIII) may include:
N-[1-[1-(3-hydroxypropyl)cyclohexylmethyl]piperidin-4-yl]-N-(5-methylpiperidin-2yl)-2-furancarboxarnide,
N-[1-[2-[1-(4-hydroxy-3-hydroxymethylbutyl)cyclohexyl [ethyl-]piperidin-4-yl]N-(5-methylpiperidin-2-yl)-2-furancarboxamide,
N-[1-[2-[1-[5-hydroxy-3,3-bis(hydroxymethyl)pentyl]cyclohexyl]ethyl]piperidin4yl]-N-(5-methylpiperidin2yl)2-furancarboxamide,
N-[1-[2-[1-(1,3-dihydroxypropan-2-yl)]cyclohexyl]ethylipiperidin-4-yl]-N-(5-methylpiperidin-2-yl)2-furancarboxamide,
N-[1-[2-[1-[1,3-dihydroxypropan-2-yl]cyclohexyl]ethyl]piperidin-4yl]-N-(p-tolyl)-2-furancarboxarnide,
N-[1-[2-[1-(4-hydroxy-3-hydroxymethylbutyl)cyclohexyl] ethyl]piperidin-4-yl]-N-(p-tolyl)-2-furancarboxamide,
5,5-bis(hydroxymethyl)-7-[1-[2-[4-[N-(5-methylpyridin2yl)-2-furancarboxamido]piperidin-1-yl] ethyl]cyclohexyl]heptanoic acid,
5,5-bis(hydroxymethyl)-7-[1-[2-[4-[N-(p-tolyl)-2-furancarboxamido]piperidin-2-yl]ethyl]cyclohexyl]heptanoic acid,
N-[1-[2-[1-(2-hydroxyethyl)cyclohexyl]ethyl]piperidin4-yl]-N-(5-methylpiperidin-2yl)-2-furancarboxamide,
N-[1-[2-[1-[5-hydroxy-3,3-bis(hydroxymethyl)pentyl]cyclohexyl]ethyl]piperidin-4-yl]-N-(p-tolyl)-2furancarboxamide,
N-[1-[2-[1-[2-[3,5bis(hydroxymethyl)phenoxy]ethyl]cyclohexyl]ethyl]piperidin4-yl]-N(p-tolyl)-2-furancarboxamide,
N-[1-[2-[1-[2-[3,5-bis(hydroxymethyl)phenoxy]ethyl]cyclohexyl]ethyl]piperidin4yl]-N(5methylpiperidin-2-yl)-2furancarboxamide,
N-[1-[2-[1-(2-hydroxyethyl)cyclohexyl]ethyl]piperidin-4-yl]-N-(p-tolyl)-2-furancarboxamide,
N-[1-[2-[1-(2-hydroxyethyl)cyclobutyl]ethyl]piperidin-4-yl]-N-(p-tolyl)-2-furancarboxamicle,
N-[1-[2-[1-(2-hydroxyethyl)cyclooctyl]ethyl]piperidin-4-yl]-N-(p-tolyl)-2-furancarboxamide,
N-[1-[2-[4-(2-hydroxyethyl)tetrahydropyran-4-yl]ethyl]piperidin-4-yl]-N-(p-tolyl)-2-furancarboxamide,
N-[1-[2-[1-benzyl-4-(2-hydroxyethyl)piperidin-4-yl]ethyl] piperidin-4-yl]-N-(p-tolyl)-2-furancarboxamide, etc.

An amine derivative represented by the general formula (XIV):

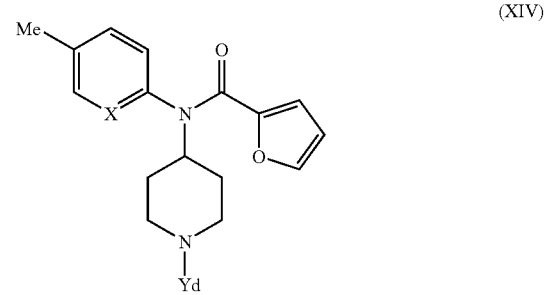

wherein
X is CH or N; and
Yd is a group of the general formula (XV):

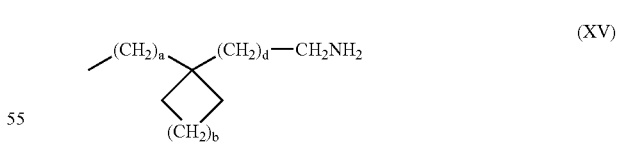

or a group of the general formula (XV-a):

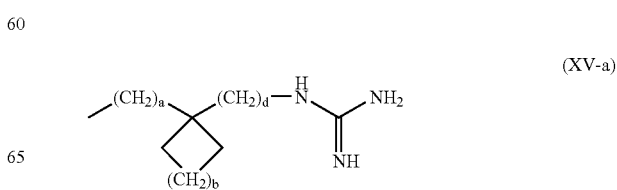

or a group of the general formula (XVI):

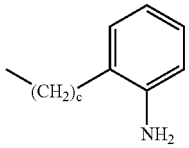

(XVI)

wherein a, b, c and d are each an integer of 0-6, which is included within the compounds of this invention represented by the general formula (I), may be prepared by deprotection of the corresponding tert-butoxycarbonyl form in the presence of an acid (e.g., hydrochloric acid or trifluoroacetic acid).

The reaction is carried out in water or an organic solvent such as methanol, ethanol, dichloromethane, 1,4-dioxane or ethyl acetate at a temperature of from ice cooling temperature to reflux temperature.

Specific examples of the compound represented by the general formula (XIV) may include:
N-[1-[2-[1-(2-aminoethyl)cyclohexyl]ethyl]piperidin-4-yl]-N-(5-methylpiperidin-2-yl)-2-furancarboxamide,
N-[1-[3-(2-aminophenyl)propyl]piperidin-4-yl]-N-(5-methylpiperidin-2-yl)-2-furancarboxamide,
N-[1-[3-(2-aminophenyl)propyl]piperidin-4-yl]-N-(p-tolyl)-2-furancarboxamide,
N-[1-[2-[1-(2-aminoethyl)cyclohexyl]ethyl]piperidin-4-yl]-N-(p-tolyl)-2-furancarboxamide,
N-[1-[2-[1-(2-guanidinoethyl)cyclohexyl]ethyl]piperidin-4-yl]-N-(5-methylpiperidin-2-yl)-2-furancarboxamide, etc.

The amine derivative represented by the general formula (XIV) wherein Yd has a general formula (XVI) may be converted to an alkyl derivative or acyl derivative by a conventional method. The amine derivative represented by the general formula (XIV) wherein Yd has a general formula (XV) may be converted to a sulfonyl derivative by a conventional method.

Specific examples of the compound thus prepared may include:
N-[2-[2-[4-[N-(p-tolyl)-2-furancarboxamido]piperidin-1-yl]ethyl]phenyl]-N-(cyclohexylacetyl)aminoacetic acid,
tert-butyl N-[2-[2-[4-[N-(p-tolyl)-2-furancarboxamido]piperidin-1-yl]ethyl]phenyl]-N-(cyclohexylacetyl)aminoacetate,
N-[2-[3-[4-[N-(p-tolyl)-2-furancarboxamido]piperidin-1-yl]propyl]phenyl]-N-(cyclohexylpropionyl)aminoacetic acid,
tert-butyl N-[2-[3-[4-[N-(p-tolyl)-2-furancarboxamido]piperidin-1-yl]propyl]phenyl]-N-(3-cyclohexylpropionyl) aminoacetate,
N-[2-[3-[4-[N-(p-tolyl)-2-furancarboxamido]piperidin-1-yl]propyl]phenyl]-N-(3-cyclohexylpropionyl)aminobutyric acid,
ethyl 3-[2-[2-[4-[N-(5-methylpyridin-2-yl)-2-furancarboxamido]piperidin-1-yl]ethyl]phenyl]-5-cyclohexylhydantoate,
3-[2-[2-[4-[N-(5-methylpyridin-2-yl)-2-furancarboxamido]piperidin-1-yl]ethyl]phenyl]-5-cyclohexylhydantoic acid,
ethyl N-[2-[2-[4-[N-(5-methylpyridin-2-yl)-2-furancarboxamido]piperidin-1-yl]ethyl]phenyl]aminoacetate,
ethyl N-[(1-methoxycarbonylmethylcyclohexyl)acetyl]-N-[2-[2-[4-[N-(5-methylpyridin-2-yl)-2-furancarboxamido]piperidin-1-yl]ethyl]phenyl]aminoacetate,
N-[(1-carboxymethylcyclohexyl)acetyl]-N-[2-[2-[4-[N-(5-methylpyridin-2-yl)-2-furancarboxamido]piperidin-1-yl]ethyl]phenyl]aminoacetic acid,
N-[1-[3-[2-(3-cyclohexylpropionamido)phenyl]propyl]piperidin-4-yl]-N-(5-methylpyridin-2-yl)-2-furancarboxamide,
N-[1-[2-[2-(3-cyclohexylureido)phenyl]ethyl]piperidin-4-yl]-N-(5-methylpyridin-2-yl)-2-furancarboxamide,
N-[1-[3-[2-(4-cyclohexylbutyramido)phenyl]propyl]piperidin-4-yl]-N-(5-methylpyridin-2-yl)-2-furancarboxamide,
methyl 1-[N-[2-[2-[4-[N-(5-methylpyridin-2-yl)-2-furancarboxamido]piperidin-2-yl]ethyl]phenyl]carbamoylmethyl]cyclohexylacetate,
1-[N-[2-[2-[4-[N-(5-methylpyridin-2-yl)-2-furancarboxamido]piperidin-1-yl]ethyl]phenyl]carbamoylmethyl]cyclohexylacetic acid,
N-[1-[3-[2-(3-cyclohexylureido)phenyl]propyl]piperidin-4-yl]-N-(p-tolyl)-2-furancarboxamide,
N-[1-[3-[2-(3-cyclohexylthioureido)phenyl]propyl]piperidin-4-yl]-N-(p-tolyl)-2-furancarboxamide,
N-[1-[2-[1-(2-methanesulfonylaminoethyl)cyclohexyl]ethyl]piperidin-4-yl]-N-(p-tolyl)-2-furancarboxamide,
N-[1-[2-[1-(p-toluenesulfonylamino)ethyl]cyclohexyl]ethyl]piperidin-4-yl]-N-(p-tolyl)-2-furancarboxamide,
N-[1-[2-[1-[2-(4-chlorobenzenesulfonylamino)ethyl]cyclohexyl]ethyl]piperidin-4-yl]-N-(p-tolyl)-2-furancarboxamide,
N-[1-[2-[1-[2-(1,2-di-tert-butoxycarbonylguanidino)ethyl]cyclohexyl]ethyl]piperidin-4-yl]-N-(5-methylpyridin-2-yl)-2-furancarboxamide, etc.

A compound represented by the general formula (V):

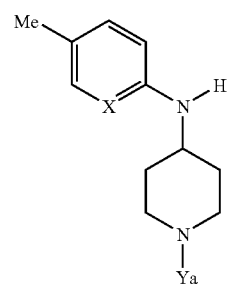

(V)

wherein
X is CH or N; and
$Y_a$ is a group of the general formula (VI):

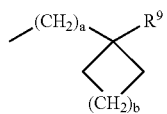

(VI)

or a group of the general formula (VI-a):

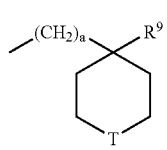

(VI-a)

wherein T is O or N—$R^{15}$ wherein $R^{15}$ is H, a C1-C6 alkyl group, a benzyl group or a phenethyl group, or a group of the general formula (VII):

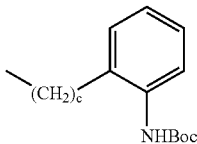
(VII)

or a group of the general formula (VIII):

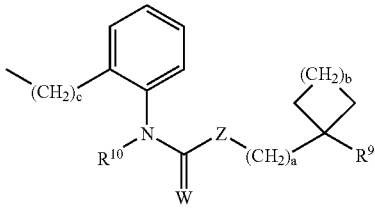
(VIII)

wherein
a, b and c are each an integer of 0-6;
Z is $CH_2$ or NH;
W is O or S;
$R^9$ is H, a C1-C6 alkoxycarbonyl group, a benzyloxycarbonyl group, a carboxy group, a 2-phenyl-1,3-dioxan-5-yl group, or a 2,2-dimethyl-1,3-dioxan-5-yl group;
$R^{10}$ is H or a group of the general formula (IX):

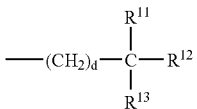
(IX)

wherein d is an integer of 0-6; and
$R^{11}$, $R^{12}$, and $R^{13}$ may be the same or different and are each independently H or —$(CH_2)_e R^{14}$ wherein e is 0-6, $R^{14}$ is a C1-C6 alkanoyloxy group, a benzoyloxy group, a 2-furoyloxy group, a C1-C6 alkoxy C1-C6 alkoxy group, a C1-C6 alkoxycarbonylphenoxy group, a di C1-C6 alkoxycarbonylphenoxy group, a di C1-C6 alkanoyloxy C1-C6 alkylphenoxy group, a C1-C6 alkyldiarylsiloxy group, a carboxy group, a C1-C6 alkoxycarbonyl group, a benzyloxycarbonyl group, a cyano group, or a C1-C6 alkylsulfonamido group, which is an intermediate compound for the synthesis of the compounds of this invention represented by the general formula (I), may be prepared by reacting a compound represented by the general formula (XVII):

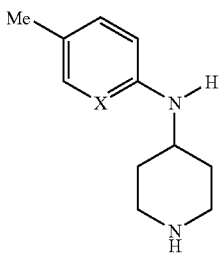
(XVII)

wherein X is CH or N, with a compound represented by the general formula (XVIII):

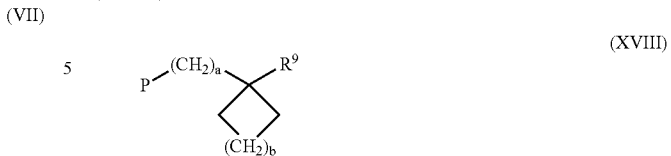
(XVIII)

or with a compound of the general formula (XIX):

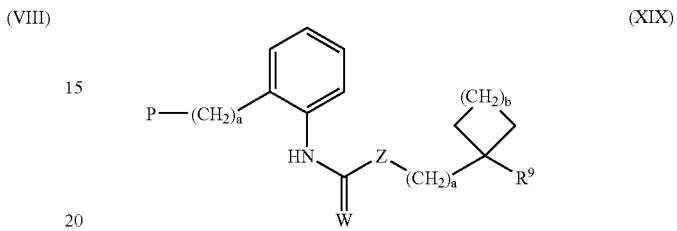
(XIX)

wherein P is a derivatized form with an activated hydroxy group as represented by a halogen atom, a methanesulfonyloxy group, or a trifluoromethanesulfonyloxy group;
a, b and c are each an integer of 0-6;
Z is $CH_2$ or NH;
W is O or S;
$R^9$ is H, a C1-C6 alkoxycarbonyl group, a benzyloxycarbonyl group, a carboxy group, a 2-phenyl-1,3-dioxan-5-yl group, or a 2,2-dimethyl-1,3-dioxan-5-yl group, or a group of the general formula (IX):

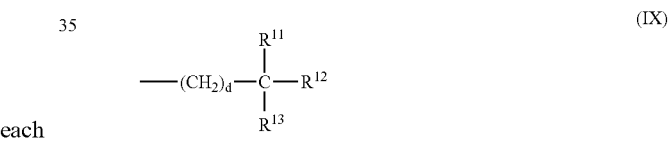
(IX)

wherein
d is an integer of 0-6; and
$R^{11}$, $R^{12}$, and $R^{13}$ may be the same or different and are each independently H or —$(CH_2)_e R^{14}$ wherein e is 0-6; and $R^{14}$ is a C1-C6 alkanoyloxy group, a benzoyloxy group, a 2-furoyloxy group, a C1-C6 alkoxy C1-C6 alkoxy group, a C1-C6 alkoxycarbonylphenoxy group, a di C1-C6 alkoxycarbonylphenoxy group, a di C1-C6 alkanoyloxy C1-C6 alkylphenoxy group, a C1-C6 alkyldiarylsiloxy group, a carboxy group, a C1-C6 alkoxycarbonyl group, a benzyloxycarbonyl group, a cyano group, or a C1-C6 alkylsulfonamido group, in the presence of abase, or alternatively by reductive amination in the presence of a reducing agent using an aldehyde compound represented by the general formula (XX), (XX-a) or (XXI), or a ketone compound represented by the general formula (XXII), or a hemiacetal compound represented by the general formula (XXIII) or (XXIII-a).

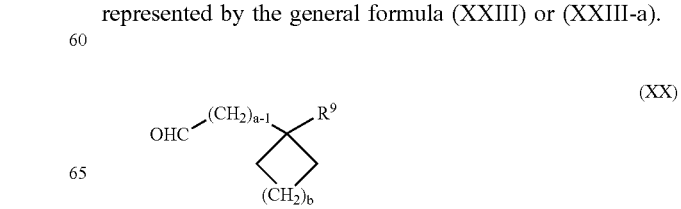
(XX)

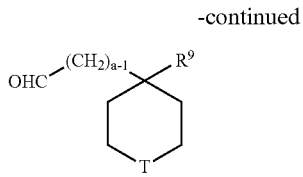

wherein T is N—R$^{15}$ wherein R$^{15}$ is H, a C1-C6 alkyl group, a benzyl group or a phenethyl group,

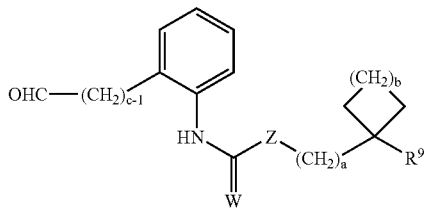

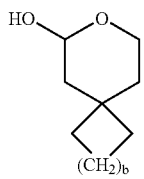

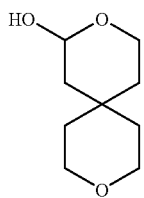

The reaction is carried out in water or an organic solvent such as 1,2-dichloroethane, dichloromethane, tetrahydrofuran, acetonitrile, 1,4-dioxane or methanol at a temperature of from ice cooling temperature to reflux temperature.

Specific examples of the compound of the general formula (V) may include:

2-[1-(cyclohexylmethyl)piperidin-4-ylamino]-5-methylpyridine,
2-[1-(2-cyclohexylethyl)piperidin-4-ylamino]-5methylpyridine,
2-[1-(3-cyclohexylpropyl)piperidin-4-ylamino]-5-methylpyridine,
2-[1-(4-cyclohexylbutyl)piperidin-4-ylamino]-5-methylpyridine,
2-[1-(2-cyclooctylethyl)piperidin-4-ylamino]5-methylpyridine,
1-(3-cyclohexyipropyl)-4-(p-toluidino)piperidine,
2-(1-cyclohexylpiperidin-4-ylamino)-5-methylpyridine,
2(1-[3-[2—(cyclohexylacetamido)phenyl]propyl]piperidin-4-ylamino]5-methylpyridine,
2-[1-[2-[2-(cyclohexylacetamido)phenyl]ethyl]piperidin-4-yl-amino]-5methylpyridine,
methyl [1-[2-[4-(5methylpyridin-2-ylamino)piperidin-1-yl]ethyl]cyclohexyl]acetate,
methyl [1-[2-[4-(5methylpyridin2-ylamino)piperidin-1-yl]ethy]cyclopentyl]acetate,
methyl 1-[2-[4-(5-methylpyridin-2-ylamino)piperidin-1-yl]-ethyl]cyclohexanecarboxylate,
1-[2-[4-(5-methylpyridin-2-ylamino)piperidin-1-yl]ethyl]cyclohexanecarboxylic acid,
methyl 4-[1-[2-[4-(5-methylpyridin-2-ylamino)piperidin-1-yl]ethyl]cyclohexyl]butyrate,
triethyl 3-[1-[2-[4-(5-methylpyridin2ylamino)piperidin-1-yl]ethy]cyclohexyl]1,1,1propanetricarboxylate,
dimethyl 3-[1-[2-[4 -(p-toluidino)piperidin-1-yl]ethyl]cyclohexyl]-1,1-propanedicarboxylate,
methyl [1-[2-[4-(p-toluidino)piperidin-1-yl]ethyl]cyclohexyl]acetate,
3-[1-[4-(5methylpyridin2ylamino)piperidin-1-yl]methylcyclohexyl]propyl acetate
2-[2-[1-[2-[4-(5methylpyridin-2-ylamino)piperidin-1-yl]ethyl]cyclohexyl]ethyl]1,3-diacetoxypropane,
2-[1-[2-[1-[4-(methoxymethoxy)-3-(methoxymethyl)butyl]cyclohexyl]ethyl]piperidin-4-ylamino]-5-methylpyridine,
2-(acetoxymethyl)-2-[2-[1-[2-[4-(5-methylpyridin2ylamino)-piperidine-1-yl]ethyl]cyclohexyl]ethyl]-1,4-diacetoxypropane,
2-[1-[2-[1-(2-phenyl-1,3-dioxan-5-yl)cyclohexyl]ethyl]piperidin-4-ylamino]-5-methylpyridine,
1-[2-[1-(2, 2-dimethyl-1,3-dioxan-5-yl)cyclohexyl]ethyl-4-(p-toluidino)piperidine,
methyl 5,5-bis(benzoyloxymethyl)-7-[1-[2-(4(5-methylpyridin-2-ylamino)piperidin-1-yl]ethyl]cyclohexyl]heptanoate,
methyl 5,5-bis(benzoyloxymethyl)-7-[1-[2-[4-(p-toluidino)-piperidin-1-yl]ethyl]cyclohexyl]heptanoate,
2-[2-[1-[4-(p-toluidino)piperidin-1-yl]ethyl]cyclohexyl]ethyl]-1,3-diacetoxypropane,
2-[1-[2-[4-(5-methylpyridin2ylamino)piperidin-1-yl]ethyl]-cyclohexyl]ethyl 2-furancarboxylate
2-[1-[2-[1(2-cyanoethyl)cyclohexyl]ethyl]piperidin-4-ylamino]-5-methylpyridine,
tert-butyl 2-[1-[2-[4-(5-methylpyridin-2ylamino)piperidin-1-yl]ethyl]cyclohexyl]ethyl]carbamate,
N-[2-[1-[2-[4-(5-methylpyridin-2-ylamino)piperidin-1-yl]ethyl]cyclohexyl]ethyl]methanesulfonamide,
N-[2-[4-(5-methylpyridin-2-ylamino) piperidin-1-ylmethyl]phenyl]cyclohexylacetamide,
N-[2-[2-[4-(p-toluidino)piperidin-1-yl]ethyl]phenyl]cyclohexylacetamide,
N-[2-[3-[4-(p-toluidino)piperidin-1-yl]propyl]phenyl]cyclohexylacetamide,
tert-butyl [2-[3-[4-(5-methylpyridin-2-ylamino)piperidin-1-yl]propyl]phenyl]carbamate,
tert-butyl [2-[3-[4-(p-toluidino)piperidin-1-yl]propyl]phenyl]carbamate,
1-[2-[1-(2-cyanoethyl)cyclohexyl]ethyl]-4-(p-toluidino)piperidine,
dimethyl 5-[2-[1-[2-[4-(p-toluidino)piperidin-1yl]ethyl]-cyclohexyl]ethoxy]isophthalate,
1,3-diacetoxymethyl-5-[2-[1-[2-[4-(p-toluidino)piperidin1-yl]ethyl]cyclohexyl]ethoxy]benzene,
1,3diacetoxymethyl-5-[2-[1-[2-[4-(5methylpyridin2ylamino)piperidin-1-yl]ethyl]cyclohexyl]ethoxy]benzene,
2-[1-[2-[4-(p-toluidino)piperidin-1-yl]ethyl]cyclohexyl]ethanol,
methyl 4-[1-[2-[4-(p-toluidino)piperidin-1-yl]ethyl]cyclohexyl]butyrate, triethyl 3-[1-[2-[4-(p-toluidino)piperidinlyl]ethyl]-cyclohexyl]-1,1,1-propanetricarboxylate,
2-[1-[2-[4-(p-toluidino)piperidin-1-yl]ethyl]cyclobutyl]ethanol,
2-[1-[2-[4-(p-toluidino)piperidin-1-yl]ethyl]cyclooctyl]ethanol,
2-[1-[2-[4-(p-toluidino)piperidin-1-yl]ethyl]tetrahydropyran-4-yl]ethanol,
1-[2-[1-benzyl-4-[2-(tertbutyldiphenylsiloxy)ethyl]piperidin-4yl]ethyl]4toluidinopiperidine, etc.

Specific examples of the compound of the general formula (XVII) may include 2-(piperidin-4-ylamino)-5-methylpyridine, 4-(p-toluidino)piperidine, etc.

Specific examples of the compound of the general formula (XVIII) may include (bromomethyl)cyclohexane, (2-bromoethyl)cyclohexane, (3-bromopropyl)cyclohexane, (4-bromobutyl)cyclohexane, methyl 1-(2-bromoethyl)cyclohexylacetate, methyl 1-(2-bromoethyl)cyclopentylacetate, 3-[1-(trifluoromethanesulfonyloxymethyl)cyclohexyl]propyl acetate, 3-[1-(2-bromoethyl)clohexyl]propionitrile, etc.

Specific examples of the compound of the general formula (XIX) may include N-[2-(2-bromoethyl)phenyl]cyclohexylacetamide, 2-nitrobenzyl bromide, (2-bromoethyl)-2-nitrobenzene, (3-bromopropyl)-2-nitrobenzene, tert-butyl [2-(3-bromopropyl)phenyl]carbamate, etc.

Specific examples of the compound of the general formula (XX) may include cyclooctylacetaldehyde, methyl 1-(formylmeth-yl)cyclohexanecarboxylate, benzyl 1-(formylmethyl)cyclohex-anecarboxylate, methyl 4-[1-(formylmethyl)cyclohexyl]butyrate, triethyl 3-[1-(formylmethyl)cyclohexyl]-1,1,1-propanetricar- boxylate, dimethyl 3-[1-(formylmethyl)cyclohexyl]-1,1-propanedicarboxylate, 2-[2-[1-(formylmethyl)cyclohexyl]eth- yl]-1,3-diacetoxypropane,1-[4-(methoxymethoxy)-3-(methoxymethoxymethyl)butyl]cyclohexylacetaldehyde, 1-(2-phenyl-1,3-dioxan-5-yl)cyclohexylacetaldehyde, 1-(2,2-dimethyl-1,3-dioxan-5yl)cyclohexylacetaldehyde, 2-(acetoxymethyl)-2-[2-[1(formylmethyl)cyclohexyl]ethyl]1,4-diacetoxybutane, methyl 5,5-bis(benzoyloxymethyl)-7-[1-(formylmethyl)cyclo- hexyl]heptanoate, N-[2-[1-(formylmethyl)cyclohex-yl]ethyl]methanesulfonamide, 1-(2-phthalimidoethyl)cyclo- hexylacetaldehyde, etc.

Specific examples of the compound of the general formula (XX-a) may include [1-benzyl-4-[2-(tert-butyldiphenylsiloxy)ethyl]piperidin-4-yl]acetaldehyde and the like.

Specific examples of the compound of the general formula (XXI) may include N-[2-(2-formylethyl)phenyl]cyclohexylacetamide and the like.

Specific examples of the compound of the general formula (XXII) may include cyclohexanone and the like.

Specific examples of the compound of the general formula (XXIII) may include 3-oxaspiro[5.5]undecan-2-ol, 7-oxaspiro-[3.5]nonan-6-ol, 3-oxaspiro[5.7]tridecan-2-ol, etc.

Specific examples of the base may include organic bases such as triethylamine, pyridine, diisopropylamine, diisopropylethylamine, and 1,8-diazabicyclo[5.4.0]-7-undecene, or inorganic bases such as sodium hydroxide, potassium hydroxide, potassium carbonate, and sodium hydrogencarbonate. Specific examples of the reducing agent may include sodium borohydride, sodium triacetoxyborohydride, sodium cyanoborohydride, etc.

The compound of the general formula (V) may also be synthesized via a phthalimide derivative (XXIV) or a nitro derivative (XXV) as shown in Reaction Scheme 1.

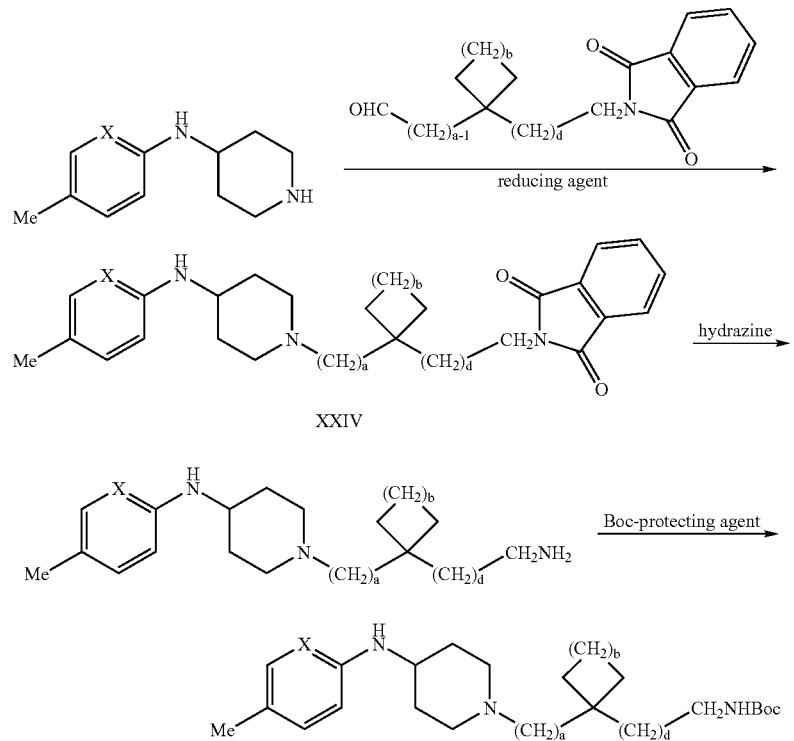

Reaction Scheme 1

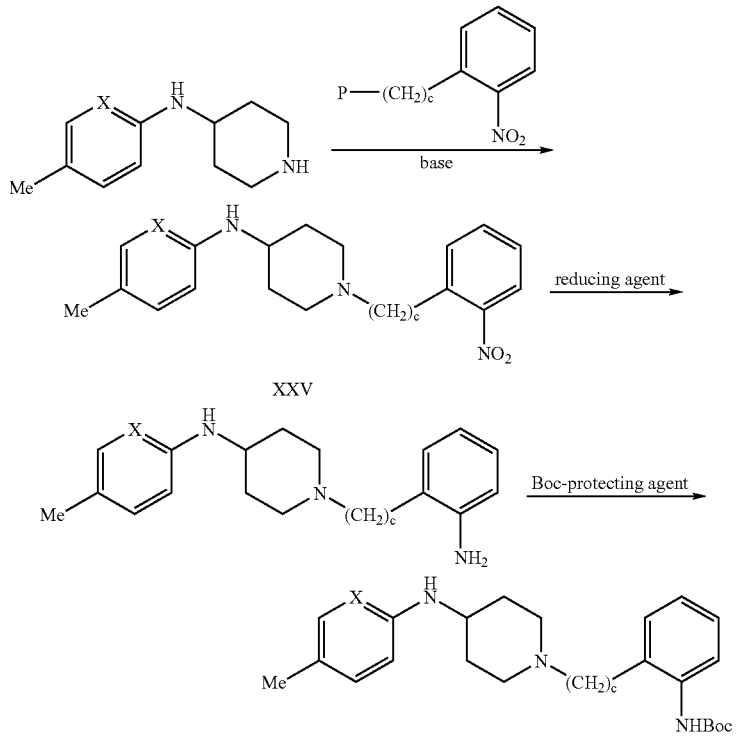

The compound of the general formula (XVIII):

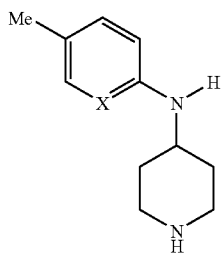
(XVIII)

may be synthesized according to the process as shown in Reaction Scheme 2.

By virtue of inhibition of the μ opioid receptors, the compounds of this invention as mentined above are useful as a therapeutic or prophylactic agent for side effects which are caused by the μ receptor agonists such as constipation, nausea/emesis, and itch, as well as for diseases such as idiopathic constipation, postoperative ileus, paralytic ileus, irritable bowel syndrome and chronic pruritus.

Some of the compounds of this invention represented by the general formula (I) are prodrugs, and thus, they may be metabolized in vivo and converted to novel opioid μ receptor antagonists. Main sites subjected to metabolism will be illustrated in the general formulae (I) to (IV):

Reaction Scheme 2

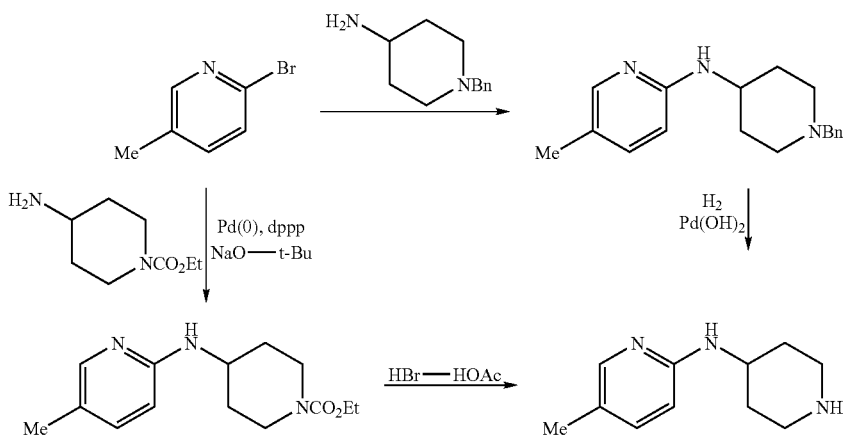

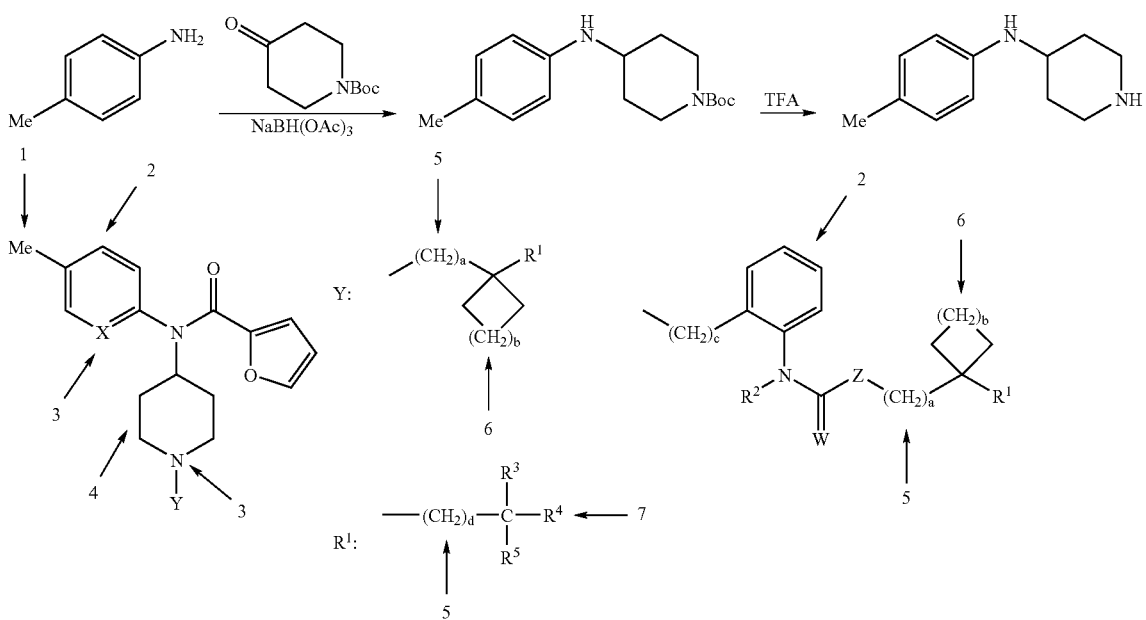

1) Hydroxylation of a methyl group
2) Hydroxylation of an aromatic ring
3) N-Oxidation of a nitrogen atom
4) Hydroxylation of a piperidine ring
5) Hydroxylation of a methylene chain
6) Hydroxylation of a cycloalkyl group
7) Hydrolysis of an ester group and hydroxylation of an alkyl chain
8) Glucuronate, sulfate or glutathione conjugates of the above compounds The compounds of this invention represented by the general formula (I) may be converted to pharmacologically acceptable acid or base addition salts, if desired, and these acid or base addition salts also fall under the scope of this invention. The acid addition salts may include salts with an inorganic acid such as hydrochloric acid, hydrobromic acid, sulfuric acid, or phosphoric acid and salts with an organic acid such as acetic acid, succinic acid, oxalic acid, malic acid, tartaric acid, fumaric acid, maleic acid, citric acid, malonic acid, lactic acid, methanesulfonic acid, p-toluenesulfonic acid, mandelic acid, suberic acid, phthalic acid, or terephthalic acid. The base addition salts may include salts with an inorganic base such as sodium salt, potassium salt or various ammonium salts and salts with an organic base.

The compounds represented by the general formula (I) when used as a medicament may be formulated into various dosage forms of preparations. More specifically, the preparations may be orally administered in the form of tablets, sugar coated tablets, hard capsules, soft capsules, enteric preparations, liquid preparations such as solutions, emulsions or suspensions. The preparations may be parenterally administered in the form of liquid preparations such as injections, suppositories, infusions, solutions, emulsions or suspensions.

In preparing these preparations, conventional additives such as excipients, stabilizers, antiseptics, solubilizing agents, humectants, emulsifying agents, lubricants, sweeteners, coloring agents, flavors, tonicity agents, and antioxidants may be added for formulating the preparations.

Administration routes and doses of the opioid μ receptors according to this invention may be adequately selected depending on various preparation forms, the gender of patients or the severity of diseases, but a daily dose of the active ingredient will be 1 to 100 mg.

BEST MODE FOR CARRYING OUT THE INVENTION

Formulation Examples will be illustrated below.

FORMULATION EXAMPLE 1

| Gelatin hard capsule | |
| --- | --- |
| Compound described in Example 4D-8 | 20 mg |
| Corn starch | 200 mg |
| Magnesium stearate | 10 mg |
| Total | 230 mg |

All the ingredients were uniformly blended and filled into a gelatin hard capsule to prepare a gelatin hard capsule with a content of 460 mg.

FORMULATION EXAMPLE 2

| Gelatin hard capsule | |
| --- | --- |
| Compound described in Example 4D-6 | 20 mg |
| Corn starch | 89 mg |
| Crystalline cellulose | 89 mg |
| Magnesium stearate | 2 mg |
| Total | 200 mg |

All the ingredients were uniformly blended and filled into a gelatin hard capsule to prepare a gelatin hard capsule with a content of 200 mg.

FORMULATION EXAMPLE 3

| Gelatin soft capsule | |
|---|---|
| (Liquid medicine) | |
| Compound described in Example 3D-3 | 20 mg |
| Middle chain fatty acid triglyceride | 160 mg |
| Polyoxyethylene hydrogenateed castor oil | 20 mg |
| Subtotal | 200 mg |
| (Coating film) | |
| Gelatin | 100 mg |
| Glycerol | 30 mg |
| Methyl parabenzoate | 0.2 mg |
| Propyl paraoxybenzoate | 0.05 mg |
| Purified water | q.s. |
| Subtotal | 140 mg |
| Total | 340 mg |

The coating film was prepared from a coating film solution previously dissolved by being heated in a rotary apparatus for preparing soft capsules, and the liquid medicament previously dissolved uniformly was encapsulated with the coating film and then molded. Thereafter, the capsules were thoroughly dried.

FORMULATION EXAMPLE 4

| Tablet | |
|---|---|
| Compound described in Example 3B-1 | 10 mg |
| Corn starch | 45 mg |
| Crystalline cellulose | 35 mg |
| Polyvinyl pyrrolidone | 4 mg |
| (in the form of a 10% aqueous solution) | |
| Carboxymethylcellulose sodium | 4.5 mg |
| Magnesium stearate | 0.5 mg |
| Talc | 1 mg |
| Total | 100 mg |

The active ingredient, starch and cellulose were sieved and blended completely. An aqueous polyvinyl pyrrolidone solution was admixed with the powder thus obtained and passed through a No. 14 mesh sieve. The granular product thus prepared was dried at 50-60° C. and passed through a No. 18 mesh sieve. Subsequently, carboxymethylcellulose sodium, magnesium stearate and talc, which had been previously passed through a No. 60 mesh sieve, were added to the granular product and blended and then compressed to tablets, each weighing 100 mg, by means of a tablet machine.

FORMULATION EXAMPLE 5

| Tablet | |
|---|---|
| Compound described in Example 2-33 | 250 mg |
| Crystalline cellulose | 400 mg |
| Thyroid | 10 mg |
| Magnesium stearate | 5 mg |
| Total | 665 mg |

All the ingredients were uniformly blended and then compressed to tablets, each weighing 665 mg, by means of a tablet machine.

FORMULATION EXAMPLE 6

A suspension containing an active ingredient at 5 mg per 5 mL of a dose was prepared as described below.

| Suspension | |
|---|---|
| Compound described in Example 2-34 | 5 mg |
| Carboxymethylcellulose sodium | 50 mg |
| Simple syrup | 1.25 mL |
| Aqueous solution of benzoic acid | 0.10 mL |
| Flavors | q.s. |
| Purified water q.v. to make up to a total volume of 5 mL | |
| Total | 5 mL |

The active ingredient was passed through a No. 45 mesh sieve and blended with carboxymethylcellulose sodium and simple syrup to prepare a paste. The aqueous solution of benzoic acid and flavors were diluted with a small amount of purified water and added to the paste obtained above with stirring. Subsequently, purified water was further added to make up to the desired volume.

The μ antagonistic activity of the compounds of this invention ($PA_2$ value) was determined according to the electric stimulation method for a specimen of the ileum longitudinal muscle of guinea pig.

The longitudinal muscle specimen was prepared by sacrificing a guinea pig (Hartley strain, male) with bleeding and then removing the ileum. The specimen was hung with a loading of 0.5 g in a Magnus equipment filled with 20 ml of a nutrient solution (Krebs-Henselite solution, 37° C., aerating with 95% $O_2$-5% $CO_2$) and isometric contraction was recorded. The specimen was equilibrated in the nutrient solution over one hour, and then, electric stimulation was given at a voltage capable of providing the maximum contraction (0.1 Hz, 1 msec duration). After contraction was stabilized, morphine (a μ receptor agonist), was cumulatively added and, after washing, dosing was discontinued for one hour. Electric stimulation was again initiated and, after contraction was stabilized, the compound of this invention was added and, 15 minutes after the addition, morphine was cumulatively added. Contraction heights (mm) before and after morphine addition were measured from the chart recording contraction by electric stimulation, and then, contraction inhibition rate (%) was calculated according to the following equation 1:

Contraction inhibition (%)=$[(a-b)/a]\times 100$ a: contraction height before morphine addition (mm)
b: contraction height after morphine addition (mm)

Morphine concentration-response curves were prepared in the absence and presence of the compound of this invention by setting logarithmic concentrations of morphine on the axis of abscissas and plotting contraction rates (%) on the axis of ordinates. At the point of 50% contraction inhibition in the morphine concentration-response curve, the distance (mm) of the morphine concentration-response curve between the presence of the compound of this invention and the absence thereof was measured. Value of Log (CR-1) in the equation 2 was determined based on the distance from a van Rossum's simplified table and pA2 value was calculated.

$$\text{Log}(CR-1)=\text{Log}[B]+pA_2 \quad \text{Equation 2}$$

[B]: Concentration of the compound of this invention

Antagonistic activity of the compounds of this invention against the μ receptors ($PA_2$ value) is shown in Table 1.

TABLE 1

| Antagonistic activity against μ receptor Example No. | $pA_2$ |
|---|---|
| Compound 10 as disclosed in Japan Kokai 264460/1988 (Compound XI as shown before) | —* |
| Example 2-3 | 8.14 |
| Example 2-6 | 8.15 |
| Example 2-15 | 8.30 |
| Example 2-17 | 8.38 |
| Example 2-18 | 8.86 |
| Example 2-26 | 8.01 |
| Example 2-31 | 8.58 |
| Example 2-33 | 8.67 |
| Example 2-34 | 8.61 |
| Example 3B-1 | 8.26 |
| Example 3C-4 | 8.15 |
| Example 3D-3 | 8.05 |
| Example 3G-2 | 8.12 |
| Example 4A-1 | 8.13 |
| Example 4A-4 | 8.36 |
| Example 4D-1 | 8.12 |
| Example 4D-2 | 8.26 |
| Example 4D-6 | 7.85 |
| Example 4D-8 | 8.61 |
| Example 5B-1 | 8.66 |
| Example 5B-4 | 8.42 |
| Example 5B-6 | 8.23 |

*μ receptor agonistic activity was noted.
$EC_{50} = 2.2 \times 10^{-7}$ M

Antagonistic activity of the compounds of this invention against the central μ receptor was determined according to the analgesic assay by pressure stimulation to mice.

This assay method is a method for measuring pain threshold with an index of pseudo-pain reaction of a mouse by pressing the mouse (ddY strain, 5 weeks old, male) at his tail head using Randall-Selitto pressing device. Pseudo-pain reaction is meant to include looking back, biting, writhing, squealing, etc.

First, the threshold pressure was measured prior to administration of the compound of this invention. Then, the compound of this invention was subcutaneously administered and 15 minutes after administration, morphine hydrochloride was subcutaneously administered at 10 mg/kg. Forty five minutes after morphine administration, the threshold pressure was measured. In order to protect the tissues from damages, a maximum pressure of 750 g (cutoff pressure) was set and the threshold pressures of the group given the compound of this invention and the control group given the solvent were measured. Analgesic effect by morphine in each group (%) was calculated according to Equation 3.

$$\text{Analgesic effect (\%)}=[(Pt-Po)/(\text{cut-off pressure 750 g}-Po)]\times 100 \quad \text{Equation 3}$$

Po: pain threshold prior to administration of the compound of this invention or a solvent (g)
Pt: pain threshold after morphine administration (g)

From the average value of analgesic effect in each administered group (5-9 cases in each group), inhibition rate (%) of the compound of this invention on morphine analgesic effect was calculated according to Equation 4.

$$\text{Inhibition rate (\%)}=[(Ao-At)/Ao]\times 100 \quad \text{Equation 4}$$

Ao: average value (%) of analgesic effect of the control group given a solvent
At: average value (%) of analgesic effect of the group given the compound of this invention A dose-response curve was prepared by setting logarithmic doses of the compound of this invention on the axis of abscissas and plotting inhibition rates (%) on the axis of ordinates. The dose of the compound of this invention to inhibit analgesic effect of morphine by 50% ($AD_{50}$ value) was calculated from the curve.

Antagonistic activity of the compounds of this invention on the peripheral μ receptor was determined by transporting ability of carbon powder.

Mice (ddY strain, 5 weeks old, male) after fasted overnight were subcutaneously administered with the compound of this invention. Thirty minutes after administration, morphine hydrochloride was subcutaneously administered at 10 mg/kg. Thirty minutes after morphine administration, 5% carbon powder was orally administered. Thirty minutes after administration of the carbon powder, mice were sacrificed, and immediately the stomach through the blind intestine was excised. The distance between the pyloric ring of the excised intestine and the tip of carbon powder and the full length of the small intestine (from the pyloric ring up to the ilocecal ring) were measured. Carbon powder moving rates for the group given the compound of this invention and the control group given the carbon powder were calculated according to Equation 5

$$\text{Moving rate (\%)}=(Mt/Mo)\times 100$$

Mo: full length of the small intestine (cm)
Mt: distance between the puloric ring and the tip of the carbon atom From the average value of moving rates in each administered group (3-6 cases in each group), improving rate (%) of the compound of this invention on the lowering effect of carbon powder transporting ability by morphine was calculated according to Equation 6.

$$\text{Improving rate (\%)}=[(Et-Em)/(En-Em)]\times 100 \quad \text{Equation 6}$$

En: average value of moving rates (%) for the group given a solvent and the group not given morphine
Em: average value of moving rates (%) for the group given a solvent and the control group given morphine
Et: average value of moving rates (%) of the group given the compound of this invention and the group given morphine A dose-response curve was prepared by setting logarithmic doses of the compound of this invention on the axis of abscissas and plotting improving rates (%) on the axis of ordinates. The dose of the compound of this invention to improve the lowering effect of morphine on transporting ability of carbon powder by 50% ($ED_{50}$ value) was calculated from the curve.

The level of peripheral selectivity of the compounds of this invention can be evaluated from the rate of $AD_{50}$ value for antagonistic activity against the central μ receptor to $ED_{50}$ value for antagonistic activity against the peripheral μ receptor ($AD_{50}/ED_{50}$). The higher the rate is, the higher the peripheral selectivity will become.

The peripheral selectivity ($AD_{50}/ED_{50}$) of the compounds of this invention is illustrated in Table 2.

TABLE 2

| Example No. | $AD_{50}$ (mg/kg) | $ED_{50}$ (mg/kg) | $AD_{50}/ED_{50}$ |
|---|---|---|---|
| Example 2-3 | 2.7 | 19.3 | 0.1 |
| Example 3B-1 | 4.0 | 3.3 | 1.2 |
| Example 3D-3 | 16.7 | 8.4 | 2.0 |
| Example 3G-2 | 5.3 | 5.3 | 1.0 |
| Example 4D-6 | 7.7 | 3.0 | 2.6 |
| Example 4D-8 | 16.3 | 5.5 | 3.0 |

This invention will be more fully explained by way of the following examples. However, these examples are provided only for the purpose of illustrating this invention, and are not to be limiting this invention.

PREPARATION EXAMPLE 1A-1

Ethyl cyclooctylideneacetate

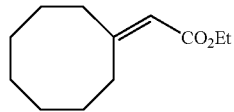

To a suspension of 60% sodium hydride/mineral oil (969 mg) in tetrahydrofuran (50 mL) was added ethyl diethylphosphonoacetate (5.48 mL) dropwise under ice cooling. After stirring the solution under ice cooling for 30 minutes, a solution of cyclooctanone (2.52 g) in tetrahydrofuran (70 mL) was added dropwise to the solution under ice cooling. The resulting solution was stirred under ice cooling for 2 hours and at room temperature for 40 hours. Water and 3N hydrochloric acid were then added to the solution, and the mixture was extracted with diethyl ether. The organic layer was washed with water and saturated sodium chloride solution, dried over anhydrous magnesium sulfate, and then, concentrated under reduced pressure. The resulting residue was purified by chromatography (silica gel, hexane:ethyl acetate=9:1) to give the title compound (1.96 g)

$^1$H-NMR (CDCl$_3$) δ: 1.27 (t, 3H, J=7.2 Hz), 1.40-1.56 (m, 6H), 1.71-1.84 (m, 4H), 2.72-2.79 (m, 2H), 4.13 (q, 2H, J=7.2 Hz), 5.72 (brs, 1H).

PREPARATION EXAMPLE 1A-2

2-Cyclooctylethanol

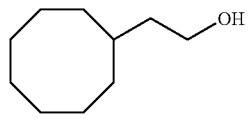

To a solution of ethyl cyclooctylideneacetate (969 mg) in ethanol (40 mL) was added 10% palladium-carbon (60 mg). The solution was stirred under hydrogen atmosphere at room temperature for 64 hours. The catalyst was filtered off and the filtrate was concentrated under reduced pressure. To a solution of the resulting residue (920 mg) in diethyl ether (40 mL) was added lithium aluminum hydride (132 mg) under ice cooling. The solution was stirred under ice cooling for 30 minutes and then water (0.13 mL), and a 15% aqueous sodium hydroxide solution (0.13 mL) were successively added thereto. The solution was stirred at room temperature for 15 minutes, to which water (0.39 mL) was then added. The solution was stirred for additional 30 minutes, dried over anhydrous magnesium sulfate and concentrated under reduced pressure. The resulting residue was purified by chromatography (silica gel, hexane:ethyl acetate=2:1) to give the title compound (680 mg).

$^1$H-NMR (CDCl$_3$) δ: 1.16-1.36 (m, 3H), 1.38-1.74 (m, 14H), 3.67 (t, 2H, J=7.2 Hz).

PREPARATION EXAMPLE 1A-3

Cyclooctylacetaldehyde

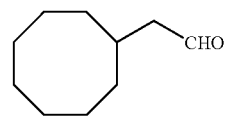

To a solution of 1,1,1-tris(acetoxy)-1,1-dihydro-1,2-benziodoxol-3(1H)-one (490 mg) in dichloromethane (3 mL) was added pyridine (0.25 mL). To the solution was added a solution of 2-cyclooctylethanol (120 mg) in dichlormethane (3 mL) under ice cooling. The reaction solution was stirred at room temperature for 3 hours. To the solution was added diethyl ether, and it was washed in turn with aqueous sodium thiosulfate, 1N hydrochloric acid, saturated aqueous sodium hydrogencarbonate and saturated aqueous sodium chloride. The solution was dried over anhydrous magnesium sulfate and concentrated under reduced pressure to give the title compound. This product was subjected to the subsequent step without further purification.

PREPARATION EXAMPLE 1B-1

1,1-Cyclohexane diacetic acid anhydride

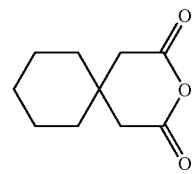

A solution of 1,1-cyclohexane diacetic acid (20.0 g) in acetic anhydride (20 mL) was heated under reflux for 5 hours. The solution was concentrated under reduced pressure, and the residue was concentrated three times azeotropically with benzene. The resulting residue was purified by column chromatography (silica gel, hexane:ethyl acetate=2:1) to give the title compound (20.1 g).

$^1$H-NMR (CDCl$_3$) δ: 1.42-1.57 (m, 10H), 2.65 (s, 4H).

PREPARATION EXAMPLE 1B-2

3-Oxa-spiro[5.5]undecan-2-one

To a solution of 1,1-cyclohexane diacetic acid anhydride (20.1 g) in THF (150 mL) was added sodium borohydride (3.78 g, 100 mmol) under ice cooling. The reaction solution was stirred at room temperature for additional 3 hours. Water was added to the solution, and it was made acidic with conc. hydrochloric acid. The solution was extracted with ethyl acetate. The organic layer was washed with water and saturated aqueous sodium chloride solution, dried over anhydrous magnesium sulfate and filtered. The filtrate was then concentrated under reduced pressure to give the title compound (17.07 g). This product was subjected to the subsequent step without further purification.

$^1$H-NMR (CDCl$_3$) δ: 1.31-1.59 (m, 10H), 1.73 (t, 2H, J=6.1 Hz), 2.37 (s, 2H), 4.32 (t, 2H, J=6.1 Hz).

PREPARATION EXAMPLE 1B-3

1-(2-Bromoethyl)cyclohexylacetic acid

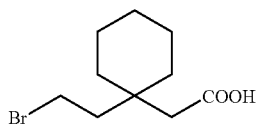

To 3-oxaspiro[5.5]undecan-2-one (16.9 g) was added a 30% hydrogen bromide/acetic acid solution (75 mL). The reaction solution was stirred at room temperature for 48 hours. Water was added to the solution, and the crystals thus separated were recovered by filtration and washed with water. The resulting crystals were dissolved in ethyl acetate, and the solution was dried over anhydrous magnesium sulfate and filtered. The filtrate was then concentrated under reduced pressure to give crude crystals. The crude crystals thus obtained were recrystallized from ethyl acetatehexane to give the title compound (20.0 g).

$^1$HNMR (CDCl$_3$) δ:1.35-1.54 (m, 10H), 2.05-2.11 (m, 2H), 2.33 (s, 2H), 3.41-3.47 (m, 2H).

PREPARATION EXAMPLE 1B-4

Methyl 1-(2-bromoethyl)cyclohexylacetate

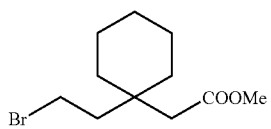

To a solution of 1-(2-bromoethyl)cyclohexylacetic acid (4.98 g) in methanol (50 mL) was added thionyl chloride (1.76 mL) dropwise under ice cooling. After completion of the dropwise addition, the reaction solution was stirred for 18 hours, while its temperature was allowed to rise to room temperature. The reaction solution was concentrated under reduced pressure, and ethyl acetate was added to the resulting residue. The solution was washed in turn with saturated aqueous sodium bicarbonate solution, water and saturated aqueous sodium chloride solution, dried over anhydrous magnesium sulfate and filtered. The filtrate was then concentrated under reduced pressure to give the title compound (5.41 g). This product was subjected to the subsequent step without further purification.

$^1$H-NMR (CDCl$_3$) δ: 1.34-1.52 (m, 10H), 1.98-2.05 (m, 2H), 2.29 (s, 2H), 3.41-3.46 (m, 2H), 3.67 (s, 3H).

PREPARATION EXAMPLE 1C-1

8-Oxa-spiro[4.5]undecan-7-one

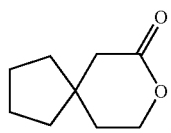

Using 8-oxaspiro[4.5]undecan-7,9-dione (10.8 g), the title compound (12.6 g) was prepared in the same manner as in Preparation Example 1B-2. This product was subjected to the subsequent step without further purification.

PRAPARATION EXAMPLE 1C-2

1-(2-Bromoethyl)cyclopentylacetic acid

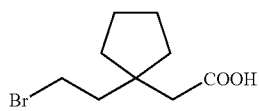

Using 8-oxaspiro[4.5]undecan7-one (3.57 g), the title compound (0.87 g) was prepared in the same manner as in $^1$HNMR (CDCl$_3$) δ: 1.51-1.67 (m, 8H), 2.08-2.12 (m, 2H), 2.34 (s, 2H), 3.41-3.46 (m, 2H).

PREPARATION EXAMPLE 1C-3

Methyl 1-(2-bromoethyl)cyclopentylacetate

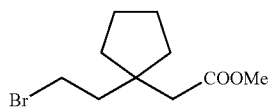

Using 1-(2-bromoethyl)cyclopentylacetic acid (2.20 g), the title compound (2.26 g) was prepared in the same manner as in Preparation Example 1B-4.

$^1$H-NMR (CDCl$_3$) δ: 1.47-1.65 (m, 8H), 2.05 (t, 2H, J=8.3 Hz), 2.30 (s, 3H), 3.43 (t, 2H, J=8.3 Hz), 3.67 (s, 3H).

PREPARATION EXAMPLE 1D-1

Methyl 1-allylcyclohexanecarboxylate

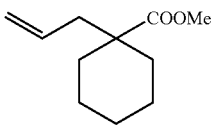

To a solution of methyl cyclohexylcarboxylate (1.42 g) and allyl bromide (3.02 g) in N,N-dimethylformamide (20 mL) was added potassium tert-butoxide (1.68 g, 15.0 mmol) under ice cooling. The solution was stirred at room temperature for 16 hours, at 50° C. for 8 hours and further at room temperature for 64 hours. Water and 3N hydrochloric acid were then added to the solution, and it was extracted with diethyl ether. The extract was washed with water and saturated aqueous sodium chloride solution, dried over anhydrous magnesium sulfate and concentrated under reduced pressure. The resulting residue was purified by column chromatography (silica gel, hexane:ethyl acetate=97:3) to give the title compound (340 mg).

PREPARATION EXAMPLE 1D-2

Methyl 1-(formylmethyl)cyclohexanecarboxylate

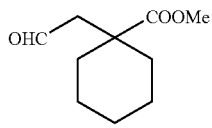

To a solution of methyl 1-allylcyclohexanecarboxylate (340 mg) in tetrahydrofuran (7 mL) were added an aqueous solution of sodium periodic acid (3.4 g, 16.0 mmol) and osmium tetraoxide (100 mg) successively under ice cooling. The solution was stirred at room temperature for 20 hours. Water was added to the reaction solution and insolubles were filtered off. The filtrate was extracted with ethyl acetate, and it was washed in turn with water, sodium thiosulfate and saturated aqueous sodium chloride solution, dried over anhydrous magnesium sulfate and concentrated under reduced pressure to give the title compound (250 mg). This product was subjected to the subsequent step without further purification.

PREPARATION EXAMPLE 1E-1

Benzyl cyclohexanecarboxylate

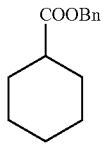

To a solution of cyclohexanecarboxylic acid (2.56 g) in dichloromethane (50 ml) and N,N-dimethylformamide (0.5 mL) was added oxalyl chloride (1.92 mL) under ice cooling. The solution was stirred at room temperature for 1 hour and then concentrated under reduced pressure. A solution of the resulting residue in dichloromethane (30 mL) was added to a solution of benzyl alcohol (2.4 g) and triethylamine (8.4 mL) in dichloromethane (30 mL) under ice cooling. The solution was stirred under ice cooling for 1 hour, and then it was washed in turn with water, saturated aqueous sodium bicarbonate solution and saturated aqueous sodium chloride solution. The solution was dried over anhydrous magnesium sulfate, and then, concentrated under reduced pressure. The resulting residue was purified by column chromatography (silica gel, hexane:ethyl acetate=9:1) to give the title compound (3.44 g).

$^1$H-NMR (CDCl$_3$) δ: 1.17-1.34 (m, 3H), 1.40-1.53 (m, 2H), 1.60-1.68 (m, 1H), 1.71-1.80 (m, 2H), 1.89-1.98 (m, 2H), 2.35 (tt, 1H, J=3.6 Hz, 11.2 Hz), 5.11 (s, 2H), 7.26-7.41 (m, 5H).

PREPARATION EXAMPLE 1E-2

Benzyl 1-allylcyclohexanecarboxylate

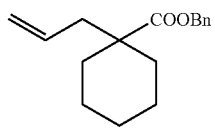

To a solution of benzyl cyclohexanecarboxylate (1.44 g) in tetrahydrofuran (40 mL) was added a 1M solution of lithium hexamethyldisilazane in tetrahydrofuran (9.9 mL) under ice cooling. The solution was stirred at room temperature for 1 hour under ice cooling, to which hexamethylphosporamide (2.3 mL) was added. The solution was then stirred for additional 10 minutes. To the solution was added allyl bromide (1.4 mL). The solution was stirred under ice cooling for 1 hour, to which allyl bromide (1.4 mL) was further added. The solution was stirred at room temperature for 18 hours. Water and 3N hydrochloric acid were added to the solution, and it was extracted with diethyl ether. The organic layer was washed in turn with water, saturated aqueous sodium bicarbonate solution and saturated aqueous sodium chloride solution. The solution was dried over anhydrous magnesium sulfate, and then, concentrated under reduced pressure. The resulting residue was purified by chromatography (silica gel, hexane:ethyl acetate=99:1) to give the title compound (550 mg). This product was subjected to the subsequent step without further purification.

PREPARATION EXAMPLE 1E-3

Benzyl 1-(formylmethyl)cyclohexanecarboxylate

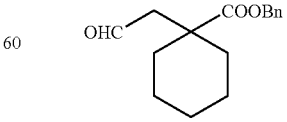

Using benzyl 1-allylcyclohexane carboxylate (1.52 g), the title compound (360 mg) was prepared in the same manner as in Preparation Example 1D-2.

$^1$H-NMR (CDCl$_3$) δ: 1.05-1.71 (m, 8H), 1.96-2.17 (m, 2H), 2.65 (d, 2H, J=2.0 Hz), 5.15 (s, 2H), 7.27-7.43 (m, 5H), 9.68 (t, 1H, J=2.0 Hz).

PREPARATION EXAMPLE 1F-1

3-Oxaspiro[5.5]undecan-2-ol

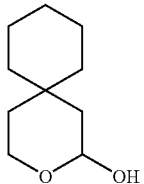

To a solution of 3-oxaspiro[5.5]undecan-2-one (1.68 g) in diethyl ether (50 mL) was added a 1M solution of diisobutylaluminum hydride in diethyl ether (15.0 mL) under ice cooling. The solution was stirred under ice cooling for 15 minutes. Diethyl ether (100 mL) was then added to the solution, followed by successive addition of water (0.6 mL) and a 15% aqueous sodium hydroxide solution (0.6 mL). The solution was stirred at room temperature for 30 minutes. Water (1.8 mL) was then added to the solution, and it was stirred for additional 15 minutes. The solution was dried over anhydrous magnesium sulfate and concentrated under reduced pressure. The resulting residue was purified by column chromatography (silica gel, hexane:ethyl acetate=1:1) to give the title compound (1.36 g).

$^1$H-NMR (CDCl$_3$) δ: 1.18-1.27 (m, 1H), 1.33-1.52 (m, 11H), 1.73-1.81 (m, 1H), 3.15 (d, 1H, J=5.6 Hz), 3.60-3.69 (m, 1H), 3.86-3.93 (m, 1H), 4.91-4.98 (m, 1H).

PREPARATION EXAMPLE 1F-2

Methyl 4-[1-(2-hydroxyethyl)cyclohexyl]butyrate

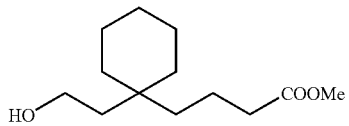

To a solution of 3oxaspiro[5.5]undecan-2-ol (460 mg) in dichloromethane (15 mL) was added methyl triphenylphosphoranylideneacetate (1.36 g). After stirring the solution under reflux for 3 hours, methyl triphenylphosphoranylideneacetate (1.36 g) was further added thereto. The solution was stirred under reflux for 14 hours. The solution was concentrated under reduced pressure, and the resulting residue was purified by chromatography (silica gel, hexane:ethyl acetate=1:1) to give a mixture of an unsaturated ester derivative and 3-oxaspiro[5.5]undecan-2-ol (520 mg) To a solution of the resulting mixture in ethanol (30 mL) was added 10% palladium-carbon (60 mg). The mixture was stirred at room temperature under hydrogen atmosphere for 63 hours. The catalyst was filtered off, concentrated under reduced pressure and the resulting residue was purified by chromatography (silica gel, hexane:ethyl acetate=1:1) to give the title compound (210 mg) $^1$HNMR (CDCl3) δ: 1.23-1.48 (m, 12H), 1.52-1.68 (m, 4H), 2.29 (t, 2H, J=7.2 Hz), 3.62-3.71 (m, 2H), 3.67 (s, 3H).

PREPARATION EXAMPLE 1F-3

Methyl 4-[1-(formylmethyl)cyclohexyl]butyrate

Using methyl 4-[1-(2-hydroxyethyl)cyclohexyl]butyrate (210 mg), the title compound (220 mg) was prepared in the same manner as in Preparation Example 1A-3. This product was subjected to the subsequent step without further purification.

$^1$H-NMR (CDCl$_3$) δ: 1.21-1.69 (m, 14H), 2.26-2.37 (m, 4H), 3.67 (s, 3H), 9.85 (t, 1H, J=3.2 Hz).

PREPARATION EXAMPLE 1G-1

(1-Allylcyclohexyl)methanol

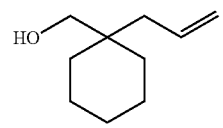

To a solution of cyclohexane carbaldehyde (2.24 g) in N,N-dimethylformamide (30 mL) were added potassium tert-butoxide (2.70 g) and allyl bromide (4.33 mL) under ice cooling. The solution was stirred under ice cooling for 30 minutes. Water and 1N hydrochloric acid were then added to the solution, and it was extracted with diethyl ether. The organic layer was washed with water and saturated aqueous sodium chloride solution, dried over anhydrous magnesium sulfate and concentrated under reduced pressure. To a solution of the resulting residue in ethanol (60 mL) was added sodium borohydride (567 mg) under ice cooling. The solution was stirred at room temperature for 16 hours. Acetic acid was added to the solution, and it was concentrated under reduced pressure. To the resulting residue was added saturated aqueous sodium bicarbonate solution, and it was extracted with diethyl ether. The organic layer was washed in turn with water and saturated aqueous sodium chloride solution, dried over anhydrous magnesium sulfate and concentrated under reduced pressure. The resulting residue was purified by column chromatography (silica gel, hexane:ethyl acetate=4:1) to give the title compound (1.47 g).

$^1$H-NMR (CDCl$_3$) δ: 1.21-1.55 (m, 10H), 2.01-2.24 (m, 2H), 3.31-3.54 (m, 2H), 5.02-5.12 (m, 2H), 5.81-5.93 (m, 1H).

PREPARATION EXAMPLE 1G-2

[1-(Allylcyclohexyl)methoxy]triethylsilane

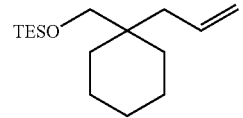

To a solution of (1-allylcyclohexyl)methanol (1.0 g) in N,N-dimethylformamide (7 mL) were added imidazole (661 mg) and triethylchlorosilane (1.41 mL) at room temperature. After stirring the solution at room temperature for 3 hours, N,N-dimethylformamide was added thereto and it was extracted with hexane. The combined hexane layer was washed with acetonitrile and concentrated under reduced pressure to give the title compound (1.70 g). This product was subjected to the subsequent step without further purification.

PREPARATION EXAMPLE 1G-3

3-[1-(Triethylsiloxymethyl)cyclohexyl]propan-1-ol

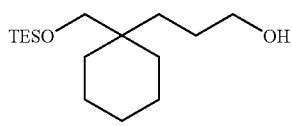

To a solution of [1-(allylcyclohexyl)methoxy]triethylsilane (1.70 g) in tetrahydrofuran (35 mL) were added a 2M borane-methyl sulfide complex solution in tetrahydrofuran (6.48 mL, 12.96 mmol) under ice cooling. The solution was stirred under ice cooling for 2 hours. To this were then added water, a 3N aqueous sodium hydroxide solution (6.5 mL) and 30% hydrogen peroxide (6.5 mL). The solution was stirred at room temperature for 16 hours. Water was added and the solution was extracted with ethyl acetate. The organic layer was washed in turn with water and saturated aqueous sodium chloride solution, dried over anhydrous magnesium sulfate and concentrated under reduced pressure. The resulting residue was purified by column chromatography (silica gel, hexane:ethyl acetate=7:3) to give the title compound (810 mg).

$^1$H-NMR (CDCl$_3$) δ: 0.58 (q, 6H, J=8.0 Hz), 0.95 (t, 9H, J=8.0 Hz), 1.22-1.61 (m, 15H), 3.35 (s, 2H), 3.56-3.66 (m, 2H).

PREPARATION EXAMPLE 1G-4

[1-(3-Acetoxypropyl)cyclohexylmethoxy]triethylsilane

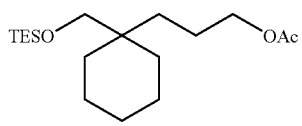

To 3-[1-(triethylsiloxymethyl)cyclohexyl]propan-1-ol (410 mg) were added acetic anhydride (3 mL) and pyridine (3 mL) at room temperature. The solution was stirred at room temperature for 2 hours and concentrated under reduced pressure. The residue was distilled with toluene azeotropically to give the title compound (480 mg). This product was subjected to the subsequent step without further pirification.

$^1$H-NMR (CDCl$_3$) δ: 0.57 (q, 6H, J=7.6 Hz), 0.95 (t, 9H, J=7.6 Hz), 1.20-1.46 (m, 12H), 1.49-1.60 (m, 2H), 2.04 (s, 3H), 3.33 (s, 2H), 4.03 (t, 2H, J=6.8 Hz).

PREPARATION EXAMPLE 1G-5

3-(1-Hydroxymethylcyclohexyl)propyl acetate

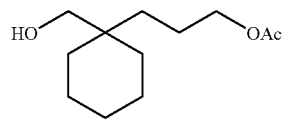

Using benzyl [1-(3-acetoxypropyl)cyclohexylmethoxy]triethylsilane (480 mg), the title compound (310 mg) was prepared in the same manner as in Preparation Example 3B-2.

$^1$H-NMR (CDCl$_3$) δ: 1.21-1.50 (m, 12H), 1.53-1.71 (m, 2H), 2.05 (s, 3H), 3.43 (s, 2H), 4.05 (t, 2H, J=7.2 Hz).

PREPARATION EXAMPLE 1H-1

[N-(tert-Butoxycarbonyl)-N-carboxymethylamino]acetic acid

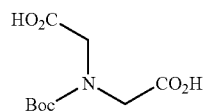

Iminodiacetic acid (10.00 g) was dissolved in a mixed solution of 1,4dioxane (160 mL) and water (80 mL). To this were added a 1N aqueous sodium hydroxide solution (160 mL) and then di-tert-butyl dicarbonate (18.04 g). The solution was stirred at room temperature for 22 hours. The solution was concentrated under reduced pressure, made to pH 3 by addition of a 5% potassium hydrogen sulfate solution and then extracted with 25% ethanol/chloroform. The extract was dried over anhydrous magnesium sulfate and the solvent was distilled off under reduced pressure. The resulting residue was washed with hexane to give the title compound (4.25 g).

1HNMR (DMSO-d$_6$) δ:1.37 (5, 9H), 3.88 (s, 2H), 3.91 (s, 2H).

PREPARATION EXAMPLE 1H-2

Ethyl [[[tert-butoxycarbonyl-[(diethoxycarbonylmethylcarbamoyl)-methyl]amino]acetyl]ethoxycarbonylmethylamino]acetate

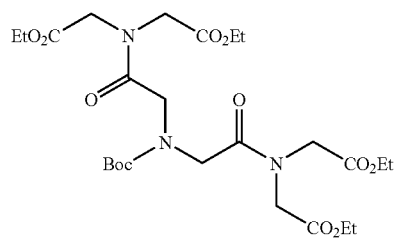

To a solution of [N-(tert-butoxycarbonyl)-N-carboxymethylamino]acetic acid (0.57 g) dissolved in dichloromethane (5 mL) were added iminodiacetic acid diethyl ester (1.40 g), N,N-diisopropylethylamine (1.59 g) and then 2-bromo-1-ethylpyridinium tetrafluoroborate (1.95 g). The solution was stirred at room temperature for 1 hour. Ethyl acetate was added to the solution and it was washed in turn with saturated aqueous sodium bicarbonate solution and saturated aqueous sodium chloride solution, dried over anhydrous magnesium sulfate and the solvent was distilled off under reduced pressure. The resulting residue was purified by column chromatography (silica gel, 5-10% methanol/dichloromethane) to give the title compound (0.79 g).

$^1$H-NMR (DMSO-$d_6$) δ: 1.17-1.24 (m, 12H), 1.35 (s, 9H), 3.96-4.26 (m, 20H).

PREPATAION EXAMPLE 1H-3

Ethyl

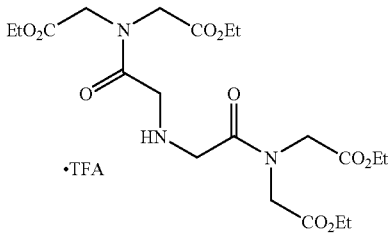

To a solution of ethyl (diothcxycarbonylmcthylc&rbamcyl) [[[tert-butoxycarbonyl-[(diethoxycarbonylmethylcarbamoyl)-methyl]amino-lacetyl]ethoxycarbonylmethylamino]etate (0.79 g) dissolved in dichloromethane (8 mL) was added trifluoroacetic acid (8.0 mL) at room temperature. The solution was stirred for 2 hours. The solvent was distilled off under reduced pressure and then, the residue was distilled with xylene azeotropically to give the title compound (0.81 g). This product was subjected to the subsequent step without further purification.

PREPARATION EXAMPLE 1I-1

2-Acetoxymethyl-2-amino-1,3-diacetoxypropane

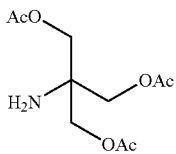

To 2-amino-2-hydroxymethyl-1,3-propanediol (10.00 g) were added acetic acid (40.0 mL), 1N hydrochloric acid/diethyl ether solution (90.0 mL) and acetic anhydride (30.0 mL) successively. The solution was heated under reflux at 110° C. for 6 hours. The solvent was distilled off under reduced pressure, and distilled to dryness with xylene azeotropically. The resulting residue was diluted with water, washed with ethyl acetate, the aqueous layer was made to pH 8 with sodium hydrogencarbonate, and it was then extracted with 25% ethanol/chloroform. The organic layer was dried over anhydrous magnesium sulfate and the solvent was distilled off under reduced pressure. The resulting residue was purified by column chromatography (silica gel, 3-4% ethanol/dichloromethane) to give the title compound (4.02 g).

$^1$H-NMR (DMSO-$d_6$) δ: 2.02 (s, 9H), 3.24 (brs, 2H), 3.94 (s, 6H).

PREPARATION EXAMPLE 1J-1

3-Acetoxy-2-(2-{[(2-acetoxy-1,1-diacetoxymethyl-ethylcarbamoyl)methyl]amino}acetylamino)-2-acetoxymethylpropyl acetate

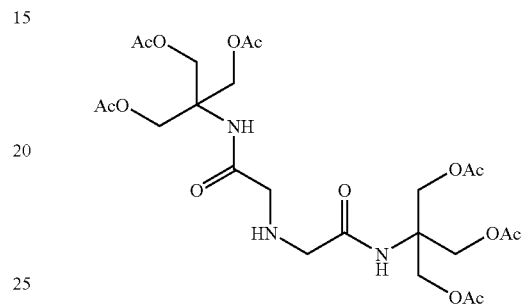

To a solution of 2acetoxymethyl-2-amino-1,3-diacetoxypropane (1.18 g) dissolved in dichioromethane (8 mL) were added [N-(tert-butoxycarbonyl)-N-carboxymethyl]acetic acid (0.56 g), N,N-diiospropylethylamine (1.54 g) and then 2-bromo-1-ethylpyridinium tetrafluoroborate (1.96 g). The solution was stirred at room temperature for 10 hours. After addition of ethyl acetate, the solution was washed in turn with a 5% aqueous potassium hydrogensulfate solution, saturated aqueous sodium bicarbonate solution and saturated aqueous sodium chloride solution, dried over anhydrous magnesium sulfate, and the solvent was distilled off under reduced pressure. The resulting residue was purified by column chromatography (silica gel, 5-10% methanol/dichloromethane). The resulting compound was dissolved in dichloromethane (5 mL), to which trifluoroacetic acid (5.0 mL) was added at room temperature. The solution was stirred for 16 hours. The solvent was distilled off under reduced pressure. The resulting residue was purified by column chromatography [silica gel, dichloromethane-methanolaqueous ammonia(90:10:0.5)]to give the title compound (0.47 g). This product was subjected to the subsequent step without further purification.

1HNMR (DMSO-$d_6$) δ: 1.82 (s, 6H), 2.01 (s, 12H), 3.48-3.53 (m, 4H), 4.25-4.31 (m, 8H), 4.33-4.38 (m, 4H).

PREPARATION EXAMPLE 1K-1

1-Methoxycarbonylmethylcyclohexylacetic acid

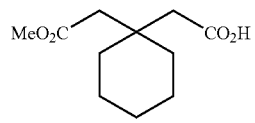

A solution of 1,1-cyclohexanediacetic acid (5.0 g) in acetic anhydride (8.0 mL) was stirred under reflux for 5 hours. The solution was then concentrated under reduced pressure and distilled with toluene azeotropically. To a solution of the resulting residue in methanol (15.2 mL) was added boron trifluoride diethyl ether complex (1.58 mL) at room temperature. The solution was stirred at room temperature for 2 hours. Saturated aqueous sodium carbonate solution was added to the solution and it was washed with diethyl ether. The aqueous layer was neutralized by addition of conc. hydrochloric acid and then extracted with ethyl acetate. The organic layer was washed with saturated aqueous sodium chloride solution, and then, dried over anhydrous magnesium sulfate. The solvent was distilled off under reduced pressure to give the title compound (4.21 g).

$^1$H-NMR (CDCl$_3$) δ: 1.38-1.60 (m, 10H), 2.56 (s, 2H), 2.58 (s, 2H), 3.68 (s, 3H).

PREPARATION EXAMPLE 1K-2

1-Methoxycarbonyimethylcyclohexyl acotic acidacetyl chloride

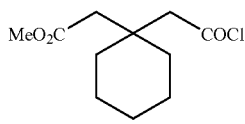

To a solution of 1-methoxycarbonylmethylcyclohexylacetic acid (265 mg) in a mixed solvent of methylene chloride (10 mL) and N,N-dimethylformamide (one drop) was added oxalyl chloride (0.12 mL) under ice cooling. After stirring the solution at room temperature for 1 hour, it was concentrated under reduced pressure to give the title compound. This product was subjected to the subsequent step without further purification.

PREPARATION EXAMPLE 2A-1

Ethyl 3-(2-nitrophenyl)acrylate

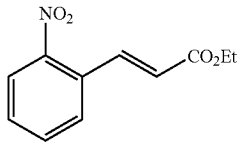

To a suspension of 60% sodium hydride/mineral oil (1.11 g) in tetrahydrofuran (40 mL) was added ethyl diethylphosphonoacetate (6.29 mL) dropwise under ice cooling. After stirring the mixture under ice cooling for 30 minutes, a solution of 2-nitrobenzaldehyde (3.0 g) in tetrahydrofuran (30 mL) was added thereto under ice cooling. The solution was stirred at room temperature for 8 hours. Water and 3N hydrochloric acid were then added to the solution and it was extracted with diethyl ether. The organic layer was washed with water and saturated aqueous sodium chloride solution, dried over anhydrous magnesium sulfate and concentrated under reduced pressure. The resulting residue was purified by column chromatography (silica gel, hexane:ethyl acetate=3:2) to give the title compound (3.74 g).

$^1$H-NMR (CDCl$_3$) δ: 1.35 (t, 3H, J=6.8 Hz), 4.29 (q, 2H, J=6.8 Hz), 6.36 (d, 1H, J=16.0 Hz), 7.50-7.59 (m, 1H), 7.61-7.69 (m, 2H), 8.04 (d, 1H, J=8.8 Hz), 8.12 (d, 1H, J=16.0 Hz).

PREPARATION EXAMPLE 2A-2

3-(2-Aminophenyl)propan-1-ol

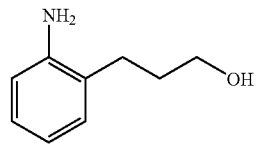

To a solution of ethyl 3-(2-nitrophenyl)acrylate (1.11 g) in diethyl ether (30 mL) was added a 1M diisobutylaluminum hydride solution in hexane (15.0 mL) under ice cooling. After stirring the solution under ice cooling for 1 hour, diethyl ether, water (0.6 mL) and a 15% aqueous sodium hydroxide solution (0.6 mL) were added thereto. The solution was stirred at room temperature for 15 minutes. Water (1.8 mL) was then added and the solution was stirred at room temperature for 15 minutes. Anhydrous magnesium sulfate was added to the solution and filtered. The filtrate was concentrated under reduced pressure. To a solution of the resulting residue in ethanol (50 mL) was added 10% palladium-carbon (200 mg). The mixture was stirred at room temperature under hydrogen atmosphere for 89 hours. The catalyst was filtered off, and the filtrate was concentrated under reduced pressure. The resulting residue was purified by column chromatography (silica gel, hexane:ethyl acetate=1:2) to give the title compound (660 mg).

$^1$H-NMR (CDCl$_3$) δ: 1.81-1.95 (m, 2H), 2.64 (t, 2H, J=7.2 Hz), 3.64 (t, 2H, J=5.2 Hz), 6.69 (d, 1H, J=7.6 Hz), 6.73-6.79 (m, 1H), 7.00-7.08 (m, 2H).

PREPARATION EXAMPLE 2A-3

2-Cyclohexyl-N-[2-(3-hydroxypropyl)phenyl]acetamide

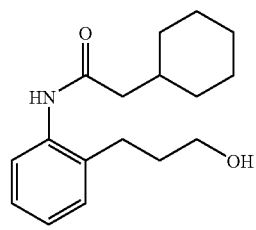

To a solution of 3-(2-aminophenyl)propan-1-ol (180 mg) and cyclohexylacetic acid (203 mg) in dichloromethane (12mL) were added 1-hydroxybenzotriazole (193 mg) and 1-ethyl-3-(3-dimethylaminopropyl)carbodiimide hydrochloride (274 mg) under ice cooling. The solution was stirred at room temperature for 113 hours. Chloroform was then added to the solution and it was washed in turn with water and saturated aqueous sodium bicarbonate solution, dried over anhydrous sodium sulfate and concentrated under reduced pressure. The resulting residue was purified by column chromatography (silica gel, hexane: ethyl acetate=1:1) to give the title compound (170 mg).

$^1$HNMR (CDCl$_3$) δ: 0.93-1.08 (m, 2H), 1.08-1.22 (m, 1H), 1.22-1.36 (m, 2H), 1.56-2.06 (m, 8H), 2.22 (d, 2H, J=7.2 Hz), 2.75 (t, 2H, J=6.8 Hz), 3.60 (t, 2H, J=5.6 Hz), 7.03-7.12 (m, 1H), 7.13-7.25 (m, 2H), 7.88 (d, 1H, J=7.6 Hz), 8.36 (brs, 1H).

PREPARATION EXAMPLE 2A-4

2-Cyclohexyl-N-[2-(2-formylethyl)phenyl]acetamide

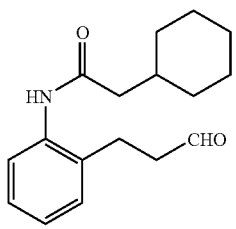

The title compound was synthesized from the compound obtained in Preparation Example 2A-3 in the same manner as in Preparation Example 1A-3.

PREPARATION EXAMPLE 2B-1

2-Cyclohexyl -N-[2-(2-hydroxyethyl) phenyl]acetamide

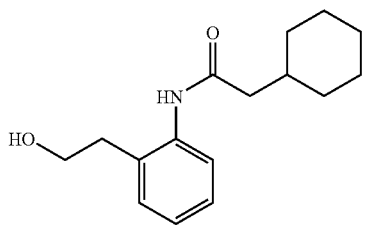

Using 2aminophenethyl alcohol (500 mg), the title compound (780 ing) was obtained in the same manner as in

PREPARATION EXAMPLE 2A-3.

$^1$HNMR (CDCl$_3$) δ 0.94-1.09 (m, 2H), 1.10-1.36 (m, 3H), 1.52-1.96 (m, 6H), 2.22 (d, 2H, J=8.4 Hz), 2.84 (t, 2H, J=5.2 Hz), 3.97 (t, 2H, J=5.2 Hz), 7.05-7.12 (m, 1H), 7.13-7.18 (m, 1H), 7.21-7.29 (m, 1H), 7.82-7.89 (m, 1H), 8.78 (brs, 1H).

PREPARATION EXAMPLE 2B-2

N-[2-(2-Bromoethyl)phenyl]-2-cyclohexylacetamide

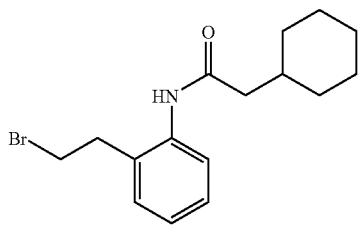

To a solution of 2-cyclohexyl-N-[2-(2-hydroxyethyl)phenyl]acetamide (780 mg) in dichloromethane (20 mL) were added triphenylphosphine (938 mg) and carbon tetrabromide (1.12 g) at room teperature. The solution was stirred at room temperature for 1 hour. Chloroform was added and the solution was washed in turn with water and saturated aqueous sodium bicarbonate solution, dried over anhydrous magnesium sulfate and concentrated under reduced pressure. The resulting residue was purified by column chromatography (silica gel, hexane:ethyl acetate=7:3) to give the title compound (450 mg).

$^1$H-NMR (CDCl$_3$) δ: 0.97-1.39 (m, 5H), 1.64-1.80 (m, 3H), 1.80-1.97 (m, 3H), 2.27 (d, 2H, J=6.8 Hz), 3.16 (t, 2H, J=7.2 Hz), 3.59 (t, 2H, J=7.2 Hz), 7.14-7.33 (m, 4H), 7.57-7.64 (m, 1H).

PREPARATION EXAMPLE 2C-1

1-(2-Bromoethyl)-2-nitrobenzene

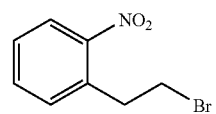

Using 1-(2-hydroxyethyl)-2-nitrobenzene (10.11 g), the title compound (21.46 g) was obtained in the same manner as in Preparation Example 2B-2. This product was subjected to the subsequent step without further purification.

$^1$H-NMR (CDCl$_3$) δ: 3.46 (t, 2H, J=7.3 Hz), 3.68 (t, 2H, J=7.3 Hz), 7.41-7.46 (m, 2H), 7.55-7.60 (m, 1H), 7.97-8.00 (m, 1H).

PREPARATION EXAMPLE 2D-1

1-(3-Hydroxy-1-propenyl)-2-nitrobenzene

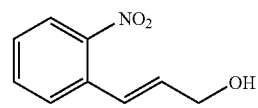

To a solution of 2-trans-nitrocinnamaldehyde (10.00 g) dissolved in ethanol (50 mL) was added sodium borohydride (2.14 g) under ice cooling. The reaction solution was stirred for 1 hour. The reaction solution was poured into saturated aqueous sodium bicarbonate solution, and it was extracted with ethyl acetate. The organic layer was washed with saturated aqueous sodium chloride solution, dried over anhydrous magnesium sulfate and the solvent was distilled off under reduced pressure. The resulting residue was purified by column chromatography (silica gel, 20-50% ethyl acetate/hexane) to give the title compound (8.00 g).

$^1$H-NMR (CDCl$_3$) δ: 1.64 (t, 1H, J=5.9 Hz), 4.38 (ddd, 2H, J=2.0 Hz, 5.4 Hz, 5.9 Hz), 6.34 (dt, 1H, J=15.6 Hz, 5.4 Hz), 7.10 (dt, 1H, J=15.6 Hz, 2.0 Hz), 7.37-7.42 (m, 1H), 7.53-7.62 (m, 2H), 7.90-7.93 (m, 1H).

PREPARATION EXAMPLE 2D-2

1-(3-Bromo-1-propenyl)-2-nitrobenzene

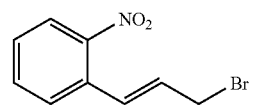

Using 1-(3-hydroxy-1-propenyl)-2-nitrobenzene (8.00 g), the title compound (17.1 g) was obtained in the same manner as in Preparation Example 2B-2. This product was subjected to the subsequent step without further purification.

PREPARATION EXAMPLE 2E-1 tert-Butyl 2-(3-hydroxypropyl)phenylcarbamate

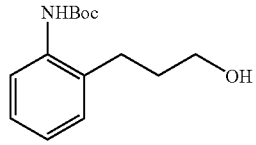

To a solution of 3-(2-aminophenyl)propan-1-ol (660 mg) in tetrahydrofuran (10 mL) were added triethylamine (1.52 mL) and di-tert-butyl dicarbonate (1.91 g) under ice cooling. The solution was stirred at room temperature for 20 hours. Ethyl acetate and water were added to carry out extraction. The organic layer was washed in turn with 1N hydrochloric acid, saturated aqueous sodium bicarbonate solution and saturated aqueous sodium chloride solution, dried over anhydrous magnesium sulfate and concentrated under reduced pressure. The resulting residue was purified by column chromatography (silica gel, hexane:ethyl acetate=60:40) to give the title compound (730 mg).

$^1$H-NMR (CDCl$_3$) δ: 1.51 (s, 9H), 1.82-19.2 (m, 2H), 2.73 (t, 2H, J=6.8 Hz), 3.59-3.67 (m, 2H), 7.00-7.07 (m, 1H), 7.11-7.23 (m, 3H), 7.75 (brd, 1H, J=8.0 Hz).

PREPARATION EXAMPLE 2E-2 tert-Butyl 2-(3-Bromopropyl)phenylcarbamate

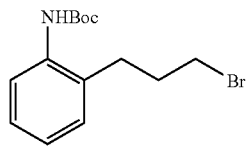

Using tert-butyl 2-(3-hydroxypropyl)phenylcarbamate (730 mg), the title compound (670 mg) was obtained in the same manner as in Preparation Example 2B-2.

$^1$H-NMR (CDCl$_3$) δ: 1.52 (s, 9H), 2.09-2.19 (m, 2H), 2.76 (t, 2H, J=7.2 Hz), 3.44 (t, 2H, J=6.4 Hz), 6.38 (brs, 1H), 7.01-7.08 (m, 1H), 7.13-7.25 (m, 2H), 7.74 (brd, 1H, J=8.4 Hz).

PREPARATION EXAMPLE 2F-1 tert-Butyl 2-(2-hydroxyethyl)phenylcarbamate

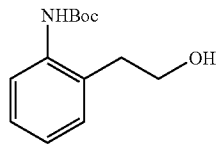

Using 2-aminophenethyl alcohol (1.0 g), the title compound (1.14 g) was obtained in the same manner as in Preparation Example 2E-1.

$^1$H-NMR (CDCl$_3$) δ: 1.51 (s, 9H), 1.95-2.05 (m, 1H), 2.84 (t, 2H, J=5.6 Hz), 3.88-3.94 (m, 2H), 7.01-7.08 (m, 1H), 7.11-7.17 (m, 1H), 7.19-7.26 (m, 1H), 7.55-7.65 (m, 1H), 7.68-7.76 (m, 1H).

PREPARATION EXAMPLE 2F-2 tert-Butyl 2-(2-bromoethyl)phenylcarbamate

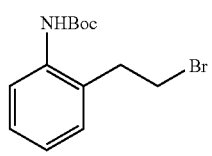

Using tert-butyl 2-(2-hydroxyethyl)phenylcarbamate (1.14 g), the title compound (0.75 g) was obtained in the same manner as in Preparation Example 2B-2.

$^1$H-NMR (CDCl$_3$) δ: 1.52 (s, 9H), 3.16 (t, 2H, J=7.2 Hz), 3.58 (t, 2H, J=7.2 Hz), 6.37 (brs, 1H), 7.08-7.15 (m, 1H), 7.16-7.21 (m, 1H), 7.23-7.29 (m, 1H), 7.63 (brd, 1H, J=8.0 Hz).

PREPARATION EXAMPLE 3A-1

2-[1-(2-Hydroxyethyl)cyclohexyl]ethanol

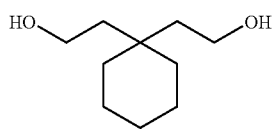

To a solution of 1,1,-cyclohexanediacetic acid (6.0 g) in tetrahydrofuran (90 mL) was added lithium aluminum hydride (2.28 g) under ice cooling. The solution was stirred under reflux for 4 hours, and then, cooled on ice, to which diethyl ether (200 mL), water (2.3 mL) and a 15% aqueous sodium hydroxide solution (2.3 mL) were added. After stirring the solution at room temperature for 30 minutes, water (6.9 mL) was added and the solution was stirred at room temperature for additional 30 minutes. Anhydrous magnesium sulfate was added to the solution, and it was filtered under reduced pressure. The filtrate was concentrated under reduced pressure. The resulting residue was purified by chromatography (silica gel, ethyl acetate) to give the title compound (4.83 g).

$^1$H-NMR (CDCl$_3$) δ: 1.23-1.50 (m, 10H), 1.64 (t, 4H, J=7.2 Hz), 1.96-2.17 (m, 2H), 3.72 (t, 4H, J=7.2 Hz).

PREPARATION EXAMPLE 3A-2

2-[1-[2-(tert-Butyldiphenylsiloxy)ethyl]cyclohexyl]ethanol

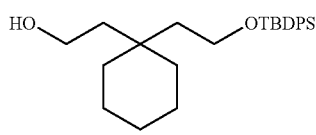

To a solution of 2-[1-(2-hydroxyethyl)cyclohexyl]ethanol (6.41 g) in dichloromethane (170 mL) were added triethylamine (6.74 mL) and tert-butyldiphenylchlorosilane (11.1 mL) at room temperature. After stirring the solution at room temperature for 18 hours, chloroform was added to the solution, and it was washed in turn with 1N hydrochloric acid, saturated aqueous sodium bicarbonate solution and saturated aqueous sodium chloride solution. The solution was dried over anhydrous magnesium sulfate, and concentrated under reduced pressure. The resulting residue was purified by chromatography (silica gel, hexane:ethyl acetate=85:15) to give the title compound (10.97 g).

$^1$H-NMR (CDCl$_3$) δ: 1.05 (s, 9H), 1.19-1.43 (m, 10H), 1.48-1.55 (m, 3H), 1.61 (t, 2H, J=7.6 Hz), 3.56 (t, 2H, J=7.6 Hz), 3.70 (t, 2H, J=7.6 Hz), 7.35-7.47 (m, 6H), 7.64-7.73 (m, 4H).

PREPARATION EXAMPLE 3A-3 tert-Butyl [2-[1-(2-iodoethyl)cyclohexyl]ethoxy]diphenylsilane

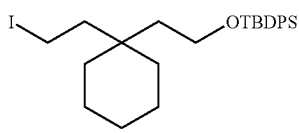

To a solution of [2-[1-(tert-butyldiphenylsiloxy)ethyl]cyclohexyl]ethanol (4.0 g) in tetrahydrofuran (60 mL) and acetonitrile (20 mL) were added triphenylphosphine (3.3 mL), imidazole (993 mg) and iodine (3.46 g) at room temperature successively. After stirring the solution at room temperature for 2 hours, diethyl ether was added to the solution, and it was washed in turn with an aqueous sodium thiosulfate solution, water, and saturated aqueous sodium chloride solution. The solution was dried over anhydrous magnesium sulfate, and then, concentrated under reduced pressure. The resulting residue was dissolved in acetonitrile. The solution was extracted with hexane. The combined hexane layer was washed with acetonitrile and concentrated under reduced pressure to give the title compound (4.83 g).

$^1$H-NMR (CDCl$_3$) δ: 1.05 (s, 9H), 1.16-1.41 (m, 8H), 1.49-1.56 (m, 4H), 1.85-1.93 (m, 2H), 2.94-3.04 (m, 2H), 3.66 (t, 2H, J=7.6 Hz), 7.35-7.47 (m, 6H), 7.63-7.71 (m, 4H).

PREPARATION EXAMPLE 3A-4

Triethyl 3-[1-[2-(tert-butyldiphenylsiloxy)ethyl]cyclohexyl]-1,1,1-propanetricarboxylate

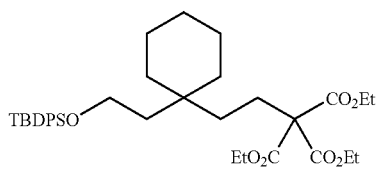

To a solution of tert-butyl [2-[1-(2-iodoethyl)cyclohexyl]ethoxy]diphenylsilane (540 mg) and ethyl methane tricarboxylate (727 mg) in N,N-dimethylformamide (5 mL) was added potassium carbonate (575 mg) at room temperature. The solution was stirred at 110° C. for 6 hours, to which water and 3N hydrochloric acid were added. The solution was extracted with ethyl acetate. The organic layer was washed in turn with a 1N aqueous sodium hydroxide solution, water and saturated aqueous sodium chloride solution, dried over anhydrous magnesium sulfate, and concentrated under reduced pressure. The resulting residue was purified by chromatography (silica gel, hexane:ethyl acetate=85:15) to give the title compound (470 mg).

$^1$H-NMR (CDCl$_3$) δ: 1.03 (s, 9H), 1.17-1.40 (m, 12H), 1.23 (t, 9H, J=6.8 Hz), 1.60 (t, 2H, J=8.0 Hz), 1.96-2.04 (m, 2H), 3.68 (t, 2H, J=8.0 Hz), 4.18 (q, 6H, J=6.8 Hz), 7.73-7.45 (m, 6H), 7.64-7.70 (m, 4H).

PREPARATION EXAMPLE 3A-5

Triethyl 3-[1-(2-hydroxyethyl)cyclohexyl]-1,1,1-propanetricarboxylate

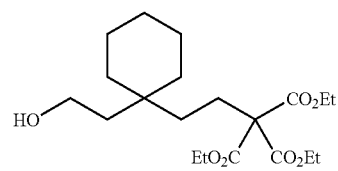

To a solution of triethyl 3-[1-[2-(tert-butyldiphenylsiloxy)ethyl]cyclohexyl]-1,1,1-propanetricarboxylate (470 mg) in methanol (10 mL)/tetrahydrofuran (5 mL) was added 3N hydrochloric acid (2.5 mL) at room temperature. After stirring the solution at room temperature for 4 hours, water was added to the solution, and it was concentrated under reduced pressure. The solution was extracted with ethyl acetate. The organic layer was washed in turn with water and saturated aqueous sodium chloride solution. The solution was dried over anhydrous magnesium sulfate, and then, concentrated under reduced pressure. The resulting residue was purified by chromatography (silica gel, hexane:ethyl acetate=1:1) to give the title compound (230 mg).

$^1$H-NMR (CDCl$_3$) δ: 1.23-1.51 (m, 12H), 1.29 (t, 9H, J=7.2 Hz), 1.56-1.64 (m, 2H), 2.03-2.11 (m, 2H), 3.68 (t, 2H, J=7.2 Hz), 4.26 (q, 6H, J=7.2 Hz).

PREPARATION EXAMPLE 3A-6

Triethyl 3-[1-(formylmethyl)cyclohexyl]-1,1,1-propanetricarboxylate

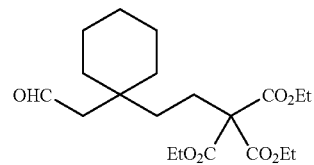

To a solution of triethyl 3-[1-(2-hydroxyethyl)cyclohexyl]-1,1,1-propanetricarboxylate (230 mg) in dichloromethane (6 mL) were added diacetic acid iodobenzene (213 mg) and 2,2,6,6-tetramethyl-1-piperidinyloxy free radical (9.3 mg) at room temperature. The solution was stirred at room temperature for 16 hours. Diethyl ether was added to the solution, and it washed in turn with an aqueous sodium thiosulfate solution, 1N hydrochloric acid, saturated aqueous sodium bicarbonate solution and saturated aqueous sodium chloride solution. The solution was dried over anhydrous magnesium sulfate, and then, concentrated under reduced pressure to give the title compound. This product was subjected to the subsequent step without further purification.

PREPARATION EXAMPLE 3B-1

Dimethyl 3-[1-[(2-tert-butyldiphenylsiloxy)ethyl]cyclohexyl]-1,1-propanedicarboxylate

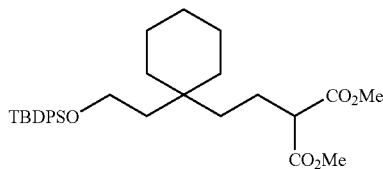

To a solution of tert-butyl 2-[1-(2-iodoethyl)cyclohexyl]ethoxy]diphenylsilane (1.5 g) and dimethyl malonate (1.90 g) in N,N-dimethylformamide (20 mL) was added potassium tert-butoxide (1.45 g) at room temperature. After stirring the solution at 60° C. for 4 hours, water and 3N hydrochloric acid were added to the solution, and it was extracted with ethyl acetate. The combined organic layer was washed in turn with water and saturated aqueous sodium chloride solution, dried over anhydrous magnesium sulfate, and then, concentrated under reduced pressure. The resulting residue was purified by chromatography (silica gel, hexane:ethyl acetate=9:1) to give the title compound (1.32 g).

$^1$H-NMR (CDCl$_3$) δ: 1.04 (s, 9H), 1.11-1.38 (m, 11H), 1.51-1.63 (m, 3H), 1.71-1.80 (m, 2H), 3.19 (t, 1H, J=8.0 Hz), 3.65 (t, 2H, J=8.0 Hz), 3.69 (s, 6H), 7.34-7.44 (m, 6H), 7.64-7.71 (m, 4H).

PREPARATION EXAMPLE 3B-2

Dimethyl 3-[1-(2-hydroxyethyl)cyclohexyl]-1,1-propanedicarboxylate

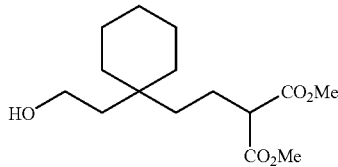

To a solution of dimethyl 3-[1-(2-(tert-butyldiphenylsiloxy)ethyl)cyclohexyl]-1,1-propanedicarboxylate (500 mg) in tetrahydrofuran (10 mL) was added a 1M tetrabutylammonium fluoride/tetrahydrofuran solution (1.9 mL) at room teperature. The solution was stirred at room temperature for 3 hours. Water was added to the solution, and it was extracted with ethyl acetate. The organic layer was washed in turn with an aqueous ammonium chloride solution, and saturated aqueous sodium chloride solution, dried over anhydrous magnesium sulfate, and then, concentrated under reduced pressure. The resulting residue was purified by chromatography (silica gel, hexane:ethyl acetate=1:1) to give the title compound (180 mg).

$^1$H-NMR (CDCl$_3$) δ: 1.21-1.49 (m, 12H), 1.55-1.68 (m, 2H), 1.80-1.91 (m, 2H), 3.30 (t, 1H, J=7.6 Hz), 3.66 (t, 2H, J=7.6 Hz), 3.75 (s, 6H).

PREPARATION EXAMPLE 3B-3

Dimethyl 2-[2-[1-(formylmethyl)cyclohexyl]ethyl]malonate

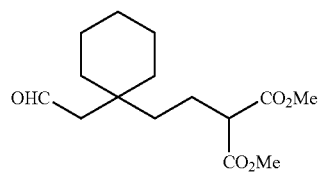

Using dimethyl 3-[1-(2-hydroxyethyl)cyclohexyl]-1,1-propanedicarboxylate (180 mg), the crude title compound was obtained in the same manner as in Preparation Example 3A-6. This product was subjected to the subsequent step without further purification.

PREPARATION EXAMPLE 3C-1

2-[2-[1-[2-(tert-butyldiphenylsiloxy)ethyl]cyclohexyl]ethylpropane-1,3-diol

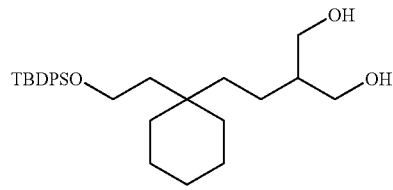

To a solution of dimethyl 3-[1-(2-(tert-butyldiphenylsiloxy)ethyl)cyclohexyl]-1,1-propanedicarboxylate (1.32 g) in diethyl ether (30 mL) was added lithium aluminum hydride (191 mg) under ice cooling. After stirring the solution under ice cooling for 2 hours, water (0.2 mL) and a 15% aqueous sodium hydroxide solution (0.2 mL) were successively added to the solution. The solution was stirred at room temperature for 15 minutes. Water (0.6 mL) was then added to the solution, and it was stirred for additional 30 minutes. The solution was dried over anhydrous magnesium sulfate, and concentrated under reduced pressure. The resulting residue was purified by chromatography (silica gel, hexane:ethyl acetate=1:1) to give the title compound (790 mg).

$^1$H-NMR (CDCl$_3$) δ: 1.04 (s, 9H), 1.11-1.41 (m, 11H), 1.50-1.61 (m, 5H), 1.99-2.08 (m, 1H), 3.54 (dd, 2H, J=7.6 Hz, 9.4 Hz), 3.65 (t, 2H, J=7.6 Hz), 3.70 (dd, 1H, J=4.6 Hz, 9.6 Hz), 7.34-7.46 (m, 6H), 7.63-7.73 (m, 4H).

PREPARATION EXAMPLE 3C-2

2-[2-[1-(2-Hydroxyethyl)cyclohexyl]ethyl]-1,3-diacetoxypropane

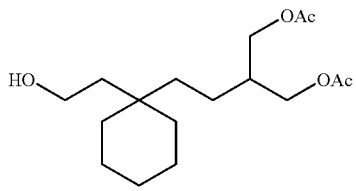

To a solution of 2-[2-[1-[2-(tert-butyldiphenylsiloxy)ethyl]cyclohexyl]ethyl]propane-1,3-diol (190 mg) in pyridine (3.0 mL) was added acetic anhydride (3.0 mL) at room temperature. After stirring the solution at room temperature for 3 hours, it was concentrated under reduced pressure. To a solution of the resulting residue in tetrahydrofuran (8 mL) was added a 1M tetrabutylammonium bromide/tetrahydrofuran solution (0.53 mL) at room temperature. The solution was stirred at room temperature for 1 hour, to which a 1M tetrabutylammonium bromide/tetrahydrofuran solution (0.53 mL) was further added at room temperature. The solution was stirred at room temperature for 1 hour, to which a 1M tetrabutylammonium bromide/tetrahydrofuran solution (0.53 mL) was still further added at room temperature. The solution was stirred at room temperature for 1 hour and water was added thereto, and it was extracted with ethyl acetate. The organic layer was washed in turn with saturated aqueous ammonium chloride solution and saturated aqueous sodium chloride solution. The solution was dried over anhydrous magnesium sulfate, and then, concentrated under reduced pressure. The resulting residue was purified by chromatography (silica gel, hexane:ethyl acetate=1:1) to give the title compound (140 mg).

$^1$H-NMR (CDCl$_3$) δ: 1.19-1.35 (m, 8H), 1.36-1.49 (m, 5H), 1.53-1.65 (m, 3H), 1.87-1.96 (m, 1H), 2.06 (s, 6H), 3.64 (t, 2H, J=8.0 Hz), 4.05 (dd, 2H, J=6.4 Hz, 11.2 Hz), 4.09 (dd, 2H, J=4.8 Hz, 11.2 Hz).

PREPARATION EXAMPLE 3C-3

2-[2-[1-(Formylmethyl)cyclohexyl]ethyl]-1,3-diacetoxypropane

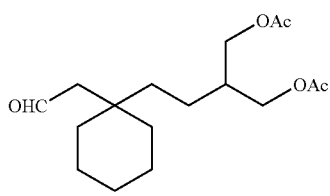

Using 2-[2-[1-(2-hydroxyethyl)cyclohexyl]ethyl]-1,3-diacetoxypropane (140 mg), the title compound (117 mg) was obtained in the same manner as in Preparation Example 1A-3. This product was subjected to the subsequent step without further purification.

PREPARATION EXAMPLE 3D-1

2-[1-(2-Benzyloxyethyl)cyclohexyl]ethanol

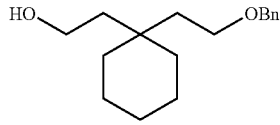

To a suspension of 60% sodium hydride/mineral oil (881 mg) in N,N-dimethylformamide (20 mL) was added 2-[1-(2-hydroxyethyl)cyclohexyl]ethanol (2.92 g) under ice cooling. To the solution was further added benzyl bromide (2.83 mL) under ice cooling, and it was stirred at room temperature for 63 hours. Water and 3N hydrochloric acid were added to the solution, and it was extracted with ethyl acetate. The organic layer was washed in turn with water and saturated aqueous sodium chloride solution, dried over anhydrous magnesium sulfate, and concentrated under reduced pressure. The resulting residue was purified by chromatography (silica gel, hexane:ethyl acetate=6:4) to give the title compound (2.93 g).

$^1$H-NMR (CDCl$_3$) δ: 1.26-1.34 (m, 4H), 1.35-1.48 (m, 6H), 1.61 (t, 2H, J=6.8 Hz), 1.69 (t, 2H, J=6.8 Hz), 1.74-1.79 (m, 1H), 3.54 (t, 2H, J=6.8 Hz), 3.64-3.73 (m, 2H), 4.50 (s, 2H), 7.26-7.39 (m, 5H).

PREPARATION EXAMPLE 3D-2

[2-[1-(2-Todoethyl)cyclohexyl]ethoxymethyl]benzene

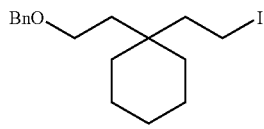

Using 2-[1-(2-benzyloxyethyl)cyclohexyl]ethanol (1.63 g), the title compound (1.87 g) was obtained in the same manner as in Preparation Example 3A-3.

$^1$H-NMR (CDCl$_3$) δ: 1.23-1.33 (m, 4H), 1.35-1.48 (m, 6H), 1.62 (t, 2H, J=7.2 Hz), 1.93-2.02 (m, 2H), 3.12-3.20 (m, 2H), 3.49 (t, 2H, J=7.2 Hz), 4.49 (s, 2H), 7.22-7.40 (m, 5H).

PREPARATION EXAMPLE 3O-3

Dimethyl 2-[2-[1-(2-benzyloxyethyl)cyclohexyl]ethyl]malonate

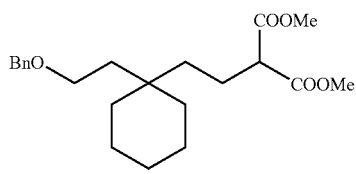

To a suspension of 60% sodium hydride/mineral oil (613 mg) in N,N-dimethylformamide (15 mL) was added malonate (1.84 mL) at room temperature. After stirring the solution at room temperature for 15 minutes, a solution of [2-[1-(2-iodoethyl)cyclohexyl]ethoxmethyl]benzene (1.5 g) in N,N-dimethylformamide (15 mL) was added thereto. The solution was stirred at 60° C. for 60 hours. Water and 3N hydrochloric acid were added to the solution, and it was extracted with ethyl acetate. The organic layer was washed in turn with water and saturated aqueous sodium chloride solution, dried over anhydrous magnesium sulfate, and then concentrated under reduced pressure. The resulting residue was purified by chromatography (silica gel, hexane:ethyl acetate=85:15) to give the title compound (1.03 g). This product was subjected to the subsequent step without further purification.

PREPARATION EXAMPLE 3D-4

2-[2-[1-(2-Benzyloxyethyl)cyclohexyl]ethyl]propane-1,3-diol

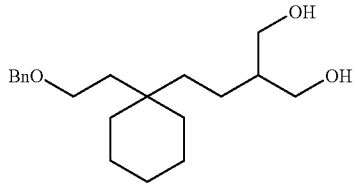

To a solution of dimethyl 2-[2-[1-(2-benzyloxyethyl)-cyclohexyl]ethyl]malonate (1.03 g) in diethyl ether (40 mL) was added lithium aluminum hydride (207 mg) under ice cooling. After stirring the solution under ice cooling for 2 hours, water (0.2 mL) and a 15% aqueous sodium hydroxide solution (0.2 mL) were successively added to the solution. The solution was stirred at room temperature for 15 minutes, water (0.6 mL) was added thereto, and it was stirred for additional 30 minutes. The solution was dried over anhydrous magnesium sulfate, and concentrated under reduced pressure. The resulting residue was purified by chromatography (silica gel, hexane:ethyl acetate=2:3) to give the title compound (320 mg)
$^1$HNMR (CDCl$_3$) δ 1.13-1.33 (m, 8H), 1.34-1.47 (m, 5H), 1.54-1.68 (m,4H), 2.23-2.37 (m, 2H), 3.47 (t, 2H, J=6.8 Hz), 3.57-3.67 Cm, 2H), 3.71-3.79 (m, 2H), 4.48 (s, 2H), 7.24-7.39 (m, 5H).

PREPARATION EXAMPLE 3D-5

2-[1-[4-(Methoxymethoxy)-3-(methoxymethoxymethyl)butyl]cyclohex-yl]ethanol

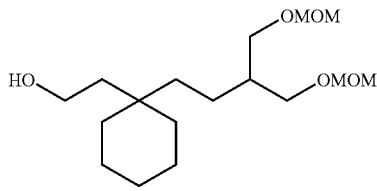

To a solution of 2-[2-[1-(2-Benzyloxyethyl)cyclohexyl]ethyl]propane-1,3-diol (320 mg) in dichloromethane (10 mL) were added diisopropylethylamine (0.69 mL) and chloromethylmethyl ether (0.23 mL) at room temperature. The solution was stirred at room temperature for 3 hours. Chloroform was added to the solution, and it was washed in turn with 1N hydrochloric acid, saturated aqueous sodium bicarbonate solution and saturated aqueous sodium chloride solution. The solution was dried over anhydrous magnesium sulfate, and then, concentrated under reduced pressure. To a solution of the resulting residue in ethanol (30 mL) was added 10% palladium-carbon (50 mg). The solution was stirred at room temperature under hydrogen atmosphere for 16 hours. The catalyst was filtered off, and the filtrate was concentrated under reduced pressure. The resulting residue was purified by chromatography (silica gel, hexane:ethyl acetate=3:2) to give the title compound (300 mg).
$^1$H-NMR (CDCl$_3$) δ: 1.20-1.48 (m, 14H), 1.53-1.65 (m, 2H), 1.73-1.82 (m, 1H), 3.37 (s, 6H), 3.49-3.58 (m, 4H), 3.65 (t, 2H, J=7.6 Hz), 4.62 (s, 4H).

PREPARATION EXAMPLE 3D-6

1-[4-(Methoxymethoxy)-3-(methoxymethoxymethyl)butyl]cyclohexylacetaldehyde

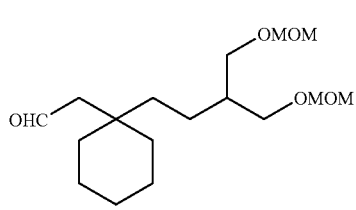

Using 2-[1-[4-(methoxymethoxy)-3-(methoxymethoxy)butyl]cyclohexyl]eth-anol (300 mg), the title compound was obtained in the same manner as in Preparation Example 1A-3. This product was subjected to the subsequent step without further purification.

PREPARATION EXAMPLE 3E-1

Dimethyl 1,1-cyclohexanediacetate

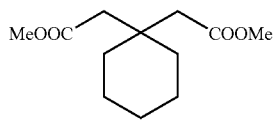

Using 1,1-cyclohexanediacetic acid (4.0 g), the title compound (4.56 g) was obtained in the same manner as in Preparation Example 1B-4.
$^1$H-NMR (CDCl$_3$) δ: 1.37-1.55 (m, 10H), 2.54 (s, 4H), 3.65 (s, 6H).

PREPARATION EXAMPLE 3E-2

Dimethyl 2-(1-methoxycarbonylmethylcyclohexyl)malonate

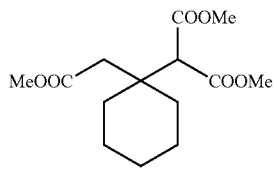

To a solution of diisopropylamine (1.01 mL, 7.2 mmol) in tetrahydrofuran (8 mL) under cooling to −78° C. were added a solution of 1.5M n-butyl lithium/hexane solution (4.4 mL). After stirring the solution at −78° C. for 1 hour, a solution of dimethyl 1,1-cyclohexanediacetate (685 mg) in tetrahydrofuran (7 mL) was added thereto. The solution was stirred at −78° C. for 1 hour. Methyl chloroformate (0.93 mL) was then added to the solution, and it was stirred at −78° C. for 1 hour. Water and 3N hydrochloric acid were added to the solution, and it was extracted with ethyl acetate. The organic layer was washed in turn with water and saturated aqueous sodium chloride solution. The solution was dried over anhydrous magnesium sulfate, and then, concentrated under reduced pressure. The resulting residue was purified by chromatography (silica gel, hexane:ethyl acetate=85:15) to give the title compound (490 mg).

$^1$H-NMR (CDCl$_3$) δ: 1.23-1.68 (m, 8H), 1.71-1.81 (m, 2H), 2.81 (s, 2H), 3.65 (s, 3H), 3.72 (s, 6H), 3.96 (s, 1H).

PREPARATION EXAMPLE 3E-3

2-[1-(2-Hydroxyethyl)cyclohexyl]propane-1,3-diol

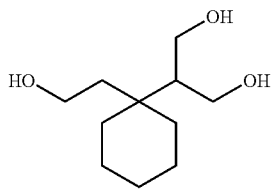

To a solution of dimethyl 2-(1-methoxycarbonylmethylcyclohexyl)malonate (490 mg) in tetrahydrofuran (15 mL) was added lithium aluminum hydride (195 mg) under ice cooling. The solution was stirred under reflux for 1 hour, and then, cooled on ice. Diethyl ether was added to the solution, followed by addition of water (0.2 mL) and a 15% aqueous sodium hydroxide solution (0.2 mL). After stirring the solution at room temperature for 15 minutes, water (0.6 mL) was added thereto, and it was stirred at room temperature for additional 30 minutes. The solution was dried over anhydrous magnesium sulfate, and then, concentrated under reduced pressure. The resulting residue was purified by chromatography (silica gel, chloroform:methanol=85:15) to give the title compound (200 mg).

$^1$H-NMR (CDCl$_3$) δ: 1.23-1.54 (m, 10H), 1.62-1.72 (m, 2H), 1.77-1.96 (m, 1H), 3.69 (t, 2H, J=11.2 Hz), 3.75-3.83 (m, 2H), 3.96 (dd, 2H, J=4.0 Hz, 11.2 Hz).

PREPARATION EXAMPLE 3E-4

2-[1-(2-Phenyl-1,3-dioxan-5-yl)cyclohexyl]ethanol

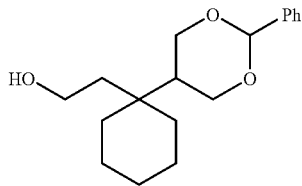

To a solution of 2-[1-(2-hydroxyethyl)cyclohexyl]propane-1,3-diol (200 mg) in N,N-dimethylformamide (8 mL) were added benzaldehyde diethyl acetal (752 mg) and p-toluenesulfonic acid pyridinium salt (48 mg) at room temperature. After stirring the solution at room temperature for 16 hours, saturated aqueous sodium bicarbonate solution was added thereto, and it was extracted with ethyl acetate. The organic layer was washed in turn with water and saturated aqueous sodium chloride solution (0.2 mL) and dried over anhydrous magnesium sulfate, and then, concentrated under reduced pressure. The resulting residue was purified by chromatography (silica gel, hexane:ethyl acetate=4:6) to give the title compound (100 mg).

$^1$H-NMR (CDCl$_3$) δ: 1.22-1.97 (m, 12H), 2.24 (tt, 1H, J=4.0 Hz, 11.6 Hz), 3.62-3.74 (m, 2H), 3.88 (t, 2H, J=11.2 Hz), 4.27 (dd, 1H, J=4.4 Hz, 11.2 Hz), 5.38 (s, 1H), 7.29-7.40 (m, 3H), 7.42-7.51 (m, 2H).

PREPARATION EXAMPLE 3E-5

[1-(2-Phenyl-1,3-dioxan-5-yl)cyclohexyl]acetaldehyde

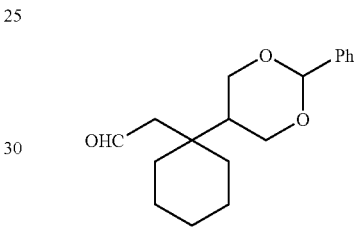

Using 2-[1-(2-phenyl-1,3-dioxan-5-yl)cyclohexyl]ethanol (100 mg), the title compound was obtained in the same manner as in Preparation Example 1A-3. This product was subjected to the subsequent step without further purification.

PREPARATION EXAMPLE 3F-1

2-[1-(2,2-Dimethyl-1,3-dioxan-5-yl)cyclohexyl]ethanol

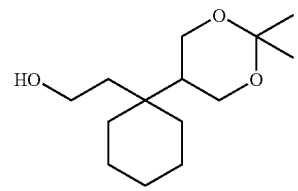

To a solution of 2-[1-(2-hydroxyethyl)cyclohexyl]propane-1,3-diol (200 mg) in acetone (10 mL) were added 2,2,-dimethoxypropane (206 mg) and p-toluenesulfonic acid (17 mg) at room temperature. After stirring the solution at room temperature for 48 hours, a saturated aqueous sodium bicarbonate solution was added thereto, and it was concentrated under reduced pressure. To the resulting residue were added diethyl ether and water, and it was extracted with diethyl ether. The organic layer was washed in turn with 0.5N hydrochloric acid, water and saturated aqueous sodium chloride solution, dried over anhydrous magnesium sulfate and then concentrated under reduced pressure. The resulting residue was purified by chromatography (silica gel, hexane:ethyl acetate=1:1 to 1:2) to give the title compound (190 mg).

1H-NMR (CDCl₃) δ: 1.24-1.56 (m, 9H), 1.37 (s, 3H), 1.42 (s, 3H), 1.66 (t, 2H, J=7.6 Hz), 2.00-2.10 (m, 1H), 2.16-2.26 (m, 3H), 3.68 (t, 2H, J=7.6 Hz), 3.80 (dd, 2H, J=4.8 Hz, 7.2 Hz), 3.88 (t, 2H, J=7.2 Hz).

PREPARATION EXAMPLE 3F-2

2-[1-(2,2-Dimethyl-1,3-dioxan-5-yl)cyclohexyl]acetaldehyde

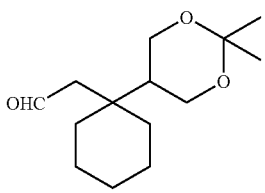

Using 2-[1-(2,2-dimethyl-1,3-dioxan-5-yl)cyclohexyl]ethanol (190 mg), the title compound was obtained in the same manner as in Preparation Example 3A-6. This product was subjected to the subsequent step without further purification.

PREPARATION EXAMPLE 3G-1

Diethyl 2-[2-[1-[2(tert-butyldiphenylsiloxy)ethyl]cyclohexyl]ethyl]-2-ethoxycarbonylsuccinate

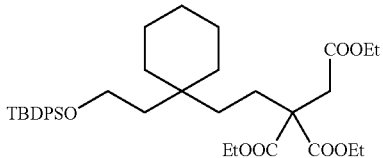

Using tert-butyl-[2-[1-(2-iodoethyl)cyclohexyl]ethoxy]diphenylsilane (1.77 g) and triethyl 1,1,2-ethanetricarboxylate (2.51 g), the title compound (1.43 g) was obtained in the same manner as in Preparation Example 3B-1. This product was subjected to the subsequent step without further purification.

PREPARATION EXAMPLE 3G-2

2-[2-[1-[2-(tert-Butyldiphenylsiloxy)ethyl]cyclohexyl]ethyl]-2-hydroxymethylbutane-1,4-diol

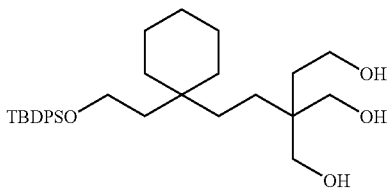

To a solution of diethyl 2-[2-[1-[2-(tert-Butyldiphenylsiloxy)ethyl]cyclohexyl]ethyl]-2-hydroxymethylbutane-1,4-diol ethoxycarbonylsuccinate (1.0 g) in diethyl ether (20 mL) was added lithium aluminum hydride (178 mg) under ice cooling. After stirring the solution under ice cooling for 1.5 hours, water (0.18 mL) and a 15% aqueous sodium hydroxide solution (0.18 mL) were successively added thereto. The solution was stirred at room temperature for 15 minutes. Water (0.54 mL) was then added to the solution, and it was stirred at room temperature for additional 30 minutes. The solution was dried over anhydrous magnesium sulfate and filtered. Chloroform was added to the solid, and the solution was stirred at room temperature for 2 hours, followed by filtration. The combined filtrate was concentrated under reduced pressure. The resulting residue was purified by chromatography (silica gel, hexane:ethyl acetate=1:4) to give the title compound (230 mg)

¹H-NMR (CDCl₃) δ: 1.01-1.44 (m, 10H), 1.04 (s, 9H), 1.52-1.62 (m, 4H), 2.94-3.19 (m, 3H), 3.40-3.50 (m, 4H), 3.58-3.68 (m, 4H), 7.35-7.46 (m, 6H), 7.64-7.73 (m, 4H).

PREPARATION EXAMPLE 3G-3

2-(Acetoxymethyl)-2-[2-[1-[2-(tert-butyldiphenylsiloxy)ethyl]cyclohexyl]ethyl]-1,4-diacetoxybutane

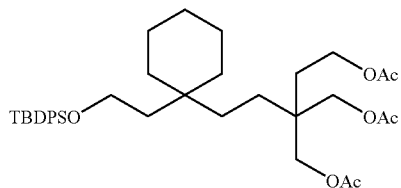

To a solution of 2-[2-[1-[2-(tert-butyldiphenylsiloxy)ethyl]cyclohexyl]ethyl]-2-hydroxymethylbutan-1,4-diol (300 mg) in pyridine (5.0 mL) was added acetic anhydride (5.0 mL) at room temperature. After stirring the solution at room temperature for 16 hours, it was concentrated under reduced pressure to give the title compound (340 mg).

¹H-NMR (CDCl₃) δ: 0.97(s, 9H), 1.03-1.39 (m, 12H), 1.51-1.65 (m, 6H), 1.98 (s, 6H), 2.01 (s, 3H), 3.64 (t, 2H, J=7.6 Hz), 3.87 (s, 4H), 4.04 (t, 2H,J=7.2 Hz), 7.35-7.46 (m, 6H), 7.64-7.71 (m, 4H).

PREPARATION EXAMPLE 3G-4

2-(Acetoxymethyl)-2-[2-[1-(2-hydroxyethyl)cyclohexyl]ethyl]-1,4-diacetoxybutane

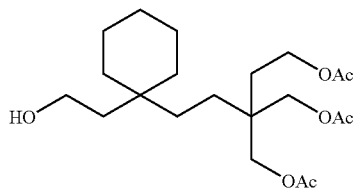

To a solution of 2-(acetoxymethyl)-2-[2-[1-[2-(tert-butyldiphenylsiloxy)ethyl]cyclohexyl]ethyl]-1,4-diacetoxybutane (340 mg) in methanol (5 mL) and tetrahydrofuran (3 mL) was added 3N hydrochloric acid (2.0 mL) at room temperature. After stirring the solution at room temperature for 5.5 hours, water was added thereto. The solution was concentrated under reduced pressure to distill off methanol and tetrahydrofuran, and it was extracted with ethyl acetate. The organic layer was washed in turn with water and saturated aqueous sodium chloride solution, dried over anhydrous magnesium sulfate, and then, concentrated under reduced pressure. The resulting residue was purified by column chromatography (silica gel, hexane:ethyl acetate=4:6) to give the title compound (110 mg).

$^1$H-NMR (CDCl$_3$) δ: 1.17-1.50 (m, 12H), 1.52-1.64 (m, 4H), 1.70 (t, 2H, J=7.2 Hz), 2.04 (s, 3H), 2.07 (s, 6H), 3.64 (t, 2H, J=8.0 Hz), 3.96 (s, 4H), 4.14 (t, 2H, J=7.2 Hz).

PREPARATION EXAMPLE 3G-5

2-(Acetoxymethyl)-2-[2-[1-(formylmethyl)cyclohexyl]ethyl]-1,4-diacetoxybutane

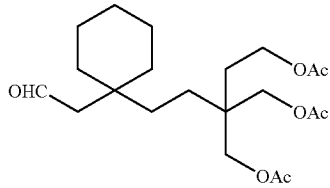

Using 2-(acetoxymethyl)-2-[2-[1-(2-hydroxyethyl)cyclohexyl]ethyl]-1,4-diacetoxybutane (110 mg), the title compound was obtained in the same manner as in Preparation Example 3A-6. This product was subjected to the subsequent step without further purification.

PREPARATION EXAMPLE 3H-1

Dimethyl 2-[2-[1-[2-(tert-butyldiphenylsiloxy)ethyl]cyclohexyl]ethyl]-2-pent-4-enylmalonate

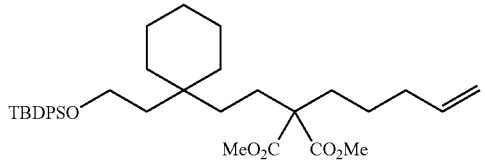

To a solution of dimethyl 2-[2-[1-[2-(tert-butyldiphenylsiloxy)ethyl]cyclohexyl]ethyl]malonate (1.30 g) in N,N-dimethylformamide (15 mL) were added 5-bromo-1-pentene (813 mg) and potassium tertbutoxide (334 mg) successively at room temperature. After stirring the solution at 60° C. for 2 hours, water and 3N hydrochloric acid were added thereto, and it was extracted with ethyl acetate. The organic layer was washed in turn with water, saturated aqueous sodium bicarbonate solution and saturated aqueous sodium chloride solution, dried over anhydrous magnesium sulfate, and then concentrated under reduced pressure. The resulting residue was purified by chromatography (silica gel, hexane:ethyl acetate=92:8) to give the title compound (910 mg).

$^1$H-NMR (CDCl$_3$) δ: 1.03 (s, 9H), 1.10-1.44 (m, 13H), 1.54-1.64 (m, 3H), 1.72-1.86 (m, 4H), 1.96-2.05 (m, 2H), 3.57-3.67 (m, 2H), 3.61 (s, 6H), 4.90-5.02 (m, 2H), 5.64-5.78 (m, 1H), 7.31-7.47 (m, 6H), 7.62-7.74 (m, 4H).

PREPARATION EXAMPLE 3H-2

2-[2-[1-[2-(tert-Butyldiphenylsiloxy)ethyl]cyclohexyl]ethyl]-2-pent-4-enylpropane-1,3-diol

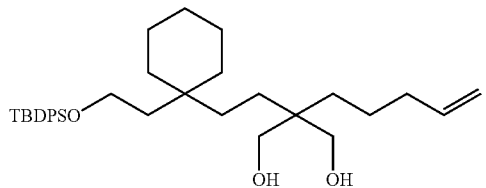

To a solution of dimethyl 2-[2-[1-[2-(tert-Butyldiphenylsiloxy)ethyl]cyclohexyl]ethyl]-2-pent-4-enylmalonate (910 mg) in diethyl ether (15 mL) was added lithium aluminum hydride (117 mg) under ice cooling. After stirring the solution at room temperature for 1 hour, water (0.12 mL) and a 15% aqueous sodium hydroxide solution (0.12 mL) were successively added thereto. The solution was stirred at room temperature for 15 minutes. Water (0.36 mL) was then added and the solution was stirred at room temperature for additional 15 minutes. The solution was dried over anhydrous magnesium sulfate and concentrated under reduced pressure. The resulting residue was purified by chromatography (silica gel, hexane:ethyl acetate=6:4) to give the title compound (640 mg).

$^1$H-NMR (CDCl$_3$) δ: 0.97-1.42 (m, 16H), 1.03 (s, 9H), 1.53-1.64 (m, 3H), 1.94-2.05 (m, 3H), 3.38-3.52 (m, 4H), 3.65 (t, 2H, J=8.0 Hz), 4.89-5.00 (m, 2H), 5.66-5.80 (m, 1H), 7.33-7.49 (m, 6H), 7.6

PREPARATION EXAMPLE 3H-3

[2-[1-[3,3-Bis(benzyloxymethyl)oct-7-enyl]cyclohexyl]ethoxy]-tert-butyldiphenylsilane

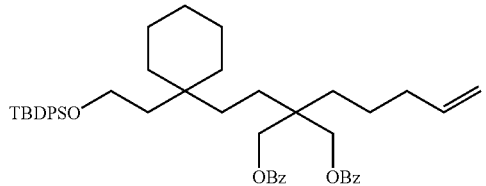

To a solution of 2-[2-[1-[2(tert-butyldiphenlsiloxy)ethyl]cyclohexyl]ethyl]-2-pent-4-enylpropane-1,3-diol (640 mg) in dichloromethane (12 mL) were added pyridine (0.67 mL) and benzoyl chloride (0.55 mL) at room temperature. After stirring the solution at room temperature for 16 hours, it was concentrated under reduced pressure. The residue was extracted by addition of diethyl ether and 1N sodium hydroxide. The organic layer was washed in turn with water, 1N hydrochloric acid, saturated aqueous sodium bicarbonate solution and saturated aqueous sodium chloride solution, dried over anhydrous magnesium sulfate, and then, concentrated under reduced pressure. The resulting residue was purified by chromatography (silica gel, hexane:ethyl acetate=94:6) to give the title compound (840 mg).

¹H-NMR (CDCl₃) δ: 1.01 (s, 9H), 1.10-1.44 (m, 18H), 1.51-1.61 (m, 2H), 1.93-2.03 (m, 2H), 3.64 (t, 2H, J=8.0 Hz), 4.18 (d, 2H, J=11.2 Hz), 4.23 (d, 2H, J=11.2 Hz), 4.85-4.99 (m, 2H), 5.61-5.75 (m, 1H), 7.32-7.45 (m, 10H), 7.49-7.57 (m, 2H), 7.60-7.69 (m, 4H), 7.95-8.03 (m, 4H).

PREPARATION EXAMPLE 3H-4

Methyl 5,5-bis(benzyloxymethyl)7-[1-[2(tert-butyl-diphenylsiloxy)-ethyl]cyclohexyl]heptanoate

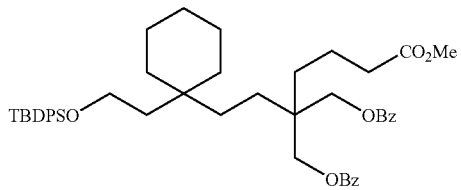

To a solution of [2-[1-[3,3-bis(benzyloxymethyl)oct-7-enyl]cyclohexyl]ethoxy]-tert-butyldiphenylsilane (840 mg) in carbon tetrachloride (3 mL), acetonitrile (3 mL) and water (4.5 mL) were added sodium periodate (1.98 g) and ruthenium trichloride.monohydrate (10.3 g) at room temperature. After stirring the solution at room temperature for 4 hours, water was added thereto and it was extracted with chloroform. The organic layer was dried over anhydrous magnesium sulfate, and then, concentrated under reduced pressure. To a solution of the resulting residue in methanol (1.5 mL)/benzene (7.5 mL) was added a 2M trimethylsilyldiazomethane/hexane solution (1.0 mL) under ice cooling. After stirring the solution under ice cooling for 30 minutes, it was concentrated under reduced pressure. The resulting residue was purified by chromatography (silica gel, hexane:ethyl acetate=85:15) to give the title compound (520 mg).

¹H-NMR (CDCl₃) δ: 1.00 (s, 9H), 1.09-1.37 (m, 14H), 1.38-1.47 (m, 2H), 1.52-1.61 (m, 4H), 2.25 (t, 2H, J=6.8 Hz), 3.57 (s, 3H), 3.65 (t, 2H, J=8.0 Hz), 4.19 (d, 2H, J=11.2 Hz), 4.23 (d, 2H, J=11.2 Hz), 7.31-7.44 (m, 10H), 7.49-7.57 (m, 2H), 7.60-7.66 (m, 4H), 7.95-8.02 (m, 4H).

PREPARATION EXAMPLE 3H-5

Methyl 5,5-bis(benzyloxymethyl)-7-[1-(2-hydroxy-ethyl)cyclohexyl]-heptanoate

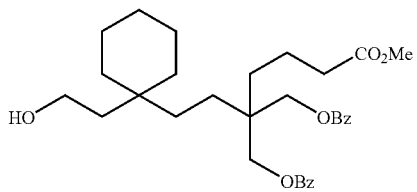

Using methyl 5,5-bis(benzyloxymethyl)-7-[1-[2-(tert-butyldiphenylsiloxy)-ethyl]cyclohexyl]heptanoate (520 mg), the title compound (360 mg) was obtained in the same manner as in Preparation Example 3B-2.

¹H-NMR (CDCl₃) δ: 1.20-1.62 (m, 18H), 1.65-1.79 (m, 2H), 2.35 (t, 2H, J=6.8 Hz), 3.55-3.67 (m, 2H), 3.63 (s, 3H), 4.30 (s, 4H), 7.40-7.47 (m, 4H), 7.53-7.60 (m, 2H), 7.98-8.05 (m, 4H).

PREPARATION EXAMPLE 3H-6

Methyl 5,5-bis(benzyloxymethyl)-7-[1-(formylm-ethyl)cyclohexyl]heptanoate

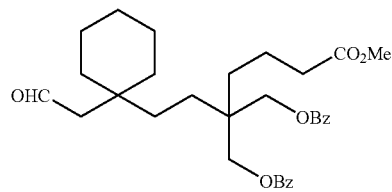

Using methyl 5,5-bis(benzyloxymethyl)-7-[1-(2-hydroxyethyl)cyclohexyl]heptanoate (170 mg), the title compound was obtained in the same manner as in Preparation Example 3A-6. This product was subjected to the subsequent step without further purification.

PREPARATION EXAMPLE 3I-1

3-[1-[2-(tert-Butyldiphenylsiloxy)ethyl]cyclohexyl] propionitrile

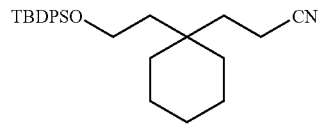

To a solution of [2-[1-[2-(tert-butyldiphenylsiloxy)ethyl] cyclohexyl]ethanol (1.25 g) dissolved in benzene (15 mL) were added acetone cyanohydrin (0.40 mL), tri-n-butylphosphine (1.08 mL) and 1,1-azobis(N,N-dimethylformamide) (754 mg). The solution was stirred at room temperature for 18 hours. The solvent was distilled off under reduced pressure, ethyl acetate was added and insolubles were filtered off. The solvent was distilled off under reduced pressure. The resulting residue was purified by column chromatography (silica gel, hexane:ethyl acetate=5:1) to give the title compound (1.07 g).

¹H-NMR (CDCl₃) δ: F1.05 (s, 9H), 1.14-1.18 (m, 2H), 1.25-1.29 (m, 2H), 1.29-1.37 (m, 6H), 1.50 (t, 2H, J=7.3 Hz), 1.60-1.64 (m, 2H), 2.03-2.07 (m, 2H), 3.64 (t, 2H, J=7.3 Hz), 7.38-7.47 (m, 6H), 7.65-7.68 (m, 4H).

PREPARATION EXAMPLE 3I-2

3-[1-(2-Hydroxyethyl)cyclohexyl]propionitrile

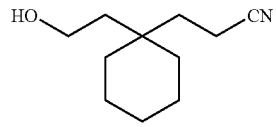

Using methyl 3-[1-[2-(tert-butyldiphenylsiloxy)ethyl]cyclohexyl]propionitrile (260 mg), the title compound (80 mg) was obtained in the same manner as in Preparation Example 3B-2.

$^1$H-NMR (CDCl$_3$) δ: 1.26-1.45 (m, 10H), 1.55-1.59 (m, 3H), 1.72-1.72 (m, 2H), 2.28-2.32 (m, 2H), 3.69 (t, 2H, J=7.3 Hz).

PREPARATION EXAMPLE 3I-3

3-[1-(2-Bromoethyl)cyclohexyl]propionitrile

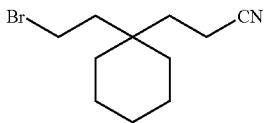

Using methyl 3-[1-(2-hydroxyethyl)cyclohexyl]propionitrile (80 mg), the title compound (98 mg) was obtained in the same manner as in Preparation Example 2B-2. This product was subjected to the subsequent step without further purification.

PREPARATION EXAMPLE 3J-1

N-[2-[1-[2-(tert-Butyldiphenylsiloxy)ethyl]cyclohexyl]ethyl]-phthalimide

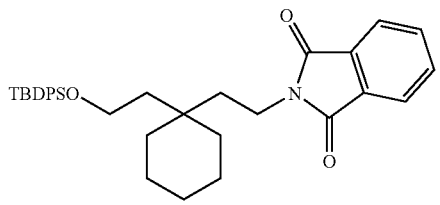

2-[1-[2-(tert-Butyldiphenylsiloxy)ethyl]cyclohexyl]ethanol (1.23 g), phthalimide (530 mg) and triphenylphosphine (1.10 g) were dissolved in tetrahydrofuran (15 mL) and stirred for 20 minutes. Diethyl azocarboxylate (0.57 mL) was then added to the solution, and it was stirred at room temperature for 18 hours. The solvent was distilled off under reduced pressure, and the resulting residue was purified by chromatography (silica gel, 15-20% ethyl acetate:hexane) to give the title compound (1.08 g).

$^1$H-NMR (CDCl$_3$) δ: 1.05 (s, 9H), 1.26-1.39 (m, 10H), 1.53 (t, 2H, J=7.3 Hz), 1.67 (t, 2H, J=7.3 Hz), 3.55 (m, 2H), 3.81 (t, 2H, J=7.3 Hz), 7.36-7.39 (m, 6H), 7.69-7.71 (m, 6H), 7.82-7.84 (m, 2H).

PREPARATION EXAMPLE 3J-2

2-[1-[2-(tert-Butyldiphenylsiloxy)ethyl]cyclohexyl]ethyl-amine

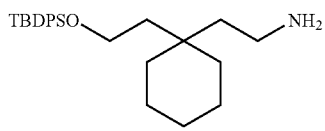

To a solution of N-[2-[1-[2(tert-butyldiphenylsiloxy)ethyl]cyclohexyl]-ethyl]phthalimide (1.52 g) dissolved in ethanol (30 mL) was added hydrazine monohydrate. The reaction solution was heated under reflux for 4 hours. To this was added diethyl ether and the insolbles were filtered off. The solvent was then distilled off under reduced pressure. To this was added chloroform, and the solution was made basic by addition of a 1N aqueous hydroxide solution. The solution was then extracted with chloroform. The organic layer was dried over anhydrous magnesium sulfate, filtered, and then, the solvent was distilled off under reduced pressure to give the title compound (1.20 g).

PREPARATION EXAMPLE 3J-3

N-[2-[1-[2-(tert-Butyldiphenylsiloxy)ethyl]cyclohexyl]ethyl]methanesulfonamide

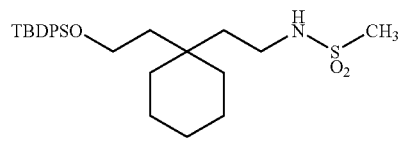

PREPARATION EXAMPLE 3J-3

N-[2 -[1-[2-(tert-Butyldiphenylsiloxy)ethyl]cyclohexyl]ethyl]methanesulfonamide

To a solution of 2-[1-[2-(tert-butyldiphenylsiloxy)ethyl]cyclohexyl]ethylamine (409 mg) dissolved in dichloromethane (10 mL) was added triethylamine (0.28 mL). Methanesulfonyl chloride (0.12 mL) was added to the solution under ice cooling, and it was stirred at that temperature for 2 hours. Saturated aqueous sodium bicarbonate solution was added to the solution, and it was extracted with chloroform. The organic layer was dried over anhydrous magnesium sulfate, filtered, and then, the solvent was distilled off under reduced pressure. The resulting residue was purified by column chromatography (silica gel, hexane:ethyl acetate=6:1) to give the title compound (327 mg).

$^1$H-NMR (CDCl$_3$) δ: 1.05 (s, 9H), 1.22-1.46 (m, 10H), 1.46-1.51 (m, 2H), 1.53-1.61 (m, 2H), 2.83 (s, 3H), 2.97-3.02 (m, 2H), 3.68-3.72 (m, 2H), 3.94 (m, 1H), 7.38-7.46 (m, 6H), 7.66-7.68 (m, 4H).

PREPARATION EXAMPLE 3J-4

N-[2-[1-(2-Hydroxyethyl)cyclohexyl]ethyl]methanesulfonamide

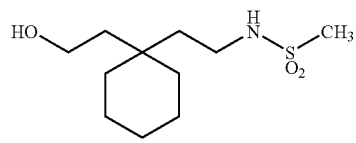

Using N-(2-[1-[2-(tert-butyldiphenylsiloxy)ethyl]cyclohexyl]ethyl)methanesulfonamide (317 mg), the title compound (153 mg) was obtained in the same manner as in Preparation Example 3B-2.

$^1$H-NMR (CDCl$_3$) δ: 1.26-1.32 (m, 4H), 1.42-1.45 m, 2H), 1.58-1.63 (m, 4H), 2.40 (brs, 1H), 2.96 (s, 3H), 3.12 (m, 2H), 3.69 (t, 2H, J=7.3 Hz), 5.13 (brs, 1H).

PREPARATION EXAMPLE 3J-5

N-[2-[1-(Formylmethyl)cyclohexyl]ethyl]methanesulfonamide

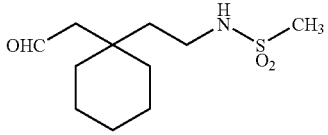

Using N-[2-[1-(2-hydroxyethyl)cyclohexyl]ethyl]methanesulfonamide (153 mg), the title compound was obtained in the same manner as in Preparation Example 1A-3. This product was subjected to the subsequent step without further purification.

PREPARATION EXAMPLE 3-K1

N-[2-[1-(2-hydroxyethyl)cyclohexyl]ethyl]phthalimide

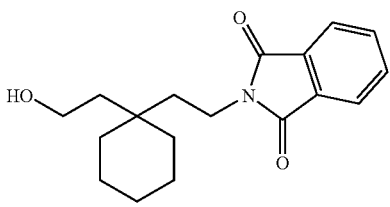

Using N-[2-[1-[2-(tert-butyldiphenylsiloxy)ethyl]cyclohexyl]ethylphthalimide (1.08 g), the title compound (340 mg) was obtained in the same manner as in Preparation Example 3B-2.

$^1$H-NMR (CDCl$_3$, 400 MHz) δ: 1.28-1.51 (m, 10H), 1.55 (t like, 1H), 1.62-1.67 (m, 2H), 1.71 (t, 2H, J=7.8 Hz), 3.67-3.71 (m, 2H), 3.79-3.84 (q like, 2H), 7.71 (d, 2H, J=8.3 Hz), 7.83 (d, 2H, J=8.3 Hz).

PREPARATION EXAMPLE 3K-2

N-[2-[1-(Formylmethyl)cyclohexyl]ethyl]phthalimide

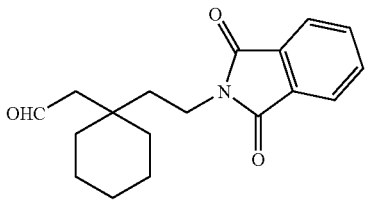

Using N-[2-[1-[2-(hydroxyethyl)cyclohexyl]ethyl]phthalimide (340 mg), the title compound was obtained in the same manner as in Preparation Example 1A-3. This product was subjected to the subsequent step without further purification.

PREPARATION EXAMPLE 4-1

2-(1-Benzylpiperidin-4-ylamino)-5-methylpyridine

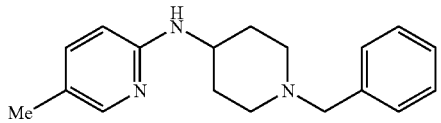

To 2-bromo-4-methylpyridine (15.5 g) was added 4-amino-1-benzylpiperidine (68.5 g). The resulting solution was stirred at 180° C. for 9 hours and then at 150° C. for 6 hours. Ethyl acetate and water were then added to the solution followed by addition of saturated aqueous sodium bicarbonate solution. After separating liquid layers, the organic layer was washed with water and saturated aqueous sodium chloride solution, dried over anhydrous sodium sulfate, and then, concentrated under reduced pressure. The resulting residue was purified by chromatography [silica gel, ethyl acetate-methanol-aqueous ammonia (90:10:0.1)] to give the title compound (11.5 g).

$^1$H-NMR (CDCl$_3$) δ: 1.45-1.56 (m, 2H), 1.97-2.07 (m, 2H), 2.16 (s, 3H), 2.13-2.23 (m, 2H), 2.78-2.89 (m, 2H), 3.52 (s, 2H), 3.48-3.62 (m, 1H), 4.22 (brd, 1H, J=8.4 Hz), 6.29 (d, 1H, J=8.4 Hz), 7.20-7.33 (m, 6H), 7.88-7.90 (m, 1H).

PREPARATION EXAMPLE 4-2

Ethyl 4-(5-methylpyridin-2-yl)piperidine-1-carboxylate

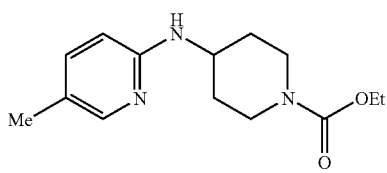

2-Bromo-5-methylpyridine (8.56 g), 1,3-bis(diphenylphosphino)propane (4.10 g) and sodium tert-butoxide (6.69 g) were suspended in toluene (500 mL), to which was added ethyl 4-amino-1-piperidinecarboxylate (10.28 g). Tris(dibenzylideneacetone)dipalladium (3.19 g) was added to the suspension, and it was stirred at 70° C. for 4 hours. Ethyl acetate was added to the reaction solution, and then, it was washed with saturated aqueous sodium chloride solution, and dried (MgSO$_4$). The solvent was distilled off under reduced pressure. The resulting residue was purified by chromatography (silica gel, ethyl acetate), and then crystallized (ethyl acetate/hexane) to give the title compound (10.13 g).

$^1$H-NMR (DMSO-d$_6$) δ; 1.19 (t, 3H, J=6.8 Hz), 1.22-1.33 (m, 2H), 1.83-1.91 (m, 2H), 2.08 (s, 3H), 2.90-3.02 (m, 2H), 3.79-3.94 (m, 3H), 4.03 (q, 2H, J=6.8 Hz), 6.07 (d, 1H, J=7.8 Hz), 6.39 (d, 1H, J=8.0 Hz), 7.17 (dd, 1H, J=2.4 Hz, 8.0 Hz), 7.77 (d, 1H, J=2.4 Hz).

PREPARATION EXAMPLE 4-3

2-(Piperidin-4-ylamino)-5-methylpyridine

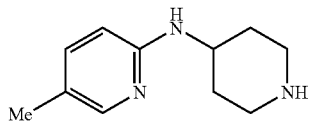

Synthetic Method 1

To a solution of 2-(1-benzylpiperidin-4-ylamino)-5-methylpyridine (11.3 g) in ethanol (250 mL) was added 20% palladium hydroxide (4 g). After stirring the solution at room temperature under hydrogen atmosphere for 48 hours, 20% palladium hydroxide (2 g) was further added. The solution was then stirred at room temperature under hydrogen atmosphere for additional 99 hours. The catalyst was filtered off. After concentration under reduced pressure, the resulting residue was purified by chromatography [NH silica gel, chloroform:methanol=10:1]. The resulting crude product was crystallized from ethyl acetate/hexane to give the title compound (5.97 g).

Synthetic Method 2

To ethyl 4-(5-methylpyridin-2-yl)piperidin-1-carboxylate (10.13 g) was added a 30% hydrobromic acid/acetic acid solution. The solution was heated under reflux for 3 hours. The solvent was distilled off under reduced pressure, and the resulting solid was washed with ethyl acetate to give the hydrobromide of the title compound as a pale purple solid. To this was added saturated aqueous sodium bicarbonate solution, and the solution was extracted with 25% ethanol/chloroform. After drying (MgSO$_4$), the solvent was distilled off under reduced pressure and then recrystallized (ethanol-chloroform-ethyl acetate) to give the title compound (3.62 g).

$^1$H-NMR (DMSO-d$_6$) δ: 1.53-1.66 (m, 2H), 2.00-2.08 (m, 2H), 2.09 (s, 3H), 2.98-3.06 (m, 2H), 3.22-3.32 (m, 2H), 3.39-3.49 (m, 1H), 6.30 (d, 1H, J=7.3 Hz), 6.42 (d, 1H, J=8.8 Hz), 7.21 (dd, 1H, J=2.4 Hz, 8.8 Hz), 7.78 (d, 1H, J=2.4 Hz).

PREPARATION EXAMPLE 4-4 tert-Butyl 4-(p-toluidino)piperidin-1-carboxylate

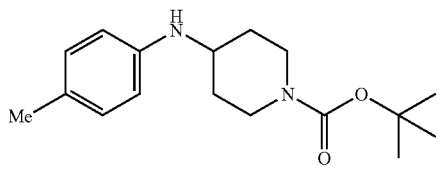

To a solution of tert-butyl 4-oxopiperidin-1-carboxylate (5.01 g) and p-toluidine (2.69 g) dissolved in tetrahydrofuran (50 mL) were added sodium triacetoxyborohydride (7.99 g) and then acetic acid (3.0 mL). The reaction solution was stirred for 2 days. The reaction solution was poured into saturated aqueous sodium bicarbonate solution, and it was extracted with ethyl acetate. The extract was washed in turn with water and saturated aqueous sodium chloride solution, and dried (MgSO$_4$). The solvent was distilled off under reduced pressure, and the resulting residue was purified by chromatography (silica gel, 20% ethyl acetate/hexane) to give the title compound (6.49 g).

$^1$H-NMR (DMSO-d$_6$) δ; 1.16-1.28 (m, 2H), 1.40 (s, 9H), 1.80-1.90 (m, 2H), 2.14 (s, 3H), 2.80-3.00 (m, 2H), 3.29-3.40 (m, 1H), 3.78-3.92 (m, 2H), 5.07 (d, 1H, J=8.3 Hz), 6.49 (d, 1H, J=8.3 Hz), 6.86 (d, 1H, J=8.3 Hz).

PREPARATION EXAMPLE 4-5

4-(p-Toluidino)piperidine

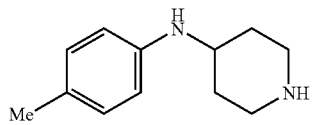

To a solution of tert-butyl 4-(p-toluidino)piperidin-1-carboxylate (32.06 g) dissolved in dichloromethane (200 mL) was added trifluoroacetic acid (100 mL) at room temperature. The solution was stirred for 1 day. The solvent was distilled off under reduced pressure, and the resulting residue was solidified with isopropyl ether and washed to give the trifluoroacetate of the title compound (42.12 g). This salt was desalted by a conventional method to give the title compound (18.03 g).

$^1$H-NMR (CDCl$_3$) δ: 1.27-1.41 (m, 2H), 2.05-2.12 (m, 2H), 2.23 (s, 3H), 2.68-2.78 (m, 2H), 3.10-3.19 (m, 2H), 3.31-3.41 (m, 1H), 6.54 (d, 1H, J=8.3 Hz), 6.93 (d, 2H, J=8.3 Hz).

EXAMPLE 1A-1

2-[1-(Cyclohexylmethyl)piperidin-4-ylamino]-5-methylpyridine

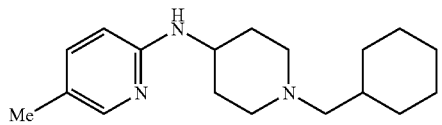

A solution of 2-(piperidin-4-ylamino)-5-methylpyridine (191 mg), diisopropylamine (202 mg) and cyclohexylmethyl bromide (212 mg) in ethanol (2 mL) was refluxed for 16 hours. To the reaction solution was added ethyl acetate, and insolubles were filtered off, and then, concentrated under reduced pressure. The resulting residue was purified by silica gel chromatography (NH silica gel, hexane:ethyl acetate=4:1) to give the title compound (216 mg).

$^1$H-NMR (CDCl$_3$) δ: 0.80-0.93 (m, 2H), 1.08-1.28 (m, 3H), 1.40-1.54 (m, 3H), 1.65-1.80 (m, 5H), 1.96-2.13 (m, 6H), 2.16 (s, 3H), 2.74-2.82 (m, 2H), 3.48-3.60 (m, 1H), 4.23 (brd, 1H, J=8.5 Hz), 6.30 (d, 1H, J=8.8 Hz), 7.23 (dd, 1H, J=2.0 Hz, 8.8 Hz), 7.89 (d, 1H, J=2.0 Hz).

EXAMPLE 1A-2

2-[1-(2-Cyclohexylethyl)piperidin-4-ylamino]-5-methylpyridine

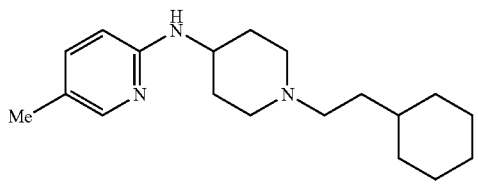

The title compound was synthesized from the compound obtained in Preparation Example 4-3 and (2-bromoethyl)cyclohexane in the same manner as in Example 1A-1.

$^1$H-NMR (CDCl$_3$) δ: 0.85-0.98 (m, 2H), 1.08-1.28 (m, 4H), 1.35-1.43 (m, 2H), 1.45-1.56 (m, 2H), 1.60-1.79 (m, 4H), 2.00-2.17 (m, 4H), 2.16 (s, 3H), 2.32-2.38 (m, 2H), 2.80-2.92 (m, 2H), 3.52-3.63 (m, 1H), 4.22 (brd, 1H, J=8.5 Hz), 6.30 (d, 1H, J=8.8 Hz), 7.23 (dd, 1H, J=2.0 Hz, 8.8 Hz), 7.89 (d, 1H, J=2.0 Hz).

EXAMPLE 1A-3

2-[1-(3-Cyclohexylpropyl)piperidin-4-ylamino]-5-methylpyridine

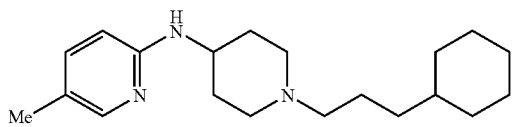

The title compound was synthesized from the compound obtained in Preparation Example 4-3 and (3-bromopropyl)cyclohexane in the same manner as in Example 1A-1.

$^1$H-NMR (CDCl$_3$) δ: 0.81-0.93 (m, 2H), 1.10-1.28 (m, 6H), 1.44-1.56 (m, 4H), 1.60-1.74 (m, 5H), 2.00-2.18 (m, 4H), 2.16 (s, 3H), 2.27-2.33 (m, 2H), 2.81-2.90 (m, 2H), 3.52-3.63 (m, 1H), 4.22 (brd, 1H, J=8.3 Hz), 6.30 (d, 1H, J=8.8 Hz), 7.23 (dd, 1H, J=2.5 Hz, 8.8 Hz), 7.89 (d, 1H, J=2.5 Hz).

EXAMPLE 1A-4

2-[1-(4-Cyclohexylbutyl)piperidin-4-ylamino]-5-methylpyridine

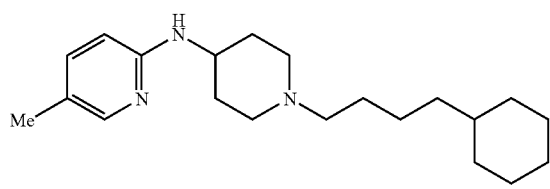

The title compound was synthesized from the compound obtained in Preparation Example 4-3 and (4-bromobutyl)cyclohexane in the same manner as in Example 1A-1.

$^1$H-NMR (CDCl$_3$) δ: 0.75-0.93 (m, 2H), 1.07-1.33 (m, 8H), 1.45-1.56 (m, 4H), 1.59-1.74 (m, 6H), 1.98-2.19 (m, 3H), 2.16 (s, 3H), 2.28-2.35 (m, 2H), 2.78-2.93 (m, 2H), 3.51-3.62 (m, 1H), 4.22 (brd, 1H, J=8.4 Hz), 6.30 (d, 1H, J=8.8 Hz), 7.23 (dd, 1H, J=2.4 Hz, 8.8 Hz), 7.90 (d, 1H, J=2.4 Hz); MS (ESI) m/z: 330 (MH$^+$).

EXAMPLE 1A-5

2-[1-[2-[2-(Cyclohexylacetamido)phenyl]ethyl]piperidin-4-yl-amino]-5-methylpyridine

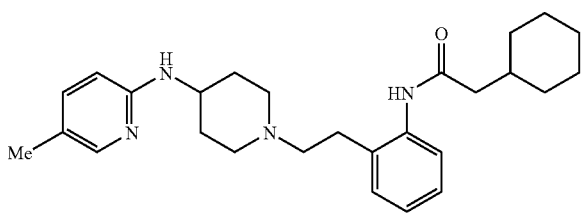

The title compound was synthesized from the compound obtained in Preparation Example 4-3 and the compound obtained in Preparation Example 2B-2 in the same manner as in Example 1A-1.

$^1$H-NMR (CDCl$_3$) δ: 0.96-1.40 (m, 5H), 1.49-2.03 (m, 8H), 2.05-2.15 (m, 2H), 2.17 (s, 3H), 2.26-2.39 (m, 4H), 2.60-2.68 (m, 2H), 2.72-2.79 (m, 2H), 2.86-2.96 (m, 1H), 3.61-3.75 (m, 1H), 4.20 (brd, 1H, J=6.8 Hz), 6.31 (d, 1H, J=8.8 Hz), 6.99-7.06 (m, 1H), 7.07-7.13 (m, 1H), 7.18-7.28 (m, 1H), 7.88-7.98 (m, 1H), 9.93 (brs, 1H).

EXAMPLE 1A-6

Methyl [1-[2-[4-(5-methylpyridin-2-ylamino)piperidin-1-yl]ethyl]cyclohexyl]acetate

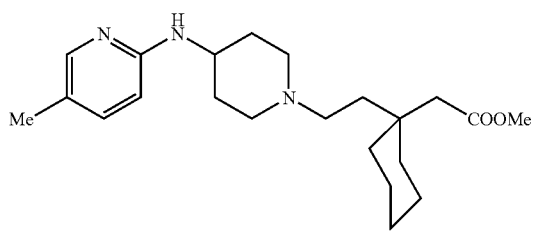

The title compound was synthesized from the compound obtained in Preparation Example 4-3 and the compound obtained in Preparation Example 1B-4 in the same manner as in Example 1A-1.

$^1$H-NMR (CDCl$_3$) δ: 1.34-1.56 (m, 12H), 1.58-1.65 (m, 2H), 2.00-2.08 (m, 2H), 2.16 (s, 3H), 2.10-2.22 (m, 2H), 2.30 (s, 2H), 2.34-2.40 (m, 2H), 2.83-2.91 (m, 2H), 3.52-3.62 (m, 2H), 3.64 (s, 3H), 4.22 (brd, 1H, J=8.3 Hz), 6.30 (d, 1H, J=8.3 Hz), 7.23 (dd, 1H, J=2.4 Hz, 8.3 Hz), 7.89 (d, 1H, J=2.4 Hz).

EXAMPLE 1A-7

Methyl [1-[2-[4-(5-methylpyridin-2-ylamino)piperidin-1-yl]ethyl]cyclopentyl]acetate

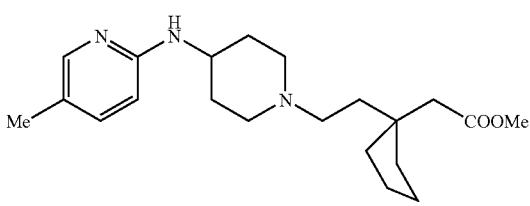

The title compound was synthesized from the compound obtained in Preparation Example 4-3 and the compound obtained in Preparation Example 1C-3 in the same manner as in Example 1A-1.

$^1$H-NMR (CDCl$_3$) δ: 1.46-1.72 (m, 12H), 2.02-2.05 (m, 2H), 2.12-2.16 (m, 5H), 2.30 (s, 2H), 2.36-2.43 (m, 2H), 2.85 (m, 2H), 3.59 (m, 1H), 3.65 (s, 3H), 4.22 (d, 1H, J=8.8 Hz), 6.30 (d, 1H, J=8.8 Hz), 7.23 (dd, 1H, J=2.4 Hz, 8.3 Hz), 7.89 (d, 1H, J=2.4 Hz); MS (ESI) m/z: 360 (MH$^+$).

EXAMPLE 1A-8 tert-Butyl [2-[3-[4-(5-methylpyridin-2-ylamino)piperidin-1-yl]propyl]phenyl]carbamate

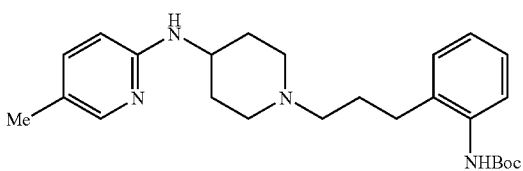

The title compound was synthesized from the compound obtained in Preparation Example 4-3 and the compound obtained in Preparation Example 2E-2 in the same manner as in Example 1A-1.

$^1$H-NMR (CDCl$_3$) δ: 1.56 (s, 9H), 1.69-1.89 (m, 4H), 2.05-2.21 (m, 6H), 2.17 (s, 3H), 2.63-2.70 (m, 2H), 2.71-2.85 (m, 2H), 3.55-3.69 (m, 1H), 4.21-4.34 (m, 1H), 6.29 (d, 1H, J=8.0 Hz), 7.00-7.08 (m, 1H), 7.09-7.28 (m, 3H), 7.59 (brd, 1H, J=8.0 Hz), 7.88-7.93 (m, 1H), 9.52 (brs, 1H).

EXAMPLE 1A-9 tert-Butyl [2-[2-[4-(5-methylpyridin-2-ylamino)piperidin-1-yl]ethyl]-phenyl]carbamate

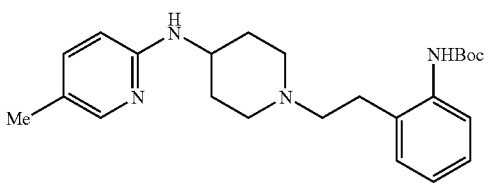

The title compound was synthesized from the compound obtained in Preparation Example 4-3 and the compound obtained in Preparation Example 2F-2 in the same manner as in Example 1A-1.

$^1$H-NMR (CDCl$_3$) δ: 1.56 (s, 9H), 1.66-1.79 (m, 2H), 2.05-2.14 (m, 2H), 2.17 (s, 3H), 2.23-2.36 (m, 2H), 2.55-2.62 (m, 2H), 2.69-2.78 (m, 2H), 2.84-2.97 (m, 2H), 3.55-3.68 (m, 1H), 4.22 (brd, 1H, J=7.6 Hz), 6.29 (d, 1H, J=8.8 Hz), 6.90-6.98 (m, 1H), 7.02-7.08 (m, 1H), 7.14-7.28 (m, 2H), 7.84 (brd, 1H, J=6.8 Hz), 7.91 (d, 1H, J=2.4 Hz), 10.36 (brs, 1H).

EXAMPLE 1B-1

1-(3-Cyclohexylpropyl)-4-(p-toluidino)piperidine

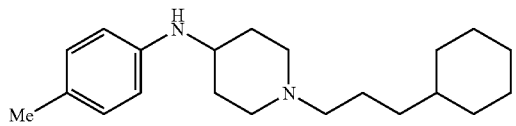

To a solution of 4-(p-toluidino)piperidine trifluoroacetate (0.7726 g) dissolved in N,N-dimethylformamide (10 mL) were added (3-bromopropyl)cyclohexane (0.57 g) and potassium carbonate (1.02 g). The reaction solution was heated with stirring at 80° C. for 5 hours. Dichloromethane was added to the reaction solution, and the insolubles were filtered off, and then, the solvent was distilled off under reduced pressure. The resulting residue was purified by chromatography [silica gel, dichloromethane-methanol-aqueous ammonia (95:5:0.3)] to give the title compound as a while solid (0.4879 g).

mp 249-252° C.; $^1$H-NMR (DMSO-d$_6$) δ: 0.79-0.92 (m, 2H), 1.09-1.26 (m, 6H), 1.27-1.46 (m, 4H), 1.56-1.72 (m, 5H), 1.80-1.90 (m, 2H), 1.93-2.03 (m, 2H), 2.13 (s, 3H), 2.19-2.27 (m, 2H), 2.73-2.82 (m, 2H), 3.06-3.15 (m, 1H), 4.97 (d, 1H, J=8.3 Hz), 6.46 (d, 2H, J=8.3 Hz), 6.85 (d, 2H, J=8.3 Hz).

EXAMPLE 1B-2

Methyl [1-[2-[4-(p-toluidino)piperidin-1-yl]ethyl] cyclohexyl]acetate

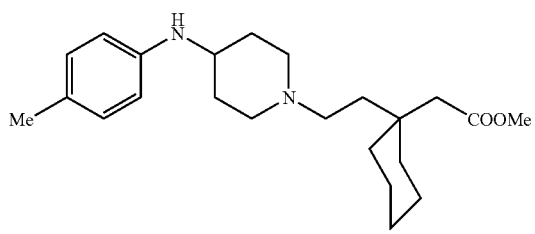

The title compound was synthesized from the compound obtained in Preparation Example 4-5 and the compound obtained in Preparation Example 1B-4 in the same manner as in Example 1B-1.

$^1$H-NMR (DMSO-d$_6$) δ: 1.25-1.47 (m, 12H), 1.47-1.53 (m, 2H), 1.81-1.89 (m, 2H), 1.95-2.03 (m, 2H), 2.13 (s, 3H), 2.24-2.30 (m, 2H), 2.29 (s, 2H), 2.75-2.82 (m, 2H), 3.06-

3.16 (m, 1H), 3.56 (S, 3H), 4.98 (d, 1H, J=8.3 Hz), 6.46 (d, 1H, J=8.3 Hz), 6.85 (d, 1H, J=8.3 Hz).

EXAMPLE 1B-3

2-[1-[2-[1-(2-Cyanoethyl)cyclohexyl]ethyl]piperidin-4-ylamino]-5-methylpyridine

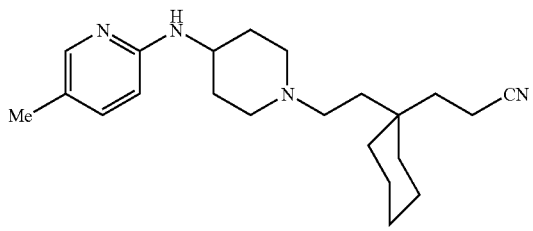

The title compound was synthesized from the compound obtained in Preparation Example 4-3 and the compound obtained in Preparation Example 3I-3 in the same manner as in Example 1B-1.

$^1$H-NMR (CDCl$_3$) δ: 1.23-1.32 (m, 4H), 1.34-1.57 (m, 10H), 1.68-1.72 (m, 2H), 2.07 (d, 2H, J=13.2 Hz), 2.16-2.18 (m, 5H), 2.24-2.31 (m, 4H), 2.90-2.96 (m, 2H), 3.63 (m, 1H), 4.25 (d, 2H, J=7.8 Hz), 6.31 (d, 1H, J=8.3 Hz), 7.23 (dd, 1H, J=2.4, 8.3 Hz), 7.89 (d, 1H, J=2.4 Hz).

EXAMPLE 1B-4

1-[2-[1-(2-Cyanoethyl)cyclohexyl]ethyl]-4-(p-toluidino)piperidine

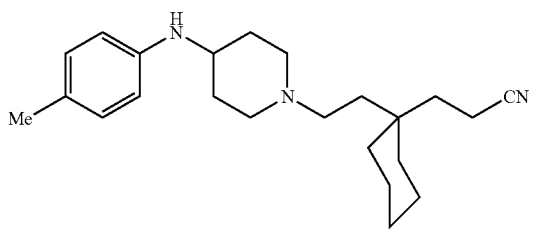

The title compound was synthesized from the compound obtained in Preparation Example 4-5 and the compound obtained in Preparation Example 3I-3 in the same manner as in Example 1B-1.

$^1$H-NMR (DMSO-d$_6$) δ: 1.29-1.45 (m, 14H), 1.56-1.63 (m, 2H), 1.82-1.90 (m, 2H), 1.96-2.04 (m, 2H), 2.13 (s, 3H), 2.17-2.24 (m, 2H), 2.33-2.40 (m, 2H), 2.78-2.85 (m, 2H), 3.06-3.17 (m, 1H), 4.99 (d, 1H, J=7.3 Hz), 6.47 (d, 2H, J=8.3 Hz), 6.85 (d, 2H, J=8.3 Hz).

EXAMPLE 1B-5 tert-Butyl [2-[3-[4-(p-toluidino)piperidine-1-yl]propyl]phenyl]carbamate

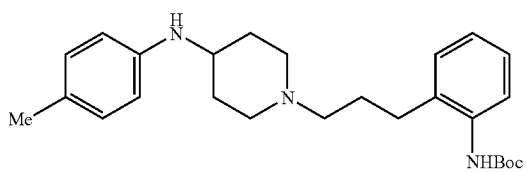

The title compound was synthesized from the compound obtained in Preparation Example 4-5 and the compound obtained in Preparation Example 2E-2 in the same manner as in Example 1B-1.

$^1$H-NMR (CDCl$_3$) δ: 1.60 (s, 9H), 1.63-1.78 (m, 2H), 1.78-1.89 (m, 2H), 1.99-2.16 (m, 6H), 2.24 (s, 3H), 2.59-2.70 (m, 2H), 2.72-2.87 (m, 2H), 3.22-3.39 (m, 1H), 6.44-6.54 (m, 2H), 6.91-7.22 (m, 5H), 7.51-7.64 (m, 1H), 9.46-9.57 (m, 1H).

EXAMPLE 1C-1

3-[1-[4-(5-Methylpyridin-2-ylamino)piperidin-1-yl]methylcyclohexyl]propyl acetate

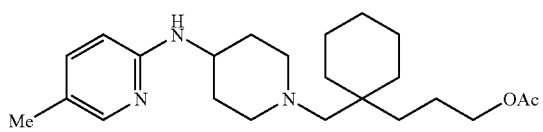

To a solution of (1-hydroxymethylcyclohexyl)propyl acetate (310 mg) in dichloromethane (15 mL) were added pyridine (0.18 mL) and anhydrous trifluoromethanesulfonic acid (0.37 mL) under ice cooling. After stirring the solution under ice cooling for 10 minutes, water and chloroform were added thereto and the liquid layers were separated. The organic layer was washed in turn with 1N hydrochloric acid, saturated aqueous sodium bicarbonate solution and saturated aqueous sodium chloride solution, dried over anhydrous magnesium sulfate, and then, concentrated under reduced pressure. To the residue was added 2-(piperidin-4-ylamino)-5-methylpyridine (416 mg) and the solution was stirred at 60° C. for 1.5 hours. After allowing the mixture to cool to room temperature, it was purified by chromatography (NH silica gel, hexane:ethyl acetate=4:1) to give the title compound (190 mg).

$^1$H-NMR (CDCl$_3$) δ: 1.21-1.68 (m, 16H), 1.89-1.99 (m, 2H), 2.04-(s, 3H), 2.13 (s, 2H), 2.16 (s, 3H), 2.32-2.41 (m, 2H), 2.68-2.76 (m, 2H), 3.44-3.55 (m, 1H), 4.03 (t, 2H, J=6.8 Hz), 4.23 (brd, 1H, J=8.0 Hz), 6.29 (d, 1H, J=8.4 Hz), 7.23 (dd, 1R, J=2.4 Hz, 8.4 Hz), 7.89 (d, 1H, J=2.4 Hz); MS (ESI) m/z: 388 (MH$^+$).

EXAMPLE 1D-1

Methyl 1-[2-[4-(5-methylpyridin-2-ylamino)piperidin-1-yl]ethyl]cyclohexanecarboxylate

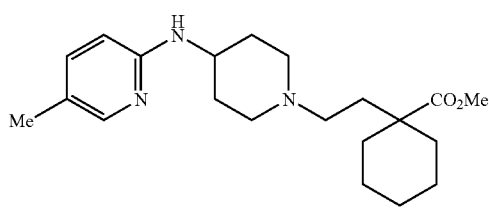

To a solution of 2-(piperidin-4-ylamino)-5-methylpyridine (191 mg) and methyl 1-(2-oxoethyl)cyclohexanecarboxylate (250 mg) in tetrahydrofuran (10 mL) were added acetic acid (150 mg) and sodium triacetoxy borohydride (424 mg) at room temperature. The solution was stirred at room temperature for 20 hours. Saturated aqueous sodium bicarbonate solution was added to the solution, and it was extracted with ethyl acetate. The extract was dried over anhydrous magnesium sulfate, and then, concentrated under reduced pressure. The resulting residue was purified by chromatography [silica gel, ethyl acetate-methanol-aqueous ammonia (90:10:0.1)] to give the title compound (30 mg).

$^1$H-NMR (CDCl$_3$) δ: 1.11-1.63 (m, 10H), 1.67-1.79 (m, 2H), 1.96-2.21 (m, 6H), 2.16 (s, 3H), 2.22-2.33 (m, 2H), 2.78-2.92 (m, 2H), 3.50-3.62 (m, 1H), 3.67 (s, 3H), 4.26 (brd, 1H, J=8.8 Hz), 6.26-6.33 (m, 1H), 7.20-7.25 (m, 1H), 7.86-7.91 (m, 1H).

EXAMPLE 1D-2

2-[1-[3-[2-(Cyclohexylacetamido)phenyl]propyl]piperidin-4-ylamino]-5-methypyridine

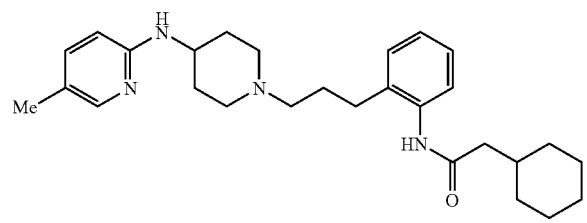

The title compound was synthesized from the compound obtained in Preparation Example 4-3 and the compound obtained in Preparation Example 2A-4 in the same manner as in Example 1D-1. This product was subjected to the subsequent step without further purification.

EXAMPLE 1D-3

2-[1-(2-Cyclooctylethyl)piperidin-4-ylamino]-5-methypyridine

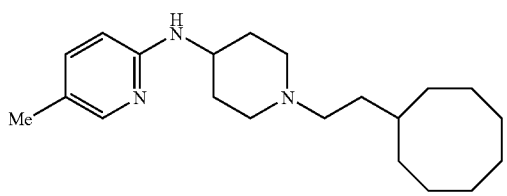

The title compound was synthesized from the compound obtained in Preparation Example 4-3 and the compound obtained in Preparation Example 1A-3 in the same manner as in Example 1D-1.

$^1$H-NMR (CDCl$_3$) δ: 1.19-1.73 (m, 19H), 2.00-2.12 (m, 2H), 2.13-2.27 (m, 2H), 2.16 (s, 3H), 2.87-2.99 (m, 2H), 3.54-3.68 (m, 1H), 4.25-4.53 (m, 1H), 6.31 (d, 1H, J=8.4 Hz), 7.23 (dd, 1H, J=2.4 Hz, 8.4 Hz), 7.85-7.91 (m, 1H).

EXAMPLE 1D-4

Methyl 4-[1-[2-[4-(5-methylpyridin-2-ylamino)piperidin-1-yl]ethyl]cyclohexyl]butyrate

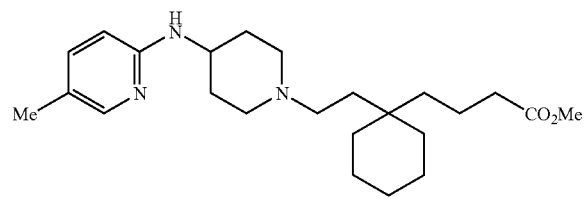

The title compound was synthesized from the compound obtained in Preparation Example 4-3 and the compound obtained in Preparation Example 1F-3 in the same manner as in Example 1D-1.

$^1$H-NMR (CDCl$_3$) δ: 1.18-1.65 (m, 16H), 2.00-2.38 (m, 10H), 2.16 (s, 3H), 2.86-2.98 (m, 2H), 3.56-3.70 (m, 1H), 3.68 (s, 3H), 4.25 (brd, 1H, J=8.8 Hz), 6.30 (d, 1H, J=8.4 Hz), 7.23 (dd, 1H, J=2.4 Hz, 8.4 Hz), 7.89 (d, 1H, J=2.4 Hz); MS (ESI) m/z: 402 (MH$^+$).

EXAMPLE 1D-5

Triethyl 3-[1-[2-[4-(5-methylpyridin-2-ylamino)piperidin-1-yl]ethyl]cyclohexyl]-1,1,1-propanetricarboxylate

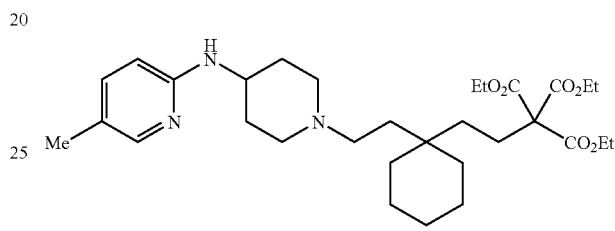

The title compound was synthesized from the compound obtained in Preparation Example 4-3 and the compound obtained in Preparation Example 3A-6 in the same manner as in Example 1D-1.

$^1$H-NMR (CDCl$_3$) δ: 1.23-1.61 (m, 25H), 2.00-2.10 (m, 4H), 2.12-2.26 (m, 2H), 2.16 (s, 3H), 2.28-2.41 (m, 2H), 2.84-3.00 (m, 2H), 2.54-3.67 (m, 1H), 4.23-4.30 (m, 1H), 6.31 (d, 1H, J=8.4 Hz), 7.23 (dd, 1H, J=2.4 Hz, 8.4 Hz), 7.86-7.92 (m, 1H); MS (ESI) m/z: 560 (MH$^+$).

EXAMPLE 1D-6

Dimethyl 3-[1-[2-[4-(p-toluidino)piperidin-1-yl]ethyl]cyclohexyl]-1,1-propanedicarboxylate

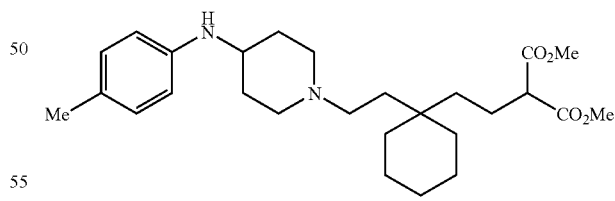

The title compound was synthesized from the compound obtained in Preparation Example 4-5 and the compound obtained in Preparation Example 3B-3 in the same manner as in Example 1D-1.

$^1$H-NMR (CDCl$_3$) δ: 1.18-1.55 (m, 16H), 1.78-1.88 (m, 2H), 2.01-2.19 (m, 3H), 2.21 (s, 3H), 2.22-2.36 (m, 2H), 2.85-2.98 (m, 2H), 3.22-3.34 (m, 2H), 3.75 (s, 6H), 6.53 (d, 2H, J=8.0 Hz), 6.98 (d, 2H, J=8.0 Hz); MS (ESI) m/z: 459 (MH$^+$).

EXAMPLE 1D-7

2-[2-[1-[2-[4-(5-Methylpyridin-2-ylamino)piperidin-1-yl]ethyl]cyclohexyl]ethyl]-1,3-diacetoxypropane

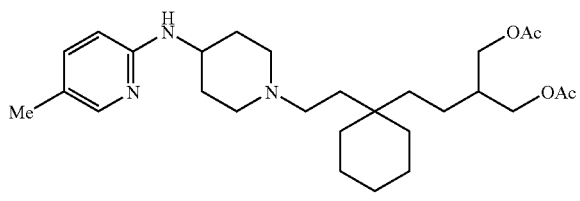

The title compound was synthesized from the compound obtained in Preparation Example 4-3 and the compound obtained in Preparation Example 3C-3 in the same manner as in Example 1D-1. This product was subjected to the subsequent step without further purification.

EXAMPLE 1D-8

2-[2-[1-[2-[4-(p-toluidino)piperidin-1-yl]ethyl]cyclohexyl]ethyl]-1,3-diacetoxypropane

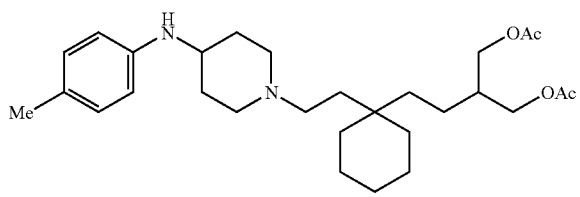

The title compound was synthesized from the compound obtained in Preparation Example 4-5 and the compound obtained in Preparation Example 3C-3 in the same manner as in Example 1D-1.

$^1$H-NMR (CDCl$_3$) δ: 1.19-1.64 (m, 19H), 1.87-1.96 (m, 1H), 2.01-2.23 (m, 4H), 2.06 (s, 6H), 2.13 (s, 3H), 2.91-3.06 (m, 2H), 3.24-3.36 (m, 1H), 4.00-4.14 (m, 4H), 6.53 (d, 2H, J=8.4 Hz), 6.98 (d, 2H, J=8.4 Hz); MS (ESI) m/z: 487 (MH$^+$).

EXAMPLE 1D-9

2-[1-[2-[1-[4-(Methoxymethoxy)-3-(methoxyinethoxyinethyl)butyl]cyclohexyl]ethyl]piperidin-4-ylamino]-5-methylpyridine

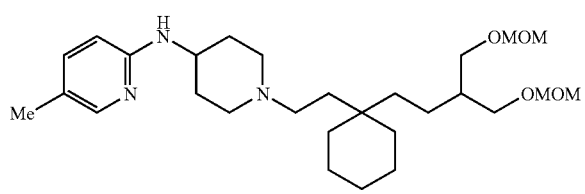

The title compound was synthesized from the compound obtained in Preparation Example 4-3 and the compound obtained in Preparation Example 3D-6 in the same manner as in Example 1D-1.

$^1$H-NMR (CDCl$_3$) δ: 1.20-1.98 (m, 19H), 2.00-2.11 (m, 2H), 2.12-2.23 (m, 2H), 2.16 (s, 3H), 2.26-2.37 (m, 2H), 2.83-2.97 (m, 2H), 3.37 (s, 6H), 3.48-3.66 (m, 5H), 4.22-4.30 (m, 1H), 4.62 (s, 4H), 6.31 (d, 1H, J=8.4 Hz), 7.23 (dd, 1H, J=2.4 Hz, 8.4 Hz), 7.86-7.92 (m, 1H); MS (ESI) m/z: 492 (MH$^+$).

EXAMPLE 1D-10

2-[1-[2-[1-(2-Phenyl-1,3-dioxan-5-yl)cyclohexyl]ethyl]piperidin-4-ylamino]-5-methylpyridine

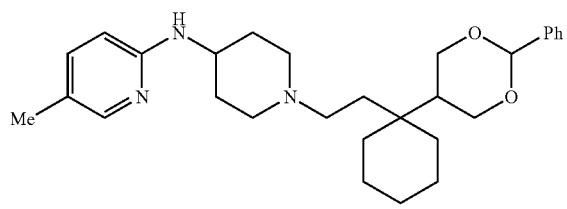

The title compound was synthesized from the compound obtained in Preparation Example 4-3 and the compound obtained in Preparation Example 3E-5 in the same manner as in Example 1D-1.

$^1$H-NMR (CDCl$_3$) δ: 1.29-1.43 (m, 5H), 1.44-1.67 (m, 9H), 2.02-2.13 (m, 2H), 2.14-2.28 (m, 3H), 2.16 (s, 3H), 2.35-2.44 (m, 2H), 2.89-2.99 (m, 2H), 3.56-3.69 (m, 1H), 3.90 (t, 2H, J=11.2 Hz), 4.23-4.37 (m, 3H), 5.39 (s, 1H), 6.31 (d, 1H, J=8.4 Hz), 7.24 (dd, 1H, J=2.4 Hz, 8.4 Hz), 7.30-7.39 (m, 3H), 7.44-7.51 (m, 2H), 7.87-7.91 (m, 1H).

EXAMPLE 1D-11

1-[2-[1-(2,2-Dimethyl-1,3-dioxan-5-yl)cyclohexyl]ethyl]-4-(p-toluidino)piperidine

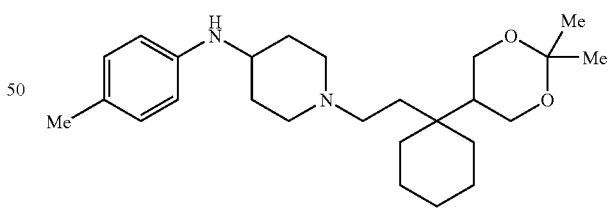

The title compound was synthesized from the compound obtained in Preparation Example 4-5 and the compound obtained in Preparation Example 3F-2 in the same manner as in Example 1D-1.

$^1$H-NMR (CDCl$_3$) δ: 1.22-1.62 (m, 14H), 1.38 (s, 3H), 1.42 (s, 3H), 1.95-2.20 (m, 5H), 2.23 (s, 3H), 2.29-2.41 (m, 2H), 2.84-2.97 (m, 2H), 3.22-3.33 (m, 1H), 3.79 (dd, 2H, J=5.2 Hz, 11.6 Hz), 3.88 (t, 2H, J=11.6 Hz), 6.52 (d, 2H, J=8.0 Hz), 6.98 (d, 2H, J=8.0 Hz); MS (ESI) m/z: 415 (MH$^+$).

EXAMPLE 1D-12

2-(Acetoxymethyl)-2-[2-[1-[2-[4-(5-methylpyridin-2-ylamino)piperidin-1-yl]ethyl]cyclohexyl]ethyl]-1,4-diacetoxybutane

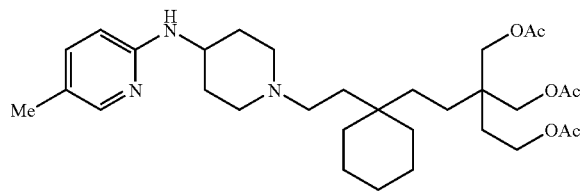

The title compound was synthesized from the compound obtained in Preparation Example 4-3 and the compound obtained in Preparation Example 3G-5 in the same manner as in Example 1D-1.

$^1$H-NMR (CDCl$_3$) δ: 1.15-1.58 (m, 16H), 1.65-1.75 (m, 4H), 1.99-2.19 (m, 4H), 2.04 (s, 6H), 2.07 (s, 3H), 2.16 (s, 3H), 2.21-2.28 (m, 4H), 2.81-2.92 (m, 2H), 3.53-3.65 (m, 1H), 3.96 (s, 4H), 4.14 (t, 2H, J=7.2 Hz), 4.21-4.29 (m, 1H), 6.31 (d, 1H, J=8.0 Hz), 7.23 (dd, 1H, J=2.4 Hz, 8.0 Hz), 7.89 (d, 1H, J=2.4 Hz).

EXAMPLE 1D-13

Methyl 5,5-bis(benzoyloxymethyl)-7-[1-[2-[4-(5-methylpyridin-2-ylamino)piperidin-1-yl]ethyl]cyclohexyl]heptanoate

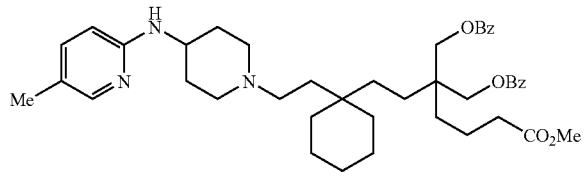

The title compound was synthesized from the compound obtained in Preparation Example 4-3 and the compound obtained in Preparation Example 3H-6 in the same manner as in Example 1D-1.

$^1$H-NMR (CDCl$_3$) δ: 1.14-1.58 (m, 20H), 1.65-1.78 (m, 2H), 1.86-2.03 (m, 4H), 2.13-2.28 (m, 2H), 2.17 (s, 3H), 2.36 (t, 2H, J=6.8 Hz), 2.69-2.85 (m, 2H), 3.40-3.55 (m, 1H), 3.63 (s, 3H), 4.20-4.38 (m, 1H), 4.29 (d, 2H, J=11.2 Hz), 4.33 (d, 2H, J=11.2 Hz), 6.28 (d, 1H, J=8.8 Hz), 7.24 (dd, 1H, J=2.4 Hz, 8.8 Hz), 7.39-7.47 (m, 4H), 7.52-7.59 (m, 2H), 7.87-7.92 (m, 1H), 7.99-8.05 (m, 4H).

EXAMPLE 1D-14

Methyl 5,5-bis(benzoyloxymethyl)-7-[1-[2-[4-(p-toluidino)piperidin-1-yl]ethyl]cyclohexyl]heptanoate

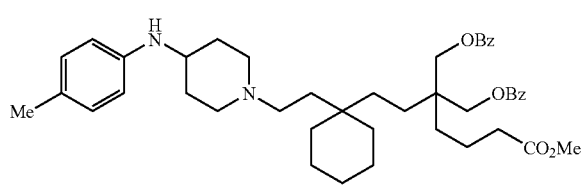

The title compound was synthesized from the compound obtained in Preparation Example 4-5 and the compound obtained in Preparation Example 3H-6 in the same manner as in Example 1D-1.

$^1$H-NMR (CDCl$_3$) δ: 1.19-1.57 (m, 20H), 1.67-1.78 (m, 2H), 1.79-1.97 (m, 4H), 2.12-2.22 (m, 2H), 2.24 (s, 3H), 2.35 (t, 2H, J=7.2 Hz), 2.67-2.79 (m, 2H), 3.04-3.15 (m, 1H), 3.62 (s, 3H), 4.28 (d, 2H, J=11.6 Hz), 4.33 (d, 2H, J=11.6 Hz), 6.50 (d, 2H, J=8.0 Hz), 6.98 (d, 2H, J=8.0 Hz), 7.39-7.47 (m, 4H), 7.51-7.60 (m, 2H), 7.99-8.07 (m, 4H).

EXAMPLE 1D-15

N-[2-[1-[2-[4-(5-Methylpyridin-2-ylamino)piperidin-1-yl]ethyl]cyclohexyl]ethyl]methanesulfonamide

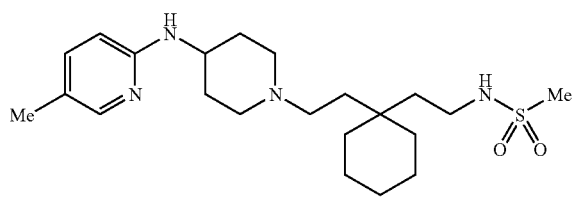

The title compound was synthesized from the compound obtained in Preparation Example 4-3 and the compound obtained in Preparation Example 3J-5 in the same manner as in Example 1D-1.

$^1$H-NMR (CDCl$_3$) δ: 1.25-1.28 (m, 5H), 1.42-1.50 (m, 8H), 1.56-1.61 (m, 4H), 2.04 (d, 2H, J=10.7 Hz), 2.15-2.18 (m, 2H), 2.15 (s, 3H), 2.29 (t, 2H, J=7.3 Hz), 2.92 (m, 2H), 2.95 (s, 3H), 3.10 (t, 2H, J=7.3 Hz), 3.61 (m, 1H), 4.38 (d, 1H, J=8.8 Hz), 6.31 (d, 1H, J=8.8 Hz), 7.22 (dd, 1H, J=2.5, 8.3 Hz), 7.87 (s, 1H)

EXAMPLE 1E-1

2-(1-Cyclohexypiperidin-4-ylamino)-5-methylpyridine

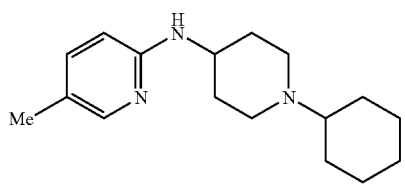

To a solution of 2-(piperidin-4-ylamino)-5-methylpyridine (192 mg) and cyclohexanone (196 mg) in tetrahydrofuran (10 mL) was added sodium triacetoxyborohydride (636 mg). The reaction solution was stirred at room temperature for 16 hours. Saturated aqueous sodium bicarbonate solution was added to the solution, and it was extracted with chloroform. The extract was dried over anhydrous sodium sulfate, and then, concentrated under reduced pressure. The resulting residue was purified by chromatography (NH silica gel, hexane:ethyl acetate=2:1) to give the title compound (170 mg).

$^1$H-NMR (CDCl$_3$) δ: 1.03-1.34 (m, 5H), 1.52-1.69 (m, 3H), 1.76-1.98 (m, 4H), 2.01-2.14 (m, 2H), 2.16 (s, 3H), 2.35-2.54 (m, 3H), 2.86-3.02 (m, 2H), 3.55-3.69 (m, 1H), 4.23 (d, 1H, J=8.4 Hz), 6.30 (d, 1H, J=8.0 Hz), 7.23 (dd, 1H, J=2.0 Hz, 8.0 Hz), 7.89 (d, 1H, J=2.0 Hz).

EXAMPLE 1F-1

2-[1-[2-[4-(5-Methylpyridin-2-ylamino)piperidin-1-yl]ethyl]cyclohexyl]ethanol

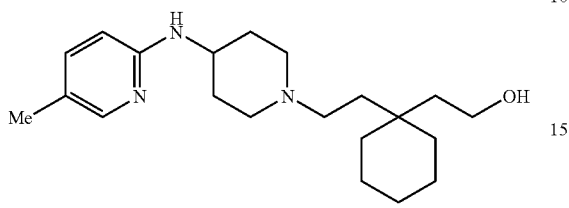

To a solution of 2-(piperidin-4-ylamino)-5-methylpyridine (191 mg) and 3-oxaspiro[5.5]undeca-2-ol (255 mg) in tetrahydrofuran (10 mL) was added sodium triacetoxyborohydride (636 mg) at room temperature. After stirring the solution at room temperature for 87 hours, saturated aqueous sodium bicarbonate solution was added thereto and it was extracted with ethyl acetate. The extract was dried over anhydrous sodium sulfate, and then, concentrated under reduced pressure. The resulting residue was purified by chromatography [silica gel, ethyl acetate-methanol-aqueous ammonia (80:20:0.1)] to give the title compound (290 mg).
$^1$H-NMR (CDCl$_3$) δ: 1.20-1.48 (m, 10H), 1.50-1.72 (m, 6H), 1.99-2.11 (m, 2H), 2.16 (s, 3H), 2.18-2.30 (m, 2H), 2.39 (t, 2H, J=6.4 Hz), 2.87-3.02 (m, 2H), 3.61-3.75 (m, 1H), 3.69 (t, 2H, J=6.4 Hz), 4.20 (brd, 1H, J=8.8 Hz), 6.28 (d, 1H, J=8.4 Hz), 7.22 (dd, 1H, J=2.4 Hz, 8.4 Hz), 7.89 (d, 1H, J=2.4 Hz); MS (ESI) m/z 346 (MH$^+$).

EXAMPLE 1G-1 tert-Butyl [2-[1-[2-[4-(5-methylpyridin-2-ylamino)piperidin-1-yl]ethyl]cyclohexyl]ethyl]carbamate

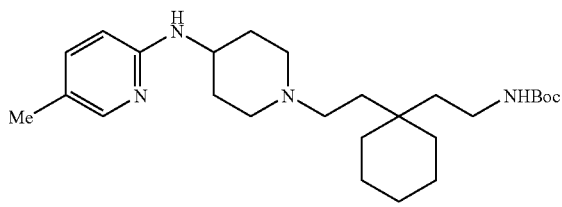

4-(5-Methylpyridin-2-yl)aminopiperidine (0.31 g) and N-[2-[1-(formylmethyl)cyclohexyl]ethyl]phthalimide obtained in Preparation Example 3K-2 were dissolved in dichloromethane (10 mL). To this was added sodium triacetoxyborohydride (0.71 g). The solution was stirred for 3 days. Saturated aqueous sodium bicarbonate solution (20 mL) was added to the reaction solution, and it was extracted with 25% ethanol/chloroform (20 mL). The extract was dried (MgSO$_4$), and then, the solvent was distilled off under reduced pressure. The resulting residue was purified by chromatography [silica gel, dichloromethane-methanol-aqueous ammonia (90:10:0.5)]to give a yellow oily substance (0.63 g). This was dissolved in ethanol (15 mL), to which hydrazine.monohydrate (0.15 g) was added. The solution was heated under reflux for 2 hours. The solvent was distilled off from the reaction solution under reduced pressure. Then, the residue was again suspended in dichloromethane (20 mL), to which triethylamine (0.32 g) and di-tert-butyl dicarbonate (0.52 g) were added. The solution was stirred at room temperature for 17 hours. The insolubles were filtered off and the solvent was distilled off under reduced pressure. The resulting residue purified by chromatography [silica gel, dichloromethane-methanol-aqueous ammonia (97:3:0.2 to 95:5:0.3)] to give the title compound (0.42 g).

EXAMPLE 1G-2

N-[2-[4-(5-Methylpyridin-2-ylamino)piperidin-1-ylmethyl]phenyl]cyclohexylacetamide

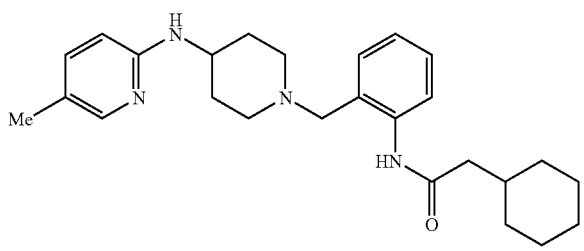

To a solution of 2-(piperidin-4-ylamino)-5-methylpyridine (150 mg) and 2-nitrobenzylbromide (339 mg) in ethanol (5 mL) was added diisopropylamine (159 mg) at room temperature. The solution was stirred under reflux for 20 hours. Ethyl acetate was then added to the solution and the insolubles were filtered off, and then, concentrated under reduced pressure. The resulting residue was purified by chromatography [silica gel, ethyl acetate:methanol:aqueous ammonia (90/10/0.1)]. The resulting residue was dissolved in ethanol (10 mL), to which platinum oxide (10 mg) was added. The solution was stirred at room temperature under hydrogen atmosphere for 4 hours. The catalyst was then filtered off and the solution was concentrated under reduced pressure. To a solution of the residue and cyclohexylacetic acid (52 mg) in dichloromethane (5 mL) were added 1-hydroxybenzotriazole (49 mg) and 1-ethyl-3-(3-dimethylaminopropyl)carbodiimide hydrochloride (69 mg) under ice cooling. The solution was stirred at room temperature for 87 hours. Chloroform was then added to the solution, and it was washed in turn with water and saturated aqueous sodium bicarbonate solution, dried over anhydrous sodium sulfate, and then, concentrated under reduced pressure. The resulting residue was purified by chromatography (NH silica gel, hexane:ethyl acetate=2:1) to give the title compound (90 mg).
$^1$H-NMR (CDCl$_3$) δ: 0.94-1.08 (m, 2H), 1.10-1.36 (m, 3H), 1.40-1.54 (m, 2H), 1.63-1.78 (m, 3H), 1.79-1.95 (m, 3H), 2.07-2.18 (m, 4H), 2.15 (s, 3H), 2.18-2.32 (m, 3H), 2.79-2.91 (m, 2H), 3.58 (s, 2H), 3.63-3.74 (m, 1H), 4.21 (brd, 1H, J=7.6 Hz), 6.32 (d, 1H, J=8.4 Hz), 6.94-7.02 (m, 1H), 7.04-7.10 (m, 1H), 7.21-7.32 (m, 2H), 7.88-7.93 (m, 1H), 8.26 (d, 1H, J=8.4 Hz), 10.15 (brs, 1H).

EXAMPLE 1G-3

N-[2-[2-[4-(p-Toluidino)piperidin-1-yl]ethyl]phenyl]cyclohexylacetamide

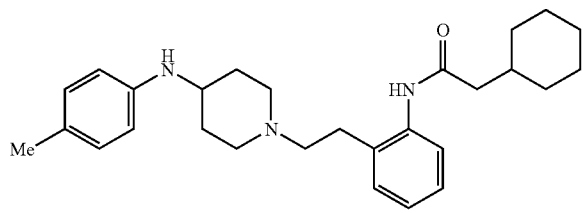

To a solution of 4-(p-tolyl)aminopiperidine trifluoroacetate (2.21 g) and (2-bromoethyl)-2-nitrobenzene (3.01 g) dissolved in N,N-dimethylformamide (20 mL) was added potassium carbonate (2.92 g). The solution was stirred under heating at 80° C. for 2 hours. Dichloromethane was added to the reaction solution and the insolubles were filtered off, and the solvent was distilled off under reduced pressure. The resulting residue was purified by chromatography [silica gel, dichloromethane-methanol-aqueous ammonia (95:5:0.3)] to give a yellow oily substance (0.6906 g). This was dissolved in acetic acid (20 mL), to which 10% palladium carbon (0.20 g) was added. The mixture was vigorously stirred at room temperature under hydrogen atmosphere for 1 hour. The catalyst was filtered off and the solvent was distilled off under reduced pressure. The resulting residue was purified by chromatography [silica gel, dichloromethane-methanol-aqueous ammonia (90:10:0.5)] to give a brown oily substance (0.5041 g). This substance, cyclohexaneacetic acid (0.35 g), 4-dimethylaminopyridine (0.50 g) and 1-ethyl-3-(3-dimethylaminopropyl)carbodiimide hydrochloride (0.62 g) were dissolved in N,N-dimethylformamide (10 mL). The solution was stirred at room temperature for 15 hours. After addition of ethyl acetate, the solution was washed in turn with saturated aqueous sodium bicarbonate solution and saturated aqueous sodium chloride solution, dried (MgSO$_4$) and the solvent was distilled off under reduced pressure. The resulting residue was purified by chromatography [silica gel, dichloromethane-methanol-aqueous ammonia (95:5:0.3)] to give the title compound (0.4453 g).

1H-NMR (DMSO-d$_6$) δ: 0.94-1.08 (m, 2H), 1.09-1.31 (m, 3H), 1.32-1.42 (m, 2H), 1.58-1.83 (m, 6H), 1.84-1.92 (m, 2H), 2.08-2.13 (m, 2H), 2.12 (9s, 3H), 2.19-2.22 (m, 2H), 2.43-2.49 (m, 2H), 2.69-2.76 (m, 2H), 2.82-2.90 (m, 2H), 3.08-3.20 (m, 1H), 5.01 (d, 1H, J=8.3 Hz), 6.48 (d, 2H, J=8.3 Hz), 6.86 (d, 2H, J=8.3 Hz), 7.02-7.24 (m, 3H), 7.32-7.40 (m, 1H), 9.39 (s, 1H).

EXAMPLE 1G-4

3-Cyclohexyl-N-[2-[3-[4-(p-toluidino)piperidin-1-yl]propyl]phenyl]propionamide

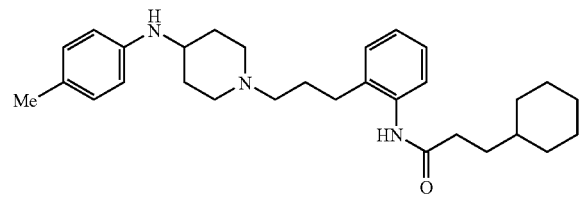

To a solution of 4-(p-tolyl)aminopiperidine trifluoroacetate (2.08 g) and (3-bromopropenyl)-2-nitrobenzene (3.01 g) dissolved in N,N-dimethylformamide (20 mL) was added potassium carbonate (2.75 g). The solution was stirred with heating at 80° C. for 2 hours. Dichloromethane was added to the reaction solution and the insolubles were filtered off, and the solvent was distilled off under reduced pressure. The resulting residue was purified by chromatography [silica gel, dichloromethane-methanol-aqueous ammonia (95:5:0.3)] to give a yellow oily substance (1.05 g). This was dissolved in acetic acid (25 mL), to which 10% palladium carbon (0.50 g) was added. The mixture was vigorously stirred at room temperature under hydrogen atmosphere for 1 hour. The catalyst was filtered off and the solvent was distilled off under reduced pressure. The resulting residue was purified by chromatography [silica gel, dichloromethane-methanol-aqueous ammonia (90:10:0.5)] to give a brown oily substance (0.5443 g). Part of the substance (0.3870 g), cyclohexaneacetic acid (0.28 g), 4-dimethylaminopyridine (0.50 g) and 1-ethyl-3-(3-dimethylaminopropyl)carbodiimide hydrochloride (0.46 g) were dissolved in N,N-dimethylformamide (5 mL). The solution was stirred at room temperature for 18 hours. After addition of ethyl acetate, the solution was washed in turn with saturated aqueous sodium bicarbonate solution and saturated aqueous sodium chloride solution, dried (MgSO$_4$), and the solvent was distilled off under reduced pressure. The resulting residue was purified by chromatography [silica gel, dichloro-methane-methanol-aqueous ammonia (97:3:0.2)] to give the title compound (0.4190 g).

1H-NMR (DMSO-d$_6$) δ: 0.82-0.97 (m, 2H), 1.08-1.30 (m, 4H), 1.30-1.42 (m, 2H), 1.47-1.56 (m, 2H), 1.57-1.78 (m, 7H), 1.84-1.92 (m, 2H), 1.96-2.04, (m, 2H), 2.13 (s, 3H), 2.25 (t, 2H, J=7.3 Hz), 2.28-2.36 (m, 2H), 2.56 (t, 2H, J=7.3 Hz), 2.74-2.82 (m, 2H), 3.08-3.19 (m, 1H), 4.98 (d, 1H, J=8.3 Hz), 6.47 (d, 2H, J=8.3 Hz), 6.85 (d, 2H, J=8.3 Hz), 7.08-7.18 (m, 2H), 7.19-7.21 (m, 1H), 7.25-7.32 (m, 1H), 9.23 (s, 1H).

EXAMPLE 1H-1

Benzyl 1-[2-[4-(5-methylpiridin-2-ylamino)piperidin-1-yl]ethyl]cyclohexanecarboxylate

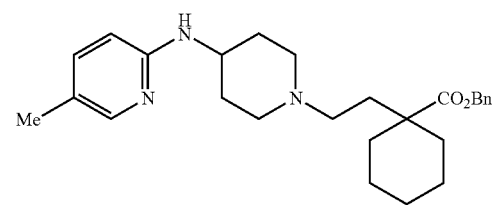

To a solution of 2-(piperidin-4-ylamino)-5-methylpyridine (277 mg) and benzyl 1-(2-oxoethyl)cyclohexanecarboxylate (360 mg) in tetrahydrofuran (15 mL) was added acetic acid (207 mg) and triacetoxyborohydride (731 mg) at room temperature. After stiring the solution for 18 hours, saturated aqueous sodium bicarbonate solution was added thereto and it was extracted with ethyl acetate. The extract was dried over anhydrous sodium sulfate, and then, concentrated under reduced pressure. The resulting residue was purified by chromatography (NH silica gel, hexane:ethyl acetate=2:1) to give the title compound (520 mg).

¹H-NMR (CDCl₃) δ: 1.18-1.65 (m, 8H), 1.68-1.91 (m, 4H), 1.93-2.05 (m, 6H), 2.13-2.24 (m, 2H), 2.16 (s, 3H), 2.67-2.81 (m, 2H), 3.45-3.58 (m, 1H), 4.19 (brd, 1H, J=8.4 Hz), 5.13 (s, 2H), 6.29 (d, 1H, J=8.4 Hz), 7.23 (dd, 1H, J=2.4 Hz, 8.4 Hz), 7.28-7.41 (m, 5H), 7.89 (d, 1H, J=2.4 Hz); MS (ESI) m/z: 436 (MH⁺);

EXAMPLE 1H-2

1-[2-[4-(5-Methylpiridin-2-ylamino)piperidin-1-yl]ethyl]cyclohexanecarboxylic acid

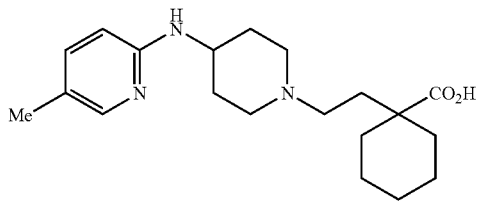

To a solution of benzyl 1-[2-[4-(5-methylpiridin-2-ylamino)piperidin-1-yl]ethyl]cyclohexanecarboxylate (160 mg, 0.37 mmol) in ethanol (16 mL) was added 10% palladium carbon (80 mg) at room temperature. The mixture was stirred at room temperature under hydrogen atmosphere for 24 hours. Acetic acid was added to the mixture, and it was filtered with Celite and concentrated under reduced pressure. Methanol and diethyl ether were added to the residue, and the solution was stirred under ice cooling for 1 hour. The crystals were recovered by filtration to give the title compound (100 mg).

¹H-NMR (DMSO-d₆) δ: 1.15-1.39 (m, 5H), 1.42-1.57 (m, 5H), 1.65-1.76 (m, 2H), 1.85-2.00 (m, 4H), 2.08 (s, 3H), 2.31-2.58 (m, 4H), 2.95-3.08 (m, 2H), 3.66-3.78 (m, 1H), 6.10 (brd, 1H, J=6.8 Hz), 6.38 (d, 1H, J=8.4 Hz), 7.18 (dd, 1H, J=2.4 Hz, 8.4 Hz), 7.74-7.79 (m, 1H).

EXAMPLE 2-1

N-[1-(Cyclohexylmethyl)piperidin-4-yl]-N-(5-methylpyridin-2-yl)-2-furancarboxamide

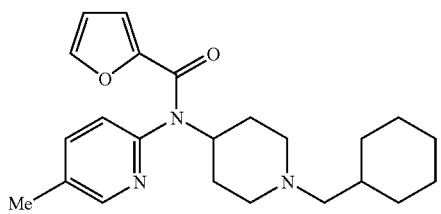

To a solution of 2-[1-(cyclohexylmethyl)piperidin-4-ylamino]-5-methylpyridine (216 mg) prepared in Preparation Example 1A-1 and triethylamine (152 mg) in dichloromethane (3 mL) was added 2-furoyl chloride (0.11 mL) dropwise under ice cooling. The solution was stirred at room temperature for 18 hours. Silica gel (NH silica gel) was added to the reaction solution, and it was concentrated under reduced pressure. The resulting residue was purified by chromatography (NH silica gel, hexane:ethyl acetate=2:1) to give the title compound as a colorless crystal (271 mg).

Free Form

¹H-NMR (CDCl₃) δ: 0.74-0.87 (m, 2H), 1.05-1.28 (m, 3H), 1.35-1.47 (m, 1H), 1.50-1.80 (m, 7H), 1.86-1.95 (m, 2H), 1.98-2.12 (m, 4H), 2.39 (s, 3H), 2.84-2.92 (m, 2H), 4.70 (tt, 1H, J=4.0 Hz, 12.5 Hz), 5.92 (d, 1H, J=3.4 Hz), 6.18 (dd, 1H, J=1.4 Hz, 3.4 Hz), 6.99 (d, 1H, J=7.8 Hz), 7.21-7.23 (m, 1H), 7.47-7.53 (m, 1H), 8.38-8.41 (m, 1H).

Hydrochloride mp 220-230° C. (dec.); ¹H-NMR (CDCl₃) δ: 0.97-1.30 (m, 5H), 1.62-1.70 (m, 1H), 1.71-1.85 (m, 3H), 1.87-1.95 (m, 2H), 2.39-2.47 (m, 2H), 2.52-2.66 (m, 2H), 2.59 (s, 3H), 2.78-2.83 (m, 2H), 3.02-3.16 (m, 2H), 3.50-3.57 (m, 2H), 5.04-5.14 (m, 1H), 6.36 (dd, 1H, J=1.5 Hz, 3.4 Hz), 6.93 (d, 1H, J=3.4 Hz), 7.12-7.13 (m, 1H), 7.69 (d, 1H, J=8.3 Hz), 8.28 (dd, 1H, J=1.5 Hz, 8.3 Hz), 8.49 (d, 1H, J=1.5 Hz), 11.55 (brs, 1H); MS (ESI) m/z: 382 (MH⁺). Anal. Calcd for $C_{23}H_{31}N_3O_2 \cdot 2HCl$: C, 60.79; H, 7.32; N, 9.25. Found: C, 60.66; H, 7.49; N, 9.08.

EXAMPLE 2-2

N-[1-(2-Cyclohexylethyl)piperidin-4-yl]-N-(5-methylpyridin-2-yl)-2-furancarboxamide

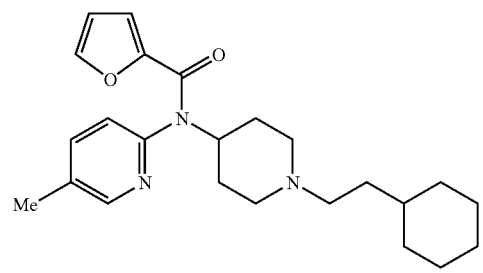

The title compound was synthesized from the compound obtained in Example 1A-2 in the same manner as in Example 2-1.

Free Form

¹H-NMR (CDCl₃) δ 0.82-0.95 (m, 2H), 1.05-1.27 (m, 4H), 1.28-1.36 (m, 2H), 1.53-1.70 (m, 7H), 1.89-1.97 (m, 2H), 2.02-2.12 (m, 2H), 2.27-2.33 (m, 2H), 2.38 (s, 3H), 2.92-2.98 (m, 2H), 4.74 (tt, 1H, J=4.0 Hz, 12.5 Hz), 5.93 (d, 1H, J=3.4 Hz), 6.18 (dd, 1H, J=1.5 Hz, 3.4 Hz), 6.99 (d, 1H, J=8.3 Hz), 7.22 (d, 1H, J=1.5 Hz), 7.50 (dd, 1H, J=2.0 Hz, 8.3 Hz), 8.38 (d, 1H, J=2.0 Hz)

Hydrochloride mp 130-140° C. (dec.); ¹H-NMR (CDCl₃) δ: 0.87-1.00 (m, 2H), 1.05-1.35 (m, 4H), 1.60-1.75 (m, 7H), 2.34-2.50 (m, 4H), 2.59 (s, 3H), 2.92-3.06 (m, 4H), 3.49-3.57 (m, 2H), 4.98-5.08 (m, 1H), 6.36 (dd, 1H, J=1.5 Hz, 3.4 Hz), 6.94 (d, 1H, J=3.4 Hz), 7.11-7.13 (m, 1H), 7.61 (d, 1H, J=7.8 Hz), 8.21 (dd, 1H, J=1.5 Hz, 7.8 Hz), 8.50 (dd, 1H, J=1.5 Hz), 12.06 (brs, 1H); MS (ESI) m/z: 396 (MH⁺). Anal. Calcd for $C_{24}H_{33}N_3O_2 \cdot 2HCl \cdot 2/3H_2O$: C, 59.99; H, 7.62; N, 8.75. Found: C, 59.99; H, 7.78; N, 8.63.

EXAMPLE 2-3

N-[1-(3-Cyclohexylpropyl)piperidin-4-yl]-N-(5-methylpyridin-2-yl)-2-furancarboxamide

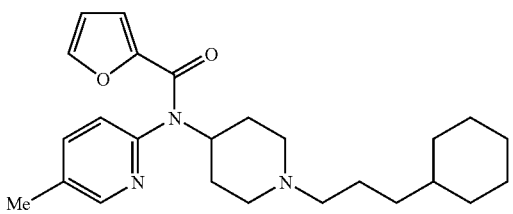

The title compound was synthesized from the compound obtained in Example 1A-3 in the same manner as in Example 2-1.

Free Form mp 90-92° C.; $^1$H-NMR (CDCl$_3$) δ: 0.77-0.90 (m, 2H), 1.08-1.24 (m, 6H), 1.38-1.47 (m, 2H), 1.54-1.70 (m, 7H), 1.90-1.97 (m, 2H), 2.03-2.12 (m, 2H), 2.22-2.28 (m, 2H), 2.38 (s, 3H), 2.92-2.98 (m, 2H), 4.74 (tt, 1H, J=4.0 Hz, 12.5 Hz), 5.93 (dd, 1H, J=0.5 Hz, 3.4 Hz), 6.19 (dd, 1H, J=1.5 Hz, 3.4 Hz), 6.99 (d, 1H, J=7.8 Hz), 7.22 (dd, 1H, J=0.5 Hz, 1.5 Hz), 7.50 (dd, 1H, J=2.4 Hz, 7.8 Hz), 8.38 (d, 1H, J=2.4 Hz); MS (ESI) m/z: 410 (MH$^+$); Anal. Calcd for C$_{25}$H$_{35}$N$_3$O$_2$: C, 73.31; H, 8.61; N, 10.26. Found: C, 73.32; H, 8.76; N, 10.34.

Hydrochloride mp 193-199° C.; $^1$H-NMR (CDCl$_3$) δ: 0.80-0.93 (m, 2H), 1.05-1.28 (m, 6H), 1.60-1.73 (m, 5H), 1.79-1.90 (m, 2H), 2.25-2.45 (m, 4H), 2.50 (s, 3H), 2.84-2.97 (m, 4H), 3.52-3.59 (m, 2H), 4.93-5.04 (m, 1H), 6.29 (dd, 1H, J=1.5 Hz, 3.4 Hz), 6.37-6.42 (m, 1H), 7.19-7.20 (m, 1H), 7.34 (d, 1H, J=8.3 Hz), 7.90 (d, 1H, J=8.3 Hz), 8.45 (s, 1H), 12.17 (brs, 1H); MS (ESI) m/z: 410 (MH$^+$); Anal. Calcd for C$_{25}$H$_{35}$N$_3$O$_2$.HCl.4/3H$_2$O: C, 63.88; H, 8.29; N, 8.94. Found: C, 63.87; H, 8.02; N, 8.84.

EXAMPLE 2-4

N-[1-(4-Cyclohexylbutyl)piperidin-4-yl]-N-(5-methylpyridin-2-yl)-2-furancarboxamide

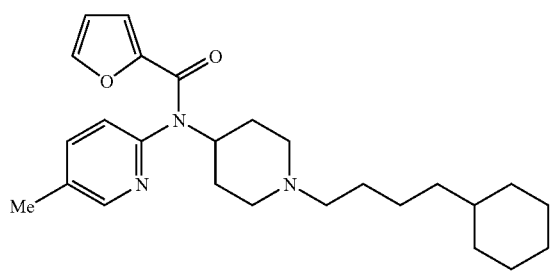

The title compound was synthesized from the compound obtained in Example 1A-4 in the same manner as in Example 2-1.

Free Form $^1$H-NMR (CDCl$_3$) δ: 0.75-0.85 (m, 2H), 1.04-1.29 (m, 8H), 1.35-1.45 (m, 2H), 1.54-1.71 (m, 7H), 1.88-1.97 (m, 2H), 2.02-2.12 (m, 2H), 2.38 (s, 3H), 2.90-2.99 (m, 2H), 4.74 (tt, 1H, J=4.0 Hz, 12.0 Hz), 5.92-5.95 (m, 1H), 6.19 (dd, 1H, J=2.4 Hz, 3.6 Hz), 6.99 (d, 1H, J=8.0 Hz), 7.21-7.24 (m, 1H), 7.50 (dd, 1H, J=2.4 Hz, 8.0 Hz), 8.38 (d, 1H, J=2.4 Hz).

Hydrochloride mp 123-126° C.; $^1$H-NMR (DMSO-d$_6$) δ 0.76-0.92 (m, 2H), 1.04-1.32 (m, 8H), 1.53-1.71 (m, 7H), 1.81-2.06 (m, 4H), 2.37 (s, 3H), 2.86-3.14 (m, 4H), 3.39-3.52 (m, 2H), 4.75 (tt, 1H, J=4.0 Hz, 11.6 Hz), 5.89 (d, 1H, J=7.6 Hz), 6.35 (dd, 1H, J=1.6 Hz, 7.6 Hz), 7.24 (d, 1H, J=8.0 Hz), 7.54-7.59 (m, 1H), 7.74 (dd, 1H, J=2.4 Hz, 8.0 Hz), 8.36-8.42 (m, 1H); MS (ESI) m/z: 424 (M++1); IR (KBr) cm−1: 3444, 2880, 1651, 1637, 1556, 1470, 1322, 1189, 752; Anal. Calcd for C$_{26}$H$_{37}$N$_3$O$_2$.HCl.2H$_2$O: C, 62.95; H, 8.53; N, 8.47. Found: C, 63.21; H, 8.52; N, 8.28.

EXAMPLE 2-5

N-[1-[2-[2-(Cyclohexylacetamido)phenyl]ethyl]piperidin-4-yl]-N-(5-methylpyridin-2-yl)-2-furancarboxamide

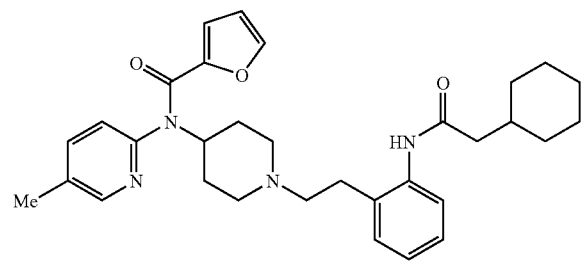

The title compound was synthesized from the compound obtained in Example 1A-5 in the same manner as in Example 2-1.

Free Form $^1$H-NMR (CDCl$_3$) δ: 0.82-0.97 (m, 2H), 1.06-1.34 (m, 4H), 1.59-1.88 (m, 9H), 1.91-2.03 (m, 4H), 2.23-2.36 (m, 2H), 2.41 (s, 3H), 2.55-2.73 (m, 4H), 2.91-3.01 (m, 2H), 4.74 (tt, 1H, J=4.0 Hz, 12.0 Hz), 5.98 (d, 1H, J=3.6 Hz), 6.21 (dd, 1H, J=1.6 Hz, 3.6 Hz), 6.95-7.10 (m, 3H), 7.16-7.24 (m, 2H), 7.50-7.57 (m, 1H), 7.87 (d, 1H, J=8.0 Hz), 8.41 (d, 1H, J=2.4 Hz), 9.86 (brs, 1H).

Hydrochloride mp 117-120° C.; $^1$H-NMR (DMSO-d$_6$) δ: 0.93-1.08 (m, 2H), 1.09-1.32 (m, 3H), 1.58-1.98 (m, 8H), 2.00-2.13 (m, 2H), 2.20-2.32 (m, 2H), 2.38 (s, 3H), 2.89-2.99 (m, 2H), 3.09-3.24 (m, 4H), 3.49-3.57 (m, 2H), 4.73-4.84 (m, 1H), 5.89-5.94 (m, 1H), 6.36 (dd, 1H, J=1.6 Hz, 3.6 Hz), 7.14-7.34 (m, 5H), 7.54-7.58 (m, 1H), 7.74 (dd, 1H, J=2.4 Hz, 8.0 Hz), 8.41 (d, 1H, J=2.4 Hz), 9.37-9.42 (m, 1H), 9.72-9.87 (m, 1H); MS (ESI) m/z: 529 (MH$^+$); IR (KBr) cm$^{−1}$: 3435, 2923, 2850, 1646, 1522, 1469, 1449, 1341, 1191.

EXAMPLE 2-6

Methyl [1-[2-[4-[N-(5-methylpyridin-2-yl)-2-furan-carboxamido]piperidin-1-yl]ethyl]cyclohexyl]acetate

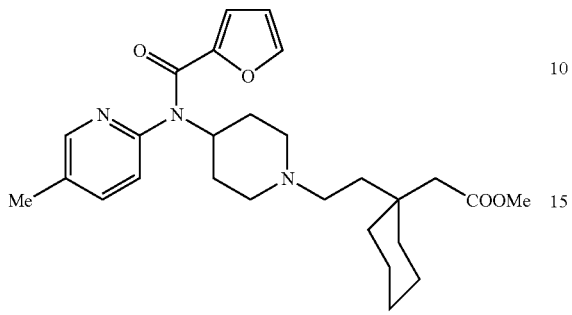

The title compound was synthesized from the compound obtained in Example 1A-6 in the same manner as in Example 2-1.

Hydrochloride mp 120-130° C. (dec); $^1$H-NMR (CDCl$_3$) δ: 1.30-1.55 (m, 10H), 1.87-1.95 (m, 2H), 2.26 (s, 2H), 2.30-2.50 (m, 4H), 2.58 (s, 3H), 2.94-3.10 (m, 4H), 3.50-3.60 (m, 2H), 3.67 (s, 3H), 4.95-5.07 (m, 1H), 6.35 (dd, 1H, J=1.5 Hz, 3.5 Hz), 6.92 (d, 1H, J=3.5 Hz), 7.12 (d, 1H, J=1.5 Hz), 7.57 (d, 1H, J=7.8 Hz), 8.18 (dd, 1H, J=1.5 Hz, 7.8 Hz), 8.51 (d, 1H, J=1.5 Hz), 12.13 (brs, 1H).

EXAMPLE 2-7

Methyl [1-[2-[4-[N-(5-methylpyridin-2-yl)-2-furan-carboxamido]piperidin-1-yl]ethyl]cyclopentyl]acetate

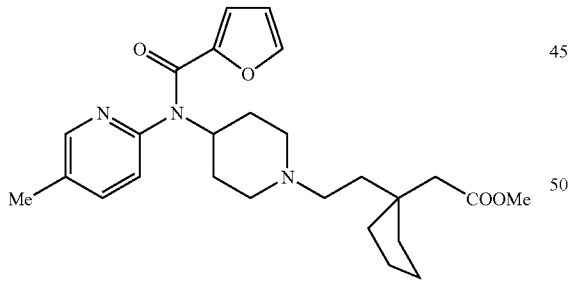

The title compound was synthesized from the compound obtained in Example 1A-7 in the same manner as in Example 2-1.

Hydrochloride $^1$H-NMR (DMSO-d$_6$) δ: 1.40-1.54 (m, 4H), 1.57-1.59 (m, 4H), 2.01-2.05 (d, 2H, J=13.2 Hz), 2.28 (s, 2H), 2.36 (s, 3H), 2.99-3.04 (m, 4H), 3.48-3.55 (m, 2H), 3.60 (s, 3H), 4.75 (m, 1H), 5.92 (d, 1H, J=3.4 Hz), 6.36 (dd, 1H, J=2.0, 3.4 Hz), 7.24 (d, 1H, J=7.8 Hz), 7.57 (s, 1H), 7.74 (d, 1H, J=7.8 Hz), 8.40 (s, 1H); MS (ESI) m/z: 454 (MH$^+$).

EXAMPLE 2-8 tert-Butyl [2-[3-[4-[N-(5-methylpyridin-2-yl)-2-furancarboxamido]piperidin-1-yl]propyl]phenyl]carbamate

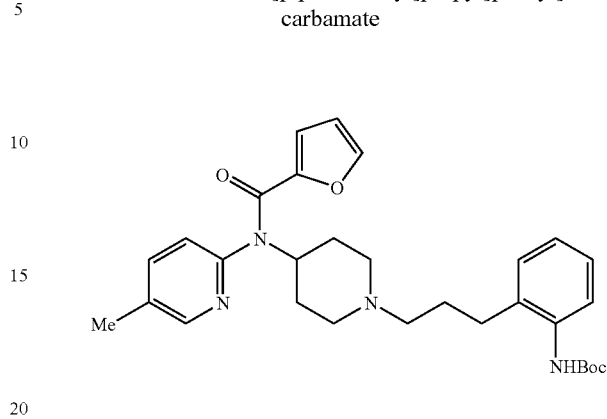

The title compound was synthesized from the compound obtained in Example 1A-8 in the same manner as in Example 2-1.

mp 87-90° C.; $^1$H-NMR (CDCl$_3$) δ: 1.45 (s, 9H), 1.69-1.83 (m, 4H), 1.84-1.94 (m, 2H), 2.08-2.18 (m, 2H), 2.19-2.26 (m, 2H), 2.41 (s, 3H), 2.59 (t, 2H, J=6.8 Hz), 2.88-2.96 (m, 2H), 4.71 (tt, 1H, J=4.0 Hz, 12.0 Hz), 5.92 (d, 1H, J=3.6 Hz), 6.19 (dd, 1H, J=1.6 Hz, 3.6 Hz), 6.96-7.02 (m, 1H), 7.03-7.16 (m, 3H), 7.20-7.25 (m, 1H), 7.47-7.57 (m, 2H), 8.40 (d, 1H, J=2.8 Hz); IR (KBr) cm−1: 3449, 2930, 1713, 1664, 1591, 1471, 1365, 1329, 1246, 1162, 1048, 1023; MS (ESI) m/z: 519 (MH$^+$); Anal. Calcd for C$_{30}$H$_{38}$N$_4$O$_4$.2/3H$_2$O: C, 67.90; H, 7.47; N, 10.56. Found: C, 67.77; H, 7.50; N, 10.37.

EXAMPLE 2-9

N-[1-(3-Cyclohexylpropyl)piperidin-4-yl]-N-(p-tolyl)-2-furancarboxamide

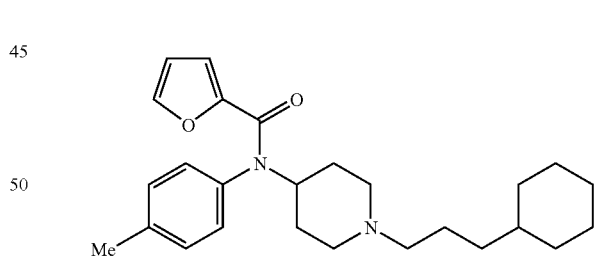

The title compound was synthesized from the compound obtained in Example 1B-1 in the same manner as in Example 2-1.

mp 249-252° C.; $^1$H-NMR (DMSO-d$_6$) δ: 0.75-0.89 (m, 2H), 1.02-1.22 (m, 6H), 1.27-1.40 (m, 4H), 1.53-1.69 (m, 5H), 1.70-1.80 (m, 2H), 1.89-2.00 (m, 2H), 2.12-2.24 (m, 2H), 2.37 (s, 3H), 2.79-2.88 (m, 2H), 4.48 (tt, 1H, J=3.9 Hz, 12.2 Hz), 5.46 (d, 1H, J=3.4 Hz), 6.28 (dd, 1H, J=1.5 Hz, 3.4 Hz), 7.08 (d, 2H, J=8.3 Hz), 7.25 (d, 2H, J=8.3 Hz), 7.58 (d, 1H, J=1.5 Hz); IR (KBr) cm$^{-1}$: 2923, 1634, 1469, 1403, 1325, 769, 756, 734; MS (ESI) m/z: 409 (MH$^+$).

EXAMPLE 2-10

Methyl [1-[2-[4-[N-(p-tolyl)-2-furancarboxamido]piperidin-1-yl]ethyl]cyclohexyl]acetate

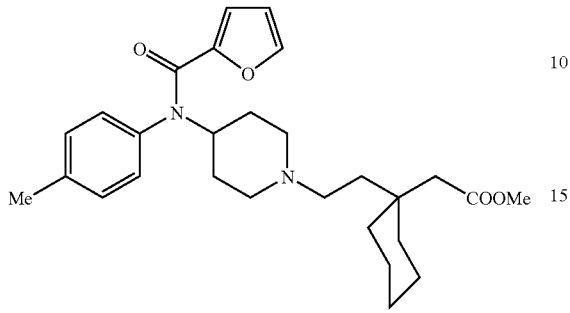

The title compound was synthesized from the compound obtained in Example 1B-2 in the same manner as in Example 2-1.

mp 118-200° C.; $^1$H-NMR (DMSO-$d_6$) δ: 1.25-1.48 (m, 10H), 1.62-1.80 (m, 4H), 1.89-2.08 (m, 2H), 2.26 (s, 2H), 2.39 (s, 3H), 2.94-3.04 (m, 2H), 3.05-3.20 (m, 2H), 3.44-3.56 (m, 2H), 3.59 (s, 3H), 4.75-4.87 (m, 1H), 5.50 (d, 1H, J=3.4 Hz), 6.32 (dd, 1H, J=2.0 Hz, 3.4 Hz), 7.16 (d, 2H, J=7.8 Hz), 7.30 (d, 2H, J=7.8 Hz), 7.63 (d, 1H, J=2.0 Hz); IR (KBr) cm$^{-1}$: 3525, 3398, 2932, 2517, 2490, 1721, 1624, 1509, 1466, 1402, 1338, 1307, 1204, 1190, 767, 759; MS (ESI) 467 m/z (MH).

EXAMPLE 2-11

N-[1-[2-[1-(2-Cyanoethyl)cyclohexyl]ethyl]piperidin-4-yl]-N-(p-tolyl)-2-furancarboxamide

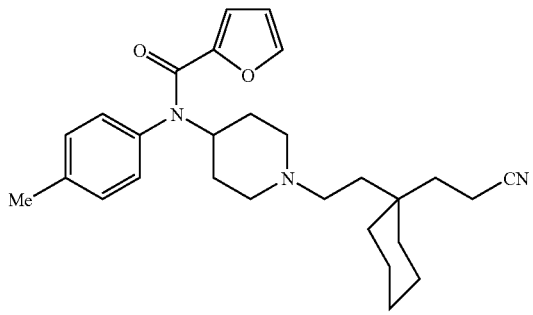

The title compound was synthesized from the compound obtained in Example 1B-4 in the same manner as in Example 2-1.

$^1$H-NMR (DMSO-$d_6$) δ: 1.10-1.44 (m, 14H), 1.49-1.58 (m, 2H), 1.70-1.79 (m, 2H), 1.92-2.02 (m, 2H), 2.10-2.20 (m, 2H), 2.27-2.34 (m, 2H), 2.37 (s, 3H), 2.84-2.94 (m, 2H), 4.48 (tt, 1H, J=3.4 Hz, 12.2 Hz), 5.47 (d, 1H, J=3.4 Hz), 6.29 (dd, 1H, J=2.0 Hz, 3.4 Hz), 7.08 (d, 2H, J=8.3 Hz), 7.25 (d, 2H, J=8.3 Hz), 7.59 (d, 1H, J=2.0 Hz).

EXAMPLE 2-12

3-[1-[4-[N-(5-Methylpyridin-2-yl)-2-furancarboxamido]piperidin-1-yl]methylcyclohexyl]propyl acetate

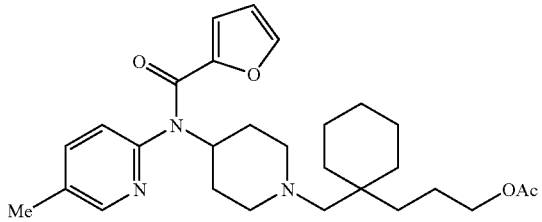

The title compound was synthesized from the compound obtained in Example 1C-1 in the same manner as in Example 2-1.

$^1$H-NMR (CDCl$_3$) δ: 1.14-1.65 (m, 16H), 1.77-1.87 (m, 2H), 2.00 (s, 3H), 2.08 (s, 2H), 2.33-2.44 (m, 2H), 2.42 (s, 3H), 2.72-2.79 (m, 2H), 3.98 (t, 2H, J=6.8 Hz), 4.63 (tt, 1H, J=4.0 Hz, 12.0 Hz), 5.93 (d, 1H, J=3.2 Hz), 6.19 (dd, 1H, J=1.6 Hz, 3.2 Hz), 6.99 (d, 1H, J=8.0 Hz), 7.19-7.24 (m, 1H), 7.53 (dd, 1H, J=2.4 Hz, 8.0 Hz), 8.14 (d, 1H, J=2.4 Hz).

EXAMPLE 2-13

Methyl 1-[2-[4-[N-(5-Methylpyridin-2-yl)-2-furancarboxamido]piperidin-1-yl]ethyl]cyclohexanecarboxylate

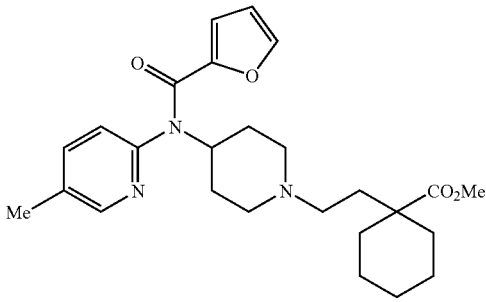

The title compound was synthesized from the compound obtained in Example 1D-1 in the same manner as in Example 2-1.

Free Form
$^1$H-NMR (CDCl$_3$) δ: 1.10-1.39 (m, 6H), 1.45-1.72 (m, 6H), 1.84-2.12 (m, 6H), 2.18-2.30 (m, 2H), 2.37 (s, 3H), 2.87-2.99 (m, 2H), 3.62 (s, 3H), 4.71 (tt, 1H, J=4.0 Hz, 12.0 Hz), 5.94 (d, 1H, J=2.4 Hz), 6.19 (dd, 1H, J=2.4 Hz, 3.6 Hz), 6.98 (d, 1H, J=8.0 Hz), 7.19-7.24 (m, 1H), 7.50 (dd, 1H, J=2.4 Hz, 8.0 Hz), 8.37 (d, 1H, J=2.4 Hz).

Hydrochloride
$^1$H-NMR (DMSO-$d_6$) δ: 1.17-1.35 (m, 5H), 1.41-1.58 (m, 3H), 1.76-1.95 (m, 6H), 1.97-2.06 (m, 2H), 2.36 (s, 3H), 2.82-2.93 (m, 2H), 3.01-3.15 (m, 2H), 3.43-3.55 (m, 2H), 3.65 (s, 3H), 4.66-4.78 (m, 1H), 5.91 (d, 1H, J=3.6 Hz), 6.36 (dd, 1H, J=2.4 Hz, 3.6 Hz), 7.23 (d, 1H, J=8.0 Hz), 7.54-7.58 (m, 1H), 7.73 (dd, 1H, J=2.4 Hz, 8.0 Hz), 8.37-8.41 (m, 1H); MS (ESI) m/z: 527 (MH+).

EXAMPLE 2-14

N-[1-[3-[2-(Cyclohexylacetamido)phenyl]propyl] piperidin-4-yl]-N-(5-methylpyridin-2-yl)-2-furancarboxamide

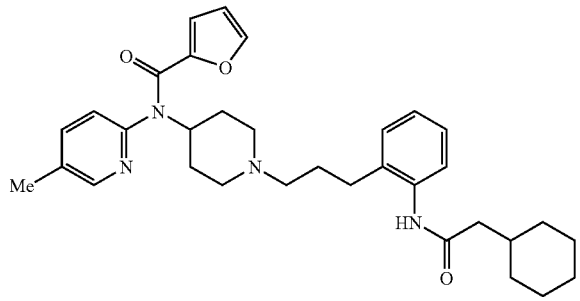

The title compound was synthesized from the compound obtained in Example 1D-2 in the same manner as in Example 2-1.

Free Form $^{1}$H-NMR (CDCl$_{3}$) δ: 0.79-1.00 (m, 2H), 1.04-1.35 (m, 3H), 1.55-1.87 (m, 10H), 1.89-1.98 (m, 2H), 2.02-2.27 (m, 6H), 2.41 (s, 3H), 2.60 (t, 2H, J=6.4 Hz), 2.89-3.00 (m, 2H), 4.70 (tt, 1H, J=4.0 Hz, 12.0 Hz), 5.97 (d, 1H, J=3.6 Hz), 6.20 (dd, 1H, J=2.0 Hz, 3.6 Hz), 6.95-7.01 (m, 1H), 7.04-7.20 (m, 3H), 7.21-7.24 (m, 1H), 7.50-7.61 (m, 2H), 8.38-8.43 (m, 1H), 8.99 (brs, 1H).

Hydrochloride mp 116-119° C.; $^{1}$H-NMR (DMSO-d$_{6}$) δ: 0.93-1.07 (m, 2H), 1.11-1.13 (m, 3H), 1.57-1.94 (m, 10H), 1.96-2.07 (m, 2H), 2.22 (d, 2H, J=6.8 Hz), 2.36 (s, 3H), 2.59 (t, 2H, J=8.0 Hz), 2.91-3.01 (m, 2H), 3.04-3.17 (m, 2H), 3.41-3.51 (m, 2H), 4.70-4.81 (m, 1H), 5.90 (d, 1H, J=3.6 Hz), 6.36 (dd, 1H, J=1.6 Hz, 3.6 Hz), 7.10-7.27 (m, 4H), 7.27-7.34 (m, 1H), 7.54-7.58 (m, 1H), 7.73 (dd, 1H, J=2.0 Hz, 8.0 Hz), 8.37-8.41 (m, 1H), 9.25 (brs, 1H), 9.53-9.65 (m, 1H); IR (KBr) cm$^{-1}$: 3426, 2923, 2849, 1644, 1523, 1469, 1449, 1340, 1322, 1189, 1031, 755; MS (ESI) m/z: 543 (MH$^{+}$).

EXAMPLE 2-15

N-[1-(2-Cyclooctylethyl)piperidin-4-yl]-N-(5-methylpyridin-2-yl)-2-furancarboxamide

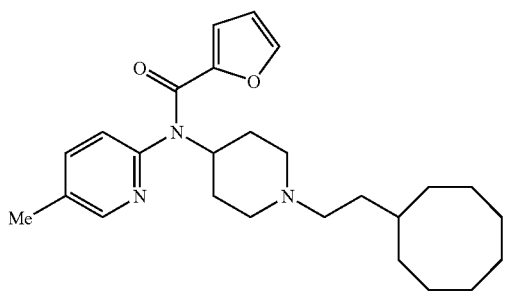

The title compound was synthesized from the compound obtained in Example 1D-3 in the same manner as in Example 2-1.

Free Form $^{1}$H-NMR (CDCl$_{3}$) δ: 1.18-1.74 (m, 19H), 1.88-1.97 (m, 2H), 2.02-2.13 (m, 2H), 2.25-2.34 (m, 2H), 2.38 (s, 3H), 2.90-3.00 (m, 2H), 4.74 (tt, 1H, J=4.0 Hz, 12.0 Hz), 5.94 (d, 1H, J=3.6 Hz), 6.19 (dd, 1H, J=1.6 Hz, 3.6 Hz), 6.99 (d, 1H, J=8.0 Hz), 7.21-7.24 (m, 1H), 7.50 (dd, 1H, J=2.4 Hz, 8.0 Hz), 8.38 (d, 1H, J=2.4 Hz).

Hydrochloride mp 107-110° C.; $^{1}$H-NMR (DMSO-d$_{6}$) δ: 1.16-1.31 (m, 2H), 1.33-1.67 (m, 15H), 1.80-1.94 (m, 2H), 1.96-2.06 (m, 2H), 2.37 (s, 3H), 2.91-3.01 (m, 2H), 3.01-3.14 (m, 2H), 3.41-3.52 (m, 2H), 4.74 (tt, 1H, J=4.0 Hz, 12.0 Hz), 5.90 (d, 1H, J=3.6 Hz), 6.35 (dd, 1H, J=1.6 Hz, 3.6 Hz), 7.24 (d, 1H, J=8.0 Hz), 7.56 (d, 1H, J=1.6 Hz), 8.23 (dd, 1H, J=2.4 Hz, 8.0 Hz), 8.39 (d, 1H, J=2.4 Hz), 9.65-9.77 (m, 1H); IR (KBr) cm$^{-1}$: 3425, 2922, 2854, 1633, 1574, 1557, 1470, 1320, 1189, 769; MS (ESI) m/z: 424 (MH$^{+}$); Anal. Calcd for C$_{26}$H$_{37}$N$_{3}$O$_{2}$.HCl.5/2H$_{2}$O: C, 61.83; H, 8.58; N, 8.32. Found: C, 61.86; H, 8.36; N, 8.16.

EXAMPLE 2-16

Methyl 4-[1-[2-[4-[N-(5-Methylpyridin-2-yl)-2-furancarboxamido]piperidin-1-yl]ethyl]cyclohexyl] butyrate

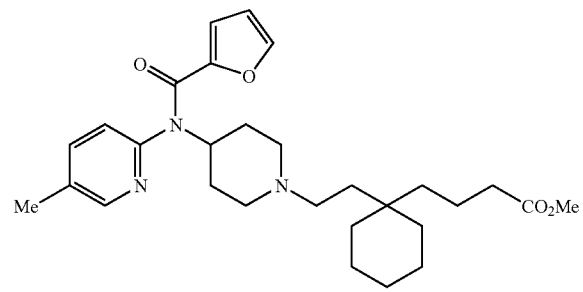

The title compound was synthesized from the compound obtained in Preparation Example 1D-4 in the same manner as in Example 2-1.

Free Form $^{1}$H-NMR (CDCl$_{3}$) δ: 1.16-1.29 (m, 6H), 1.31-1.44 (m, 8H), 1.46-1.72 (m, 4H), 1.90-1.98 (m, 2H), 2.03-2.13 (m, 2H), 2.18-2.30 (m, 4H), 2.38 (s, 3H), 2.93-3.02 (m, 2H), 3.67 (s, 3H), 4.74 (tt, 1H, J=4.0 Hz, 12.0 Hz), 5.94 (d, 1H, J=3.6 Hz), 6.19 (dd, 1H, J=1.6 Hz, 3.6 Hz), 6.99 (d, 1H, J=8.0 Hz), 7.22 (d, 1H, J=1.6 Hz), 7.50 (dd, 1H, J=2.4 Hz, 8.0 Hz), 8.37 (d, 1H, J=2.4 Hz).

Hydrochloride mp 123-126° C.; $^{1}$H-NMR (DMSO-d$_{6}$) δ: 1.10-1.29 (m, 6H), 1.31-1.49 (m, 8H), 1.53-1.62 (m, 2H), 1.78-1.94 (m, 2H), 1.98-2.08 (m, 2H), 2.29 (t, 2H, J=6.8 Hz), 2.37 (s, 3H), 2.86-2.96 (m, 2H), 3.03-3.15 (m, 2H), 3.48-3.57 (m, 2H), 3.59 (s, 3H), 4.74 (tt, 1H, J=4.0 Hz, 12.0 Hz), 5.91 (d, 1H, J=3.6 Hz), 6.36 (dd, 1H, J=1.6 Hz, 3.6 Hz), 7.24 (d, 1H, J=8.0 Hz), 7.56 (d, 1H, J=1.6 Hz), 7.74 (dd, 1H, J=2.4 Hz, 8.0 Hz), 8.40 (d, 1H, J=2.4 Hz), 9.41-9.56 (m, 1H); IR (KBr) cm$^{-1}$: 3425, 2928, 1729, 1633, 1469, 1321, 1191, 1031, 769; MS (ESI) m/z: 496 (MH$^{+}$); Anal. Calcd for C$_{29}$H$_{42}$ClN$_{3}$O$_{3.4}$.2H$_{2}$O: C, 61.31; H, 8.16; N, 7.40. Found: C, 61.11; H, 8.06; N, 7.34.

EXAMPLE 2-17

Triethyl 3-[1-[2-[4-[N-(5-methylpyridin-2-yl)-2-furancarboxamido]piperidin-1-yl]ethyl]cyclohexyl]-1,1,1-propanetricarboxylate

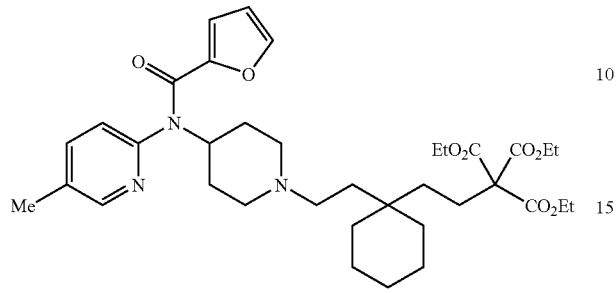

The title compound was synthesized from the compound obtained in Example 1D-5 in the same manner as in Example 2-1.

Free Form $^1$H-NMR (CDCl$_3$) δ: 1.20-1.46 (m, 13H), 1.28 (t, 9H, J=7.2 Hz), 1.53-1.70 (m, 4H), 1.90-2.13 (m, 5H), 2.20-2.29 (m, 2H), 2.38 (s, 3H), 2.94-3.03 (m, 2H), 4.25 (q, 6H, J=7.2 Hz), 4.74 (tt, 1H, J=4.0 Hz, 12.4 Hz), 5.93 (d, 1H, J=3.6 Hz), 6.19 (dd, 1H, J=1.6 Hz, 3.6 Hz), 6.99 (d, 1H, J=8.4 Hz), 7.20-7.24 (m, 1H), 7.47-7.53 (m, 1H), 8.38 (d, 1H, J=2.4 Hz).

Hydrochloride mp 131-134° C.; $^1$H-NMR (DMSO-d$_6$) δ: 1.15-1.28 (m, 4H), 1.20 (t, 9H, J==7.2 Hz), 1.29-1.47 (m, 8H), 1.53-1.63 (m, 2H), 1.77-1.95 (m, 4H), 1.99-2.09 (m, 2H), 2.37 (s, 3H), 2.87-2.97 (m, 2H), 3.06-3.18 (m, 2H), 3.46-3.58 (m, 2H), 4.19 (q, 6H, J=7.2 Hz), 4.76 (tt, 1H, J=4.0 Hz, 12.0 Hz), 5.92 (d, 1H, J=3.6 Hz), 6.36 (dd, 1H, J=1.6 Hz, 3.6 Hz), 7.24 (d, 1H, J=8.0 Hz), 7.54-7.58 (m, 1H), 7.74 (dd, 1H, J=2.4 Hz, 8.0 Hz), 8.40 (d, 1H, J=2.4 Hz), 9.13-9.25 (m, 1H); IR (KBr) cm$^{-1}$: 3451, 2932, 1755, 1732, 1660, 1646, 1469, 1324, 1265, 1253, 1210, 773 cm$^{-1}$; MS (ESI) m/z: 654 (MH$^+$); Anal. Calcd for C$_{36}$H$_{52}$ClN$_3$O$_8$.2H$_2$O: C, 59.53; H, 7.77; N, 5.79. Found: C, 59.42; H, 7.50; N, 5.65.

EXAMPLE 2-18

Dimethyl 3-[1-[2-[4-[N-(p-tolyl)-2-furancarboxamido]-piperidin-1-yl]ethyl]cyclohexyl]-1,1-propanedicarboxylate

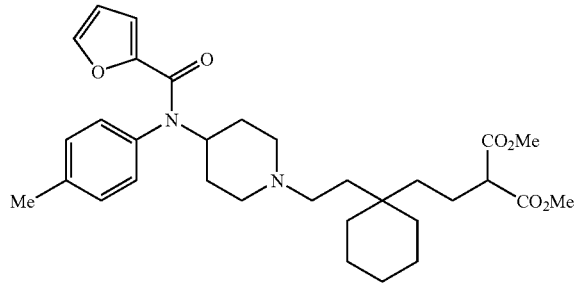

The title compound was synthesized from the compound obtained in Example 1D-6 in the same manner as in Example 2-1.

Free Form $^1$H-NMR (CDCl$_3$) δ: 1.15-1.45 (m, 14H), 1.45-1.59 (m, 2H), 1.67-1.90 (m, 4H), 2.06-2.16 (m, 2H), 2.17-2.26 (m, 2H), 2.39 (s, 3H), 2.92-3.03 (m, 2H), 3.26 (t, 1H, J=7.2 Hz), 3.74 (s, 6H), 4.72-4.83 (m, 1H), 5.30-5.40 (m, 1H), 6.13 (dd, 1H, J=1.6 Hz, 3.2 Hz), 7.02 (d, 2H, J=8.0 Hz), 7.18 (d, 2H, J=8.0 Hz), 7.33-7.38 (m, 1H); MS (ESI) m/z: 553 (MH$^+$).

EXAMPLE 2-19

2-[2-[1-[2-[4-[N-(5-Methylpyridin-2-yl)-2-furancarboxamido]piperidin-1-yl]ethyl]cyclohexyl]ethyl]-1,3-diacetoxypropane

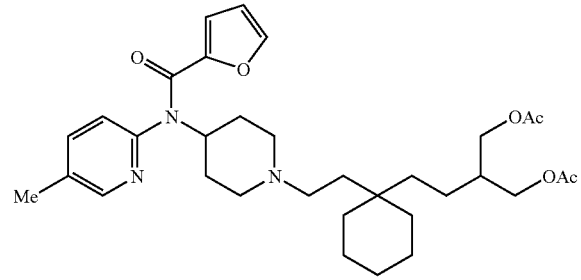

The title compound was synthesized from the compound obtained in Example 1D-7 in the same manner as in Example 2-1.

Free Form $^1$H-NMR (CDCl$_3$) δ: 1.14-1.47 (m, 15H), 1.53-1.70 (m, 2H), 1.84-2.15 (m, 6H), 2.05 (s, 6H), 2.16-2.27 (m, 2H), 2.38 (s, 3H), 2.92-3.04 (m, 2H), 4.02 (dd, 1H, J=4.8 Hz, 11.6 Hz), 4.07 (dd, 2H, J=4.8 Hz, 9.8 Hz), 4.73 (tt, 1H, J=4.0 Hz, 12.0 Hz), 5.94 (d, 1H, J=3.6 Hz), 6.19 (dd, 1H, J=1.6 Hz, 3.6 Hz), 6.99 (d, 1H, J=8.0 Hz), 7.20-7.24 (m, 1H), 7.50 (dd, 1H, J=2.4 Hz, 8.0 Hz), 8.37 (d, 1H, J=2.4 Hz).

Hydrochloride $^1$H-NMR (DMSO-d$_6$) δ: 1.10-1.66 (m, 17H), 1.78-1.95 (m, 2H), 1.97-2.09 (m, 2H), 2.01 (s, 6H), 2.37 (s, 3H), 2.84-2.94 (m, 2H), 3.03-3.16 (m, 2H), 3.47-3.56 (m, 2H), 3.78-4.07 (m, 4H), 4.69-4.80 (m, 1H), 5.91 (d, 1H, J=3.6 Hz), 6.36 (dd, 1H, J=1.6 Hz, 3.6 Hz), 7.24 (d, 1H, J=8.0 Hz), 7.54-7.58 (m, 1H), 7.73 (dd, 1H, J=2.4 Hz, 8.0 Hz), 8.40 (d, 1H, J=2.4 Hz), 9.50-9.71 (m, 1H); MS (ESI) m/z: 582 (MH$^+$).

EXAMPLE 2-20

2-[2-[1-[2-[4-[N-(p-Tolyl)-2-furancarboxamido]piperidin-1-yl]ethyl]cyclohexyl]ethyl]-1,3-diacetoxypropane

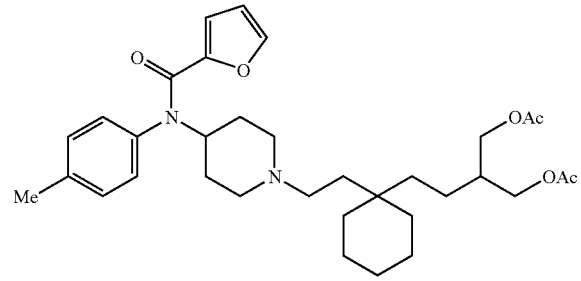

The title compound was synthesized from the compound obtained in Example 1D-8 in the same manner as in Example 2-1.

¹H-NMR (CDCl₃) δ: 1.15-1.30 (m, 8H), 1.31-1.66 (m, 10H), 1.81-1.94 (m, 3H), 2.03-2.13 (m, 2H), 2.05 (s, 6H), 2.15-2.23 (m, 2H), 2.39 (s, 3H), 2.92-3.00 (m, 2H), 4.01 (dd, 2H, J=6.4 Hz, 11.2 Hz), 4.07 (dd, 2H, J=5.2 Hz, 11.2 Hz), 4.77 (tt, 1H, J=4.0 Hz, 12.0 Hz), 5.32-5.39 (m, 1H), 6.13 (dd, 1H, J=1.6 Hz, 3.6 Hz), 7.01 (d, 2H, J=8.0 Hz), 7.18 (d, 2H, J=8.0 Hz), 7.33-7.36 (m, 1H); M (ESI) m/z: 581 (MH⁺).

EXAMPLE 2-21

N-[1-[2-[1-[4-(Methoxymethoxy)-3-(methoxymethoxymethyl)butyl]cyclohexyl]ethyl]piperidin-4-yl]-N-(5-methylpyridin-2-yl)-2-furancarboxamide

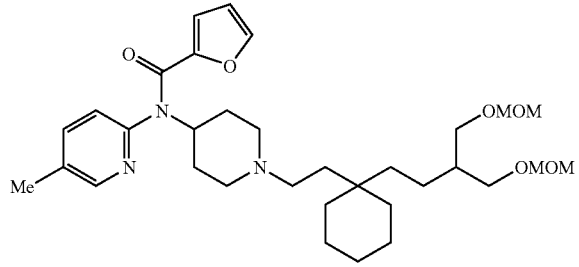

The title compound was synthesized from the compound obtained in Example 1D-9 in the same manner as in Example 2-1.

¹H-NMR (CDCl₃) δ: 1.19-1.46 (m, 16H), 1.54-1.67 (m, 2H), 1.70-1.79 (m, 1H), 1.89-1.98 (m, 2H), 2.03-2.13 (m, 2H), 2.18-2.27 (m, 2H), 2.38 (s, 3H), 2.92-3.02 (m, 2H), 3.36 (s, 6H), 3.46-3.56 (m, 4H), 4.61 (s, 4H), 4.74 (tt, 1H, J=4.0 Hz, 12.0 Hz), 5.93 (d, 1H, J=3.6 Hz), 6.19 (dd, 1H, J=2.0 Hz, 3.6 Hz), 6.99 (d, 1H, J=8.4 Hz), 7.20-7.24 (m, 1H), 7.50 (dd, 1H, J=2.4 Hz, 8.4 Hz), 8.38 (d, 1H, J=2.4 Hz); MS (ESI) m/z: 586 (MH⁺).

EXAMPLE 2-22

N-[1-[2-[1-(2-Phenyl-1,3-dioxan-5-yl)cyclohexyl]ethyl]piperidin-4-yl]-N-(5-methylpyridin-2-yl)-2-furancarboxamide

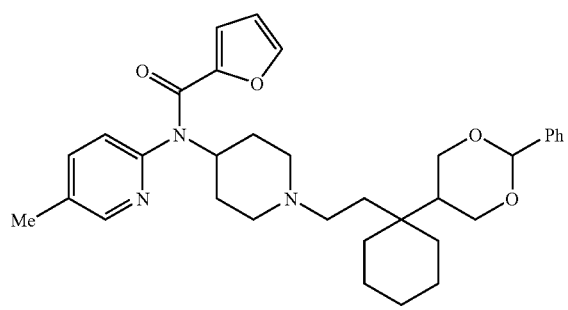

The title compound was synthesized from the compound obtained in Example 1D-10 in the same manner as in Example 2-1.

¹H-NMR (CDCl₃) δ: 1.24-1.40 (m, 5H), 1.40-1.55 (m, 7H), 1.55-1.69 (m, 2H), 1.91-2.01 (m, 2H), 2.08-2.26 (m, 3H), 2.27-2.35 (m, 2H), 2.37 (s, 3H), 2.94-3.06 (m, 2H), 3.87 (t, 2H, J=11.2 Hz), 4.24 (dd, 2H, J=4.4 Hz, 11.2 Hz), 4.75 (tt, 1H, J=4.4 Hz, 12.4 Hz), 5.36 (s, 1H), 5.94 (d, 1H, J=3.6 Hz), 6.19 (dd, 1H, J=1.6 Hz, 3.6 Hz), 6.99 (d, 1H, J=7.6 Hz), 7.21-7.24 (m, 1H), 7.29-7.35 (m, 3H), 7.44-7.52 (m, 3H), 8.38 (d, 1H, J=2.4 Hz).

EXAMPLE 2-23

N-[1-[2-[1-(2,2-Dimethyl-1,3-dioxan-5-yl)cyclohexyl]ethyl]piperidin-4-yl]-N-(p-tolyl)-2-furancarboxamide

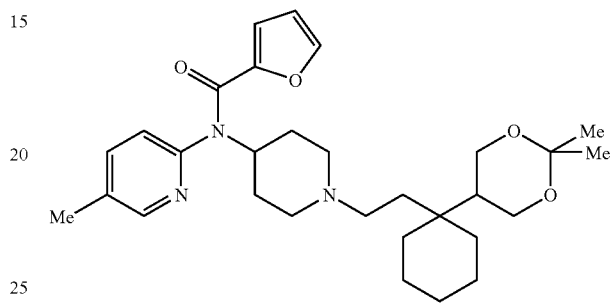

The title compound was synthesized from the compound obtained in Example 1D-11 in the same manner as in Example 2-1.

¹H-NMR (CDCl₃) δ: 1.19-1.60 (m, 14H), 1.36 (s, 3H), 1.39 (s, 3H), 1.81-1.92 (m, 2H), 1.95-2.07 (m, 1H), 2.08-2.18 (m, 2H), 2.22-2.31 (m, 2H), 2.39 (s, 3H), 2.92-3.02 (m, 2H), 3.76 (dd, 2H, J=4.8 Hz, 11.6 Hz), 3.84 (t, 2H, J=11.6 Hz), 4.78 (tt, 1H, J=4.0 Hz, 12.0 Hz), 5.30-5.40 (m, 1H), 6.14 (dd, 1H, J=1.6 Hz, 3.6 Hz), 7.02 (d, 1H, J=8.0 Hz), 7.19 (d, 2H, J=8.0 Hz), 7.33-7.38 (m, 1H); MS (ESI) m/z: 509 (MH⁺).

EXAMPLE 2-24

2-(Acetoxymethyl)-2-[2-[1-[2-[4-[N-(5-methylpyridin-2-yl)-2-furancarboxamido]piperidin-1-yl]ethyl]cyclohexyl]ethyl]-1,4-diacetoxybutane

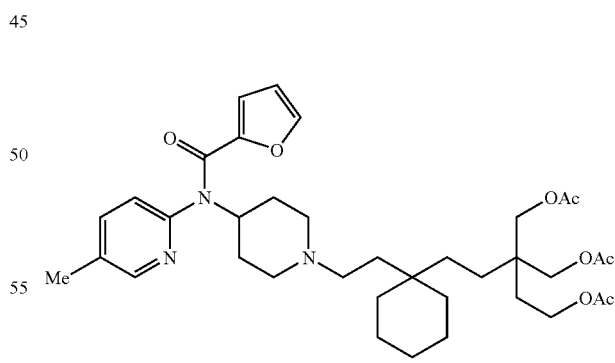

The title compound was synthesized from the compound obtained in Example 1D-12 in the same manner as in Example 2-1.

¹H-NMR (CDCl₃) δ: 1.12-1.46 (m, 16H), 1.55-1.73 (m, 5H), 1.91-1.99 (m, 2H), 2.01-2.12 (m, 1H), 2.04 (s, 3H), 2.06 (s, 6H), 2.16-2.24 (m, 2H), 2.38 (s, 3H), 2.93-3.01 (m, 2H), 3.94 (s, 4H), 4.12 (t, 2H, J=7.2 Hz), 4.68-4.79 (m, 1H), 5.93 (d, 1H, J=3.6 Hz), 6.19 (dd, 1H, J=1.6 Hz, 3.6 Hz), 6.99

(d, 1H, J=8.0 Hz), 7.20-7.25 (m, 1H), 7.50 (dd, 1H, J=2.0 Hz, 8.0 Hz), 8.38 (d, 1H, J=2.0 Hz); MS (ESI) m/z: 668 (MH⁺).

EXAMPLE 2-25

Methyl 5,5-bis(benzoyloxymethyl)-7-[1-[2-[4-[N-(5-methylpyridin-2-yl)-2-furancarboxamido]piperidin-1-yl]ethyl]cyclohexyl]heptanoate

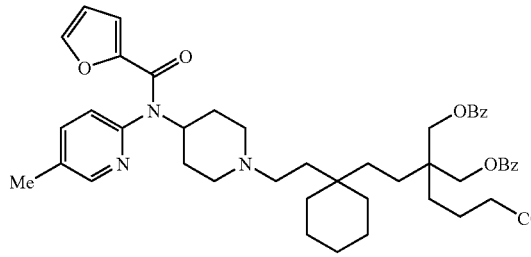

The title compound was synthesized from the compound obtained in Example 1D-13 in the same manner as in Example 2-1.

$^1$H-NMR (CDCl$_3$) δ: 1.14-1.55 (m, 19H), 1.61-1.82 (m, 7H), 2.03-2.13 (m, 2H), 2.34 (t, 2H, J=7.2 Hz), 2.39 (s, 3H), 2.73-2.82 (m, 2H), 3.62 (s, 3H), 4.26 (d, 2H, J=11.6 Hz), 4.31 (d, 2H, J=11.6 Hz), 4.57-4.69 (m, 1H), 5.28-5.34 (m, 1H), 6.14 (dd, 1H, J=1.6 Hz, 3.6 Hz), 6.99 (d, 2H, J=8.0 Hz), 7.18 (d, 2H, J=8.0 Hz), 7.37 (d, 1H, J=1.6 Hz), 7.41-7.49 (m, 4H), 7.56-7.64 (m, 2H), 7.98-8.05 (m, 4H).

EXAMPLE 2-26

N-[1-[2-[1-(2-Cyanoethyl)cyclohexyl]ethyl]piperidin-4-yl]-N-(5-methylpyridin-2-yl)-2-furancarboxamide

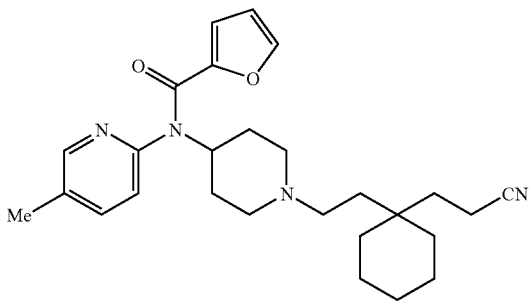

The title compound was synthesized from the compound obtained in Example 1B-3 in the same manner as in Example 2-1.

Hydrochloride $^1$H-NMR (DMSO-d$_6$) δ: 1.18-1.40 (m, 12H), 1.55-1.60 (m, 4H), 1.81-1.91 (m, 2H), 2.03 (d, 2H, J=13.2 Hz), 2.37 (s, 3H), 2.43 (t, 2H, J=7.8 Hz), 2.91 (m, 2H), 3.03-3.12 (m, 2H), 3.53 (d, 2H, J=12.2 Hz), 4.73 (t, 1H, J=12.2 Hz), 5.87 (d, 1H, J=2.9 Hz), 6.38 (dd, 1H, J=1.9, 3.4 Hz), 7.27 (d, 1H, J=8.3 Hz), 7.59 (d, 1H, J=1.0 Hz), 7.75 (dd, 1H, J=2.0, 8.3 Hz), 8.41 (d, 1H, J=2.0 Hz); IR (KBr) cm$^{-1}$: 3431, 2928, 2638, 2528, 2244, 1623, 1593, 1469, 1400, 1339, 1229, 1190, 1030, 754; MS (ESI) m/z: 449 (MH⁺).

EXAMPLE 2-27

N-[1-[2-[1-(2-Methanesulfonamidoethyl)cyclohexyl]ethyl]piperidin-4-yl]-N-(5-methylpyridin-2-yl)-2-furancarboxamide

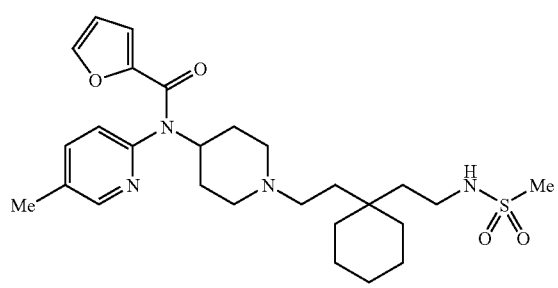

The title compound was synthesized from the compound obtained in Example 1D-15 in the same manner as in Example 2-1.

Hydrochloride $^1$H-NMR (DMSO-d$_6$) δ: 1.19-1.25 (m, 4H), 1.32-1.48 (m, 8H), 1.64 (m, 2H), 1.88 (q like, 2H), 2.03 (brd, 2H, J=12.7 Hz), 2.38 (s, 3H), 2.26 (s, 2H), 2.91-3.00 (m, 7H), 3.10 (q like, 2H), 3.53 (d, 2H, J=11.3 Hz), 4.76 (t like, 1H), 5.86 (d, 1H, J=3.5 Hz), 6.36 (m, 1H), 6.88-7.00 (m, 1H), 7.26 (d, 1H, J=8.3 Hz), 7.58 (s, 1H), 7.75 (d, 1H, J=7.8 Hz), 8.41 (s, 1H), 9.78-9.87 (m, 1H).

EXAMPLE 2-28

N-(1-Cyclohexylpiperidin-4-yl)-N-(5-methylpyridin-2-yl)-2-furancarboxamide

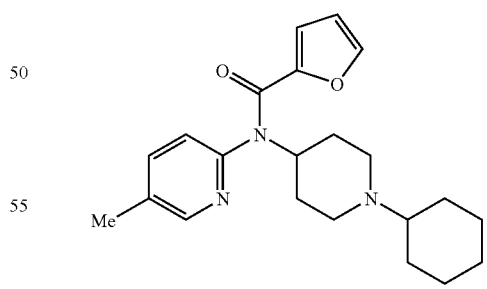

The title compound was synthesized from the compound obtained in Example 1E-1 in the same manner as in Example 2-1.

$^1$H-NMR (CDCl$_3$) δ: 0.99-1.33 (m, 5H), 1.49-1.66 (m, 2H), 1.71-1.89 (m, 3H), 1.91-2.02 (m, 2H), 2.18-2.53 (m, 3H), 2.37 (s, 3H), 2.93-2.96 (m, 2H), 4.71 (tt, 1H, J=4.0 Hz, 12.4 Hz), 5.92 (d, 1H, J=3.6 Hz), 6.18 (dd, 1H, J=1.6 Hz, 3.6 Hz), 7.00 (d, 1H, J=8.0 Hz), 7.21-7.24 (m, 1H), 7.48-7.52 (m, 1H), 8.37-8.39 (m, 1H).

Hydrochloride mp 213-216° C.; $^1$H-NMR (DMSO-$d_6$) δ: 1.01-1.15 (m, 1H), 1.16-1.42 (m, 4H), 1.54-1.65 (m, 1H), 1.74-2.08 (m, 8H), 2.37 (s, 3H), 3.01-3.23 (m, 3H), 3.38-3.42 (m, 2H), 4.78 (tt, 1H, J=4.0 Hz, 12.0 Hz), 5.87-5.89 (m, 1H), 6.35 (dd, 1H, J=2.0 Hz, 7.2 Hz), 7.25 (d, 1H, J=8.2 Hz), 7.55-7.58 (m, 1H), 7.74 (dd, 1H, J=2.0 Hz, 8.2 Hz), 8.38-8.41 (m, 1H); IR (KBr) cm$^{-1}$: 2641, 2502, 1652, 1644, 1620, 1464, 1319, 1191, 770; MS (ESI) m/z: 368 (MH$^+$); Anal. Calcd for $C_{22}H_{29}N_3O_2 \cdot 2HCl$: C, 60.00; H, 7.09; N, 9.54. Found: C, 60.11; H, 7.23; N, 9.54.

EXAMPLE 2-29

N-[1-[2-(Cyclohexylacetamido)benzyl]piperidin-4-yl]-N-(5-methylpyridin-2-yl)-2-furancarboxamide

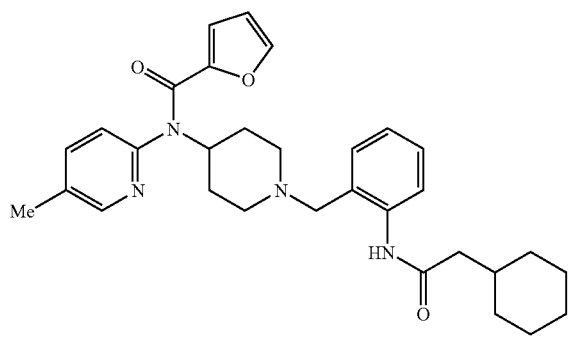

The title compound was synthesized from the compound obtained in Example 1G-2 in the same manner as in Example 2-1.

Free Form $^1$H-NMR (CDCl$_3$) δ: 0.81-0.96 (m, 2H), 1.07-1.32 (m, 4H), 1.53-1.86 (m, 7H), 1.95-2.06 (m, 4H), 2.17-2.27 (m, 2H), 2.40 (s, 3H), 2.86-2.96 (m, 2H), 3.56 (s, 2H), 4.78 (tt, 1H, J=4.0 Hz, 12.0 Hz), 6.01 (d, 1H, J=3.2 Hz), 6.21 (dd, 1H, J=1.6 Hz, 3.2 Hz), 6.93-7.00 (m, 2H), 7.02-7.08 (m, 1H), 7.21-7.28 (m, 2H), 7.52 (dd, 1H, J=2.4 Hz, 8.4 Hz), 8.24 (d, 1H, J=8.4 Hz), 8.41 (d, 1H, J=2.4 Hz), 10.77 (brs, 1H).

Hydrochloride mp 141-144° C.; $^1$H-NMR (DMSO-$d_6$) δ: 0.93-1.09 (m, 2H), 1.10-1.31 (m, 3H), 1.56-2.06 (m, 10H), 2.27-2.39 (m, 2H), 2.35 (s, 3H), 3.14-3.27 (m, 2H), 3.28-3.38 (m, 2H), 4.15-4.24 (m, 2H), 4.72-4.83 (m, 1H), 5.88 (d, 1H, J=3.6 Hz), 6.35 (dd, 1H, J=1.6 Hz, 3.6 Hz), 7.21 (d, 1H, J=8.4 Hz), 7.24-7.31 (m, 1H), 7.38-7.46 (m, 2H), 7.52-7.59 (m, 2H), 7.71 (dd, 1H, J=2.4 Hz, 8.4 Hz), 8.36 (d, 1H, J=2.4 Hz), 9.87 (brs, 1H), 9.95-10.05 (m, 1H); IR (KBr) cm$^{-1}$: 3444, 2923, 2849, 1651, 1470, 1454, 1336, 1322, 1189; MS (ESI) m/z: 515 (MH$^+$); Anal. Calcd for $C_{31}H_{42}Cl_2N_4O_4 \cdot H_2O$: C, 61.48; H, 6.99; N, 9.25. Found: C, 61.63; H, 7.05; N, 9.14.

EXAMPLE 2-30

Methyl 5,5-bis(benzoyloxymethyl)-7-[1-[2-[4-[N-(p-tolyl)-2-furancarboxamide]piperidin-1-yl]ethyl]cyclohexyl]heptanoate

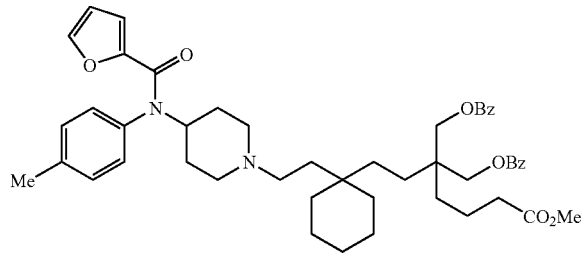

The title compound was synthesized from the compound obtained in Example 1D-14 in the same manner as in Example 2-1.

$^1$H-NMR (CDCl$_3$) δ: 1.15-1.56 (m, 19H), 1.62-1.84 (m, 7H), 2.03-2.14 (m, 2H), 2.34 (t, 2H, J=6.8 Hz), 2.38 (s, 3H), 2.74-2.84 (m, 2H), 3.62 (s, 3H), 4.26 (d, 2H, J=11.2 Hz), 4.31 (d, 2H, J=11.2 Hz), 4.54-4.65 (m, 1H), 5.87 (d, 1H, J=3.6 Hz), 6.19 (dd, 1H, J=1.6 Hz, 3.6 Hz), 6.97 (d, 1H, J=8.4 Hz), 7.22-7.26 (m, 1H), 7.41-7.53 (m, 5H), 7.56-7.63 (m, 2H), 7.97-8.05 (m, 4H), 8.38 (d, 1H, J=2.0 Hz).

EXAMPLE 2-31

2-[1-[2-[4-[N-(5-Methylpyridin-2-yl)-2-furancarboxamido]piperidin-1-yl]ethyl]cyclohexyl]ethyl 2-furancarboxylate

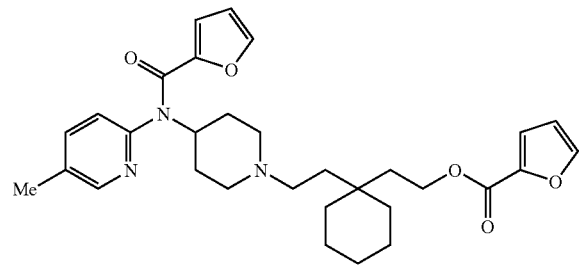

The title compound was synthesized from the compound obtained in Example 1F-1 in the same manner as in Example 2-1.

Free Form $^1$H-NMR (CDCl$_3$) δ: 1.24-1.52 (m, 12H), 1.54-1.68 (m, 2H), 1.69-1.77 (m, 2H), 1.89-1.98 (m, 2H), 2.05-2.15 (m, 2H), 2.26-2.35 (m, 2H), 2.38 (s, 3H), 2.93-3.03 (m, 2H), 4.73 (tt, 1H, J=4.0 Hz, 12.0 Hz), 5.94 (d, 1H, J=3.6 Hz), 6.19 (dd, 1H, J=1.6 Hz, 3.6 Hz), 6.49 (dd, 1H, 1.6 Hz, 3.6 Hz), 6.99 (d, 1H, J=8.0 Hz), 7.18 (d, 1H, J=3.6 Hz), 7.21-7.24 (m, 1H), 7.50 (dd, 1H, J=2.4 Hz, 8.0 Hz), 7.55-7.59 (m, 1H), 8.38 (d, 1H, J=2.4 Hz).

Hydrochloride mp 123-126° C.; $^1$H-NMR (DMSO-$d_6$) δ: 1.22-1.48 (m, 10H), 1.61-1.72 (m, 4H), 1.77-1.95 (m, 2H), 1.99-2.09 (m, 2H), 2.37 (s, 3H), 2.95-3.16 (m, 4H), 3.47-3.60 (m, 2H), 4.28 (t, 2H, J=7.2 Hz), 4.68-4.79 (m, 1H), 5.92 (d, 1H, J=3.2 Hz), 6.36 (dd, 1H, J=1.6 Hz, 3.2 Hz), 6.68 (dd, 1H, J=1.6 Hz, 3.2 Hz), 7.22-7.28 (m, 2H), 7.56 (d, 1H, J=1.6 Hz), 7.74 (dd, 1H, J=2.4 Hz, 8.0 Hz), 7.92-7.96 (m, 1H), 8.40 (d, 1H, J=2.4

Hz), 9.33-9.47 (m, 1H); IR (KBr) cm$^{-1}$: 3440, 2929, 2507, 1717, 1673, 1621, 1556, 1471, 1303, 1174, 1122, 758; MS (ESI) m/z: 534 (MH$^+$); Anal. Calcd for $C_{31}H_{41}Cl_2N_3O_5 \cdot 1/2H_2O$: C, 60.48; H, 6.88; N. 6.83. Found: C, 60.60; H, 6.99; N, 6.79.

EXAMPLE 2-32 tert-Butyl [2-[1-[2-[4-[N-(5-methylpyridin-2-yl)-2-furancarboxamido]piperidin-1-yl]ethyl]cyclohexyl]ethyl]carbamate

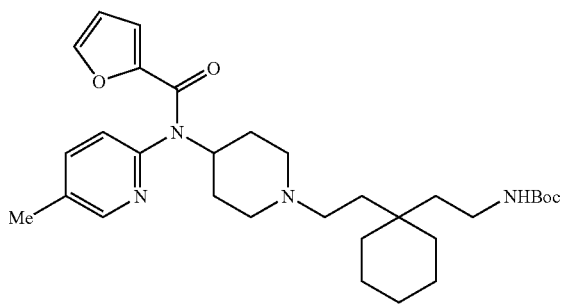

The title compound was synthesized from the compound obtained in Example 1G-1 in the same manner as in Example 2-1.

$^1$H-NMR (DMSO-d$_6$) δ: 1.16-1.26 (m, 4H), 1.27-1.40 (m, 10H), 1.36 (s, 9H), 1.41-1.52 (m, 2H), 1.70-1.80 (m, 2H), 1.90-2.00 (m, 2H), 2.14-2.23 (m, 2H), 2.35 (s, 3H), 2.80-2.91 (m, 4H), 4.43 (tt, 1H, J=3.9 Hz, 12.2 Hz), 5.85 (d, 1H, J=3.4 Hz), 6.33 (dd, 1H, J=2.0 Hz, 3.4 Hz), 6.50-6.60 (m, 1H), 7.16 (d, 1H, J=7.8 Hz), 7.68 (dd, 1H, J=2.4 Hz, 7.8 Hz), 8.35 (d, 1H, J=2.4 Hz).

EXAMPLE 2-33

N-[1-[2-[2-(Cyclohexylacetamido)phenyl]ethyl]piperidin-4-yl]-N-(p-tolyl)-2-furancarboxamide

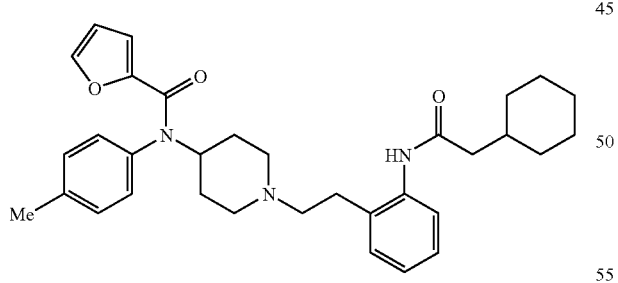

The title compound was synthesized from the compound obtained in Example 1G-3 in the same manner as in Example 2-1.

Hydrochloride mp 201-204° C.; $^1$H-NMR (DMSO-d$_6$) δ: 0.95-1.09 (m, 2H), 1.10-1.32 (m, 4H), 1.60-1.84 (m, 7H), 2.00-2.12 (m, 2H), 2.20-2.29 (m, 2H), 2.39 (s, 3H), 2.88-2.98 (m, 2H), 3.12-3.24 (m, 4H), 3.50-3.60 (m, 2H), 4.78-4.89 (m, 1H), 5.46-5.52 (m, 1H), 6.31-6.32 (m, 1H), 7.16-7.33 (m, 8H), 7.62-7.63 (m, 1H), 9.39-9.40 (m, 1H); IR (KBr) cm$^{-1}$: 3426, 3216, 3174, 2921, 2848, 2533, 2488, 1674, 1645, 1524, 1513, 1473, 1447, 1401, 1338, 754; MS (ESI+) m/z: 528 (MH$^+$).

EXAMPLE 2-34

N-[1-[3-[2-(3-Cyclohexylpropionamido)phenyl]propyl]piperidin-4-yl]-N-(p-tolyl)-2-furancarboxamide

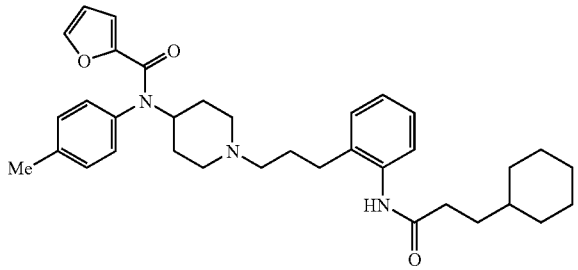

The title compound was synthesized from the compound obtained in Example 1G-4 in the same manner as in Example 2-1.

Hydrochloride mp 113-117° C.; $^1$H-NMR (DMSO-d$_6$) δ: 0.85-0.97 (m, 2H), 1.11-1.32 (m, 4H), 1.44-1.53 (m, 2H), 1.58-1.80 (m, 7H), 1.84-1.94 (m, 2H), 1.97-2.08 (m, 2H), 2.29-2.39 (m, 2H), 2.38 (s, 3H), 2.52-2.63 (m, 2H), 2.90-3.00 (m, 2H), 3.07-3.12 (m, 2H), 3.40-3.52 (m, 2H), 4.75-4.89 (m, 1H), 5.48-5.50 (m, 1H), 6.29-6.32 (m, 1H), 7.00-7.40 (m, 8H), 7.60-7.62 (m, 1H), 9.26 (s, 1H); IR (KBr) cm$^{-1}$: 3432, 3246, 2932, 2849, 1686, 1635, 1519, 1467, 1449, 1392, 1330, 1246, 1184, 1157, 761; MS (ESI+) m/z: 556 (MH$^+$).

EXAMPLE 2-35

1-[2-[4-[N-(5-Methylpyridin-2-yl)-2-furancarboxamido]piperidin-1-yl]ethyl]cyclohexanecarboxylic acid

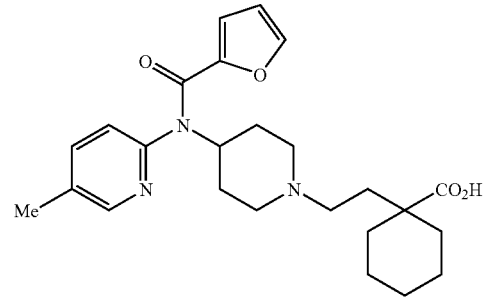

The title compound was synthesized from the compound obtained in Example 1H-2 in the same manner as in Example 2-1.

Free Form $^1$H-NMR (DMSO-d$_6$) δ: 1.07-1.35 (m, 5H), 1.38-1.57 (m, 7H), 1.70-1.80 (m, 2H), 1.81-1.91 (m, 2H), 1.93-2.05 (m, 2H), 2.15-2.24 (m, 2H), 2.35 (s, 3H), 2.80-2.92 (m, 2H), 4.44 (tt, 1H, J=4.0 Hz, 12.0 Hz), 5.84 (d, 1H, J=3.2 Hz), 6.33

(dd, 1H, J=1.6 Hz, 3.2 Hz), 7.17 (d, 1H, J=8.0 Hz), 7.50-7.55 (m, 1H), 7.65-7.70 (m, 1H), 8.33-8.37 (m, 1H).

Hydrochloride $^1$H-NMR (DMSO-d$_6$) δ: 1.16-1.38 (m, 5H), 1.42-1.58 (m, 3H), 1.77-1.92 (m, 6H), 1.96-2.05 (m, 2H), 2.36 (s, 3H), 2.86-2.96 (m, 2H), 3.04-3.16 (m, 2H), 3.44-3.53 (m, 2H), 4.73 (tt, 1H, J=3.6 Hz, 12.4 Hz), 5.90 (d, 1H, J=3.6 Hz), 6.36 (dd, 1H, J=1.6 Hz, 3.6 Hz), 7.24 (d, 1H, J=8.0 Hz), 7.57 (d, 1H, J=1.6 Hz), 7.73 (dd, 1H, J=2.0 Hz, 8.0 Hz), 8.39 (d, 1H, J=2.0 Hz), 9.59-9.73 (m, 1H); IR (KBr) cm$^{-1}$: 3417, 2934, 2858, 1713, 1633, 1469, 1318, 1190, 1130, 1031, 769; MS (ESI) m/z: 440 (MH$^+$).

EXAMPLE 2-36 tert-Butyl [2-[3-[4-[N-(p-tolyl)-2-furancarboxamido]piperidin-1-yl]propyl]phenyl]carbamate

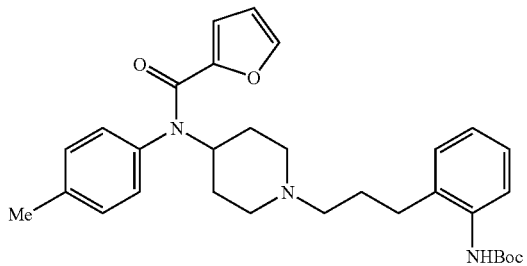

The title compound was synthesized from the compound obtained in Example 1B-5 in the same manner as in Example 2-1.

$^1$H-NMR (CDCl$_3$) δ: 1.44 (s, 9H), 1.54-1.70 (m, 2H), 1.71-1.85 (m, 4H), 2.07-2.19 (m, 2H), 2.23 (t, 2H, J=6.4 Hz), 2.42 (s, 3H), 2.57 (t, 2H, J=6.4 Hz), 2.84-2.96 (m, 2H), 4.73 (tt, 1H, J=4.0 Hz, 12.0 Hz), 5.27-5.39 (m, 1H), 6.14 (dd, 1H, J=2.0 Hz, 3.6 Hz), 6.93-7.16 (m, 5H), 7.16-7.25 (m, 2H), 7.31-7.37 (m, 1H), 7.45-7.56 (m, 1H), 8.00-8.38 (m, 1H).

EXAMPLE 2-37 tert-Butyl [2-[2-[4-[N-(5-methylpyridin-2-yl)-2-furancarboxamido]piperidin-1-yl]ethyl]phenyl]carbamate

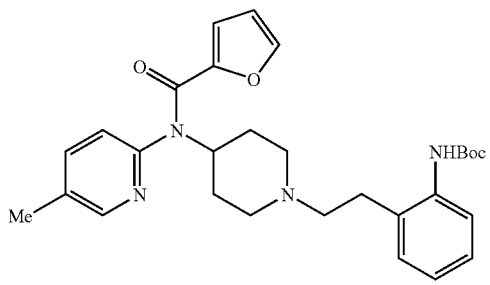

The title compound was synthesized from the compound obtained in Example 1A-9 in the same manner as in Example 2-1.

$^1$H-NMR (CDCl$_3$) δ: 1.44 (s, 9H), 1.68-1.82 (m, 2H), 1.88-1.97 (m, 2H), 2.21-2.32 (m, 2H), 2.41 (s, 3H), 2.53-2.60 (m, 2H), 2.64-2.71 (m, 2H), 2.97-3.06 (m, 2H), 4.71 (tt, 1H, J=4.0 Hz, 12.0 Hz), 5.93 (d, 1H, J=3.6 Hz), 6.20 (dd, 1H, J=1.6 Hz, 3.6 Hz), 6.94-7.09 (m, 3H), 7.14-7.20 (m, 1H), 7.21-7.24 (m, 1H), 7.53 (dd, 1H, J=2.4 Hz, 8.0 Hz), 7.60-7.67 (m, 1H), 8.40 (d, 1H, J=2.4 Hz); IR (KBr) cm$^{-1}$: 2945, 2815, 1718, 1640, 1591, 1482, 1331, 1297, 1253, 1166, 1029, 761; M (ESI) m/z: 505 (MH$^+$); Anal. Calcd for C$_{29}$H$_{36}$N$_4$O$_4$·1/2H$_2$O: C, 67.81; H, 7.26; N, 10.91. Found: C, 67.57; H, 7.16; N, 10.83.

EXAMPLE 3A-1

[2-[1-[2-[4-[N-(5-Methylpyridin-2-yl)-2-furancarboxamido]piperidin-1-yl]ethyl]cyclohexyl]acetamido]acetic acid

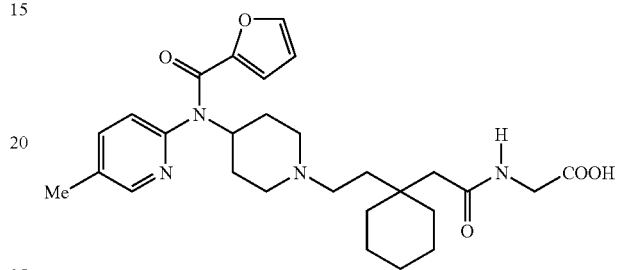

Ethyl [2-[1-[2-[4-[N-(5-methylpyridin-2-yl)-2-furancarboxamido]piperidin-1-yl]ethyl]cyclohexyl]acetamido]acetate (221 mg) was dissolved in methanol (5 mL). A 2N aqueous sodium hydroxide solution (2.1 mL) was added to the solution, and it was stirred at room temperature for 16 hours. The solution was neutralized by addition of acetic acid (0.25 mL) (to pH of about 6). The solvent was distilled off under reduced pressure, and the resulting residue was extracted with 20% ethanol/chloroform. The organic layer was dried over anhydrous magnesium sulfate and the solvent was distilled off under reduced pressure to give the title compound (170 mg).

Hydrochloride $^1$H-NMR (DMSO-d$_6$) δ: 1.22-1.39 (m, 11H), 1.70-1.73 (m, 2H), 1.82-1.90 (m, 2H), 1.97-2.01 (d like, 2H), 2.07 (s, 2H), 2.35 (s, 3H), 3.06-3.11 (m, 4H), 3.47 (d, 2H, J=11.7 Hz), 3.59 (s, 2H), 4.74 (t like, 1H), 5.84 (d, 1H, J=3.4 Hz), 6.36 (dd, 1H, J=1.5, 3.4 Hz), 7.26 (d, 1H, J=8.3 Hz), 7.59 (s, 1H), 7.74 (d, 1H, J=8.3 Hz), 8.39 (s, 1H), 9.84-9.94 (m, 1H); IR (KBr) cm$^{-1}$: 3418, 2928, 2856, 2706, 1742, 1651, 1556, 1470, 1403, 1384, 1319, 1210, 1189, 1034, 769; MS (ESI) m/z: 511 (MH$^+$).

EXAMPLE 3A-2

3-[2-[1-[2-[4-[N-(5methylpyridin-2-yl)-2-furancarboxamido]-piperidin-1-yl]ethyl]cyclohexyl]acetamido]propionic acid

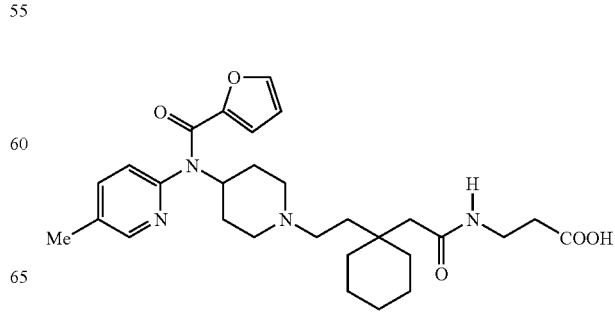

EXAMPLE 3A-3

[1-[2-[4-[N-(5-Methylpyridin-2-yl)-2-furancarboxamido]piperidin-1-yl]ethyl]cyclohexyl]acetic acid

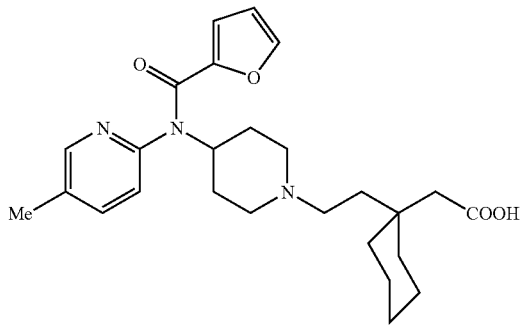

The title compound was synthesized from the compound obtained in Example 2-6 in the same manner as in Example 3A-1.

Free Form mp 220-222° C. (dec); $^1$H-NMR (DMSO-d$_6$) δ: 1.17-1.55 (m, 14H), 1.75-1.83 (m, 2H), 2.05-2.14 (m, 4H), 2.28-2.36 (m, 5H), 2.93-3.00 (m, 2H), 4.43-4.53 (m, 1H), 5.79 (d, 1H, J=3.5 Hz), 6.33 (dd, 1H, J=1.5 Hz, 3.5 Hz), 7.18 (d, 1H, J=7.8 Hz), 7.55 (d, 1H, J=1.5 Hz), 7.70 (dd, 1H, J=2.0 Hz, 7.8 Hz), 8.36 (d, 1H, J=2.0 Hz).

Hydrochloride mp 120-130° C. (dec); $^1$H-NMR (CDCl$_3$) δ: 1.30-1.55 (m, 10H), 1.90-1.98 (m, 2H), 2.20-2.38 (m, 6H), 2.47 (s, 3H), 3.00-3.14 (m, 4H), 3.53-3.63 (m, 2H), 4.95-5.05 (m, 1H), 6.21-6.28 (m, 2H), 7.22 (brs, 1H), 7.27-7.33 (m, 1H), 7.81-7.87 (m, 1H), 8.45 (brs, 1H), 11.59 (brs, 1H).

EXAMPLE 3A-4

[1-[2-[4-[N-(5-Methylpyridin-2-yl)-2-furancarboxamido]piperidin-1-yl]ethyl]cyclopentyl]acetic acid

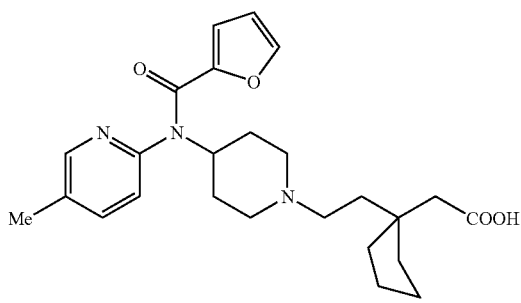

The title compound was synthesized from the compound obtained in Example 2-7 in the same manner as in Example 3A-1.

Hydrochloride $^1$H-NMR (DMSO-d$_6$) δ: 1.38-1.57 (m, 8H), 1.72-1.82 (m, 4H), 2.00-2.03 (m, 2H), 2.18 (s, 1H), 2.35 (s, 3H), 2.99-3.09 (m, 4H), 3.48 (d, 2H, J=6.8 Hz), 4.70-4.77 (m, 1H), 5.87 (d, 2H, J=2.9 Hz), 6.37 (dd, 1H, J=5.4 Hz), 7.26 (d, 1H, J=7.8 Hz), 7.59 (d, 1H, J=1.4 Hz), 7.74 (d, 1H, J=7.3 Hz), 8.40 (s, H); MS (ESI) m/z: 440 (MH$^+$).

EXAMPLE 3B-1

[1-[2-[4-[N-(p-Tolyl)-2-furancarboxamido]piperidin-1-yl]ethyl]cyclohexyl]acetic acid

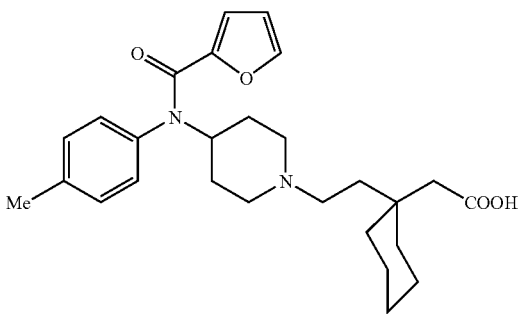

To methyl [1-[2-[4-[N-(p-tolyl)-2-furancarboxamido]piperidin-1-yl]ethyl]cyclohexyl]acetate (0.5241 g) and lithium hydroxide monohydrate (0.94 g) were added 1,4-dioxane (20 mL) and water (5 mL). The resulting suspension was stirred at room temperature for 3 days. The reaction solution was brought to dryness and the residue was diluted with water. Acetic acid (1.0 mL) was then added to the solution and it was extracted with 25% ethanol/chloroform. The extract was dried over (MgSO$_4$) and the solvent was distilled off under reduced pressure. The resulting residue was purified by chromatography (silica gel, 10% methanol/chloroform) to give the title compound (0.36 g), which was then converted to its hydrochloride by hydrochloric acid to give the title compound as a white solid (0.3805 g).

Hydrochloride mp 235-240° C.; $^1$H-NMR (DMSO-d$_6$) δ: 0.25-1.49 (m, 10H), 1.63-1.81 (m, 4H), 1.97-2.06 (m, 2H), 2.16 (s, 2H), 2.38 (s, 3H), 2.93-3.04 (m, 2H), 3.05-3.19 (m, 2H), 3.40-3.53 (m, 2H), 4.73-4.86 (m, 1H), 5.50 (d, 1H, J=3.4 Hz), 6.32 (dd, 1H, J=2.0 Hz, 3.4 Hz), 7.16 (d, 1H, J=7.8 Hz), 7.30 (d, 1H, J=7.8 Hz), 7.63 (d, 1H, J=2.0 Hz); IR (KBr) cm$^{-1}$: 2931, 2650, 1721, 1642, 1151, 1469, 1396, 1343, 1316, 1235, 1188, 1129, 1032, 948, 770, 757; MS (ESI) 453 m/z: (MH$^+$).

EXAMPLE 3B-2

3-[1-[2-[4-[N-(p-Tolyl)-2-furancarboxamido]piperidin-1-yl]ethyl]cyclohexyl]-1,1-propanedicarboxylic acid

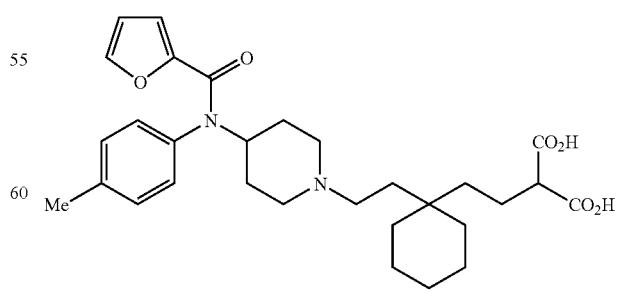

The title compound was synthesized from the compound obtained in Example 2-18 in the same manner as in Example 3B-1.

Free Form $^1$H-NMR (CDCl$_3$) δ: 1.03-1.66 (m, 18H), 1.72-1.87 (m, 1H), 1.97-2.21 (m, 3H), 2.41 (s, 3H), 2.75-3.03 (m, 3H), 3.48-3.69 (m, 2H), 4.79-4.99 (m, 1H), 5.88-6.02 (m, 1H), 6.14-6.29 (m, 1H), 6.90-7.02 (m, 1H), 7.48-7.64 (m, 1H), 8.30-8.44 (m, 1H).

Hydrochloride mp 136-139° C.; $^1$H-NMR (DMSO-d$_6$) δ: 1.12-1.29 (m, 6H), 1.30-1.48 (m, 6H), 1.53-1.70 (m, 4H), 1.78-1.94 (m, 2H), 1.98-2.09 (m, 2H), 2.37 (s, 3H), 2.86-2.97 (m, 2H), 3.02-3.22 (m, 3H), 3.48-3.58 (m, 2H), 4.68-4.80 (m, 1H), 5.91 (d, 1H, J=3.6 Hz), 6.36 (dd, 1H, J=1.6 Hz, 3.6 Hz), 7.24 (d, 1H, J=8.4 Hz), 7.54-7.57 (m, 1H), 7.73 (dd, 1H, J=2.4 Hz, 8.4 Hz), 8.38-8.42 (m, 1H), 9.35-9.51 (m, 1H), 12.29-12.85 (m, 2H); IR (KBr) cm$^{-1}$: 3424, 2928, 1726, 1633, 1469, 1402, 1339, 1229, 1192, 755; MS (ESI) m/z: 526 (MH$^+$).

EXAMPLE 3B-3

4-[2-[1-[2-[4-[N-(p-Tolyl)-2-furancarboxamido]-piperidin-1-yl]ethyl]cyclohexyl]acetamido]butyric acid

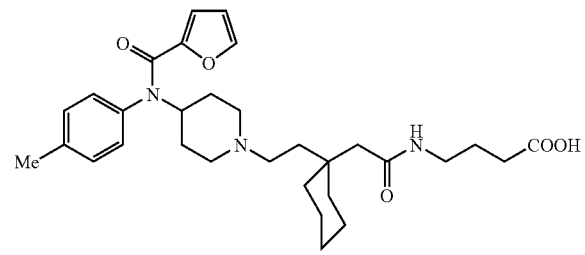

The title compound was synthesized from the compound obtained in Example 4B-3 in the same manner as in Example 3B-1.

Hydrochloride $^1$H-NMR (DMSO-d$_6$) δ: 1.20-1.50 (m, 10H), 1.59-1.80 (m, 6H), 1.98-2.08 (m, 4H), 2.19-2.24 (m, 2H), 2.38 (s, 3H), 3.00-3.18 (m, 6H), 3.44-3.55 (m, 2H), 4.75-4.88 (m, 1H), 5.50 (d, 1H, J=3.4 Hz), 6.32 (dd, 1H, J=1.5 Hz, 3.4 Hz), 7.15 (d, 2H, J=8.3 Hz), 7.29 (d, 2H, J=8.3 Hz), 7.62 (d, 1H, J=1.5 Hz), 7.90-7.96 (m, 1H); IR (NaCl film) cm$^{-1}$: 3387, 2928, 2859, 1719, 1637, 1630, 1468, 757, 734; MS (ESI) m/z: 538 (MH$^+$).

EXAMPLE 3B-4

2-[1-[2-[4-[N-(5-Methylpyridin-2-yl)-2-furancarboxamido]piperidin-1-yl]ethyl]cyclohexyl]acetyliminodiacetic acid

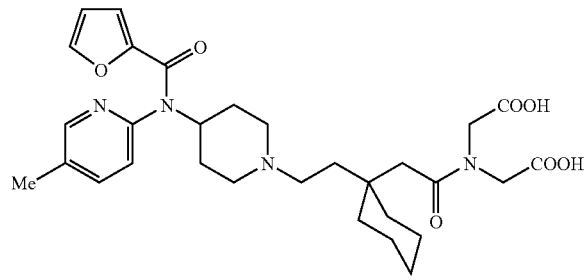

The title compound was synthesized from the compound obtained in Example 4C-1 in the same manner as in Example 3B-1.

Hydrochloride $^1$H-NMR (DMSO-d$_6$) δ: 1.25-1.50 (m, 10H), 1.75-1.96 (m, 4H), 1.98-2.06 (m, 2H), 2.15-2.28 (m, 2H), 2.37 (s, 3H), 2.90-3.12 (m, 4H), 3.40-3.52 (m, 2H), 3.60-3.70 (m, 2H), 4.20-4.40 (m, 2H), 4.68-4.80 (m, 1H), 5.89 (d, 1H, J=3.4 Hz), 6.35 (dd, 1H, J=1.5 Hz, 3.4 Hz), 7.23 (d, 1H, J=7.8 Hz), 7.56 (d, 1H, J=1.5 Hz), 7.72-7.75 (m, 1H), 8.39-8.40 (m, 1H); IR (KBr) cm$^{-1}$: 3444, 1738, 1634, 1469, 1406; MS (ESI) 569 m/z: (MH$^+$).

EXAMPLE 3B-5

N-[1-[2-[1-[N-[Tris(hydroxymethyl)methyl]carbamoylmethyl]cyclohexyl]ethyl]piperidin-1-yl]-N-(5-methylpyridin-4-yl)-2-furancarboxamide

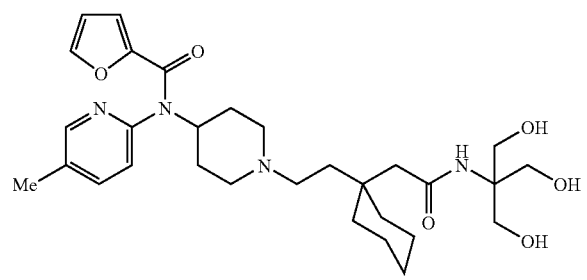

The title compound was synthesized from the compound obtained in Example 4B-5 in the same manner as in Example 3B-1.

Hydrochloride mp 83-88° C. (dec.); $^1$H-NMR (DMSO-d$_6$) δ: 0.80-0.98 (m, 2H), 1.09-1.28 (m, 3H), 1.55-1.77 (m, 6H), 1.98-2.12 (m, 4H), 2.36 (s, 3H), 3.00-3.08 (m, 2H), 3.20-3.33 (m, 2H), 3.39-3.50 (m, 2H), 3.54-3.67 9 m, 2H), 4.39-4.50 (m, 2H), 4.73-4.84 (m, 1H), 5.90 (d, 1H, J=3.9 Hz), 6.36 (dd, 1H, J=2.0 Hz, 3.9 Hz), 7.06 (t, 1H, J=7.8 Hz), 7.16 (d, 1H, J=7.8 Hz), 7.25 (d, 1H, J=7.8 Hz), 7.40-7.52 (m, 2H), 7.56 (d, 1H, J=2.0 Hz), 7.73 (dd, 1H, J=2.0 Hz, 7.8 Hz), 8.18-8.26 (m, 1H), 8.39 (d, 1H, J=2.0 Hz); IR (KBr) cm$^{-1}$: 3426, 2923, 2849, 1643, 1470, 1448, 1317, 755; MS (ESI) m/z: 557 (MH$^+$).

EXAMPLE 3B-6

N-[(1-Carboxymethylcyclohexyl)acetyl]-N-[2-[2-[4-[N-(5-methylpyridin-2-yl)-2-furancarboxamido]piperidin-1-yl]ethyl]phenyl]aminoacetic acid

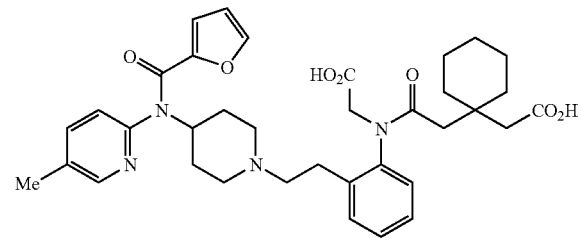

The title compound was synthesized from the compound obtained in Example 5B-5 in the same manner as in Example 3B-1.

Hydrochloride
mp 146-149° C.; $^1$H-NMR (DMSO-$d_6$) δ: 1.09-1.48 (m, 11H), 1.86-2.19 (m, 6H), 2.27-2.40 (m, 1H), 2.37 (s, 3H), 2.55-2.70 (m, 1H), 2.86-3.07 (m, 2H), 3.10-3.29 (m, 4H), 3.41-3.98 (m, 3H), 4.70-4.83 (m, 1H), 5.96 (d, 1H, J=3.6 Hz), 6.35 (dd, 1H, J=2.0 Hz, 3.6 Hz), 7.23 (d, 1H, J=8.4 Hz), 7.31-7.46 (m, 4H), 7.51-7.55 (m, 1H), 7.68-7.75 (m, 1H), 8.35-8.41 (m, 1H), 9.87-10.12 (m, 1H); IR (KBr) cm$^{-1}$: 3425, 2929, 1727, 1644, 1469, 1403, 1388, 1192, 770; MS (ESI) m/z: 645 (MH$^+$).

EXAMPLE 3B-7

3-[2-[2-[4-[N-(5-Methylpyridin-2-yl)-2-furancarboxamido]piperidin-1-yl]ethyl]phenyl]-5-cyclohexylhydantoic acid

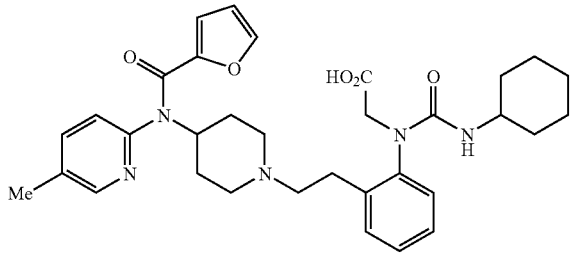

The title compound was synthesized from the compound obtained in Example 5B-8 in the same manner as in Example 3B-1.

Hydrochloride
$^1$H-NMR (DMSO-$d_6$) δ: 0.92-1.37 (m, 4H), 1.46-2.15 (m, 10H), 2.37 (s, 3H), 2.87-3.04 (m, 2H), 3.10-3.60 (m, 6H), 3.76-3.94 (m, 1H), 4.29-4.46 (m, 2H), 4.71-4.86 (m, 1H), 5.87-5.95 (m, 1H), 6.33-6.39 (m, 1H), 7.25 (d, 1H, J=8.0 Hz), 7.30-7.46 (m, 4H), 7.56 (brs, 1H), 7.70-7.77 (m, 1H), 8.36-8.43 (m, 1H), 9.67-10.14 (m, 1H); IR (KBr) cm$^{-1}$: 3427, 2931, 2854, 1703, 1644, 1469, 1386, 1339, 1190, 756; MS (ESI) m/z: 588 (MH$^+$); Anal. Calcd for $C_{33}H_{42}ClN_5O_6 \cdot 1/2H_2O$: C, 62.60; H, 6.85; N, 11.06. Found: C, 62.68; H, 6.89; N, 11.01.

EXAMPLE 3C-1

4-[1-[2-[4-[N-(5-Methylpyridin-2-yl)-2-furancarboxamido]piperidin-1-yl]ethyl]cyclohexyl]butyric acid

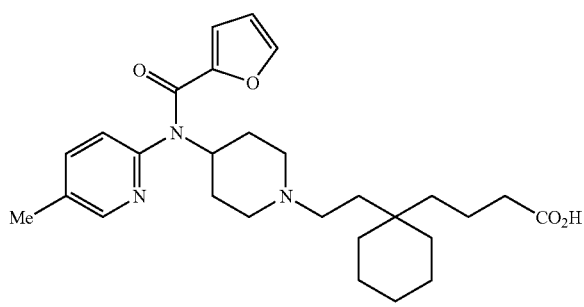

To a solution of methyl 4-[1-[2-[4-[N-(5-methylpyridin-2-yl)-2-furancarboxamido]piperidin-1-yl]ethyl]cyclohexyl]butyrate (210 mg) in methanol (10 mL) was added a 3N aqueous sodium hydroxide solution (1.4 mL) at room temperature. After stirring the solution at room temperature for 3 hours, a 3N aqueous sodium hydroxide solution (0.7 mL) was added thereto at room temperature. The solution was stirred at room temperature for 2 hours. Water (5 mL) and acetic acid (0.36 mL) were then added to the solution and it was concentrated under reduced pressure to distill off the methanol. The solution was extracted with 20% ethanol/chloroform. The organic layer was dried over anhydrous sodium sulfate and concentrated under reduced pressure to give the title compound (180 mg).

Free Form
$^1$H-NMR (CDCl$_3$) δ: 1.14-1.30 (m, 6H), 1.32-1.46 (m, 8H), 1.48-1.56 (m, 2H), 1.82-2.01 (m, 4H), 2.05-2.11 (m, 2H), 2.26 (s, 3H), 2.40-2.51 (m, 2H), 2.57-2.66 (m, 2H), 3.34-3.44 (m, 2H), 4.74-4.87 (m, 1H), 5.96 (d, 1H, J=3.6 Hz), 6.20 (dd, 1H, J=1.6 Hz, 3.6 Hz), 6.99 (d, 1H, J=8.4 Hz), 7.23 (d, 1H, J=1.6 Hz), 7.52 (dd, 1H, J=2.4 Hz, 8.4 Hz), 8.38 (d, 1H, J=2.4 Hz).

Hydrochloride
mp 134-137° C.; $^1$H-NMR (DMSO-$d_6$) δ: 1.11-1.47 (m, 14H), 1.52-1.64 (m, 2H), 1.79-1.95 (m, 2H), 1.97-2.08 (m, 2H), 2.19 (t, 2H, J=7.2 Hz), 2.37 (s, 3H), 2.86-2.97 (m, 2H), 3.02-3.15 (m, 2H), 3.47-3.57 (m, 2H), 4.74 (tt, 1H, J=4.0 Hz, 12.0 Hz), 5.91 (d, 1H, J=3.6 Hz), 6.36 (dd, 1H, J=1.6 Hz, 3.6 Hz), 7.24 (d, 1H, J=8.4 Hz), 7.56 (d, 1H, J=1.6 Hz), 7.74 (dd, 1H, J=2.4 Hz, 8.4 Hz), 8.36-8.42 (m, 1H), 9.65-9.79 (m, 1H) IR (KBr) cm$^{-1}$: 3426, 2928, 1714, 1633, 1470, 1385, 1322, 1191, 768; MS (ESI) m/z: 482 (MH$^+$).

EXAMPLE 3C-2

5,5-Bis(hydroxymethyl)-7-[1-[2-[4-[N-(5-methylpyridin-2-yl)-2-furancarboxamido]piperidin-1-yl]ethyl]cyclohexyl]heptanoic acid

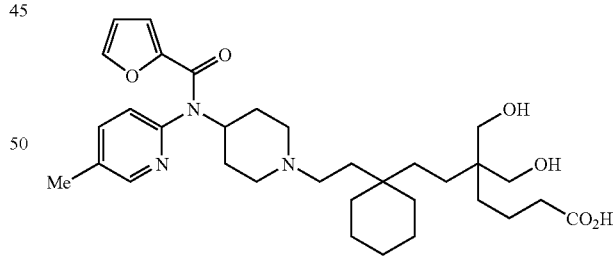

The title compound was synthesized from the compound obtained in Example 2-25 in the same manner as in Example 3C-1.

$^1$H-NMR (DMSO-$d_6$) δ: 0.90-1.28 (m, 10H), 1.30-1.61 (m, 10H), 1.77-1.93 (m, 2H), 1.95-2.07 (m, 2H), 2.15 (t, 2H, J=7.6 Hz), 2.37 (s, 3H), 2.87-2.98 (m, 2H), 3.00-3.13 (m, 2H), 3.18 (d, 2H, J=10.8 Hz), 3.22 (d, 2H, J=10.8 Hz), 3.46-3.56 (m, 2H), 4.74 (tt, 1H, J=4.0 Hz, 12.0 Hz), 5.91 (d, 1H, J=3.6 Hz), 6.36 (dd, 1H, J=1.6 Hz, 3.6 Hz), 7.24 (d, 1H, J=8.0 Hz), 7.56 (d, 1H, J=1.6 Hz), 7.73 (dd, 1H, J=2.4 Hz, 8.0 Hz), 8.36-8.42 (m, 1H), 9.33-9.50 (m, 1H).

EXAMPLE 3C-3

5,5-Bis(hydroxymethyl)-7-[1-[2-[4-[N-(p-tolyl)-2-furancarboxamido]piperidin-1-yl]ethyl]cyclohexyl]heptanoic acid

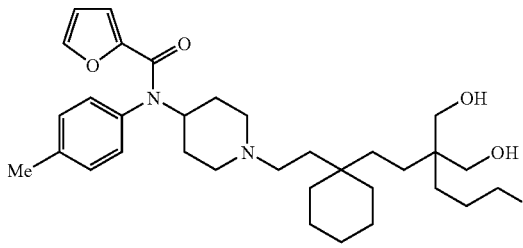

The title compound was synthesized from the compound obtained in Example 2-30 in the same manner as in Example 3C-1.

Free Form
$^1$H-NMR (CDCl$_3$) δ: 0.99-1.47 (m, 18H), 1.50-1.62 (m, 2H), 1.74-1.98 (m, 4H), 1.99-2.08 (m, 2H), 2.40 (s, 3H), 2.58 (t, 2H, J=12.0 Hz), 2.69-2.85 (m, 2H), 3.30-3.55 (m, 6H), 4.82-4.94 (m, 1H), 5.36 (d, 1H, J=3.2 Hz), 6.15 (dd, 1H, J=1.6 Hz, 3.2 Hz), 6.99 (d, 2H, J=8.0 Hz), 7.21 (d, 2H, J=8.0 Hz), 7.37 (d, 1H, J=1.6 Hz).

EXAMPLE 3C-4

N-[1-[2-[1-(2-Hydroxyethyl)cyclohexyl]ethyl]piperidin-4-yl]N-(5-methylpyridin-2-yl)-2-furancarboxamide

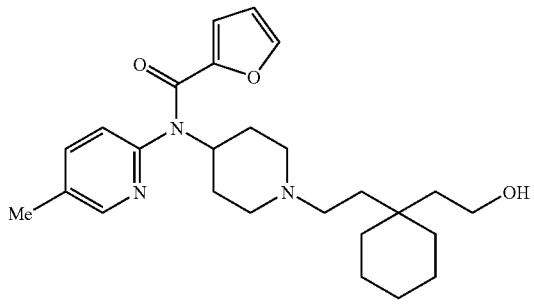

The title compound was synthesized from the compound obtained in Example 2-31 in the same manner as in Example 3C-1.

Free Form
$^1$H-NMR (CDCl$_3$) δ: 1.19-1.32 (m, 4H), 1.32-1.48 (m, 8H), 1.50-1.64 (m, 4H), 1.89-1.98 (m, 2H), 2.06-2.16 (m, 2H), 2.24-2.31 (m, 2H), 2.38 (s, 3H), 2.95-3.02 (m, 2H), 3.61 (t, 2H, J=6.8 Hz), 4.72 (tt, 1H, J=4.0 Hz, 12.0 Hz), 5.92 (d, 1H, J=3.6 Hz), 6.19 (dd, 1H, J=1.6 Hz, 3.6 Hz), 6.98 (d, 1H, J=8.0 Hz), 7.20-7.24 (m, 1H), 7.50 (dd, 1H, J=2.4 Hz, 8.0 Hz), 8.35-8.40 (m, 1H).

Hydrochloride
$^1$H-NMR (DMSO-d$_6$) δ: 1.20-1.30 (m, 4H), 1.31-1.46 (m, 8H), 1.56-1.67 (m, 2H), 1.79-1.94 (m, 2H), 1.98-2.07 (m, 2H), 2.37 (s, 3H), 2.90-3.02 (m, 2H), 3.02-3.15 (m, 2H), 3.44 (t, 2H, J=7.6 Hz), 3.47-3.56 (m, 2H), 4.74 (tt, 1H, J=4.0 Hz, 12.0 Hz), 5.91 (d, 1H, J=3.6 Hz), 6.36 (dd, 1H, J=1.6 Hz, 3.6 Hz), 7.24 (d, 1H, J=8.4 Hz), 7.54-7.57 (m, 1H), 7.73 (dd, 1H, J=2.4 Hz, 8.4 Hz), 8.37-8.41 (m, 1H), 9.44-9.59 (m, 1H); IR (KBr) cm$^{-1}$: 3425, 2927, 2857, 1633, 1593, 1574, 1469, 1402, 1339, 1191, 1034, 754; MS (ESI) m/z: 440 (MH$^+$); Anal. Calcd for C$_{26}$H$_{38}$ClN$_3$O$_3$.2H$_2$O: C, 60.98; H, 8.27; N, 8.21. Found: C, 61.08; H, 8.39; N, 8.05.

EXAMPLE 3C-5

1-[N-[2-[2-[4-[N-(5-Methylpyrydin-2-yl)-2-furan-carboxamido]piperidin-1-yl]ethyl]phenyl]carbamoylmethyl]cyclohexylacetic acid

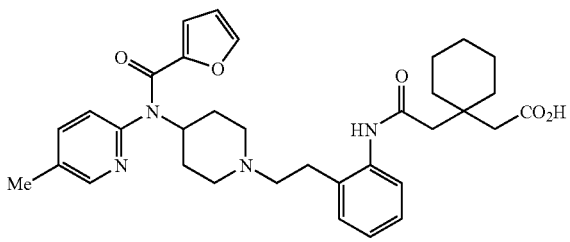

The title compound was synthesized from the compound obtained in Example 5B-4 in the same manner as in Example 3C-1.

Free Form
$^1$H-NMR (CDCl$_3$) δ: 1.36-1.63 (m, 10H), 1.89-2.12 (m, 4H), 2.38 (s, 3H), 2.41 (s, 2H), 2.53-2.69 (m, 4H), 3.37-3.46 (m, 2H), 4.77-4.89 (m, 1H), 5.96 (d, 1H, J=3.6 Hz), 6.21 (dd, 1H, J=1.6 Hz, 3.6 Hz), 6.94 (d, 1H, J=8.0 Hz), 7.01-7.12 (m, 2H), 7.12-7.29 (m, 2H), 7.52 (dd, 1H, J=2.4 Hz, 8.0 Hz), 7.93 (d, 1H, J=7.6 Hz), 8.38 (d, 1H, J=2.4 Hz), 10.03-10.19 (m, 1H).

Hydrochloride
mp 138-141° C.; $^1$H-NMR (DMSO-d$_6$) δ: 1.32-1.60 (m, 10H), 1.82-1.97 (m, 2H), 2.02-2.12 (m, 2H), 2.38 (s, 3H), 2.52-2.62 (m, 4H), 2.90-3.00 (m, 2H), 3.10-3.25 (m, 4H), 3.49-3.60 (m, 2H), 4.72-4.85 (m, 1H), 5.91 (d, 1H, J=3.6 Hz), 6.36 (dd, 1H, J=1.6 Hz, 3.6 Hz), 7.14-7.41 (m, 5H), 7.53-7.59 (m, 1H), 7.71-7.78 (m, 1H), 8.36-8.44 (m, 1H), 9.37-9.46 (m, 1H), 9.68-9.83 (m, 1H); IR (KBr) cm$^{-1}$: 3444, 2929, 1714, 1633, 1470, 1454, 1403, 1342, 1192, 756; M (ESI) m/z: 587 (MH$^+$).

EXAMPLE 3-1

N-[1-[1-(3-Hydroxypropyl) cyclohexylmethyl]piperidin-4-yl]-N-(5-methylpyridin-2-yl)-2-furancarboxamide

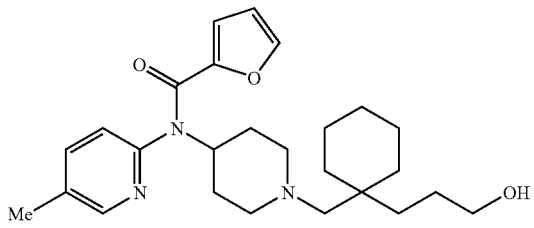

To a solution of acetic acid 3-[1-[4-[N-(5-methylpyridin-2-yl)-2-furancarboxamido]piperidin-1-yl]methyl]cyclohexyl]propyl ester (180 mg) in methanol (10 mL) was added potassium carbonate (10 mg) at room temperature. After stirring the solution at room temperature for 16 hours, it was concentrated under reduced pressure. Water was added to the residue and it was extracted with chloroform. The organic layer was dried over anhydrous sodium sulfate and concentrated under reduced pressure. The residue was purified by chromatography (NH silica gel, hexane:ethyl acetate=2:8) to give the title compound (180 mg).

Free Form $^1$H-NMR (CDCl$_3$) δ: 1.15-1.49 (m, 14H), 1.50-1.64 (m, 2H), 1.79-1.88 (m, 2H), 2.12 (s, 2H), 2.27-2.38 (m, 2H), 2.41 (s, 3H), 2.78-2.86 (m, 2H), 3.55 (t, 2H, J=6.4 Hz), 4.64 (tt, 1H, J=4.0 Hz, 12.0 Hz), 5.91 (d, 1H, J=3.6 Hz), 6.19 (dd, 1H, J=2.0 Hz, 3.6 Hz), 6.99 (d, 1H, J=8.0 Hz), 7.22 (d, 1H, J=2.0 Hz), 7.53 (dd, 1H, J=2.4 Hz, 8.0 Hz), 8.41 (d, 1H, J=2.4 Hz).

Hydrochloride mp 113-116° C.; $^1$H-NMR (DMSO-d$_6$) δ: 1.20-1.54 (m, 14H), 1.88-2.17 (m, 4H), 2.37 (s, 3H), 2.89-3.02 (m, 2H), 3.26-3.43 (m, 4H), 3.45-3.55 (m, 2H), 4.59-4.85 (m, 1H), 5.86-5.96 (m, 1H), 6.33-6.38 (m, 1H), 7.23-7.29 (m, 1H), 7.53-7.58 (m, 1H), 7.70-7.78 (m, 1H), 8.29-8.43 (m, 2H); IR (KBr) cm$^{-1}$: 3420, 2933, 2861, 1627, 1559, 1469, 1402, 1324, 1191, 769; MS (ESI) m/z: 440 (MH$^+$); Anal. Calcd for C$_{26}$H$_{38}$ClN$_3$O$_3$5/2H$_2$O: C, 59.93; H, 8.32; N, 8.06. Found: C, 60.14; H, 8.32; N, 8.06.

EXAMPLE 3D-2

N-[1-[2-[1-(4-Hydroxy-3-hydroxymethylbutyl)cyclohexyl]ethyl]piperidin-4-yl]-N-(p-tolyl)-2-furancarboxamide

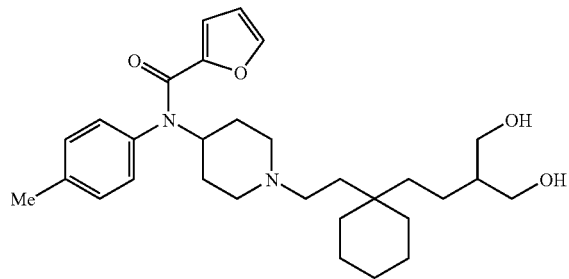

The title compound was synthesized from the compound obtained in Example 2-20 in the same manner as in Example 3D-1.

Free Form $^1$H-NMR (CDCl$_3$) δ: 1.10-1.28 (m, 8H), 1.31-1.44 (m, 8H), 1.46-1.66 (m, 3H), 1.79-1.90 (m, 2H), 2.03-2.14 (m, 2H), 2.16-2.25 (m, 2H), 2.40 (s, 3H), 2.92-3.01 (m, 2H), 3.62 (dd, 2H, J=7.2 Hz, 10.8 Hz), 3.77 (dd, 2H, J=3.2 Hz, 10.8 Hz), 4.74 (tt, 1H, J=4.0 Hz, 12.0 Hz), 5.32-5.39 (m, 1H), 6.14 (dd, 1H, J=1.6 Hz, 3.6 Hz), 7.02 (d, 2H, J=8.0 Hz), 7.19 (d, 2H, J=8.0 Hz), 7.35 (d, 1H, J=1.6 Hz).

Hydrochloride $^1$H-NMR (DMSO-d$_6$) δ: 1.09-1.28 (m, 8H), 1.29-1.46 (m, 7H), 1.51-1.63 (m, 2H), 1.65-1.80 (m, 2H), 1.94-2.07 (m, 2H), 2.38 (s, 3H), 2.82-2.96 (m, 2H), 3.02-3.18 (m, 2H), 3.32-3.57 (m, 6H), 4.73-4.85 (m, 1H), 5.44-5.55 (m, 1H), 6.31 (dd, 1H, J=1.6 Hz, 3.6 Hz), 7.15 (d, 2H, J=8.0 Hz), 7.29 (d, 2H, J=8.0 Hz), 7.62 (d, 1H, J=1.6 Hz), 9.56-9.77 (m, 1H); IR (KBr) cm$^{-1}$: 3406, 2926, 2859, 1633, 1604, 1511, 1469, 1403, 1341, 1189, 1032, 757; MS (ESI) m/z: 497 (MH$^+$); Anal. Calcd for C$_{30}$H$_{45}$ClN$_2$O$_4$.1/2H$_2$O: C, 66.46; H, 8.55; N, 5.17. Found: C, 66.43; H, 8.71; N, 5.01.

EXAMPLE 3D-3

N-[1-[2-[1-[5-Hydroxy-3,3-bis(hydroxymethyl)pentyl]cyclohexyl]ethyl]piperidin-4-yl]-N-(5-methylpyridin-2-yl)-2-furancarboxamide

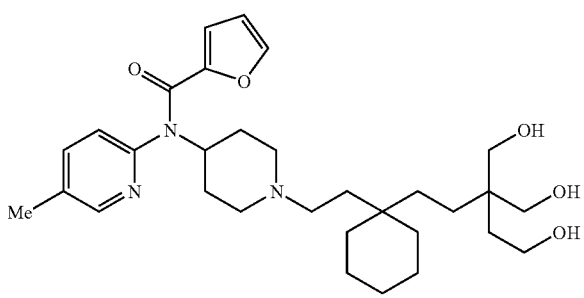

The title compound was synthesized from the compound obtained in Example 2-24 in the same manner as in Example 3D-1.

Free Form $^1$H-NMR (CDCl$_3$) δ: 1.07-1.29 (m, 8H), 1.32-1.46 (m, 8H), 1.55-1.74 (m, 4H), 1.87-1.96 (m, 2H), 2.02-2.13 (m, 2H), 2.17-2.26 (m, 2H), 2.39 (s, 3H), 2.94-3.02 (m, 2H), 3.47 (d, 2H, J=10.8 Hz), 3.51 (d, 2H, J=10.8 Hz), 3.73 (t, 2H, J=5.6 Hz), 4.63-4.75 (m, 1H), 5.93 (d, 1H, J=3.6 Hz), 6.19 (dd, 1H, J=1.6 Hz, 3.6 Hz), 6.99 (d, 1H, J=8.4 Hz), 7.20-7.24 (m, 1H), 7.51 (dd, 1H, J=2.4 Hz, 8.4 Hz), 8.38 (d, 1H, J=2.4 Hz).

Hydrochloride mp 102-105° C.; $^1$H-NMR (DMSO-d$_6$) δ: 1.01-1.18 (m, 4H), 1.19-1.28 (m, 4H), 1.30-1.45 (m, 8H), 1.49-1.59 (m, 2H), 1.75-1.92 (m, 2H), 1.98-2.08 (m, 2H), 2.37 (s, 3H), 2.87-3.01 (m, 2H), 3.01-3.13 (m, 2H), 3.15-3.35 (m, 4H), 3.43-3.56 (m, 4H), 4.69-4.80 (m, 1H), 5.92 (d, 1H, J=3.6 Hz), 6.36 (dd, 1H, J=1.2 Hz, 3.6 Hz), 7.24 (d, 1H, J=8.0 Hz), 7.56 (d, 1H, J=1.2 Hz), 7.73 (dd, 1H, J=2.4 Hz, 8.0 Hz), 8.40 (d, 1H, J=2.4 Hz), 9.02-9.16 (m, 1H); IR (KBr) cm$^{-1}$: 3388, 2929, 1643, 1470, 1402, 1338, 1031, 754; MS (ESI) m/z: 542 (MH$^+$); Anal. Calcd for C$_{31}$H$_{48}$ClN$_3$O$_5$4/5H$_2$O: C, 62.83; H, 8.44; N, 7.09. Found: C, 62.74; H, 8.45; N, 7.01.

EXAMPLE 3E-1

2-[1-[2-[4-[N-(p-Tolyl)-2-furancarboxamido]piperidin-1-yl]ethyl]cyclohexyl]acetylimino-N,N-bis(acetyliminodiacetate)

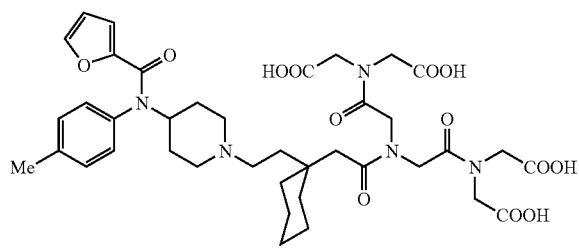

Tetraethyl 2-[1-[2-[4-[N-(p-tolyl)-2-furancarboxamido]piperidin-1-yl]ethyl]cyclohexyl]-acetylimino-N,N-bis(acetyliminodiacetic acid) (0.2597 g) was dissolved in 6N hydrochloric acid (20 mL) The solvent was then distilled off under reduced pressure. This procedure was repeated twice. The residue was freeze-dried to give the hydrochloride of the title compound (0.2322 g).

Hydrochloride

¹H-NMR (DMSO-d₆) δ: 1.25-1.50 (m, 10H), 1.62-1.86 (m, 4H), 1.97-2.07 (m, 2H), 2.08 (s, 2H), 2.38 (s, 3H), 2.87-2.97 (m, 2H), 3.00-3.13 (m, 2H), 3.41-3.54 (m, 2H), 3.98-4.30 (12H), 4.74-4.84 (m, 1H), 5.51 (d, 1H, J=3.4 Hz), 6.32 (dd, 1H, J=1.5 Hz, 3.4 Hz), 7.16 (d, 2H, J=8.3 Hz), 7.30 (d, 2H, J=8.3 Hz), 7.62 (d, 1H, J=1.5 Hz); IR (NaCl film) cm⁻¹: 2930, 2859, 1736, 1637, 1469, 1406, 1190; MS (ESI) m/z: 798 (MH⁺).

EXAMPLE 3E-2

N-[1-[2-[1-[N,N-Bis[N-[tris(hydroxymethyl)methyl]carbamoylmethyl]carbamoylmethyl]cyclohexyl]ethyl]piperidine-4-yl]-N-(5-methylpyridin-2-yl)-2-furancarboxamide

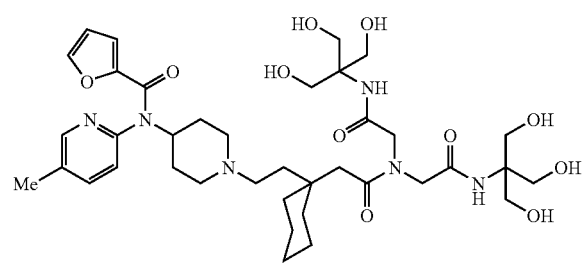

The title compound was synthesized from the compound obtained in Example 4B-6 in the same manner as in Example 3E-1.

Hydrochloride

¹H-NMR (DMSO-d₆) δ: 1.20-1.53 (m, 12H), 1.72-1.97 (m, 4H), 1.98-2.07 (m, 2H), 2.14-2.24 (m, 2H), 2.37 (s, 3H), 2.90-3.20 (m, 4H), 3.30-4.50 (brm, 16H), 4.69-4.82 (m, 1H), 5.90 (d, 1H, J=3.4 Hz), 6.35 (dd, 1H, J=1.5 Hz, 3.4 Hz), 7.24 (d, 1H, J=7.8 Hz), 7.55 (d, 1H, J=1.5 Hz), 7.60-7.77 (m, 3H), 8.38-8.40 (m, 1H); IR (NaCl film) cm⁻¹: 3342, 2927, 2854, 1734, 1647, 1636, 1466, 1458, 1398, 1187, 1059, 754; MS (ESI) m/z: 775 (MH⁺).

EXAMPLE 3E-3

N-[2-[3-[4-[N-(p-Tolyl)-2-furancarboxamido]piperidin-1-yl]propyl]phenyl]-N-(3-cyclohexylpropionyl)aminobutyric acid

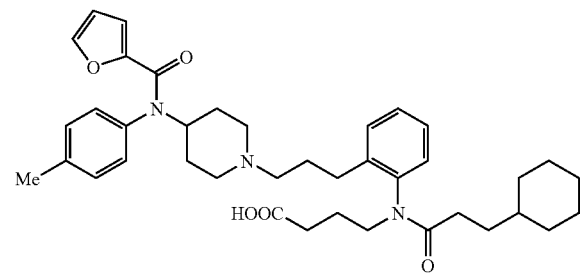

The title compound was synthesized from the compound obtained in Example 5B-3 in the same manner as in Example 3E-1.

Hydrochloride mp 105-115° C.; ¹H-NMR (DMSO-d₆) δ: 0.64-0.77 (m, 2H), 0.95-2.08 (m, 21H), 2.16-2.22 (m, 2H), 2.38 (s, 3H), 2.41-2.51 (m, 2H), 2.94-3.22 (m, 5H), 3.44-3.56 (m, 2H), 3.97-4.06 (m, 1H), 4.76-4.86 (m, 1H), 5.49 (d, 1H, J=3.4 Hz), 6.31 (dd, 1H, J=1.5 Hz, 3.4 Hz), 7.16 (d, 2H, J=8.3 Hz), 7.15-7.20 (m, 1H), 7.30 (d, 2H, J=8.3 Hz), 7.30-7.48 (m, 3H), 7.62 (d, 1H, J=1.5 Hz); IR (KBr) cm⁻¹: 3433, 2923, 2850, 1725, 1639, 1470, 1450, 1405, 757, 736; MS (ESI) m/z: 642 (MH⁺).

EXAMPLE 3F-1

N-[2-[2-[4-[N-(p-Tolyl)-2-furancarboxamido]piperidin-1-yl]ethyl]phenyl]-N-(cyclohexylacetyl)aminoacetic acid

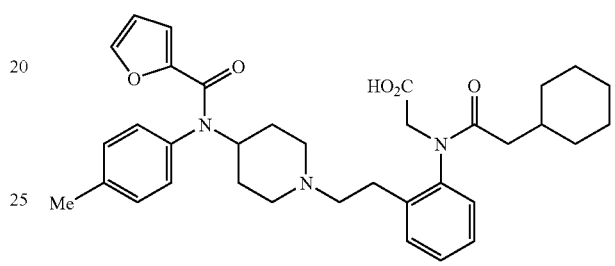

tert-Butyl N-[2-[2-[4-[N-(p-tolyl)-2-furancarboxamido]piperidin-1-yl]-ethyl]phenyl]-N-(cyclohexylacetyl)aminoacetate (0.1318 g) was dissolved in a 4N hydrochloric acid/1,4-dioxane solution (6.0 mL). The solution was stirred at room temperature for 3 days. The solvent was distilled off under reduced pressure. The residue was solidified in ethyl acetate to give the hydrochloride of the title compound (0.0871 g)

Hydrochloride mp 140-147° C.; ¹H-NMR (DMSO-d₆) δ: 0.61-0.78 (m, 2H), 0.95-1.28 (m, 3H), 1.51-1.83 (m, 10H), 2.00-2.11 (m, 2H), 2.39 (s, 3H), 2.82-2.99 (m, 2H), 3.10-3.30 (m, 4H), 3.503.62 (m, 2H), 3.80 (d, 1H, J=16.6 Hz), 4.50 (d, 1H, J=16.6 Hz), 4.77-4.86 (m, 1H), 5.52 (d, 1 H, J=3.4 Hz), 6.31 (dd, 1H, J=1.5 Hz, 3.4 Hz), 7.18 (d, 2H, J=8.3 Hz), 7.31 (d, 2H, J=8.3 Hz), 7.33-7.44 (m, 4H), 7.62 (d, 1H, J=1.5 Hz); IR (KBr) cm¹: 3430, 2923, 1732, 1634, 1470, 1450, 1403, 1190, 1028, 758; MS (ESI) m/z: 586 (MH⁺).

EXAMPLE 3F-2

N-[2-[3-[4-[N-(p-Tolyl)-2-furancarboxamido]piperidin-1-yl]propyl]phenyl]-N-(3-cyclohexylpropionyl)aminoacetic acid

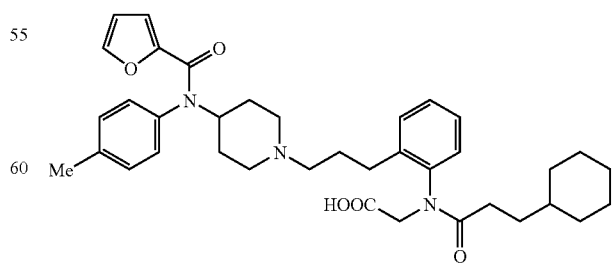

The title compound was synthesized from the compound obtained in Example 5C-2 in the same manner as in Example 3F-1.

Hydrochloride mp 125-130° C.; $^1$H-NMR (DMSO-d$_6$) δ: 0.64-0.79 (m, 2H), 0.98-1.19 (m, 4H), 1.22-1.40 (m, 2H), 1.40-1.49 (m, 2H), 1.50-1.61 (m, 3H), 1.65-1.98 (m, 6H), 1.99-2.0 (m, 2H), 2.38 (s, 3H), 2.45-2.68 (m, 2H), 2.98-3.18 (m, 4H), 3.40-3.55 (m, 2H), 3.72 (d, 1H, J=17.1 Hz), 4.50 (d, 1H, J=17.1 Hz), 4.74-4.84 (m, 1H), 5.58 (d, 1H, J=3.4 Hz), 6.29 (dd, 1H, J=1.5 Hz, 3.4 Hz), 7.14 (d, 2H, J=8.3 Hz), 7.28 (d, 2H, J=8.3 Hz), 7.29-7.44 (m, 4H), 7.57 (d, 1H, J=1.5 Hz); IR (KBr) cm$^{-1}$: 3432, 2923, 2850, 1734, 1639, 1470, 1451, 1405, 1187, 1025, 757; MS (ESI) m/z: 614 (MH$^+$).

EXAMPLE 3F-3

[2-[1-[2-[4-[N-(p-Tolyl)-2-furancarboxamido]piperidin-1-yl]ethyl]cyclohexyl]acetamido]acetic acid

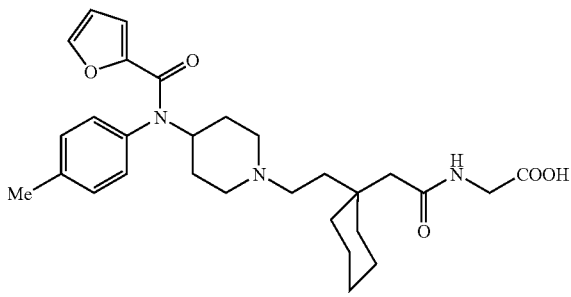

The title compound was synthesized from the compound obtained in Example 4B-2 in the same manner as in Example 3F-1.

Hydrochloride mp 216-219° C.; $^1$H-NMR (DMSO-d$_6$) δ: 1.27-1.51 (m, 10H), 1.62-1.80 (m, 4H), 1.98-2.06 (m, 2H), 2.09 (s, 2H), 2.38 (s, 3H), 3.00-3.17 (m, 4H), 3.45-3.58 (m, 2H), 3.70-3.75 (m, 2H), 4.73-4.83 (m, 1H), 5.50 (d, 1H, J=3.4 Hz), 6.31 (dd, 1H, J=1.5 Hz, 3.4 Hz), 7.15 (d, 2H, J=8.3 Hz), 7.30 (d, 2H, J=8.3 Hz), 7.62 (d, 1H, J=1.5 Hz), 8.18 (t, 1H, J=5.9 Hz); IR (KBr) cm$^{-1}$: 3427, 2927, 2859, 1737, 1640, 1557, 1512, 1469, 1402, 1343, 1189, 1032, 758; MS (ESI) m/z: 510 (MH$^+$).

EXAMPLE 3F-4

2-[1-[2-[4-[N-(p-Tolyl)-2-furancarboxamido]piperidin-1-yl]ethyl]cyclohexyl]acetyliminodiacetic acid

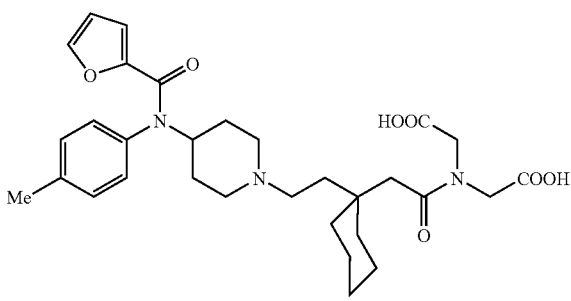

The title compound was synthesized from the compound obtained in Example 4B-1 in the same manner as in Example 3F-1.

Hydrochloride $^1$H-NMR (DMSO-d$_6$) δ: 1.26-1.51 (m, 10H), 1.61-1.77 (m, 2H), 1.78-1.88 (m, 2H), 1.99-2.08 (m, 2H), 2.19 (s, 2H), 2.39 (s, 3H), 2.90-2.99 (m, 2H), 3.01-3.16 (m, 2H), 3.42-3.54 (m, 2H), 3.95 (s, 2H), 4.20 (s, 2H), 4.74-4.87 (m, 1H), 5.51 (d, 1H, J=3.4 Hz), 6.31 (dd, 1H, J=1.5 Hz, 3.4 Hz), 7.15 (d, 2H, J=8.3 Hz), 7.30 (d, 2H, J=8.3 Hz), 7.62 (d, 1H, J=1.5 Hz).

EXAMPLE 3F-5

N-[1-[2-[1-(2-Aminoethyl)cyclohexyl]ethyl]piperidin-4-yl]-N-(5-methylpyridin-2-yl)-2-furancarboxamide

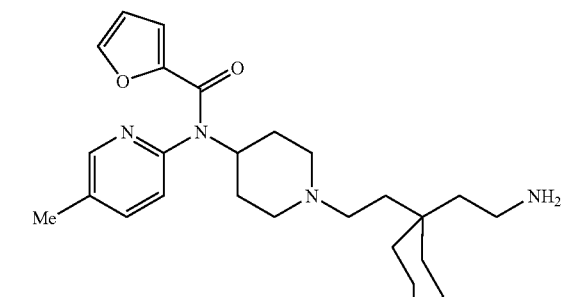

tert-Butyl [2-[1-[2-[4-[N-(5-methylpyridin-2-yl)-2-furancarboxamido]piperidin-1-yl]ethyl]cyclohexyl]ethyl]carbamate (0.4760 g) was dissolved in a 4N hydrochloric acid/1,4-dioxane solution (10.0 mL) and methanol (5 mL). The solution was stirred at room temperature for 2 hours. The solvent was distilled off under reduced pressure to give the title compound (0.5036 g).

Hydrochloride $^1$H-NMR (DMSO-d$_6$) δ: 1.28-1.30 (m, 4H), 1.31-1.50 (m, 6H), 1.52-1.68 (m, 4H), 1.83-2.08 (m, 2H), 2.09-2.18 (m, 2H), 2.37 (s, 3H), 2.70-2.82 (m, 2H), 3.00-3.16 (m, 4H), 3.53-3.62 (m, 2H), 4.69-4.79 (m, 1H), 5.90 (d, 1H, J=3.4 Hz), 6.35 (dd, 1H, J=1.5 Hz, 3.4 Hz), 7.24 (d, 1H, J=7.8 Hz), 7.55 (d, 1H, J=1.5 Hz), 7.74 (dd, 1H, J=2.0 Hz, 7.8 Hz), 7.90-8.15 (brm, 3H), 8.39 (d, 1H, J=2.0 Hz), 9.90-10.15 (brm, 1H); IR (KBr) cm$^{-1}$: 3424, 2927, 2858, 1632, 1557, 1470, 1385, 1320, 1189, 768; MS (ESI) m/z: 439 (MH$^+$).

EXAMPLE 3G-1

3-[1-[2-[4-[N-(5-Methylpyridin-2-yl)-2-furancarboxamido]piperidin-1-yl]ethyl]cyclohexyl]-1,1-propanedicarboxylic acid

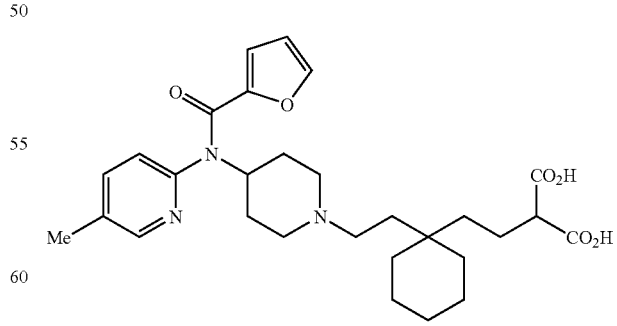

To a solution of triethyl 3-[1-[2-[4-[N-(5-methylpyridin-2-yl)-2-furancarboxamido]piperidin-1-yl]ethyl]cyclohexyl]-1,1,1-propanetricarboxylate (200 mg) in 1,4-dioxane (9 mL) and water (3 mL) was added lithium hydroxide (100 mg). After stirring the solution at room temperature for 7 hours, water was added thereto and it was concentrated under reduced pressure. Acetic acid (0.14 mL) was added to the residue, and the solution was further concentrated under reduced pressure and to dryness. The residue was purified by chromatography (DIAION HP20 manufactured by Mitubishi Chemical Corporation, methanol) to give the title compound (150 mg).

Free Form $^1$H-NMR (CDCl$_3$) δ: 1.03-1.66 (m, 18H), 1.72-1.87 (m, 1H), 1.97-2.21 (m, 3H), 2.41 (s, 3H), 2.75-3.03 (m, 3H), 3.48-3.69 (m, 2H), 4.79-4.99 (m, 1H), 5.88-6.02 (m, 1H), 6.14-6.29 (m, 1H), 6.90-7.02 (m, 1H), 7.48-7.64 (m, 1H), 8.30-8.44 (m, 1H).

Hydrochloride mp 136-139° C.; $^1$H-NMR (DMSO-d$_6$) δ: 1.12-1.29 (m, 6H), 1.30-1.48 (m, 6H), 1.53-1.70 (m, 4H), 1.78-1.94 (m, 2H), 1.98-2.09 (m, 2H), 2.37 (s, 3H), 2.86-2.97 (m, 2H), 3.02-3.22 (m, 3H), 3.48-3.58 (m, 2H), 4.68-4.80 (m, 1H), 5.91 (d, 1H, J=3.6 Hz), 6.36 (dd, 1H, J=1.6 Hz, 3.6 Hz), 7.24 (d, 1H, J=8.4 Hz), 7.54-7.57 (m, 1H), 7.73 (dd, 1H, J=2.4 Hz, 8.4 Hz), 8.38-8.42 (m, 1H), 9.35-9.51 (m, 1H), 12.29-12.85 (m, 2H); IR (KBr) cm$^{-1}$: 3424, 2928, 1726, 1633, 1469, 1402, 1339, 1229, 1192, 755; MS (ESI) m/z: 526 (MH$^+$).

EXAMPLE 3G-2

N-[1-[2-[1-(4-Hydroxy-3-hydroxymethylbutyl)cyclohexyl]ethyl]piperidin-4-yl]-N-(5-methylpyridin-2-yl)-2-furancarboxamide

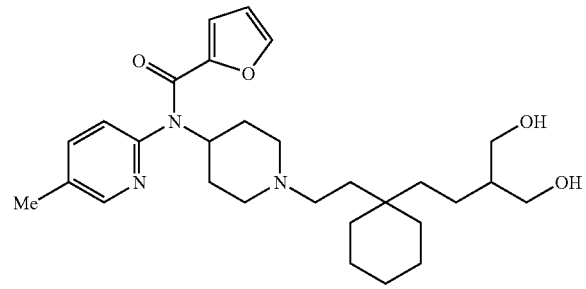

To a solution of N-[1-[2-[1-[4-(methoxymethoxy)-3-(methoxymethoxymethyl)butyl]cyclohexyl]ethyl]piperidin-4-yl]-N-(5-methylpyridin-2-yl)-2-furancarboxamide (300 mg) in methanol (10 mL) was added conc. hydrochloric acid (0.17 mL) at room temperature. The solution was stirred at room temperature for 16 hours. conc. Hydrochloric acid (0.17 mL) was further added to the solution, and it was stirred at 50 ° C. for 6 hours. The solution was concentrated under reduced pressure, saturated aqueous sodium bicarbonate solution was added to the residue, and it was extracted with chloroform. The extract was dried over anhydrous sodium sulfate, and then, concentrated under reduced pressure. The residue was purified by chromatography [silica gel, chloroform-methanol-aqueous ammonia (90:10:0.1)]to give the title compound (260 mg).

Free form $^1$H-NMR (CDCl$_3$) δ: 1.12-1.30 (m, 9H), 1.31-1.46 (m, 7H), 1.55-1.72 (m, 3H), 1.88-1.97 (m, 2H), 2.02-2.13 (m, 2H), 2.19-2.28 (m, 2H), 2.38 (s, 3H), 2.93-3.04 (m, 2H), 3.64 (dd, 2H, J=7.2 Hz, 10.8 Hz), 3.78 (dd, 2H, J=3.6 Hz, 10.8 Hz), 4.71 (tt, 1H, J=4.0 Hz, 12.0 Hz), 5.94 (d, 1H, J=3.6 Hz), 6.19 (dd, 1H, J=1.6 Hz, 3.6 Hz), 6.90 (d, 1H, J=8.0 Hz), 7.23 (d, 1H, J=1.6 Hz), 7.51 (dd, 1H, J=2.4 Hz, 8.0 Hz), 8.38 (d, 1H, J=2.4 Hz).

Hydrochloride mp 112-115° C.; $^1$H-NMR (DMSO-d$_6$) δ: 1.05-1.46 (m, 15H), 1.51-1.62 (m, 2H), 1.76-1.92 (m, 2H), 1.96-2.07 (m, 2H), 2.37 (s, 3H), 2.82-2.97 (m, 2h), 3.01-3.17 (m, 2H), 3.27-3.43 (m, 4H), 3.47-3.56 (m, 2H), 4.68-4.80 (m, 1H), 5.91 (d, 1H, J=3.2 Hz), 6.35 (dd, 1H, J=2.0 Hz, 3.2 Hz), 7.24 (d, 1H, J=8.0 Hz), 7.51-7.58 (m, 1H), 7.73 (dd, 1H, J=2.4 Hz, 8.0 Hz), 8.36-8.42 (m, 1H), 9.29-9.46 (m, 1H); IR (KBr) cm$^{-1}$: 3406, 2928, 1651, 1633, 1556, 1470, 1323, 1191, 1032, 768; MS (ESI) m/z: 498 (MH$^+$); Anal. Calcd for C$_{29}$H$_{44}$ClN$_3$O$_4$5/2H$_2$O: C, 60.14; H, 8.53; N, 7.26. Found: C, 60.06; H, 8.36; N, 6.98.

EXAMPLE 3G-3

N-[1-[2-[1-[1,3-Dihydroxypropan-2-yl]cyclohexyl]ethyl]piperidin-4-yl]-N-(5-methylpyridin-2-yl)-2-furancarboxamide

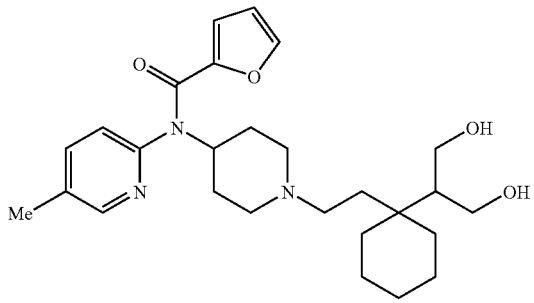

To a solution of N-[1-[2-[1-(2-phenyl-1,3-dioxan-5-yl)cyclohexyl]ethyl]piperidin-4-yl]-N-(5-methylpyridin-2-yl)-2-furancarboxamide (110 mg) in methanol (5 mL) was added 4N hydrochloric acid (0.5 mL). After stirring the solution at room temperature for 2 hours, it was concentrated under reduced pressure. Saturated aqueous sodium bicarbonate solution was added to the residue and it was extracted with chloroform. The combined organic layer was dried over anhydrous sodium sulfate and concentrated under reduced pressure to give the title compound. To a solution of the residue in ethyl acetate (10 mL) was added a 4N hydrochloric acid/ethyl acetate solution (0.15 mL), and the solution was stirred at room temperature for 1 hour. The crystals thus separated out were then filtered to give its hydrochloride (60 mg).

Hydrochloride $^1$H-NMR (DMSO-d$_6$) δ: 1.16-1.32 (m, 3H), 1.35-1.49 (m, 8H), 1.67-1.77 (m, 2H), 1.77-1.91 (m, 2H), 1.97-2.07 (m, 2H), 2.37 (s, 3H), 2.91-3.02 (m, 2H), 3.03-3.16 (m, 2H), 3.42-3.56 (m, 4H), 3.59 (dd, 2H, J=4.0 Hz, 11.2 Hz), 4.69-4.79 (m, 1H), 5.92 (d, 1H, J=3.6 Hz), 6.36 (dd, 1H, J=1.6 Hz, 3.6 Hz), 7.24 (d, 1H, J=7.6 Hz), 7.54-7.58 (m, 1H), 7.74 (dd, 1H, J=2.4 Hz, 7.6 Hz), 8.40 (d, 1H, J=2.4 Hz), 9.07-9.21 (m, 1H); MS (ESI) m/z: 470 (MH$^+$).

EXAMPLE 3G-4

N-[1-[2-[1-[1,3-Dihydroxypropan-2-yl]cyclohexyl]ethyl]piperidin-4-yl]-N-(p-tolyl)-2-furancarboxamide

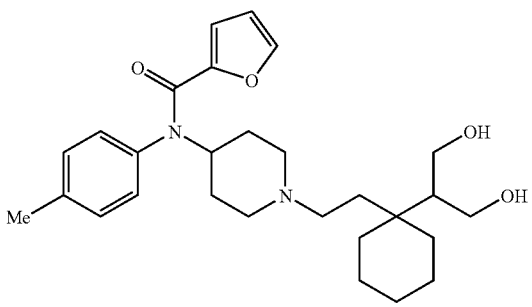

To a solution of N-[1-[2-[1-[2,2-dimethyl-1,3-dioxan-5-yl]cyclohexyl]ethyl]piperidin-4-yl]-N-(p-tolyl)-2-furancarboxamide (340 mg) in methanol (5 mL) was added 3N hydrochloric acid (1.1 mL) at room temperature. After stirring the solution for 1 hour, it was concentrated under reduced pressure. A solution of the residue in chloroform/diethyl ether was stirred under ice cooling for 1 hour and the crystals thus separated out was then filtered to give the hydrochloride of the title compound (240 mg).

Hydrochloride m.p. 118-121° C.; $^1$H-NMR (DMSO-d$_6$) δ: 1.14-1.50 (m, 12H), 1.62-1.79 (m, 4H), 1.94-2.07 (m, 2H), 2.39 (s, 3H), 2.88-3.03 (m, 2H), 3.04-3.17 (m, 2H), 3.40-3.64 (m, 6H), 4.24-4.42 (m, 1H), 4.72-4.86 (m, 1H), 5.44-5.54 (m, 1H), 6.25-6.35 (m, 1H), 7.09-7.20 (m, 1H), 7.24-7.34 (m, 1H), 7.57-7.67 (m, 1H), 9.24-9.40 (m, 1H); IR (KBr) cm$^{-1}$: 3396, 2929, 2863, 1636, 1604, 1511, 1470, 1402, 1340, 1312, 1189, 1022, 954, 757, 735; MS (ESI) m/z: 469 (MH$^+$). Anal. Calcd for $C_{28}H_{41}ClN_2O_4 \cdot 3/7H_2O$: C, 66.58; H, 8.23; N, 5.46. Found: C, 65.64; H, 8.42; N, 5.32.

EXAMPLE 4A-1

Ethyl 4-[2-[1-[2-[4-[N-(5-methylpyridin-2-yl)-2-furancarboxamido]piperidin-1-yl]ethyl]cyclohexyl]acetamido]butyrate

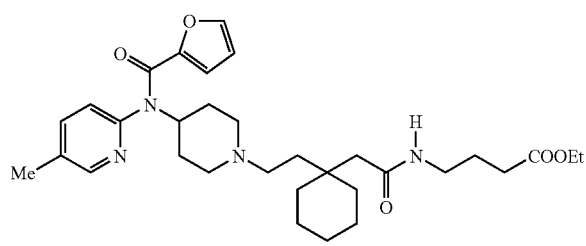

[1-[2-[4-[N-(5-Methylpyridin-2-yl)-2-furancarboxamido]piperidin-1-yl]ethyl]cyclohexyl]acetic acid (133 mg) and triethylamine (0.04 mL) were suspended in N,N-dimethylformamide (10 mL), to which ethyl 4-aminobutyrate hydrochloride (69 mg) was added. To the suspension were added 1-ethyl-3-(3-dimethylaminopropyl)carbodiimide hydrochloride (78 mg, 0.41 mmol) and 1-hydroxybenzotriazole hydrate (63 mg) under ice cooling. The solution was stirred at that temperature for 30 minutes. After allowing the temperature to rise to room temperature, the solution was stirred at that temperature for 15 hours. Water and saturated aqueous sodium bicarbonate solution were added to the solution and it was extracted with chloroform. The organic layer was dried over anhydrous magnesium sulfate and concentrated under reduced pressure. The resulting residue was purified by chromatography (NH silica gel, chloroform:methanol=10:1) to give the title compound (142 mg).

Hydrochloride $^1$H-NMR (DMSO-d$_6$) δ: 1.18 (t, 3H, J=7.4 Hz), 1.27-1.42 (m, 10H), 1.64 (t like, 2H), 1.75-1.91 (m, 5H), 2.01-2.04 (m, 4H), 2.26-2.28 (m, 2H), 2.37 (s, 3H), 3.03-3.15 (m, 5H), 3.58 (d, 2H, J=5.8 Hz), 4.04 (q like, 2H), 4.77 (t like, 1H), 5.86 (d, 1H, J=3.4 Hz), 6.36 (s, 1H), 7.25 (d, 1H, J=9.8 Hz), 7.59 (s, 1H), 7.74 (d, 1H, J=7.8 Hz), 8.00 (s, 1H), 8.41 (s, 1H), 9.55 (m, 1H); IR (KBr) cm$^{-1}$: 3425, 2928, 2644, 1727, 1644, 1557, 1470, 1319, 1188, 1030, 769; MS (ESI) m/z: 567 (MH$^+$).

EXAMPLE 4A-2

Ethyl [2-[1-[2-[4-[N-(5-methylpyridin-2-yl)-2-furancarboxamido]piperidin-1-yl]ethyl]cyclohexyl]acetamido]acetate

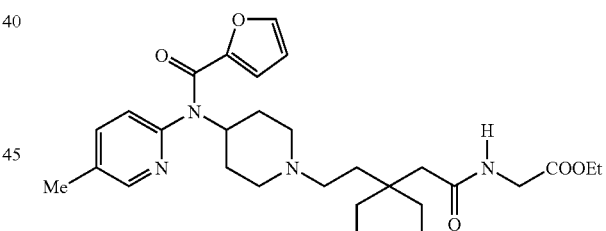

The title compound was synthesized from the compound obtained in Example 3A-3 in the same manner as in Example 4A-1 except that ethyl aminoacetate was used instead of ethyl aminobutyrate.

Hydrochloride $^1$H-NMR (DMSO-d$_6$) δ: 1.16 (t, 3H, J=7.3 Hz), 1.30-1.39 (m, 10H), 1.70-1.74 (m, 2H), 1.79-1.85 (m, 2H), 1.97 (d like, 3H), 2.06 (s, 2H), 2.35 (s, 3H), 3.05-3.08 (m, 4H), 3.71 (d, 2H, J=5.9 Hz), 4.01 (q, 2H, J=7.3 Hz), 4.71-4.77 (m, 1H), 5.84 (d, 1H, J=3.4 Hz), 6.37 (t, 1H, J=1.9 Hz), 7.25 (d, 1H, J=7.8 Hz), 7.59 (s, 1H), 7.74 (d, 1H, J=8.3 Hz), 8.28 (t, 1H, J=5.9 Hz), 8.39 (s, 1H), 9.47-9.57 (m, 1H); IR (KBr) cm$^{-1}$: 3418, 3317, 2926, 2855, 1738, 1673, 1635, 1469, 1398, 1343, 1329, 1192, 1177, 1164, 757; MS (ESI) m/z: 511 ([M-Et]$^+$).

EXAMPLE 4A-3

Ethyl 3-[2-[1-[2-[4-[N-(5-methylpyridin-2-yl)-2-furancarboxamido]piperidin-1-yl]ethyl]cyclohexyl]acetamido]propionate

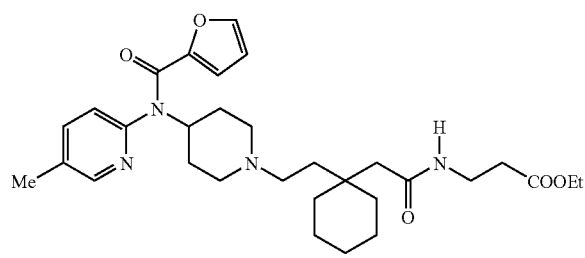

The title compound was synthesized from the compound obtained in Example 3A-3 in the same manner as in Example 4A-1 except that ethyl 3-aminopropionate was used instead of ethyl 4-aminobutyrate.

Hydrochloride $^1$H-NMR (DMSO-d$_6$) δ: 1.08 (t, 3H, J=7.3 Hz), 1.27-1.40 (m, 10H), 1.71-1.75 (m, 2H), 1.79-1.88 (m, 2H), 1.99-2.04 (m, 4H), 2.37 (s, 3H), 2.42-2.44 (m, 2H), 3.06-3.15 (m, 4H), 3.21-3.27 (m, 2H), 3.49-3.52 (m, 4H), 4.05 (q like, 2H), 4.77 (t like, 1H), 5.86 (d, 1H, J=3.4 Hz), 6.37 (dd, 1H, J=2.0, 3.4 Hz), 7.26 (d, 1H, J=7.8 Hz), 7.59 (s, 1H), 7.74 (dd, 1H, J=2.0, 5.8 Hz), 8.07 (m, 1H), 8.40 (d, 1H, J=2.0 Hz), 9.51-9.61 (m, 1H); IR (KBr) cm$^{-1}$: 3440, 2927, 1731, 1651, 1644, 1633, 1557, 1470, 1190, 1031; MS (ESI) m/z: 553 (MH$^+$).

EXAMPLE 4A-4

Ethyl 4-[2-[1-[2-[4-[N-(5-methylpyridin-2-yl)-2-furancarboxamido]piperidin-1-yl]ethyl]cyclopentyl]acetamido]butyrate

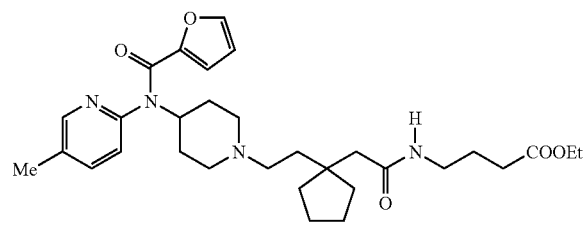

The title compound was synthesized from the compound obtained in Example 3A-4 in the same manner as in Example 4A-1.

$^1$H-NMR (CDCl$_3$) δ: 1.57 (t, 3H, J=7.3 Hz), 1.30-1.33 (m, 3H), 1.51-1.60 (m, 11H), 1.70-1.86 (m, 5H), 2.00 (m, 5H), 2.20-2.35 (m, 7H), 3.00-3.12 (m, 8H), 3.46 (d, 1H, J=10.7 Hz), 4.03 (q, 2H, J=6.8, 10.2 Hz), 4.74 (m, 1H), 5.83 (d, 1H, J=3.4 Hz), 6.36 (dd, 1H, J=1.9, 3.4 Hz), 7.25 (d, 1H, J=8.3 Hz), 7.59 (d, 1H, J=1.0 Hz), 7.73 (d, 1H, J=1.9H), 8.02 (m, 1H), 8.39 (s, 1H); IR (KBr) cm$^{-1}$: 3426, 2950, 1728, 1643, 1470, 1338, 1190, 1030, 755; MS (ESI) m/z: 553 (MH$^+$).

EXAMPLE 4B-1

Di-tert-butyl 2-[1-[2-[4-[N-(p-tolyl)-2-furancarboxamido]piperidin-1-yl]ethyl]cyclohexyl]acetyliminodiacetate

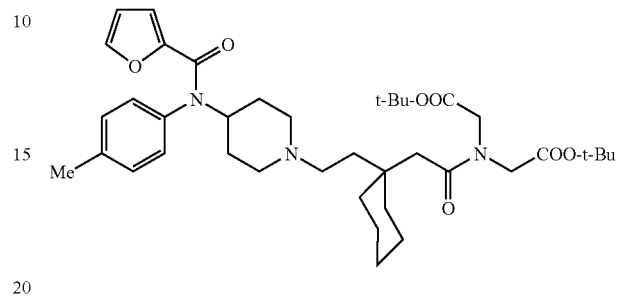

[1-[2-[4-[N-(p-Tolyl)-2-furancarboxamido]piperidin-1-yl]ethyl]cyclohexyl]acetic acid (0.2144 g) and di-tert-butyl iminodiacetate (0.2389 g) were dissolved in dichloromethane (5 mL). To this were added N,N-diisopropylethylamine (0.18 g) and then 2-bromo-1-ethylpyridinium tetrafluoroborate (0.26 g) at room temperature. The solution was stirred for 20 hours. After addition of ethyl acetate (60 mL), the solution was washed in turn with saturated aqueous sodium bicarbonate solution and saturated aqueous sodium chloride solution. It was dried over (MgSO$_4$), and the solvent was distilled off under reduced pressure. The resulting residue was purified by chromatography [silica gel, dichloromethane-methanol-aqueous ammonia (90:3:0.2 to 95:5:0.3)] to give the title compound (0.2722 g).

$^1$H-NMR (DMSO-d$_6$) δ: 1.20-1.50 (m, 12H), 1.38 (s, 9H), 1.42 (s, 9H), 1.50-1.60 (m, 2H), 1.68-1.78 (m, 2H), 1.87-2.01 (m, 2H), 2.15 (s, 2H), 2.10-2.22 (m, 2H), 2.37 (s, 3H), 2.80-2.93 (m, 2H), 3.86 (s, 2H), 4.07 (s, 2H), 4.43-4.54 (m, 1H), 5.47 (d, 1H, J=3.4 Hz), 6.28 (dd, 1H, J=1.5 Hz, 3.4 Hz), 7.07 (d, 2H, J=8.3 Hz), 7.25 (d, 2H, J=8.3 Hz), 7.58 (d, 1H, J=1.5 Hz).

EXAMPLE 4B-2 tert-Butyl [2-[1-[2-[4-[N-(p-tolyl)-2-furancarboxamido]piperidin-1-yl]ethyl]cyclohexyl]acetamido]acetate

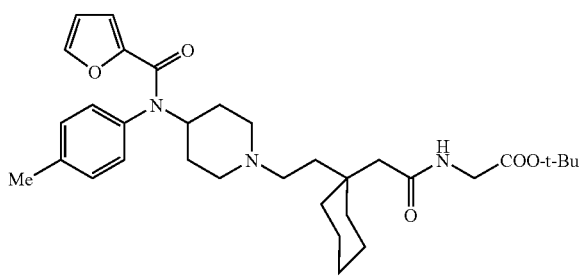

The title compound was synthesized from the compound obtained in Example 3B-1 in the same manner as in Example 4B-1. This product was subjected to the subsequent step without further purification.

EXAMPLE 4B-3

Ethyl 4-[2-[1-[2-[4-[N-(p-tolyl)-2-furancarboxamido]piperidin-1-yl]ethyl]cyclohexyl]acetamido]butyrate

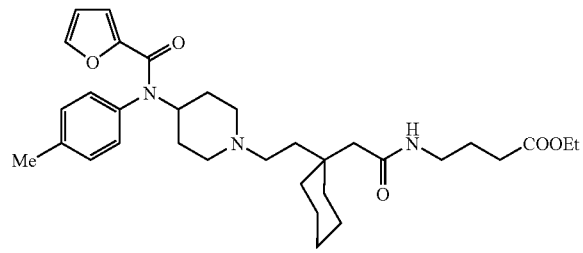

The title compound was synthesized from the compound obtained in Example 3B-1 in the same manner as in Example 4B-1.

$^1$H-NMR (DMSO-$d_6$) δ: 1.18 (t, 3H, J=7.3 Hz), 1.16-1.52 (m, 12H), 1.56-1.64 (m, 2H), 1.71-1.82 (m, 2H), 1.90-2.10 (brm, 2H), 1.98 (s, 2H), 2.16-2.34 (m, 4H), 2.37 (s, 3H), 2.84-3.02 (m, 4H), 3.10-3.35 (brm, 2H), 4.04 (q, 2H, J=7.3 Hz), 4.44-4.56 (m, 1H), 5.47 (d, 1H, J=3.4 Hz), 6.28 (dd, 1H, J=1.5 Hz, 3.4 Hz), 7.09 (d, 2H, J=8.3 Hz), 7.25 (d, 2H, J=8.3 Hz), 7.59 (d, 1H, J=1.5 Hz), 7.70-7.76 (m, 1H).

EXAMPLE 4B-4

Tetraethyl 2-[1-[2-[4-[N-(p-tolyl)-2-furancarboxamido]piperidin-1-yl]ethyl]cyclohexyl]acetylimino-N,N-bis(acetyliminodiacetate)

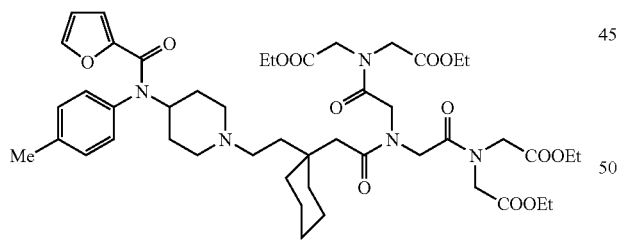

The title compound was synthesized from the compound obtained in Example 3B-1 in the same manner as in Example 4B-1.

$^1$H-NMR (DMSO-$d_6$) δ: 1.15-1.24 (m, 12H), 1.25-1.39 (brm, 10H), 1.40-1.48 (brm, 2H), 1.49-1.61 (m, 2H), 1.66-1.82 (brm, 2H), 1.83-2.00 (brm, 2H), 2.07 (s, 2H), 2.07-2.22 (brm, 2H), 2.37 (s, 3H), 2.80-2.95 (brm, 2H), 4.04-4.31 (m, 20H), 4.41-4.55 (brm, 1H), 5.46 (d, 1H, J=3.4 Hz), 6.29 (dd, 1H, J=2.0 Hz, 3.4 Hz), 7.09 (d, 2H, J=8.3 Hz), 7.26 (d, 2H, J=8.3 Hz), 7.59 (d, 1H, J=2.0 Hz); IR (NaCl film) cm$^{-1}$: 2928, 1744, 1676, 1643, 1470, 1405, 1189, 1025, 757, 736; MS (ESI) m/z: 910 (MH$^+$).

EXAMPLE 4B-5

2-Acetoxymethyl-2-[1-[2-[4-[N-(5-methylpyridin-2-yl)-2-furancarboxamido]piperidin-1-yl]ethyl]cyclohexyl]acetamido-1,3-diacetoxypropane

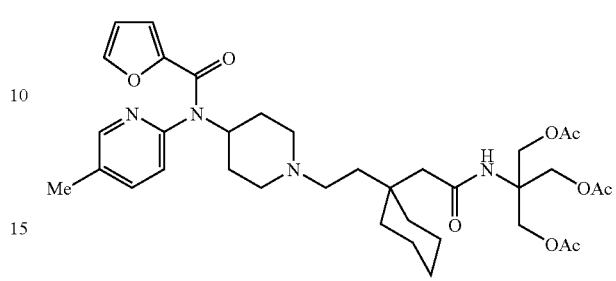

The title compound was synthesized from the compound obtained in Example 3A-3 in the same manner as in Example 4A-1. This product was subjected to the subsequent step without further purification.

EXAMPLE 4B-6

N-[1-[2-[1-[N,N-Bis[N-[tris (acetoxymethyl)methyl]carbamoylmethyl]carbamoylmethyl]cyclohexyl]ethyl]piperidin-4-yl]-N-(5-methylpyridin-2-yl)-2-furancarboxamide

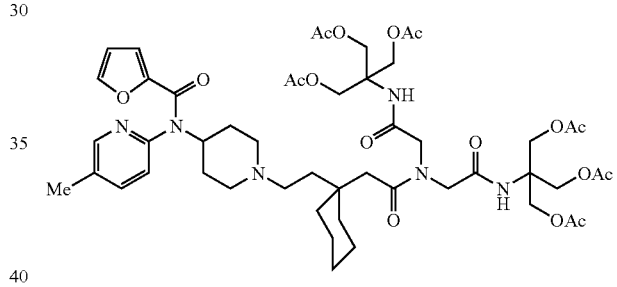

The title compound was synthesized from the compound obtained in Example 3A-3 in the same manner as in Example 4A-1. This product was subjected to the subsequent step without further purification.

EXAMPLE 4C-1

Diethyl 2-[1-[2-[4-[N-(5-methylpyridin-2-yl)-2-furancarboxamido]piperidin-1-yl]ethyl]cyclohexyl]acetyliminodiacetate

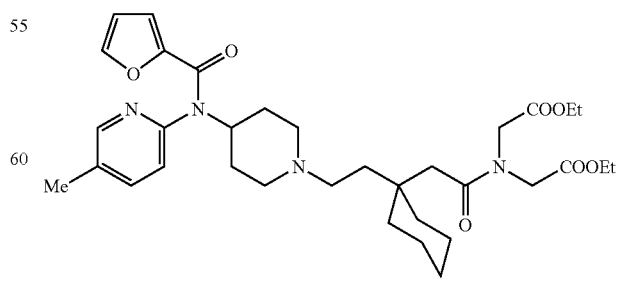

[1-[2-[4-[N-(5-Methylpyridin-2-yl)-2-furancarboxamido]piperidin-1-yl]ethyl]cyclohexyl]acetic acid (0.2527 g) was dissolved in dichloromethane (5 mL) and N,N-dimethylformamide (5 drops) under ice cooling. Oxalyl chloride (0.10 mL) was added to the solution dropwise. The temperature was allowed to rise to room temperature, at which the solution was stirred for 1 hour. The solvent was distilled off under reduced pressure, and dichloromethane (3 mL) was added under ice cooling to dissolve the residue. To this was added a solution of ethyl iminodiacetate (0.21 g) and triethylamine (0.23 g) in dichloromethane (2 mL), which was then stirred at room temperature for 2 days. The reaction solution without any pre-treatment was purified by chromatography [silica gel, dichloromethane-methanol-aqueous ammonia (95:5:0.3)] to give the title compound (0.1702 g).

$^1$H-NMR (DMSO-d$_6$) δ: 1.17 (t, 3H, J=7.3 Hz), 1.21 (t, 3H, J=7.3 Hz), 1.25-1.50 (m, 12H), 1.52-1.59 (m, 2H), 1.70-1.78 (m, 2H), 1.88-1.96 (m, 2H), 2.11-2.20 (m, 2H), 2.19 (s, 2H), 2.35 (s, 3H), 2.82-2.89 (m, 2H), 3.99 (s, 2H), 4.06 (q, 2H, J=7.3 Hz), 4.13 (q, 2H, J=7.3 Hz), 4.25 (s, 2H), 4.42 (tt, 1H, J=3.4 Hz, 12.2 Hz), 5.84 (d, 1H, J=3.4 Hz), 6.32 (dd, 1H, J=1.5 Hz, 3.4 Hz), 7.16 (d, 1H, J=8.3 Hz), 7.52 (d, 1H, J=1.5 Hz), 7.67 (dd, 1H, J=2.4 Hz, 8.3 Hz), 8.35 (d, 1H, J=2.4 Hz); IR (NaCl, film) cm$^{-1}$: 2927, 1746, 1650, 1645, 1470, 1189, 1028, 754; MS (ESI) m/z: 625 (MH$^+$).

EXAMPLE 4D-1

N-[1-[2-[1-(Carbamoylmethyl)cyclohexyl]ethyl]piperidin-4-yl]-N-(5-methylpyridin-2-yl)-2-furancarboxamide

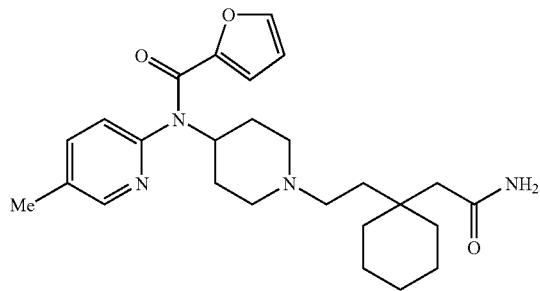

[1-[2-[4-[N-(5-Methylpyridin-2-yl)-2-furancarboxamido]piperidin-1-yl]ethyl]cyclohexyl]acetic acid (909 mg), ammonium chloride (216 mg), benzotriazol-1-yloxytrispyrrolidinophosphonium hexafluorophosphate (1.56 g), 1-hydroxybenzotriazole hydrate (470 mg) and N,N-diisoprpoylamine (1.4 mL) were dissolved in N,N-dimethylformamide (8 mL). The solution was stirred at room temperature for 22 hours. Saturated aqueous sodium bicarbonate solution was added to the solution, and it was extracted with chloroform. The organic layer was dried over anhydrous magnesium sulfate, filtered, and then, the solvent was distilled off under reduced pressure. The resulting residue was purified by chromatography (silica gel, chloroform:methanol=10:1) to give the title compound (652 mg).

Hydrochloride
$^1$H-NMR (DMSO-d$_6$) δ: 1.29-1.42 (m, 10H), 1.73-1.87 (m, 4H), 1.99-2.05 (m, 4H), 2.37 (s, 3H), 3.06-3.11 (m, 4H), 3.52 (d, 1H, J=12.2 Hz), 4.77 (t like, 1H), 5.87 (d, 1H, J=3.4 Hz), 6.36 (dd, 1H, J=1.5, 2.9 Hz), 6.85 (s, 1H), 7.25 (d, 1H, J=7.8 Hz), 7.38 (s, 1H), 7.59 (s, 1H), 7.75 (d, 1H, J=7.8 Hz), 8.40 (s, 1H); IR (KBr) cm$^{-1}$: 3417, 2927, 1651, 1469, 1402, 1338, 1230, 1191, 1031, 754; MS (ESI): m/z 453 (MH$^+$).

EXAMPLE 4D-2

N-[1-[2-[1-(Cyanomethyl)cyclohexyl]ethyl]piperidin-4-yl]-N-(5-methylpyridin-2-yl)-2-furancarboxamide

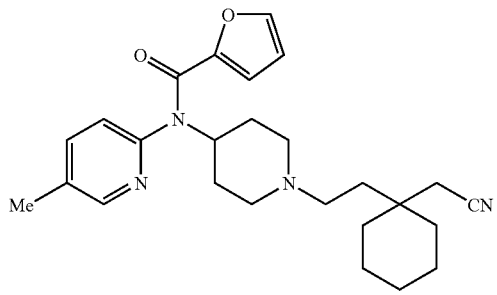

To a solution of N-[1-[2-[1-(carbamoylmethyl)cyclohexyl]ethyl]piperidin-4-yl]-N-(5-methylpyridin-2-yl)-2-furancarboxamide (154 mg) dissolved in dichloromethane (3 mL) was added triethylamine (0.10 mL). Methanesulfonyl chloride (0.038 mL) was added to the solution under ice cooling. After allowing the temperature to rise to room temperature, the solution was stirred for 24 hours. Triethylamine (0.14 mL) and methanesulfonyl chloride (0.063 mL) were further added to the solution under ice cooling. The solution was stirred at room temperature for 24 hours. Water was added to he solution and it was extracted with chloroform. The organic layer was dried over anhydrous magnesium sulfate, and then, the solvent was distilled off under reduced pressure. The resulting residue was purified by chromatography (silica gel, chloroform:methanol=20:1) to give the title compound (133 mg).

Hydrochloride
$^1$H-NMR (DMSO-d$_6$) δ: 1.22-1.40 (m, 10H), 1.70-1.73 (m, 2H), 1.75-1.88 (m, 2H), 2.01 (d, 1H, J=13.7 Hz), 2.35 (s, 3H), 2.54 (s., 2H), 2.97 (m, 2H), 3.09 (q like, 2H), 4.75 (t like, 1H), 5.84 (d, 1H, J=3.4 Hz), 6.36 (dd, 1H, J=1.9, 3.9 Hz), 7.25 (d, 1H, J=8.3 Hz), 7.59 (d, 1H, J=2.4 Hz), 7.74 (dd, 1H, J=2.0, 7.8 Hz), 8.39 (d, 1H, J=7.8 Hz), 9.87 (m, 1H); IR (KBr) cm$^{-1}$: 3426, 2927, 2855, 2639, 2239, 1643, 1470, 1401, 1336, 1190, 1031, 754; MS (ESI) m/z: 435 (MH$^+$).

EXAMPLE 4D-3 tert-Butyl

[1-[2-[4-[N-(5-methylpyridin-2-yl)-2-furancarboxamido]piperidin-1-yl]ethyl]cyclohexyl]acetohydroxamate

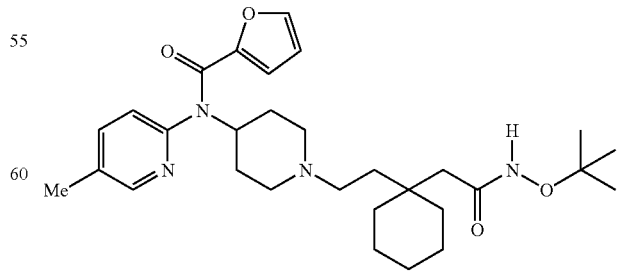

[1-[2-[4-[N-(5-Methylpyridin-2-yl)-2-furancarboxamido]piperidin-1-yl]ethyl]cyclohexyl]acetic acid (366 mg), O-(tert-butyl)hydroxylamine hydrochloride (304 mg), 1-hydroxybenzotriazole hydrate (187 mg) and triethylamine (0.56 mg) were dissolved in dichloromethane (15 mL). To this was added 1-ethyl-3-(3-dimethylaminopropyl)carbodiimide hydrochloride (239 mg) under cooling and the solution was stirred for 1 hour. The temperature was gradually allowed to rise to room temperature, and the solution was stirred for 44 hours. The solvent was distilled off under reduced pressure. The resulting residue was purified by chromatography (silica gel, chloroform:methanol=95:5) to give the title compound (390 mg).

Free Form $^1$H-NMR (DMSO-$d_6$) δ: 1.11 (s, 9H), 1.24-1.27 (m, 3H), 1.35-1.65 (m, 12H), 1.96 (d, 2H, J=12.7 Hz), 2.07 (s, 2H), 2.13-2.18 (m, 2H), 2.32-2.35 (m, 2H), 2.39 (s, 3H), 3.06 (d, 1H, J=11.3 Hz), 4.72 (tt, 1H, J=3.9, 7.8, 12.2 Hz), 5.93 (d, 1H, J=3.4 Hz), 6.19 (dd, 1H, J=1.9, 3.4 Hz), 6.99 (d, 1H, J=7.8 Hz), 7.22 (d, 1H, J=0.9 Hz), 7.52 (dd, 1H, J=2.5, 7.8 Hz), 8.38 (d, 1H, J=2.0 Hz), 9.60 (m, 1H); IR (KBr) cm$^{-1}$: 3443, 3239, 2926, 2857, 1651, 1592, 1573, 1470, 1365, 1329, 1249, 1233, 1189, 1029, 754; MS (ESI) m/z: 525 (MH$^+$).

EXAMPLE 4D-4

[1-[2-[4-[N-(5-Methylpyridin-2-yl)-2-furancarboxamido]piperidin-1-yl]ethyl]cyclohexyl]acetohydroxamic acid

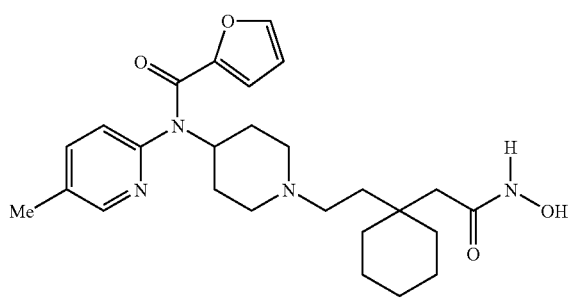

To tert-butyl [1-[2-[4-[N-(5-methylpyridin-2-yl)-2-furancarboxamido]piperidin-1-yl]ethyl]cyclohexyl]acetohydroxamate (266 mg) was added trifluoroacetic acid (3.0 mL), and the solution was stirred at room temperature for 23 hours. The solution was then stirred at 40° C. for 2 hours and trifluoroacetic acid (2.0 mL) was further added. The solution was stirred at 50° C. for 3 hours. The trifluoroacetic acid was distilled off by azeotropic distillation with xylene. Water and chloroform were added to the residue and the solution was neutralized with saturated aqueous sodium hydrogencarbonate solution. The solution was extracted with 20% ethanol/chloroform. The organic layer was dried over anhydrous magnesium sulfate, filtered, and then, the solvent was distilled off under reduced pressure. The resulting residue was purified by chromatography (silica gel, chloroform:methanol=85:15) to give the title compound (75 mg).

Hydrochloride $^1$H-NMR (DMSO-$d_6$) δ: 1.27-1.41 (m, 10H), 1.72-1.85 (m, 4H), 1.91 (s, 2H), 2.03 (d, 2H, J=11.2 Hz), 2.37 (s, 3H), 3.06-3.12 (m, 3H), 3.52 (d, 2H, J=12.2 Hz), 4.78 (t like, 1H), 5.87 (d, 1H, J=3.5 Hz), 6.37 (dd, 1H, J=1.5, 3.0 Hz), 7.26 (d, 1H, J=7.8 Hz), 7.59 (s, 1H), 7.75 (d, 1H, J=5.3 Hz), 8.41 (s, 1H), 8.73 (s, 1H), 9.32 (m, 1H), 10.46 (s, 1H); IR (KBr) cm$^{-1}$: 3426, 3191, 2928, 1644, 1469, 1400, 1341, 1911, 1034, 755; MS (ESI) m/z: 469 (MH$^+$).

EXAMPLE 4D-5 tert-Butyl [1-[2-[4-[N-(p-tolyl)-2-furancarboxamido]piperidin-1-yl]ethyl]cyclohexyl]acetohydroxamate

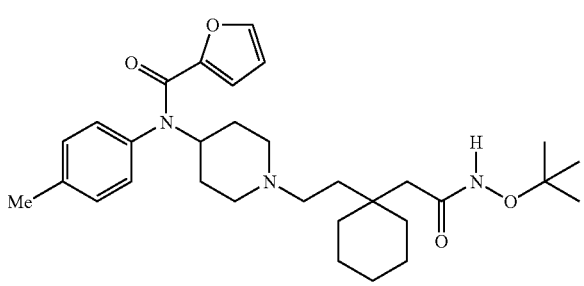

The title compound was synthesized from the compound obtained in Example 3B-1 in the same manner as in Example 4D-3.

$^1$H-NMR (CDCl$_3$) δ: 1.03 (s, 9H), 1.24 (d, 2H, J=11.7 Hz), 1.33-1.50 (m, 12H), 1.87 (d, 2H, J=11.7 Hz), 2.06 (s, 2H), 2.15 (t, 2H, J=11.7 Hz), 2.31-2.35 (m, 2H), 2.40 (s, 3H), 3.05 (d, 2H, J=11.7 Hz), 4.79 (t, 1H, J=12.2 Hz), 5.34 (s, 1H), 6.14 (dd, 1H, J=1.5 Hz, 3.4 Hz), 7.01 (d, 2H, J=8.3 Hz), 7.20 (d, 2H, J=7.9 Hz), 7.35 (d, 1H, J=1.4 Hz), 9.61-9.71 (m, 1H).

EXAMPLE 4D-6 [1-[2[4-[N-(p-tolyl)-2-furancarboxamido]piperidin-1-yl]ethyl cyclohexyl]acetohydroxamic acid

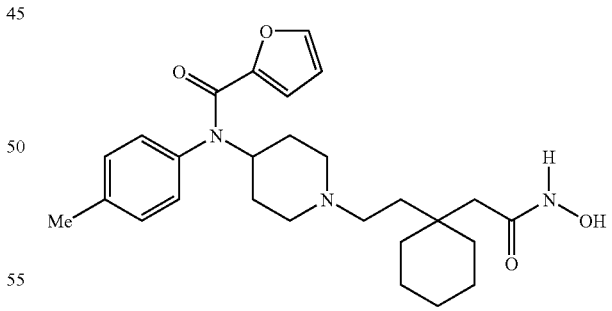

The title compound was synthesized from the compound obtained in Example 4D-5 in the same manner as in Example 4D-4.

$^1$H-NMR (DMSO-$d_6$) δ: 1.25-1.39 (m, 10H), 1.65-1.73 (m, 4H), 1.88 (brs, 2H), 2.01 (d, 2H, J=13.7 Hz), 2.37 (s, 3H), 3.01-3.06 (m, 2H), 3.08-3.14 (m, 2H), 3.39-3.51 (m, 4H), 4.80 (t like, 1H), 5.41 (brs, 1H), 6.33 (dd, 1H, J=1.9 Hz, 3.9 Hz), 7.16 (d, 2H, J=7.8 Hz), 7.29 (d, 2H, J=8.3 Hz), 7.66 (d, 1H, J=1.0 Hz), 9.40-9.51 (m, 1H), 10.47 (s, 1H).

EXAMPLE 4D-7

N-[1-[2-[1-(2-Tetrazolylethyl)cyclohexyl]ethyl]piperidin-4-yl]-N-(5-methylpyridin-2-yl)-2-furancarboxamide

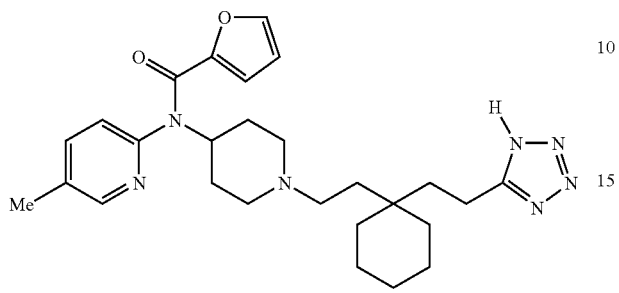

To a solution of N-[1-[2-[1-(2-cyanoethyl)cyclohexyl]ethyl]piperidin-4-yl]-N-(5-methylpyridin-2-yl) -2-furancarboxamide (355 mg) dissolved in toluene (2 mL) were added trimethylsilylazide (0.21 mL) and di-n-butyltin oxide (19.7 mg). The solution was heated under reflux for 11 hours. Trimethylsilylazide (0.42 mL) and di-n-butyltin oxide (98.0 mg) were further added to the solution and it was heated under reflux for 4 hours. The solvent was distilled off under reduced pressure (by azeotropic distillation with methanol). The resulting residue was purified by chromatography (silica gel, chloroform:methanol=80:20) to give the title compound (385 mg).

Hydrochloride $^1$H-NMR (DMSO-$d_6$) δ: 1.25-1.42 (m, 10H), 1.60-1.68 (m, 4H), 1.78-1.91 (m, 3H), 2.03 (d, 2H, J=8.8 Hz), 2.37 (s, 3H), 2.80 (d, 2H, J=8.7 Hz), 3.01 (m, 2H), 3.11-3.15 (m, 2H), 3.59 (d, 2H, J=10.7 Hz), 4.74 (m, 1H), 5.87 (d, 1H, J=3.4 Hz), 6.35 (d like, 1H), 7.59 (s, 1H), 7.75 (d like, 1H), 8.41 (m, 1H); MS (ESI) m/z: 492 (MH$^+$).

EXAMPLE 4D-8

N-[1-[2-[1-(2-Tetrazolylethyl)cyclohexyl]ethyl]piperidin-4-yl]-N-(p-tolyl)-2-furancarboxamide

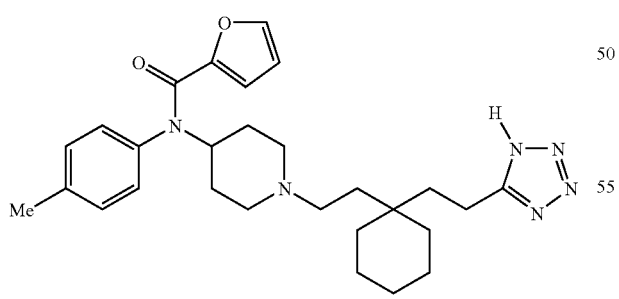

The title compound was synthesized from the compound obtained in Example 2-11 in the same manner as in Example 4D-7.

Hydrochloride mp 90-92° C.; $^1$H-NMR (DMSO-$d_6$) δ: 1.22-1.51 (m, 10H), 1.59-1.80 (m, 6H), 1.98-2.10 (m, 2H), 2.38 (s, 3H), 2.77-2.86 (m, 2H), 2.99-3.08 (m, 2H), 3.10-3.22 (m, 2H), 3.52-3.63 (m, 2H), 4.72-4.84 (m, 1H), 5.51 (d, 1H, J=3.4 Hz), 6.31 (dd, 1H, J=1.5 Hz, 3.4 Hz), 7.17 (d, 2H, J=8.3 Hz), 7.30 (d, 2H, J=8.3 Hz), 7.62 (d, 1H, J=1.5 Hz); IR (KBr) cm$^{-1}$: 3431, 2926, 2855, 1633, 1557, 1512, 1470, 1404, 1044, 757, 735; MS (ESI) m/z: 491 (MH$^+$).

EXAMPLE 5A-1

N-[1-[3-(2-Aminophenyl)propyl]piperidin-4-yl]-N-(5-methylpyridin-2-yl)-2-furancarboxamide

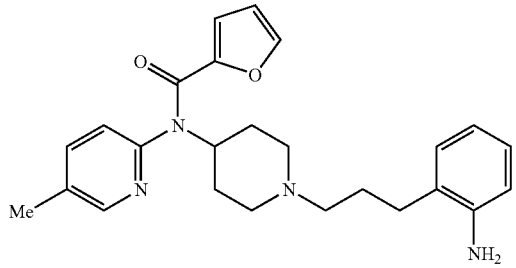

To a solution of tert-butyl [2-[3-[4-[N-(5-metylpyridin-2-yl)-2-furancarboxamido]piperidin-1-yl]propyl]phenyl]carbamate (790 mg) in methanol (15 mL) was added a 4N hydrochloric acid/ethyl acetate solution (2.3 mL) at room temperature. The solution was stirred at room temperature for 16 hours. The solution was then concentrated under reduced pressure. Saturated aqueous sodium bicarbonate solution was added to the residue and the solution was extracted with chloroform. The extract was dried over over anhydrous sodium sulfate, and then, concentrated under reduced pressure to give the title compound (700 mg).

$^1$H-NMR (CDCl$_3$) δ: 1.52-1.67 (m, 2H), 1.71-1.83 (m, 2H), 1.90-1.99 (m, 2H), 2.04-2.16 (m, 2H), 2.26-2.33 (m, 2H), 2.40 (s, 3H), 2.50 (t, 2H, J=7.2 Hz), 2.90-3.02 (m, 2H), 4.73 (tt, 1H, J=4.0 Hz, 12.0 Hz), 5.95 (d, 1H, J=3.2 Hz), 6.20 (dd, 1H, J=1.6 Hz, 3.2 Hz), 6.58-6.64 (m, 1H), 6.65-6.72 (m, 1H), 6.95-7.03 (m, 3H), 7.19-7.25 (m, 1H), 7.52 (dd, 1H, J=2.4 Hz, 7.6 Hz), 8.38-8.43 (m, 1H).

EXAMPLE 5A-2

N-[1-[3-(2-Aminophenyl)ethyl]piperidin-4-yl]-N-(5-methylpyridin-2-yl)-2-furancarboxamide

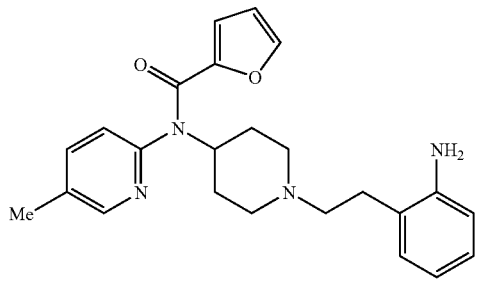

The title compound was synthesized from the compound obtained in Example 2-37 in the same manner as in Example 5A-1.

$^1$H-NMR (DMSO-d$_6$) δ: 1.85-2.01 (m, 2H), 2.02-2.11 (m, 2H), 2.37 (s, 3H), 3.08-3.25 (m, 6H), 3.32-3.40 (m, 2H), 3.56-3.67 (m, 2H), 4.72-4.83 (m, 1H), 5.91 (d, 1H, J=3.6 Hz), 6.36 (dd, 1H, J=1.6 Hz, 3.6 Hz), 7.24-7.43 (m, 5H), 7.54-7.59 (m, 1H), 7.75 (dd, 1H, J=2.4 Hz, 8.4 Hz), 8.41 (d, 1H, J=2.4 Hz); IR (KBr) cm$^{-1}$: 3426, 2927, 1624, 1572, 1559, 1469, 1320, 1190, 767; MS (ESI) m/z: 405 (MH$^+$). Anal. Calcd for C$_{24}$H$_{31}$Cl$_3$N$_4$O$_2$.1/3H$_2$O: C, 55.45; H, 6.14; N, 10.78. Found: C, 55.32; H, 6.31; N, 10.55.

EXAMPLE 5A-3

N-[1-[3-(2-Aminophenyl)propyl]piperidin-4-yl]-N-(p-tolyl)-2-furancarboxamide

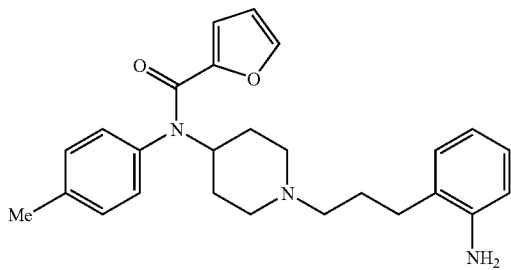

The title compound was synthesized from the compound obtained in Example 2-36 in the same manner as in Example 5A-1.

$^1$H-NMR (CDCl$_3$) δ: 1.40-1.59 (m, 2H), 1.71-1.82 (m, 2H), 1.83-1.92 (m, 2H), 2.05-2.20 (m, 2H), 2.24-2.36 (m, 2H), 2.42 (s, 3H), 2.49 (t, 2H, J=7.2 Hz), 2.89-3.05 (m, 2H), 3.84-4.29 (m, 2H), 4.77 (tt, 1H, J=4.0 Hz, 12.0 Hz), 5.29-5.41 (m, 1H), 6.09-6.17 (m, 1H), 6.60 (d, 1H, J=7.2 Hz), 6.68 (d, 1H, J=7.2 Hz), 6.97-7.04 (m, 4H), 7.21 (d, 2H, J=8.0 Hz), 7.31-7.38 (m, 1H).

EXAMPLE 5B-1

N-[1-[3-[2-(3-Cyclohexylpropionamido)phenyl]propyl]piperidin-4-yl]-N-(5-methylpyridin-2-yl)-2-furancarboxamide

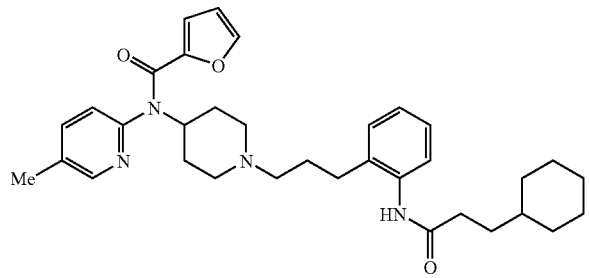

To a solution of N-[1-[3-(2-aminophenyl)propyl]piperidin-4-yl]-N-(5-methylpyridin-2-yl)-2-furancarboxamide (100 mg) and cyclohexylpropionic acid (49 mg) in dichloromethane (3 mL) were added 1-hydroxybenzotriazole (42 mg) and 1-ethyl-3-(3-dimethylaminopropyl)carbodiimide hydrochloride (60 mg) under ice cooling. The solution was stirred at room temperature for 64 hours. Chloroform was then added to the solution and the solution was washed in turn with water and saturated aqueous sodium bicarbonate solution. The solution was dried over anhydrous sodium sulfate, and then, concentrated under reduced pressure. The residue was purified by chromatography (NH silica gel, hexane:ethyl acetate=1:2) to give the title compound (120 mg).

Free Form $^1$H-NMR (CDCl$_3$) δ: 0.77-0.93 (m, 2H), 1.08-1.33 (m, 5H), 1.44-1.53 (m, 2H), 1.55-1.76 (m, 6H), 1.77-1.86 (m, 2H), 1.90-2.00 (m, 2H), 2.03-2.20 (m, 6H), 2.42 (s, 3H), 2.55-2.62 (m, 2H), 2.87-2.98 (m, 2H), 4.66-4.80 (m, 1H), 5.96-6.01 (m, 1H), 6.18-6.23 (m, 1H), 6.96-7.02 (m, 1H), 7.03-7.20 (m, 3H), 7.21-7.25 (m, 1H), 7.51-7.60 (m, 2H), 8.39-8.45 (m, 1H), 9.10-9.15 (m, 1H).

Hydrochloride mp 99-102° C.; $^1$H-NMR (DMSO-d$_6$) δ: 0.82-0.97 (m, 2H), 1.08-1.31 (m, 4H), 1.45-1.55 (m, 2H), 1.56-1.77 (m, 5H), 1.79-1.96 (m, 4H), 1.97-2.07 (m, 2H), 2.28-2.41 (m, 2H), 2.36 (s, 3H), 2.54-2.63 (m, 2H), 2.91-3.03 (m, 2H), 3.04-3.18 (m, 2H), 3.41-3.52 (m, 2H), 4.70-4.81 (m, 1H), 5.90 (d, 1H, J=3.2 Hz), 6.35 (dd, 1H, J=1.6 Hz, 3.2 Hz), 7.10-7.33 (m, 5H), 7.53-7.58 (m, 1H), 7.73 (dd, 1H, J=2.4 Hz, 8.0 Hz), 8.39 (d, 1H, J=2.4 Hz), 9.26 (brs, 1H), 9.38-9.78 (m, 1H); IR (KBr) cm$^{-1}$: 3425, 2922, 2849, 1651, 1520, 1470, 1453, 1322, 1189, 1131, 756; MS (ESI) m/z: 557 (MH$^+$). Anal. Calcd for C$_{34}$H$_{45}$ClN$_4$O$_3$.2H$_2$O: C, 64.90; H, 7.85; N, 8.90. Found: C, 65.07; H, 7.77; N, 8.69.

EXAMPLE 5B-2

N-[1-[3-[2-(4-Cyclohexylbutyramido)phenyl]propyl]piperidin-4-yl]-N-(5-methylpyridin-2-yl)-2-furancarboxamide

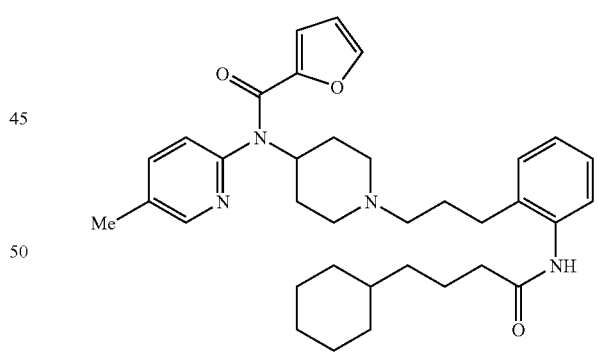

The title compound was synthesized from the compound obtained in Example 5A-1 in the same manner as in Example 5B-1.

Free Form $^1$H-NMR (CDCl$_3$) δ: 0.78-0.93 (m, 2H), 1.08-1.29 (m, 6H), 1.52-1.75 (m, 9H), 1.77-1.87 (m, 2H), 1.91-2.01 (m, 2H), 2.01-2.18 (m, 6H), 2.42 (s, 3H), 2.55-2.63 (m, 2H), 2.90-2.99 (m, 2H), 4.68-4.79 (m, 1H), 5.98 (d, 1H, J=3.6 Hz), 6.21 (dd, 1H, J=1.6 Hz, 3.6 Hz), 6.96-7.02 (m, 1H), 7.04-7.20 (m, 3H), 7.21-7.25 (m, 1H), 7.51-7.59 (m, 2H), 8.39-8.44 (m, 1H), 9.22 (brs, 1H).

Hydrochloride

¹H-NMR (DMSO-d₆,) δ: 0.80-0.94 (m, 2H), 1.06-1.29 (m, 6H), 1.53-1.74 (m, 7H), 1.80-1.95 (m, 4H), 1.96-2.06 (m, 2H), 2.25-2.35 (m, 2H), 2.36 (s, 3H), 2.55-2.63 (m, 2H), 2.91-3.01 (m, 2H), 3.04-3.17 (m, 2H), 3.41-3.51 (m, 2H), 4.75 (tt, 1H, J=4.0 Hz, 12.0 Hz), 5.89 (d, 1H, J=3.6 Hz), 6.35 (dd, 1H, J=2.0 Hz, 3.6 Hz), 7.09-7.26 (m, 4H), 7.27-7.34 (m, 1H), 7.54-7.58 (m, 1H), 7.73 (dd, 1H, J=2.4 Hz, 8.0 Hz), 8.36-8.41 (m, 1H), 9.27 (brs, 1H), 9.63-9.77 (m, 1H); IR (KBr) cm⁻¹: 3426, 2922, 2848, 1642, 1523, 1470, 1449, 1401, 1340, 1190, 1133, 1030, 754; MS (ESI) m/z: 571 (MH⁺). Anal. Calcd for $C_{35}H_{47}ClN_4O_3 \cdot 1/2H_2O$: C, 68.22; H, 7.85; N, 9.09. Found: C, 68.17; H, 8.11; N, 8.93.

EXAMPLE 5B-3

Ethyl N-[2-[3-[4-[N-(p-tolyl)-2-furancarboxaimdo]piperidin-1-yl]propyl]phenyl]-N-(3-cyclohexylpropionyl)aminobutyrate

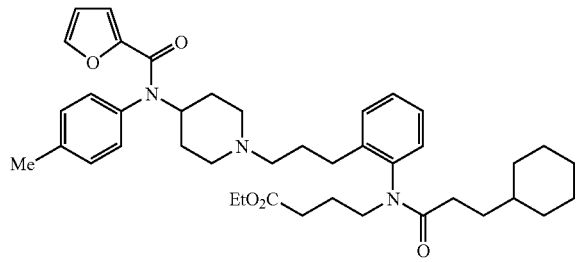

To a solution of ethyl N-[2-[3-[4-[N-(p-tolyl)-2-furancarboxaimdo]piperidin-1-yl]propyl]phenyl]aminobutyrate (0.2552 g) dissolved in dichloromethane (10 mL) were added 3-cyclohexanepropionic acid (0.11 g), N,N-diisopropylethylamine (0.31 g) and 2-bromo-1-ethylpyridinium tetrafluoroborate (0.39 g) successively. The solution was stirred at room temperature for 5 days. After addition of ethyl acetate (50 mL), the solution was washed in turn with saturated aqueous sodium bicarbonate solution and saturated aqueous sodium chloride solution, dried over (MgSO₄) and the solvent was distilled off under reduced pressure. The resulting residue was purified by chromatography [silica gel, dichloromethane-methanol-aqueous ammonia (97:3:0.2)] to give the title compound. This product was subjected to the subsequent step without further purification.

EXAMPLE 5B-4

Methyl 1-[N-[2-[2-[4-[N-(5-methylpyridin-2-yl)-2-furancarboxamido]piperidin-1-yl]ethyl]phenyl]carbamoylmethyl]cyclohexylacetate

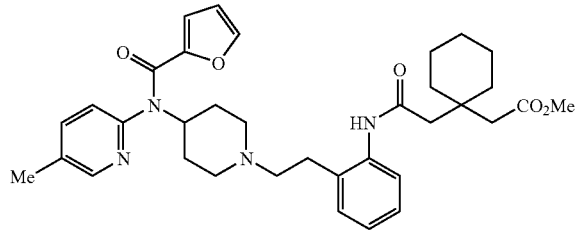

To a solution of 1-methoxycarbonylmethylcyclohexylacetic acid (265 mg) in dichloromethane (10 mL) was added N,N-dimethylformamide (one drop) and then oxalyl chloride (0.12 ML) under ice cooling. The solution was stirred at room temperature for 1 hour and concentrated under reduced pressure. After addition of triethylamine (0.29 mL), a solution of the residue in dichloromethane (5 mL) was added to a solution of N-[1-[3-(2-aminophenyl)ethyl]piperidin-4-yl]-N-(5-methylpyridin-2-yl)-2-furancarboxamide (250 mg) in dichloromethane (5 mL) under ice cooling. After stirring the solution under ice cooling for 1 hour, saturated aqueous sodium bicarbonate solution and chloroform were added to the solution, and then, it was separated to liquid layers. The organic layer was washed in turn with 1N hydrochloric acid, saturated aqueous sodium bicarbonate solution and saturated aqueous sodium chloride solution, dried over anhydrous magnesium sulfate and concentrated under reduced pressure. The resulting residue was purified by chromatography (silica gel, hexane:ethyl acetate=6:4) to give the title compound (320 mg).

Free Form

¹H-NMR (CDCl₃) δ: 1.37-1.59 (m, 8H), 1.60-1.74 (m, 2H), 1.88-2.03 (m, 4H), 2.22-2.33 (m, 2H), 2.42 (s, 3H), 2.43 (s, 2H), 2.52-2.63 (m, 4H), 2.69-2.78 (m, 2H), 2.95-3.04 (m, 2H), 3.68 (s, 3H), 4.74 (tt, 1H, J=4.0 Hz, 12.0 Hz), 5.95 (d, 1H, J=3.6 Hz), 6.20 (dd, 1H, J=1.6 Hz, 3.6 Hz), 6.96-7.06 (m, 2H), 7.09-7.14 (m, 1H), 7.14-7.21 (m, 1H), 7.21-7.24 (m, 1H), 7.53 (dd, 1H, J=2.4 Hz, 8.0 Hz), 7.82-7.89 (m, 1H), 8.41 (d, 1H, J=2.4 Hz), 9.30 (brs, 1H).

Hydrochloride mp104-107° C.; ¹H-NMR (DMSO-d₆) δ: 1.30-1.60 (m, 10H), .1.79-1.98 (m, 2H), 2.01-2.13 (m, 2H), 2.37 (s, 3H), 2.54 (s, 2H), 2.58 (s, 2H), 2.89-2.98 (m, 2H), 3.13-3.24 (m, 4H), 3.50-3.61 (m, 2H), 3.58 (s, 3H), 4.73-4.84 (m, 1H), 5.92 (d, 1H, J=3.6 Hz), 6.36 (dd, 1H, J=1.6 Hz, 3.6 Hz), 7.14-7.32 (m, 5H), 7.54-7.59 (m, 1H), 7.74 (dd, 1H, J=2.4 Hz, 8.0 Hz), 8.41 (d, 1H, J=2.4 Hz), 9.35-9.40 (m, 1H), 9.50-9.61 (m, 1H); IR (KBr) cm⁻¹: 3426, 2928, 2856, 1727, 1642, 1516, 1469, 1452, 1340, 1191, 755; MS (ESI) m/z: 601 (MH⁺). Anal. Calcd for $C_{35}H_{45}ClN_4O_5 \cdot 2/3H_2O$: C, 64.75; H, 7.19; N, 8.63. Found: C, 64.76; H, 7.38; N, 8.59.

EXAMPLE 5B-5

Ethyl N-[(1-methoxycarbonylmethylcyclohexyl)acetyl]-N-[2-[2-[4-[N-(5-methylpyridin-2-yl)-2-furancarboxamido]piperidin-1-yl]ethyl]phenyl]aminoacetate

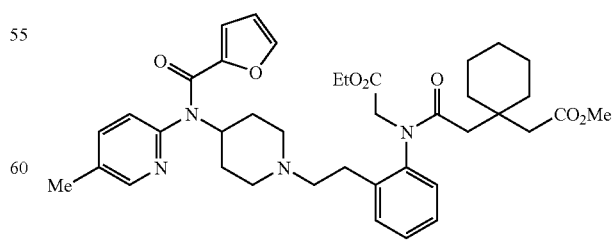

The title compound was synthesized from the compound obtained in Example 5D-2 in the same manner as in Example 5B-4.

Free Form

¹H-NMR (CDCl₃) δ: 1.18-1.53 (m, 11H), 1.55-1.70 (m, 2H), 1.90-2.00 (m, 2H), 2.14-2.30 (m, 3H), 2.39 (s, 3H), 2.46-2.79 (m, 6H), 2.93-3.05 (m, 2H), 3.54-3.59 (m, 1H), 3.57 (s, 3H), 4.15-4.24 (m, 2H), 4.69-4.83 (m, 2H), 5.96 (d, 1H, J=3.6 Hz), 6.20 (dd, 1H, J=1.6 Hz, 3.6 Hz), 7.00 (d, 1H, J=8.0 Hz), 7.20-7.33 (m, 4H), 7.46 (d, 1H, J=8.0 Hz), 7.52 (dd, 1H, J=2.4 Hz, 8.0 Hz), 8.40 (d, 1H, J=2.4 Hz).

EXAMPLE 5B-6

N-[1-[2-[1-[5-Hydroxy-3,3-bis(hydroxymethyl)pentyl]cyclohexyl]ethyl]piperidin-4-yl]-N-(5-methylpyridin-2-yl)-2-furancarboxamide

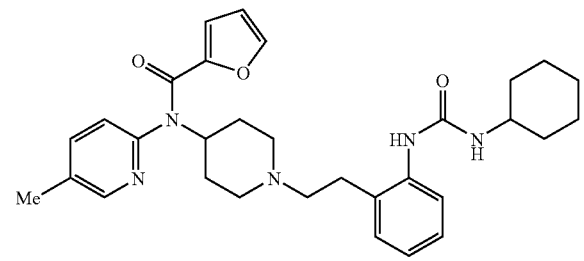

To a solution of N-[1-[3-(2-aminophenyl)ethyl]piperidin-4-yl]-N-(5-methylpyridin-2-yl)-2-furancarboxamide (82 mg) in 1,2-dichloroethane (2 mL) was added cyclohexyl isocyanate (38 mg) at room temperature. The solution was stirred at 50° C. for 5 hours. The solution was then concentrated under reduced pressure. The residue was purified by chromatography (NH silica gel, ethyl acetate) to give the title compound (70 mg).

Free Form

¹H-NMR (CDCl₃) δ: 1.05-1.19 (m, 3H), 1.20-1.43 (m, 2H), 1.56-1.74 (m, 3H), 1.85-2.11 (m, 6H), 2.13-2.26 (m, 2H), 2.40 (s, 3H), 2.54 (t, 2H, J=6.4 Hz), 2.71 (t, 2H, J=6.4 Hz), 2.97-3.09 (m, 2H), 3.60-3.73 (m, 1H), 4.51-4.63 (m, 1H), 4.74-4.88 (m, 1H), 6.02 (d, 1H, J=3.6 Hz), 6.21 (dd, 1H, J=1.6 Hz, 3.6 Hz), 6.98-7.05 (m, 2H), 7.08-7.13 (m, 1H), 7.15-7.24 (m, 2H), 8.20 (brs, 1H), 8.39 (d, 1H, J=2.4 Hz).

Hydrochloride mp 99-102° C.; ¹H-NMR (DMSO-d₆) δ: 0.82-0.97 (m, 2H), 1.08-1.31 (m, 4H), 1.45-1.55 (m, 2H), 1.56-1.77 (m, 5H), 1.79-1.96 (m, 4H), 1.97-2.07 (m, 2H), 2.28-2.41 (m, 2H), 2.36 (s, 3H), 2.54-2.63 (m, 2H), 2.91-3.03 (m, 2H), 3.04-3.18 (m, 2H), 3.41-3.52 (m, 2H), 4.70-4.81 (m, 1H), 5.90 (d, 1H, J=3.2 Hz), 6.35 (dd, 1H, J=1.6 Hz, 3.2 Hz), 7.10-7.33 (m, 5H), 7.53-7.58 (m, 1H), 7.73 (dd, 1H, J=2.4 Hz, 8.0 Hz), 8.39 (d, 1H, J=2.4 Hz), 9.26 (brs, 1H), 9.38-9.78 (m, 1H); IR (KBr) cm⁻¹: 3425, 2922, 2849, 1651, 1520, 1470, 1453, 1322, 1189, 1131, 756; MS (ESI) m/z: 557 (MH⁺); H). Anal. Calcd for C₃₄H₄₅ClN₄O₃.2H₂O: C, 64.90; H, 7.85; N, 8.90. Found: C, 65.07; H, 7.77; N, 8.69.

EXAMPLE 5B-7

N-[1-[3-[2-(3-Cyclohexylureido)phenyl]propyl]piperidin-4-yl]-N-(p-tolyl)-2-furancarboxamide

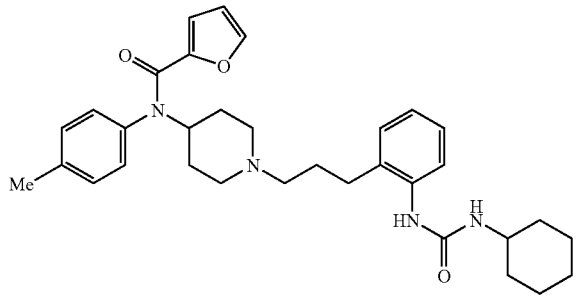

The title compound was synthesized from the compound obtained in Example 5A-1 in the same manner as in Example 5B-6.

Hydrochloride mp 112-115° C.; ¹H-NMR (DMSO-d₆) δ: 1.05-1.38 (m, 5H), 1.47-1.60 (m, 1H), 1.63-1.93 (m, 8H), 1.96-2.07 (m, 2H), 2.38 (s, 3H), 2.58-2.68 (m, 2H), 3.00-3.21 (m, 4H), 3.41-3.56 (m, 3H), 4.75-4.89 (m, 1H), 5.49 (d, 1H, J=3.6 Hz), 6.31 (dd, 1H, J=1.6 Hz, 3.6 Hz), 6.79-6.86 (m, 1H), 6.86-6.93 (m, 1H), 7.05-7.21 (m, 4H), 7.25-7.34 (m, 2H), 7.60-7.65 (m, 1H), 7.75-7.82 (m, 1H), 7.83-7.89 (m, 1H), 9.34-9.49 (m, 1H); IR (KBr) cm⁻¹: 3426, 2929, 1694, 1635, 1544, 1471, 1449, 1404, 1339, 1316, 1226, 1186, 759. Anal. Calcd for C₃₃H₄₃ClN₄O₃.1/3H₂O: C, 67.73; H, 7.52; N, 9.57. Found: C, 67.75; H, 7.67; N, 9.29.

EXAMPLE 5B-8

Ethyl 3-[2-[2-[4-[N-(5-methylpyridin-2-yl)-2-furancarboxamido]piperidin-1-yl]ethyl]phenyl]-5-cyclohexylhydantoate

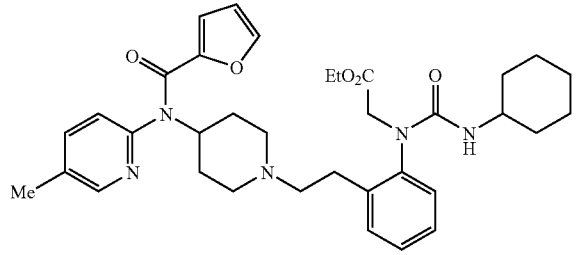

The title compound was synthesized from the compound obtained in Example 5D-2 in the same manner as in Example 5B-6.

Free Form

¹H-NMR (CDCl₃) δ: 0.81-1.10 (m, 2H), 1.25 (t, 3H, J=6.8 Hz), 1.28-1.37 (m, 2H), 1.47-1.77 (m, 5H), 1.77-1.89 (m, 2H), 1.90-2.02 (m, 2H), 2.12-2.25 (m, 2H), 2.40 (s, 3H), 2.45-2.61 (m, 2H), 2.66-2.77 (m, 2H), 2.93-3.06 (m, 2H), 3.53-3.69 (m, 2H), 3.91-4.02 (m, 1H), 4.10-4.28 (m, 2H), 4.69-4.83 (m, 2H), 5.94 (d, 1H, J=3.6 Hz), 6.20 (dd, 1H, J=1.6 Hz, 3.6 Hz), 7.01 (d, 1H, J=8.4 Hz), 7.21-7.33 (m, 4H), 7.49-7.57 (m, 2H), 8.40 (d, 1H, J=2.0 Hz); MS (ESI) m/z: 616 (MH⁺).

EXAMPLE 5B-9

N-[1-[3-[2-(3-Cyclohexylthioureido)phenyl]propyl]piperidin-4-yl]-N-(p-tolyl)-2-furancarboxamide

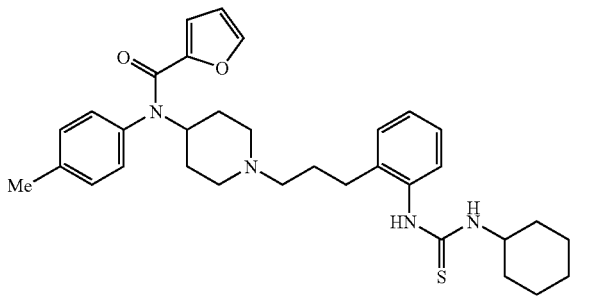

To a solution of N-[1-[3-(2-aminophenyl)propyl]piperidin-4-yl]-N-(p-tolyl)-2-furancarboxamide (0.42 g) dissolved in 1,2-dichloroethane (5 mL) was added cyclohexyl isothiocyanate (0.42 g) at room temperature. The solution was then heated under reflux for 8 hours. The solution was purified by chromatography [silica gel, dichloromethane-methanol-aqueous ammonia (97:3:0.2-95:5:0.3)] to give the title compound (0.2458 g).

$^1$H-NMR (DMSO-$d_6$) δ: 1.09-1.43 (m, 7H), 1.50-1.68 (m, 5H) 1.69-1.77 (m, 2H), 1.81-1.89 (m, 2H), 1.90-1.98 (m, 2H), 2.18-2.24 (m, 2H), 2.37 (s, 3H), 2.43-2.50 (m, 2H), 2.80-2.89 (m, 2H), 3.98-4.12 (m, 1H), 4.48 (tt, 1H, J=3.9 Hz, 12.2 Hz), 5.45 (d, 1H, J=3.4 Hz), 6.28 (dd, 1H, J=1.5 Hz, 3.4 Hz), 7.08 (d, 2H, J=8.3 Hz), 7.10-7.20 (m, 5H), 7.25 (d, 2H, J=8.3 Hz), 7.59 (d, 1H, J=1.5 Hz), 8.85 (s, 1H); IR (NaCl film) cm$^{-1}$: 2927, 2852, 1636, 1515, 1471, 1327, 1305, 756, 735; MS (ESI) m/z: 559 (MH$^+$).

EXAMPLE 5C-1 tert-Butyl

N-[2-[2-[4-[N-(p-tolyl)-2-furancarboxamido]piperidin-1-yl]ethyl]phenyl]-N-(cyclohexylacetyl)aminoacetate

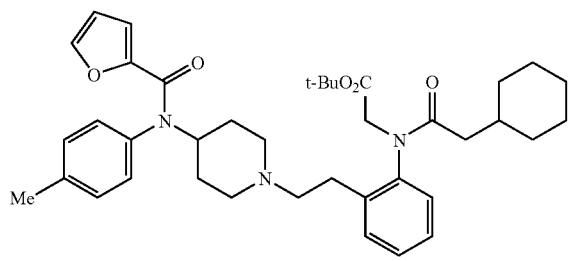

N-[1-[2-[2-(Cyclohexylacetamido)phenyl]ethyl]piperidin-4-yl]-N-(p-tolyl)-2-furancarboxamide (0.3464 g) and tert-butyl bromoacetate (0.38 g) were dissolved in N,N-dimethylformamide (5 mL). To this was added 60% sodium hydride/mineral oil (0.0622 g) and the solution was stirred at room temperature for 17 hours. After diluting with ethyl acetate (50 mL), the solution was washed with saturated aqueous sodium chloride solution, dried over (MgSO$_4$), and the solvent was distilled off under reduced pressure. The resulting residue was purified by chromatography (silica gel, ethyl acetate) to give the title compound (0.1318 g).

$^1$H-NMR (DMSO-$d_6$) δ: 0.62-1.88 (m, 17H), 1.40 (s, 9H), 2.02-2.12 (m, 2H), 2.37 (s, 3H), 2.44-2.54 (m, 2H), 2.55-2.63 (m, 2H), 2.88-2.96 (m, 2H), 3.60 (d, 1H, J=17.1 Hz), 4.45 (d, 1H, J=17.1 Hz), 4.46-4.54 (m, 1H), 5.46 (d, 1H, J=3.4 Hz), 6.28 (dd, 1H, J=1.5 Hz, 3.4 Hz), 7.09 (d, 2H, J=8.3 Hz), 7.25 (d, 2H, J=8.3 Hz), 7.26-7.48 (m, 4H), 7.59 (d, 1H, J=1.5 Hz).

EXAMPLE 5C-2 tert-Butyl

N-[2-[3-[4-[N-(p-tolyl)-2-furancarboxamido]piperidin-1-yl]propyl]phenyl]-N-(3-cyclohexylpropionyl)aminoacetate

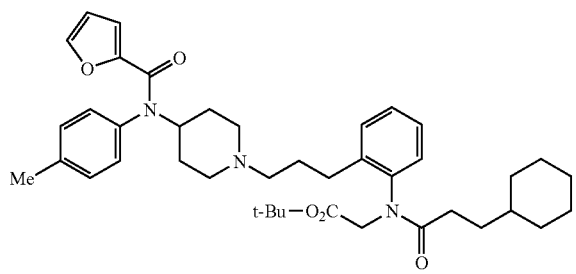

The title compound was synthesized from the compound obtained in Example 2-34 in the same manner as in Example 5C-1.

$^1$H-NMR (DMSO-$d_6$) δ: 0.60-0.75 (m, 2H), 0.95-1.12 (m, 4H), 1.40 (s, 9H), 1.20-1.48 (m, 7H), 1.49-1.69 (m, 4H), 1.70-1.82 (m, 3H), 1.84-2.01 (m, 3H), 2.20-2.31 (m, 2H), 2.37 (s, 3H), 2.40-2.52 (m, 2H), 2.79-2.89 (m, 2H), 3.60 (d, 1H, J=16.6 Hz), 4.41 (d, 1H, J=16.6 Hz), 4.42-4.53 (m, 1H), 5.46 (d, 1H, J=3.4 Hz), 6.28 (dd, 1H, J=2.0 Hz, 3.4 Hz), 7.08 9 d, 2H, J=8.3 Hz), 7.25 (d, 2H, J=8.3 Hz), 7.21-7.37 (m, 4H), 7.58 (d, 1H, J=2.0 Hz).

EXAMPLE 5D-1

Ethyl

N-[2-[3-[4-[N-(p-tolyl)-2-furancarboxamido]piperidin-1-yl]propyl]phenyl]aminobutyrate

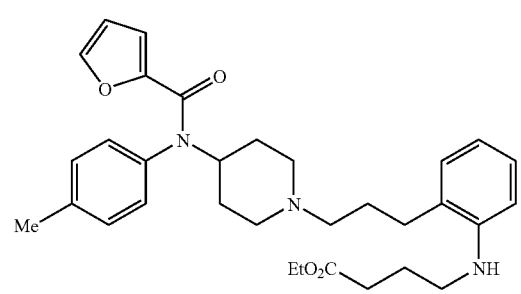

To a solution of N-[1-[3-(2-aminophenyl)propyl]piperidin-4-yl]-N-(p-tolyl)-2-furancarboxamide (0.3211 g) dissolved in ethanol (3 mL) were added ethyl 4-bromobutyrate (0.23 g) and then diisopropylamine (0.16 g). The solution was heated under reflux for 5 hours. After addition of ethyl acetate (10 mL), the solution was washed with saturated aqueous sodium chloride solution, dried over (MgSO$_4$), and the solvent was distilled off under reduced pressure. The resulting residue was purified by chromatography [silica gel, dichloromethane-methanol-aqueous ammonia (97:3:0.2)] to give the title compound (0.2552 g).

$^1$H-NMR (DMSO-$d_6$) δ: 1.17 (t, 3H, J=7.3 Hz), 1.39-1.42 (m, 2H), 1.56-1.67 (m, 2H), 1.70-1.83 (m, 4H), 1.90-2.10 (m, 2H), 2.19-2.33 (m, 4H), 2.37 (s, 3H), 2.35-2.43 (m, 2H), 2.83-2.94 (m, 2H), 2.98-3.06 (m, 2H), 4.05 (q, 2H, J=7.3 Hz), 4.46-4.58 (m, 1H), 4.86-4.92 (m, 1H), 5.47 (d, 1H, J=3.4 Hz), 6.29 (dd, 1H, J=1.5 Hz, 3.4 Hz), 6.46-6.51 (m, 2H), 6.87-6.90 (m, 1H), 6.93-6.98 (m, 1H), 7.10 (d, 2H, J=8.3 Hz), 7.26 (d, 2H, J=8.3 Hz), 7.59 (d, 1H, J=1.5 Hz).

EXAMPLE 5D-2

Ethyl N-[2-[2-[4-[N-(5-methylpyridyl-2-yl)-2-furancarboxamido]piperidin-1-yl]ethyl]phenyl]aminoacetate

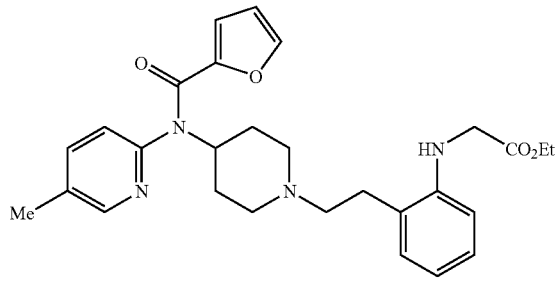

The title compound was synthesized from the compound obtained in Example 5A-2 in the same manner as in Example 5D-1.

$^1$H-NMR (CDCl$_3$) δ: 1.26 (t, 3H, J=7.2 Hz), 1.58-1.75 (m, 2H), 1.90-2.01 (m, 2H), 2.40 (s, 3H), 2.58 (t, 2H, J=6.4 Hz), 2.70 (t, 2H, J=6.4 Hz), 3.02-3.13 (m, 2H), 3.79 (s, 2H), 4.18 (q, 2H, J=7.2 Hz), 4.76 (tt, 1H, J=4.0 Hz, 12.0 Hz), 5.98 (d, 1H, J=3.6 Hz), 6.20 (dd, 1H, J=1.6 Hz, 3.6 Hz), 6.42 (d, 1H, J=8.0 Hz), 6.63-6.70 (m, 1H), 6.96-7.02 (m, 2H), 7.05-7.12 (m, 1H), 7.21-7.25 (m, 1H), 7.51 (dd, 1H, J=2.4 Hz, 8.0 Hz), 8.40 (d, 1H, J=2.4 Hz).

EXAMPLE 6

N-[1-[2-[1-[2-(N$^2$-Hydroxycarbamidoyl)ethyl]cyclohexyl]ethyl]piperidin-4-yl]-N-(p-tolyl)-2-furancarboxamide

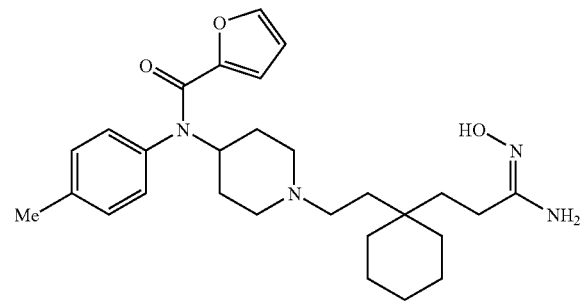

To a solution of N-[1-[2-[1-(2-cyanoethyl)cyclohexyl]ethyl]piperidin-4-yl]-N-(p-tolyl)-2-furancarboxamide (synthesized in Example 2-11) (1.75 g) dissolved in ethanol (15 mL) were added an aqueous solution (5 mL) of hydroxylamine hydrochloride (0.82 g) and then an aqueous solution (10 mL) of potassium carbonate (1.62 g). The solution was heated to 90° C. for 24 hours. Silica gel (15 g) was added to the reaction solution, and then, the solvent was distilled off under reduced pressure. The resulting residue was purified by chromatography [silica gel, dichloromethane-methanol-aqueous ammonia (0:10:0.5)] to give the title compound (1.4660 g).

Hydrochloride mp 185-195° C. (dec.); $^1$H-NMR (DMSO-$d_6$) δ: 1.17-1.48 (m, 10H), 1.49-1.66 (m, 4H), 1.67-1.81 (m, 2H), 1.98-2.09 (m, 2H), 2.30-2.40 (m, 2H), 2.39 (s, 3H), 3.04-3.26 (m, 4H), 3.56-3.68 (m, 2H), 4.71-4.84 (m, 1H), 5.49 (d, 1H, J=3.4 Hz), 6.31 (dd, 1H, J=1.5 Hz, 3.4 Hz), 7.16 (d, 2H, J=7.8 Hz), 7.29 (d, 2H, J=7.8 Hz), 7.62 (d, 1H, J=1.5 Hz); IR (KBr) cm$^{-1}$: 3426, 2929, 2857, 1681, 1620, 1556, 1511, 1469, 1409, 1190, 1034, 757, 735; MS (ESI) m/z: 481 (MH$^+$).

EXAMPLE 7

Methyl 1-[1-hydroxyimino-3-[1-[2-[4-[N-(p-tolyl)-2-furancarboxamido]piperidin-1-yl]ethyl]cyclohexyl]propyl]carbamate

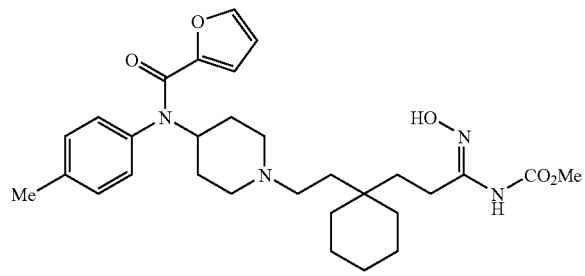

N-[1-[2-[1-[2-(N$^2$-Hydroxycarbamidoyl)ethyl]cyclohexyl]ethyl]piperidin-4-yl]-N-(p-tolyl)-2-furancarboxamide (synthesized in Example 6) (0.4740 g) was dissolved in N,N-dimethylformamide and pyridine (0.12 g). To this was added methyl chloroformate (0.092 g) under ice cooling. The solution was stirred at room temperature for 1 hour. After addition of water, the reaction solution was extracted with 25% ethanol-chloroform. The extract was dried over anhydrous magnesium sulfate, and then, the solvent was distilled off under reduced pressure. The resulting residue was purified by chromatography [silica gel, dichloromethane-methanol-aqueous ammonia (95:5:0.3)] to give the title compound (0.4535 g).

Hydrochloride mp 150-160° C. (dec.); $^1$H-NMR (DMSO-$d_6$) δ: 1.18-1.52 (m, 12H), 1.54-1.64 (m, 2H), 1.65-1.77 (m, 2H), 1.95-2.08 (m, 4H), 2.39 (s, 3H), 2.92-3.02 (m, 2H), 3.04-3.19 (m, 2H), 3.50-3.58 (m, 2H), 3.71 (s, 3H), 4.73-4.83 (m, 1H), 5.49 (d, 1H, J=3.4 Hz), 6.31 (dd, 1H, J=2.0 Hz, 3.4 Hz), 7.16 (d, 2H, J=7.8 Hz), 7.30 (d, 2H, J=7.8 Hz), 7.62 (d, 1H, J=2.0 Hz); IR (KBr) cm$^{-1}$: 3426, 2928, 2855, 1760, 1644, 1557, 1511, 1469, 1405, 1254, 1190, 1033, 952, 885, 757; MS (ESI) m/z: 539 (MH$^+$).

EXAMPLE 8

N-[1-[2-[1-[2-(2H-5-Thioxo-1,2,4-oxadiazol-3-yl)ethyl]cyclohexyl]ethyl]piperidin-4-yl]-N-(p-tolyl)-2-furancarboxamide

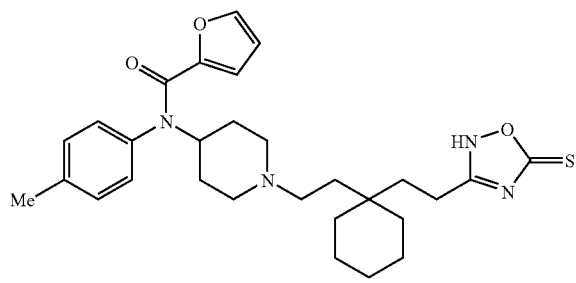

To a solution of N-[1-[2-[1-[2-(N$^2$-hydroxycarbamidoyl)ethyl]cyclohexyl]ethyl]piperidin-4-yl]-N-(p-tolyl)-2-furancarboxamide (synthesized in Example 6) (0.3097 g) dissolved in acetonitrile (10 mL) was added 1,1-thiocarbonyldiimidazole (0.17 g). The orange reaction solution was changed to a yellow suspension, to which 1,8-diazabicyclo[5.4.0]-7-undecene (0.39 g) was added. The solution was heated under reflux for 4 hours. Water was added to the reaction solution, and it was extracted with 25% ethanol-chloroform. The extract was dried over anhydrous magnesium sulfate, and then, the solvent was distilled off under reduced pressure. The resulting residue was purified by chromatography [silica gel, dichloromethane-methanol-aqueous ammonia (90:10:0.5)] to give the title compound (0.2810 g).

Hydrochloride mp 201-206° C. (dec.); $^1$H-NMR (DMSO-d$_6$) δ: 1.20-1.48 (m, 10H), 1.53-1.77 (m, 6H), 2.00-2.09 (m, 2H), 2.38 (s, 3H), 2.48-2.58 (m, 2H), 2.92-3.01 (m, 2H), 3.08-3.20 (m, 2H), 3.49-3.61 (m, 2H), 4.73-4.84 (m, 1H), 5.51 (d, 1H, J=3.4 Hz), 6.32 (dd, 1H, J=1.5 Hz, 3.4 Hz), 7.17 (d, 2H, J=8.3 Hz), 7.30 (d, 2H, J=8.3 Hz), 7.62 (d, 1H, J=1.5 Hz); IR (KBr) cm$^{-1}$: 3444, 2925, 2853, 2674, 2644, 1635, 1598, 1470, 1401, 1167, 758; MS (ESI) m/z: 523 (MH$^+$).

EXAMPLE 9

N-[1-[2-[1-[2-(2H-5-Oxo-1,2,4-oxadiazol-3-yl)ethyl]cyclohexyl]ethyl]piperidin-4-yl]-N-(p-tolyl)-2-furancarboxamide

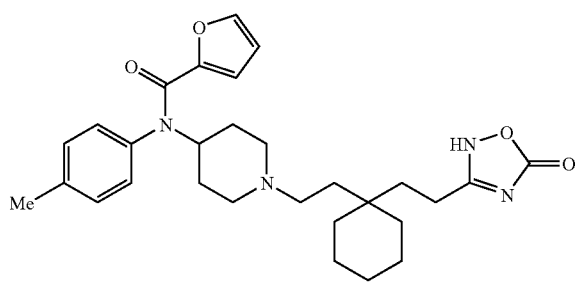

To a solution of methyl 1-[1-hydroxyimino-3-[1-[2-[4-[N-(p-tolyl)-2-furancarboxamido]piperidin-1-yl]ethyl]cyclohexyl]propyl]carbamate hydrochloride (synthesized in Example 7) (0.3565 g) dissolved in acetonitrile (10 mL) was added 1,8-diazabicyclo[5.4.0]-7-undecene (0.50 g). The solution was heated under reflux for 1 hour. Water (30 mL) was added to the reaction solution, and it was extracted with 25% ethanol-chloroform. The extract was dried over anhydrous magnesium sulfate, and then, the solvent was distilled off under reduced pressure. The resulting residue was purified by chromatography [silica gel, dichloromethane-methanol-aqueous ammonia (90:10:0.5)] to give the title compound (0.2818 g).

Hydrochloride mp 162-168° C. (dec.); $^1$H-NMR (DMSO-d$_6$) δ: 1.19-1.48 (m, 10H), 1.49-1.81 (m, 6H), 1.98-2.09 (m, 2H), 2.30-2.48 (m, 2H), 2.39 (s, 3H), 2.90-3.04 (m, 2H), 3.05-3.21 (m, 2H), 3.50-3.68 (m, 2H), 4.72-4.84 (m, 1H), 5.47-5.53 (m, 1H), 6.29-6.33 (m, 1H), 7.16 (d, 2H, J=8.3 Hz), 7.30 (d, 2H, J=8.3 Hz), 7.59-7.63 (m, 1H); IR (KBr) cm$^{-1}$: 3431, 2927, 2857, 1775, 1621, 1602, 1557, 1511, 1470, 1408, 1344, 1190, 1033, 953, 757, 735.

EXAMPLE 10

N-[1-[2-[1-(1-Methanesulfonylcarbamoylmethyl)cyclohexyl]ethyl]piperidin-4-yl]-N-(p-tolyl)-2-furancarboxamide

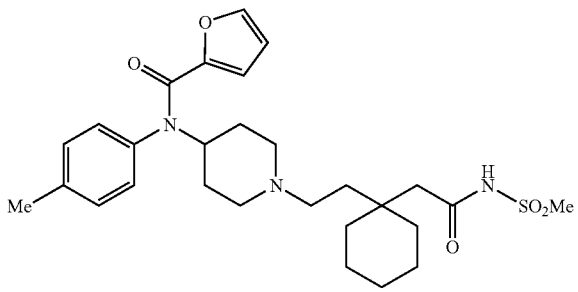

[1-[2-[4-[N-(p-Tolyl)-2-furancarboxamido]-piperidin-1-yl]ethyl]cyclohexyl]acetic acid (synthesized in Example 3B-1) (203 mg), methanesulfonamide (84 mg), 1,3-dicyclohexylcarbodiimide (101 mg) and 4-dimethylaminopyridine (59 mg) were dissolved in dichloromethane (5 mL). The solution was stirred at room temperature for 4 days. The reaction solution was concentrated under reduced pressure. The resulting residue was purified by chromatography [silica gel, dichloromethane-methanol (10:1)] to give the title compound (233 mg).

Free Form $^1$H-NMR (CDCl$_3$) δ: 1.21 (d, 2H, J=10.3 Hz), 1.32-1.62 (m, 10H), 1.68 (d like, 2H), 1.92-1.99 (m, 4H), 2.17 (s, 2H), 2.41 (s, 3H), 2.62-2.76 (m, 2H), 2.99 (s, 3H), 3.21 (d, 2H, J=12.2 Hz), 4.74 (t like, 1H), 5.41 (d, 1H, J=3.4 Hz), 6.15 (dd, 1H, J=1.5 Hz, 3.4 Hz), 7.05 (d, 2H, J=7.8 Hz), 7.22 (d, 2H, J=8.3 Hz), 7.35 (d, 1H, J=0.9 Hz).

Hydrochloride $^1$H-NMR (DMSO-d$_6$) δ: 1.24-1.49 (m, 10H), 1.67-1.84 (m, 4H), 1.97-2.07 (m, 2H), 2.23 (s, 2H), 2.39 (s, 3H), 2.99-3.08 (m, 2H), 3.13-3.18 (m, 2H), 3.24 (s, 3H), 3.45-3.53 (m, 2H), 4.77-4.87 (m, 1H), 5.42 (s, 1H), 6.31 (dd, 1H, J=1.5 Hz, 3.4 Hz), 7.16 (d, 2H, J=7.8 Hz), 7.30 (d, 2H, J=7.8 Hz), 7.65 (s, 1H), 9.70-9.98 (m, 1H), 11.71-11.81 (m, 1H).

EXAMPLE 11

N-[1-[2-[1-(1,1-Dimethylcarbamoylmethyl)cyclohexyl]ethyl]piperidin-4-yl]-N-(p-tolyl)-2-furancarboxamide

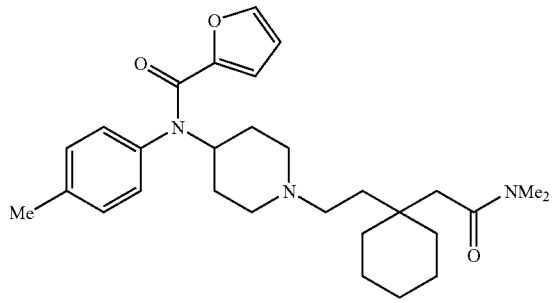

To a solution of [1-[2-[4-[N-(p-tolyl)-2-furancarboxamido]piperidin-1-yl]ethyl]cyclohexyl]acetic acid (synthesized in Example 3B-1) (678 mg) in dichloromethane (15 mL) was added dropwise N,N-dimethylformamide (2 drops) and then oxalyl chloride (0.16 mL) under ice cooling. The solution was stirred under ice cooling for 2 hours. A 5 mL-aliquot of the reaction solution was taken and then added dropwise to a 50% aqueous dimethylamine solution under ice cooling. The reaction solution was stirred for 48 hours while the temperature was allowed to rise to room temperature. NH Silica gel was then added to the solution and concentrated under reduced pressure. The residue was purified by chromatography [NH silica gel, hexane:ethyl acetate (1:1)] to give the title compound (164 mg).

Hydrochloride
$^1$H-NMR (CDCl$_3$) δ: 1.20-1.80 (m, 12H), 2.00-2.25 (m, 6H), 2.22 (s, 2H), 2.41 (s, 3H), 2.92 (s, 3H), 2.88-3.00 (m, 2H), 3.02-3.13 (m, 2H), 3.06 (s, 3H), 3.50-3.60 (m, 2H), 4.83-4.93 (m, 1H), 5.30-5.45 (m, 1H), 6.14-6.17 (m, 1H), 7.04 (d, 2H, J=7.8 Hz), 7.24 (d, 2H, J=7.8 Hz), 7.38 (s, 1H)

EXAMPLE 12

N-[1-[2-[1-(2-Morpholin-4-yl-2-oxoethyl)cyclohexyl]ethyl]piperidin-4-yl]-N-(p-tolyl)-2-furancarboxamide

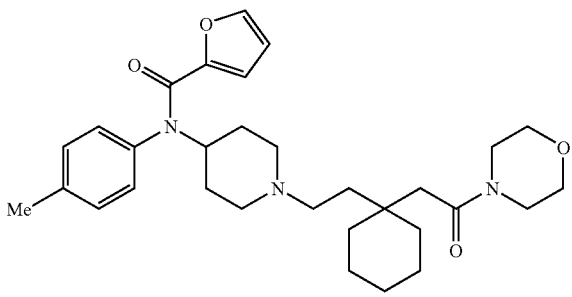

To a solution of [1-[2-[4-[N-(p-tolyl)-2-furancarboxamido]piperidin-1-yl]ethyl]cyclohexyl]acetic acid (synthesized in Example 3B-1) (200 mg) dissolved in dichloromethane (4 mL) was added N,N-dimethylformamide (1 drop) and then oxalyl chloride (0.050 mL) dropwise under ice cooling. The solution was stirred under ice cooling for 1 hour. The reaction solution was concentrated under reduced pressure to give the corresponding acid chloride.

To a solution of morpholine (61 mg) dissolved in dichloromethane (4 mL) was added triethylamine (0.13 mL) dropwise. To this was added a solution of the acid chloride in dichloromethane (3 mL) dropwise, and it was stirred for 1 hour. After allowing the temperature to rise to room temperature, the solution was stirred for 19 hours. Ethyl acetate was added to the solution, and then, it was washed in turn with a 10% aqueous citric acid solution, saturated aqueous sodium bicarbonate solution and saturated aqueous sodium chloride solution. The organic layer was dried over anhydrous magnesium sulfate, filtered and concentrated under reduced pressure. The aqueous layer was again extracted with chloroform, and the organic layer was dried over anhydrous magnesium sulfate and filtered. The combined organic layer was then distilled under reduced pressure. The resulting residue was subjected to column chromatography [NH silica gel, hexane-ethyl acetate (2:1)] to give the title compound (116 mg).

Free Form
$^1$H-NMR (CDCl$_3$) δ: 1.33-1.53 (m, 12H), 1.64-1.68 (m, 2H), 1.85 (brd, 2H, J=11.7 Hz), 2.10 (t, 2H, J=11.7 Hz), 2.25-2.30 (m, 4H), 2.40 (s, 3H), 2.97 (brd, 2H, J=10.2 Hz), 3.46-3.48 (m, 2H), 3.54-3.67 (m, 6H), 4.73-4.79 (t like, 1H), 5.37 (s, 1H), 6.13 (dd, 1H, J=1.4 Hz, 3.4 Hz), 7.01 (d, 2H, J=8.3 Hz), 7.18 (d, 2H, J=8.3 Hz), 7.34 (s, 1H).

Hydrochloride
$^1$H-NMR (DMSO-d$_6$) δ: 1.20-1.49 (m, 10H), 1.62-1.75 (m, 2H), 1.79-1.89 (m, 2H), 2.02-2.09 (brd, 2H, J=12.7 Hz), 2.23 (s, 2H), 2.39 (s, 3H), 2.95-3.01 (m, 2H), 3.06-3.15 (m, 2H), 3.46-3.59 (m, 10H), 4.78-4.90 (m, 1H), 5.44 (m, 1H), 6.31 (dd, 1H, J=1.5 Hz, 3.5 Hz), 7.16 (d, 2H, J=7.8 Hz), 7.30 (d, 2H, J=7.8 Hz), 7.63 (s, 1H), 9.19-9.32 (m, 1H).

EXAMPLE 13

2-(Acetoxymethyl)-2-[2-[1-[2-[4-(p-toluidino)piperidin-1-yl]ethyl]cyclohexyl]ethyl]-1,4-diacetoxybutane

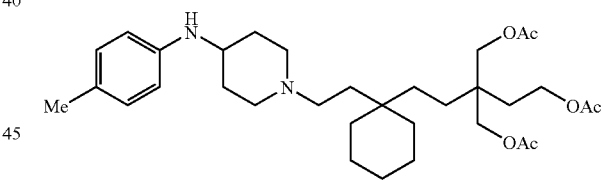

2-(Acetoxymethyl)-2-[2-[1-(formylmethyl)cyclohexyl]ethyl]-1,4-diacetoxybutane (synthesized in Example 3G-5) (280 mg) and 4-(p-toluidino)piperidine ditrifluoroacetate (synthesized in Preparation Example4-5) (356 mg) were suspended in dichloromethane (15 mL). Triethylamine (0.23 mL) was added to the suspension at room temperature to form a homogenous solution, to which acetic acid (0.048 mL) was then added. The solution was stirred for 15 minutes. Sodium triacetoxyborohydride (377 mg) was added to the solution under ice cooling and the temperature was allowed to rise to room temperature. The solution was stirred for 16 hours. Saturated aqueous sodium bicarbonate solution was added to the solution and the solution was extracted with chloroform. The organic layer was dried over anhydrous sodium sulfate, filtered and concentrated under reduced pressure. The residue was purified by chromatography [NH silica gel, 33% ethyl acetate/hexane] to give the title compound (334 mg).

$^1$H-NMR (CDCl$_3$) δ: 1.18-1.28 (m, 10H), 1.35-1.48 (m, 10H), 2.02-2.14 (m, 13H), 2.23-2.29 (m, 5H), 2.82-2.92 (m,

2H), 3.22-3.31 (m, 1H), 3.96 (s, 4H), 4.11-4.16 (m, 3H), 6.52 (d, 2H, J=8.3 Hz), 6.97 (d, 2H, J=8.3 Hz).

EXAMPLE 14

2-(Acetoxymethyl)-2-[2-[1-[2-[4-[N-(p-tolyl)-2-furancarboxamido]piperidin-1-yl]ethyl]cyclohexyl]ethyl]-1,4-diacetoxybutane

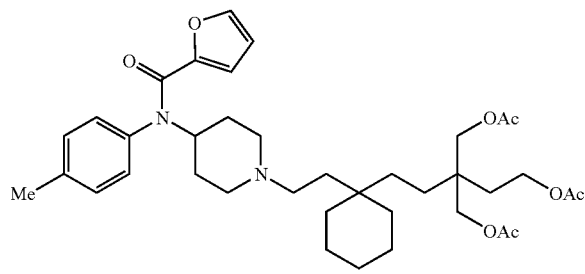

To a solution of 2-(acetoxymethyl)-2-[2-[1-[2-[4-(p-toluidino)piperidin-1-yl]ethyl]cyclohexyl]ethyl]-1,4-diacetoxybutane (synthesized in Example 13) (324 mg) dissolved in dichloromethane (4 mL) was added triethylamine (0.16 mL). 2-Furoyl chloride (0.084 mL) was added to the solution under ice cooling, and the temperature was then allowed to rise to room temperature. The solution was stirred for 17 hours. A 10% aqueous citric acid solution was added to the solution and the solution was extracted with chloroform. The organic layer was dried over anhydrous magnesium sulfate, filtered and concentrated under reduced pressure. The residue was purified by chromatography [NH silica gel, hexane-ethyl acetate (1:1)] to give the title compound (356 mg).

$^1$H-NMR (CDCl$_3$) δ: 1.14-1.28 (m, 6H), 1.29-1.47 (m, 8H), 1.47-1.59 (m, 2H), 1.86 (d, 2H, J=10.3 Hz), 2.04-2.11 (m, 12H), 2.17-2.21 (m, 2H), 2.40 (s, 3H), 2.96 (d, 2H, J=11.7 Hz), 3.94 (s, 4H), 4.10-4.20 (m, 2H), 4.74-4.79 (t like, 1H), 5.35 (brs, 1H), 6.13 (dd, 1H, J=2.0 Hz, 3.4 Hz), 7.01 (d, 2H, J=8.3 Hz), 7.18 (d, 2H, J=7.8 Hz), 7.35 (s, 1H); MS (ESI) m/z: 667 (MH$^+$).

EXAMPLE 15

N-[1-[2-[1-[5-Hydroxy-3,3-bis(hydroxymethyl)pentyl]cyclohexyl]ethyl]piperidin-4-yl]-N-(p-tolyl)-2-furancarboxamide

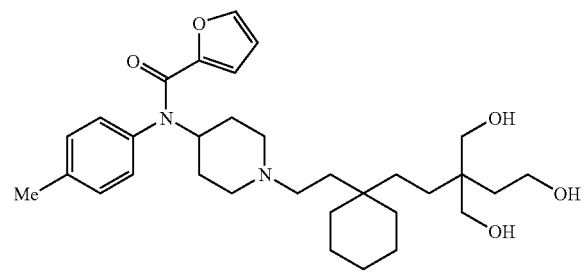

To a solution of 2-(acetoxymethyl)-2-[2-[1-[2-[4-[N-(p-tolyl)-2-furancarboxamido]piperidin-1-yl]ethyl]cyclohexyl]ethyl]-1,4-diacetoxybutane (synthesized in Example 14) (313 mg) dissolved in methanol (5 mL) was added potassium carbonate (39 mg) at room temperature. The solution was stirred for 20 hours. The reaction solution was concentrated under reduced pressure. Water was added to the resulting residue and extracted with a mixed solvent of chloroform-ethanol (80:20). The organic layer was dried over anhydrous magnesium sulfate, filtered and then concentrated under reduced pressure to give the title compound (252 mg).

Hydrochloride $^1$H-NMR (DMSO-d$_6$) δ: 1.05-1.12 (m, 4H), 1.12-1.23 (m, 5H), 1.23-1.39 (m, 8H), 1.52-1.59 (m, 2H), 1.63-1.79 (m, 2H), 1.98-2.04 (m, 3H), 2.39 (s, 3H), 2.92-3.08 (m, 2H), 3.11-3.21 (m, 2H), 3.22-3.35 (m, 4H), 3.45-3.57 (m, 5H), 4.77-4.81 (t like, 1H), 5.40 (brs, 1H), 6.32 (dd, 1H, J=2.0 Hz, 3.2 Hz), 7.16 (d, 2H, J=7.8 Hz), 7.30 (d, 2H, J=8.3 Hz), 7.66 (s, 1H), 9.77-9.93 (brm, 1H); IR (KBr) cm$^{-1}$: 3388, 2926, 2860, 1633, 1512, 1470, 1403, 1342, 1243, 1189, 1032, 757; MS (ESI) m/z: 541 (MH$^+$).

EXAMPLE 16 tert-Butyl 2-[1-[2-[4-(p-toluidino)piperidin-1-yl]ethyl]cyclohexyl]ethylcarbamate

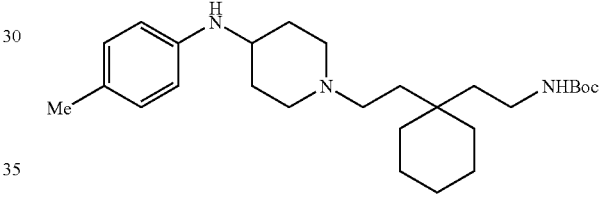

To a solution of 4-(p-toluidino)piperidine (synthesized in Preparation Example 4-5), N-[2-[1-(formylmethyl)cyclohexyl]ethyl]phthalimide (synthesized in Preparation Example 3K-2) (0.77 g) and acetic acid (0.30 mL) in 1,2-dichloroethane (10 mL) was added sodium triacetoxyborohydride (0.82 g). The solution was stirred at room temperature for 1.5 hours. Saturated aqueous sodium bicarbonate solution was added to the solution and it was extracted with a mixed solvent of chloroform-ethanol (10:1). The organic layer was dried over anhydrous sodium sulfate, filtered and concentrated under reduced pressure. The residue was purified by chromatography [silica gel, chloroform-methanol (20:1)] to give a colorless oily substance (1.32 g).

$^1$H-NMR (CDCl$_3$) δ: 1.35-1.63 (m, 16H), 2.05-2.08 (m, 2H), 2.15-2.23 (m, 2H), 2.23 (s, 3H), 2.42-2.46 (m, 2H), 2.94-2.98 (m, 2H), 3.25-3.30 (m, 1H), 3.64-3.68 (m, 2H), 6.53 (d, 2H, J=8.3 Hz), 6.97 (d, 2H, J=7.8 Hz), 7.69-7.72 (m, 2H), 7.81-7.86 (m, 2H).

To a solution of the resulting oily substance (1.32 g) in ethanol (20 mL) was added hydrazine monohydrate (0.37 mL). The solution was heated under reflux for 1 hour. The reaction solution was concentrated under reduced pressure (by azeotropic distillation with toluene). Dichloromethane (20 mL), triethylamine (1.0 mL) and di-tert-butyl dicarbonate (1.00 g) were successively added to the resulting residue. The solution was stirred at room temperature for 13 hours. The reaction solution was filtered with Celite and the filtrate was concentrated under reduced pressure. The residue was purified by chromatography [silica gel, chloroform-methanol (100:1)] to give the title compound (1.08 g).

¹H-NMR (CDCl₃) δ: 1.22-1.51 (m, 16H), 1.44 (s, 9H), 2.03-2.15 (m, 4H), 2.23 (s, 3H), 2.28-2.33 (m, 2H), 2.87-2.90 (m, 2H), 3.06-3.10 (m, 2H), 3.24-3.28 (m, 1H), 4.62 (br, 1H), 6.52 (d, 2H, J=8.3 Hz), 6.97 (d, 2H, J=7.8 Hz).

EXAMPLE 17 tert-Butyl

2-[1-[2-[4-[N-(p-tolyl)-2-furancarboxamido]piperidin-1-yl]-ethyl]cyclohexyl]ethylcarbamate

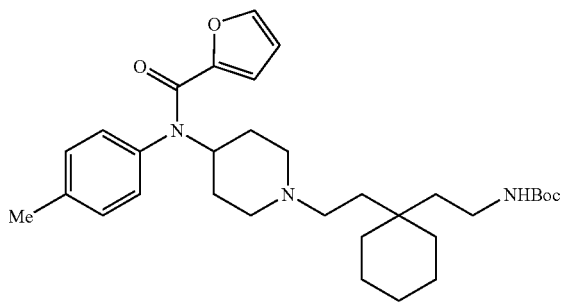

To a solution of tert-butyl 2-[1-[2-[4-(p-toluidino)piperidin-1-yl]ethyl]cyclohexyl]ethylcarbamate (synthesized in Example 16) (1.08 g) in dichloromethane (5 mL) were added triethylamine (0.68 mL) and then 2-furoyl chloride (0.31 mL). The solution was stirred at room temperature for 1 hour. NH Silica gel was added to the reaction solution and the solvent was distilled off under reduced pressure. The resulting residue was purified by chromatography [NH silica gel, hexane-ethyl acetate (4:1)] to give the title compound (1.14 g).

¹H-NMR (CDCl₃) δ: 1.24-1.59 (m, 16H), 1.43 (s, 9H), 1.83-1.86 (m, 2H), 2.04-2.13 (m, 2H), 2.22-2.26 (m, 2H), 2.39 (s, 3H), 2.95-3.05 (m, 4H), 4.50 (br, 1H), 4.72-4.80 (m, 1H), 5.37 (s, 1H), 6.13 (dd, 1H, J=1.5 Hz, 3.4 Hz), 7.01 (d, 2H, J=7.8 Hz), 7.18 (d, 2H, J=7.8 Hz), 7.34 (s, 1H).

EXAMPLE 18

N-[1-[2-[1-(2-Aminoethyl)cyclohexyl]ethyl]piperidin-4-yl]-N-(p-tolyl)-2-furancarboxamide

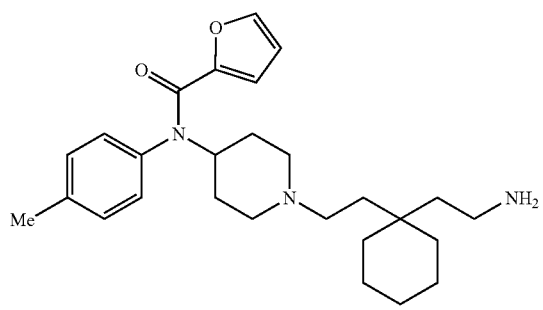

To a solution of tert-butyl 2-[1-[2-[4-[N-(p-tolyl)-2-furancarboxamido]piperidin-1-yl]ethyl]cyclohexyl]ethylcarbamate (synthesized in Example 17) (1.14 g) in methanol (4 mL) was added a 4N hydrochloric acid/dioxane solution (3 mL). The solution was stirred at room temperature for 12 hours. The reaction solution was concentrated under reduced pressure. The resulting residue was purified by chromatography [NH silica gel, chloroform-methanol (20:1)] to give the title compound (1.01 g).

Free Form

¹H-NMR (CDCl₃) δ: 1.23-1.57 (m, 16H), 1.83-1.86 (m, 2H), 2.04-2.12 (m, 2H), 2.22-2.27 (m, 2H), 2.39 (s, 3H), 2.59-2.64 (m, 2H), 2.94-2.98 (m, 2H), 4.72-4.81 (m, 1H), 5.37 (s, 1H), 6.13 (dd, 1H, J=2.0 Hz, 3.4 Hz), 7.01 (d, 2H, J=7.8 Hz), 7.17 (d, 2H, J=7.8 Hz), 7.34 (d, 1H, J=2.0 Hz).

Hydrochloride

¹H-NMR (DMSO-d₆) δ: 1.18-1.73 (m, 16H), 2.02-2.05 (m, 2H), 2.39 (s, 3H), 2.67-2.78 (m, 2H), 3.00-3.16 (m, 4H), 3.56-3.59 (m, 2H), 4.76-4.83 (m, 1H), 5.42 (s, 1H), 6.33 (dd, 1H, J=1.5 Hz, 3.4 Hz), 7.17 (d, 2H, J=7.8 Hz), 7.31 (d, 2H, J=8.3 Hz), 7.66 (s, 1H), 7.95 (br, 2H), 9.69 (br, 1H); MS (ESI) m/z: 438 (MH⁺).

EXAMPLE 19

N-[1-[2-[1-(2-Methanesulfonylaminoethyl)cyclohexyl]ethyl]-piperidin-4-yl]-N-(p-tolyl)-2-furancarboxamide

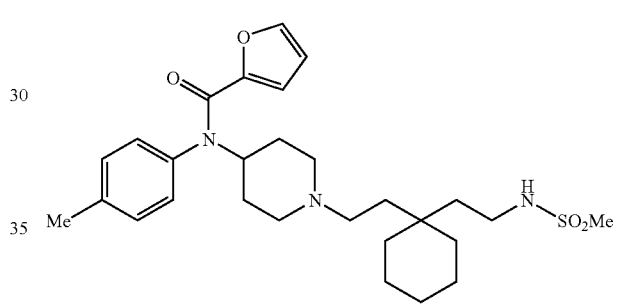

To a solution of N-[1-[2-[1-(2-aminoethyl) cyclohexyl] ethyl]piperidin-4-yl]-N-(p-tolyl)-2-furancarboxamide (synthesized in Example 18) (260 mg) in dichloromethane (3 mL) were added triethylamine (0.15 mL) and methanesulfonyl chloride (56 μL) successively. The solution was stirred at room temperature for 6 hours. The reaction solution was filtered and the filtrate was concentrated under reduced pressure. The resulting residue was purified by chromatography [NH silica gel, hexane-ethyl acetate (7:3 to 1:1 to 1:2] to give the title compound (214 mg).

Free form

¹-HNMR (CDCl₃) δ: 1.22-1.27 (m, 4H), 1.34-1.43 (m, 8H), 1.51-1.60 (m, 4H), 1.83-1.87 (m, 2H), 2.08-2.14 (m, 2H), 2.21-2.26 (m, 2H), 2.39 (s, 3H), 2.81 (s, 3H), 2.85-2.99 (m, 2H), 3.03-3.08 (m, 2H), 4.71-4.79 (m, 1H), 5.37 (s, 1H), 6.13 (dd, 1H, J=1.5 Hz, 3.9 Hz), 7.02 (d, 2H, J=8.3 Hz), 7.19 (d, 2H, J=8.3 Hz), 7.34 (s, 1H).

Hydrochloride mp 235-238° C.; ¹HNMR (DMSOd₆) δ: 1.24-1.44 (m, 12H), 1.58-1.73 (m, 4H), 1.98-2.05 (m, 2H), 2.39 (s, 3H), 2.85-2.97 (m, 4H), 2.90 (s, 3H), 3.07-3.16 (m, 2H), 3.51-3.54 (m, 2H), 4.76-4.85 (m, 1H), 5.43 (s, 1H), 6.32-6.33 (m, 1H), 6.91 (t, 1H, J=5.6 Hz), 7.17 (d, 2H, J=7.8 Hz), 7.31 (d, 2H, J=7.8 Hz), 7.66 (s, 1H), 9.54 (br, 1H); IR (KBr) cm⁻¹: 3445, 3113, 2931, 2858, 2641, 1642, 1557, 1511, 1471, 1398, 1313, 1187, 1153, 772, 523; MS (EST) m/z: 516 (MH⁺).

EXAMPLE 20

N-[1-[2-[1-[2-(p-Toluenesulfonylamino)ethyl]cyclohexyl]ethyl]piperidin-4-yl]-N-(p-tolyl)-2-furancarboxamide

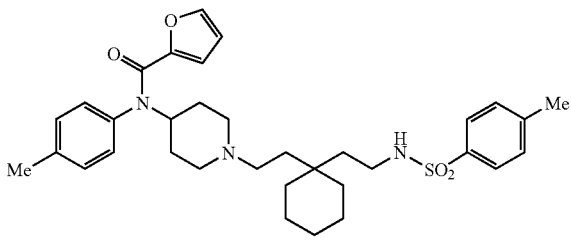

To a solution of N-[1-[2-[1-(2-aminoethyl)cyclohexyl]ethyl]piperidin-4-yl]-N-(p-tolyl)-2-furancarboxamide (synthesized in Example 18) (228 mg) in dichloromethane (3 mL) were added 1,4-diazabicyclo[2.2.2]octane (108 mg) and p-toluenesulfonyl chloride (120 mg) successively. The solution was stirred at room temperature for 6 hours. The reaction solution was filtered and the filtrate was concentrated under reduced pressure. The resulting residue was purified by chromatography [NH silica gel, hexane-ethyl acetate (7:3 to 1:2)] to give the title compound (265 mg).

Free Form
$^1$H-NMR (CDCl$_3$) δ: 1.16-1.44 (m, 14H), 1.51-1.62 (m, 2H), 1.81-1.85 (m, 2H), 1.99-2.05 (m, 2H), 2.10-2.14 (m, 2H), 2.37 (s, 3H), 2.43 (s, 3H), 2.83-2.92 (m, 4H), 4.70-4.79 (m, 1H), 5.37 (s, 1H), 6.14 (dd, 1H, J=1.5 Hz, 3.4 Hz), 7.03 (d, 2H, J=8.3 Hz), 7.18 (d, 2H, J=8.3 Hz), 7.26 (d, 2H, J=6.8 Hz), 7.35 (d, 1H, J=1.5 Hz), 7.62 (d, 2H, J=8.3 Hz).

Hydrochloride
mp 230-235° C.; $^1$H-NMR (DMSO-d$_6$) δ: 1.09-1.39 (m, 12H), 1.48-1.56 (m, 2H), 1.63-1.72 (m, 2H), 1.98-2.03 (m, 2H), 2.39 (s, 3H), 2.57-2.72 (m, 2H), 2.83-2.90 (m, 2H), 3.04-3.11 (m, 2H), 3.46-3.49 (m, 2H), 4.76-4.83 (m, 1H), 5.43 (s, 1H), 6.33 (dd, 1H, J=1.5 Hz, 3.4 Hz), 7.17 (d, 2H, J=8.3 Hz), 7.31 (d, 2H, J=8.3 Hz), 7.39 (d, 2H, J=7.8 Hz), 7.51 (t, 1H, J=5.1 Hz), 7.65 (s, 1H), 7.69 (d, 2H, J=8.3 Hz), 9.57 (br, 1H); IR (KBr) cm$^{-1}$: 3443, 3142, 2928, 2855, 2633, 2534, 1638, 1510, 1473, 1448, 1408, 1325, 1188, 1158, 1091, 1057, 807, 766, 726, 616; MS (ESI) m/z: 592 (MH$^+$).

EXAMPLE 21

N-[1-[2-[1-[2-(4-Chlorobenzenesulfonylamino)ethyl]cyclohexyl]ethyl]piperidin-4-yl]-N-(p-tolyl)-2-furancarboxamide

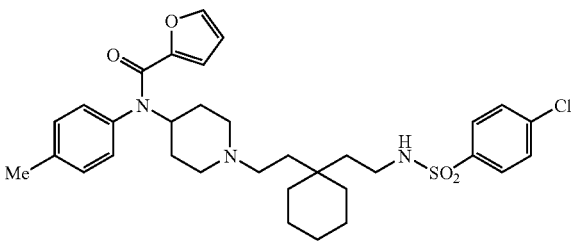

To a solution of N-[1-[2-[1-(2-aminoethyl)cyclohexyl]ethyl]piperidin-4-yl]-N-(p-tolyl)-2-furancarboxamide (synthesized in Example 18) (199 mg) in dichloromethane (3 mL) were added 1,4-diazabicyclo[2.2.2]octane (100 mg) and p-chlorobenzenesulfonyl chloride (100 mg) successively. The reaction solution was stirred at room temperature for 2 hours. The reaction solution was diluted with chloroform, washed in turn with saturated aqueous sodium bicarbonate solution and saturated aqueous sodium chloride solution, and dried over anhydrous sodium sulfate. The solvent was distilled off under reduced pressure. The resulting residue was purified by chromatography [NH silica gel, hexane-ethyl acetate (7:3)] to give the title compound (181 mg).

Free Form
$^1$H-NMR (CDCl$_3$) δ: 1.11-1.64 (m, 16H), 1.83-1.87 (m, 2H), 2.04-2.18 (m, 4H), 2.37 (s, 3H), 2.87 (t, 2H, J=6.8 Hz), 2.91-2.95 (m, 2H), 4.72-4.80 (m, 1H), 5.37 (s, 1H), 6.14 (dd, 1H, J=1.5 Hz, 3.4 Hz), 7.05 (d, 2H, J=8.3 Hz), 7.19 (d, 2H, J=7.8 Hz), 7.34 (s, 1H), 7.40 (d, 2H, J=8.3 Hz), 7.60 (d, 2H, J=8.3 Hz).

Hydrochloride
mp 235-241° C.; $^1$H-NMR (DMSO-d$_6$) δ: 1.10-1.40 (m, 12H), 1.52-1.55 (m, 2H), 1.61-1.71 (m, 2H), 2.00-2.04 (m, 2H), 2.39 (s, 3H), 2.69-2.75 (m, 2H), 2.83-2.92 (m, 2H), 3.04-3.12 (m, 2H), 3.47-3.50 (m, 2H), 4.77-4.83 (m, 1H), 5.43 (s, 1H), 6.33 (dd, 1H, J=1.5 Hz, 3.4 Hz), 7.17 (d, 2H, J=8.3 Hz), 7.31 (d, 2H, J=7.8 Hz), 7.66 (s, 1H), 7.67 (d, 2H, J=8.3 Hz), 7.73 (t, 1H, J=5.4 Hz), 7.82 (d, 2H, J=8.3 Hz), 9.45 (br, 1H); IR (KBr) cm$^{-1}$: 3450, 3131, 2927, 2855, 2634, 2543, 1638, 1474, 1335, 1161, 1092, 1083, 758, 615, 563; MS (ESI) m/z: 612 (MH$^+$).

EXAMPLE 22

2-[2-[1-[2-[4-[N-(p-Tolyl)-2-furancarboxamido]piperidin-1-yl]ethyl]cyclohexyl]acetylamino]benzoic acid

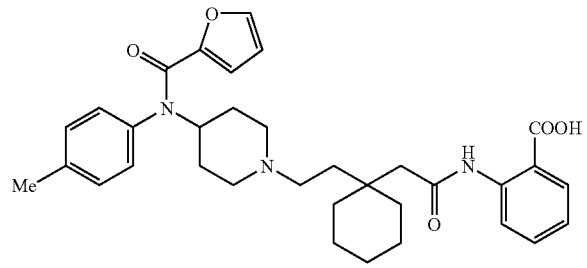

To a solution of [1-[2-[4-[N-(p-tolyl)-2-furancarboxamido]piperidin-1-yl]ethyl]cyclohexyl]acetic acid (synthesized in Preparation Example 3B-1) (678 mg) in dichloromethane (15 mL) was added N,N-dimethylformamide (2 drops) dropwise. Oxalyl chloride (228 mg) was then added to the solution under ice cooling. The solution was stirred under ice cooling for 2 hours. A 5-mL aliquot of the reaction solution was taken and was added to a solution of methyl anthranilate (99 mg) and triethylamine (182 mg) in dichloromethane (15 mL) dropwise under ice cooling. The reaction solution was stirred for 18 hours while the temperature was allowed to rise to room temperature. NH Silica gel was then added to the reaction solution, and it was concentrated under reduced pressure. The residue was purified by chromatography [silica gel, chloroform-methanol (20:1)] to give methyl 2-[2-[1-[2-[4-[N-(p-tolyl)-2-furancarboxamido]piperidin-1-yl]ethyl]cyclohexyl]acetylamino]benzoate (150 mg).

To a solution of this product in methanol (5 mL) was added an aqueous sodium hydroxide (51 mg) solution (3 mL) dropwise at room temperature. The solution was stirred at room temperature for 18 hours. After neutralizing the solution with 2N hydrochloric acid, silica gel was added thereto and it was concentrated under reduced pressure. The resulting residue was purified by chromatography [silica gel, chloroform-methanol (10:1)] to give the title compound (148 mg).

Free Form
$^1$H-NMR (CDCl$_3$) δ: 1.25-1.55 (m, 10H), 1.82-1.90 (m, 2H), 1.93-2.05 (m, 4H), 2.21 (s, 2H), 2.32 (s, 3H), 2.76-2.88 (m, 2H), 3.08-3.16 (m, 2H), 3.52-3.60 (m, 2H), 4.85-4.96 (m, 1H), 5.32-5.37 (m, 1H), 6.12-6.15 (m, 1H), 6.95 (d, 2H, J=8.3 Hz), 6.97-7.03 (m, 1H), 7.09 (d, 2H, J=8.3 Hz), 7.33-7.39 (m, 2H), 7.82 (brd, 1H, J=7.8 Hz), 8.54 (brd, 1H, J=8.3 Hz), 12.68 (brs, 1H).

Hydrochloride
$^1$H-NMR (CDCl$_3$) δ: 1.25-1.55 (m, 10H), 1.93-2.10 (m, 4H), 2.11-2.26 (m, 2H), 2.34 (s, 2H), 3.05 (s, 3H), 3.00-3.14 (m, 2H), 3.16-3.26 (m, 2H), 3.50-3.60 (m, 2H), 4.88-4.98 (m, 1H), 5.32-5.36 (m, 1H), 6.18 (dd, 1H, J=1.5 Hz, 3.5 Hz), 7.03 (d, 2H, J=8.3 Hz), 7.09-7.15 (m, 1H), 7.24 (d, 2H, J=8.3 Hz), 7.38-7.41 (m, 1H), 7.51-7.57 (m, 1H), 8.09-8.12 (m, 1H), 8.57-8.60 (m, 1H), 11.10 (brs, 1H).

EXAMPLE 23

N-[1-[2-[1-[1-(pirazin-2-yl)carbamoylmethyl]cyclohexyl]ethyl]piperidin-4-yl]-N-(p-tolyl)-2-furancarboxamide

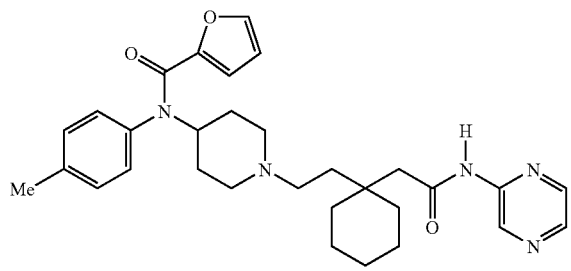

To a solution of [1-[2-[4-[N-(p-tolyl)-2-furancarboxamido]piperidin-1-yl]ethyl]cyclohexyl]acetic acid (synthesized in Example 3B-1) (201 mg) dissolved in dichloromethane (6 mL) was added N,N-dimethylformamide (2 drops). Oxalyl chloride (0.060 mL) was then added to the solution dropwise under ice cooling. The solution was stirred for 1.5 hours. After addition of triethylamine (0.12 mL) at that temperature, the solution was stirred for 20 minutes. 2-Aminopyrazine (128 mg) was then added to the solution and it was stirred at that temperature. The temperature was allowed to rise to room temperature and the solution was stirred for 16 hours. NH Silica gel was added to the reaction solution, and it was concentrated under reduced pressure. The resulting residue was purified by chromatography [at the first stage; NH silica gel, hexane-ethyl acetate (2:1) and at the second stage; silica gel, chloroform-methanol (10:1)] to give the title compound (116 mg).

Free form
$^1$H-NMR (CDCl$_3$) δ: 1.28-1.65 (m, 10H), 1.71-1.84 (m, 6H), 2.27-2.40 (m, 9H), 3.10 (brd, 2H, J=11.7 Hz), 4.75-4.81 (t like, 1H), 5.31 (s, 1H), 6.12 (d, 1H, J=1.9 Hz), 6.94 (d, 2H, J=8.3 Hz), 7.06 (d, 2H, J=7.9 Hz), 7.33 (s, 1H), 7.87 (s, 1H), 8.21 (d, 1H, J=2.4 Hz), 9.38 (s, 1H), 10.27 (brs, 1H).

Hydrochloride
$^1$H-NMR (DMSO-d$_6$) δ: 1.35-1.56 (m, 12H), 1.67-1.76 (m, 2H), 1.82-1.91 (m, 2H), 2.02 (d, 2H, J=16.1 Hz), 2.38-2.41 (m, 5H), 3.11-3.17 (m, 4H), 3.18 (s, 2H), 4.79-4.86 (m, 1H), 5.43 (s, 1H), 6.32 (s, 1H), 7.16 (d, 2H, J=8.3 Hz), 7.31 (d, 2H, J=7.8 Hz), 7.65 (s, 1H), 8.34 (s, 1H), 8.39 (s, 1H), 9.34 (s, 1H), 9.54-9.66 (m, 1H), 10.77 (s, 1H).

EXAMPLE 24

Dimethyl

5-[2-[1-[2-(tert-butyldiphenylsiloxy)ethyl]cyclohexyl]ethoxy]isophthalate

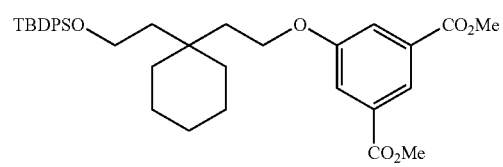

2-[1-[2-(tert-Butyldiphenylsiloxy)ethyl]cyclohexyl]ethanol (synthesized in Preparation Example 3A-2) (2.03 g) and dimethyl 5-hydroxyisophthalate (1.26 g) were dissolved in benzene (50 mL). To this was added triphenylphosphine (1.56 g). Diethyl azocarboxylate (0.95 mL) was further added to the solution at room temperature dropwise. The solution was stirred for 3 hours. The reaction solution was concentrated under reduced pressure. The resulting residue was purified by chromatography [silica gel, hexane-ethyl acetate (4:1)] to give the title compound (1.84 g).

$^1$H-NMR (CDCl$_3$) δ: 1.02 (s, 9H), 1.31-1.45 (m, 10H), 1.65 (t, 2H, J=7.3 Hz), 1.77 (t, 2H, J=7.3 Hz), 3.74 (t, 2H, J=7.3 Hz), 3.96 (t, 2H, J=7.3 Hz), 3.94 (s, 6H), 7.33-7.40 (m, 6H), 7.65-7.69 (m, 6H), 8.27 (d, 1H, J=1.5 Hz).

EXAMPLE 25

Dimethyl

5-[2-[1-(2-hydroxyethyl)cyclohexyl]ethoxy]isophthalate

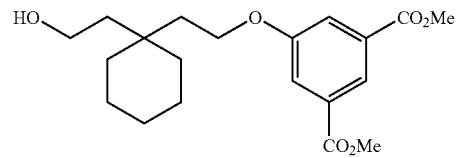

To a solution of dimethyl 5-[2-[1-[2-(tert-butyldiphenylsiloxy)ethyl]cyclohexyl]ethoxy]isophthalate (synthesized in Example 24) (0.53 g) dissolved in tetrahydrofuran (6 mL) was added a 1M tetrabutylammonium fluoride/tetrahydrofuran solution (1.32 mL) dropwise at room temperature. The solution was stirred for 3 hours. A 10% aqueous citric acid solution was added to the solution and it was extracted with ethyl acetate. The organic layer was washed with saturated aqueous sodium bicarbonate solution and saturated aqueous sodium chloride solution, dried over anhydrous magnesium sulfate, and filtered. The filtrate was then concentrated under reduced pressure. The resulting residue was purified by chromatography [silica gel, hexane-ethyl acetate (1:1)] to give the title compound (255 mg).

$^1$H-NMR (CDCl$_3$) δ: 1.38-1.55 (m, 11H), 1.69 (t, 2H, J=7.3 Hz), 1.86 (t, 2H, J=7.3 Hz), 3.74-3.80 (m, 2H), 3.94 (s, 6H), 4.12 (t, 2H, J=7.3 Hz), 7.74 (d, 2H, J=0.9 Hz), 8.27 (s, 1H).

EXAMPLE 26

Dimethyl

5-[2-[1-(formylmethyl)cyclohexyl]ethoxy]isophthalate

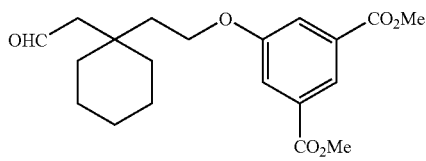

1,1,1-Tris(acetoxy)-1,1-dihydro-1,2-benziodooxol-3 (1H)-one (444 mg) was suspended in dichloromethane (4 mL). Pyridine (196 mg) was added to the suspension to form a nearly homogenous solution. A solution of dimethyl 5-[2-[1-(2-hydroxyethyl)cyclohexyl]ethoxy]isophthalate (synthesized in Example 25) (253 mg) dissolved in dichloromethane (4 mL) was added to the solution dropwise under ice cooling. The solution was stirred at that temperature for 1.5 hours. After allowing the temperature to rise to room temperature, diethyl ether (50 mL) was added to the solution and it was washed in turn with a 10% aqueous sodium thiosulfate solution (15 mL), 1N hydrochloric acid (20 mL), saturated aqueous sodium bicarbonate solution (20 mL) and saturated aqueous sodium chloride solution (30 mL). The organic layer was dried over anhydrous magnesium sulfate, and filtered. The filtrate was concentrated under reduced pressure to give the title compound (253 mg). This product was subjected to the subsequent step without further purification.

EXAMPLE 27

Dimethyl

5-[2-[1-[2-[4-(p-toluidino)piperidin-1-yl]ethyl]cyclohexyl]ethoxy]isophthalate

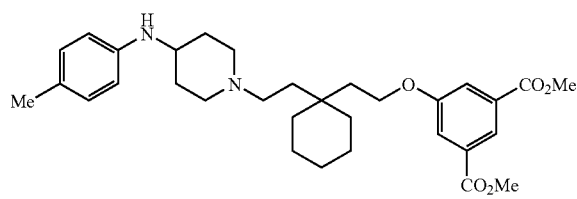

Dimethyl 5-[2-[1-(formylmethyl)cyclohexyl]ethoxy] isophthalate (synthesized in Example 26) (253 mg) and 4-(p-toluidino)piperidine ditrifluoroacetate (synthesized in Preparation Example 4-5) were suspended in 1,2-dichloroethane (8 mL). Triethylamine (170 mg) was added to the suspension at room temperature to form a homogenous solution. Acetic acid (51 mg) was added to the solution and it was stirred for 10 minutes. After addition of sodium triacetoxyborohydride (371 mg) under ice cooling, the solution was allowed to rise to room temperature and stirred for 3 hours. Saturated aqueous sodium bicarbonate solution was added to the solution and it was extracted with chloroform. The organic layer was dried over anhydrous sodium sulfate and filtered. The filtrate was then concentrated under reduced pressure. The resulting residue was purified by chromatography [NH silica gel, chloroform-methanol (10:1)] to give the title compound (296 mg).

$^1$H-NMR (CDCl$_3$) δ: 1.28-1.48 (m, 12H), 1.55-1.59 (m, 2H), 1.81-1.85 (t like, 2H), 2.05-2.12 (m, 5H), 2.22 (s, 3H), 2.34-2.40 (m, 2H), 2.84-2.95 (m, 2H), 3.22-3.31 (m, 1H), 3.94 (s, 6H), 4.06-4.10 (t like, 2H), 6.52 (d, 2H, J=8.3 Hz), 6.96 (d, 2H, J=8.3 Hz), 7.74 (s, 2H), 8.27 (s, 1H).; MS (ESI) m/z 537 (MH$^+$).

EXAMPLE 28

Dimethyl

5-[2-[1-[2-[N-[4-(p-tolyl)-2-furancarboxamido]piperidin-1-yl]ethyl]cyclohexyl]ethoxy]isophthalate

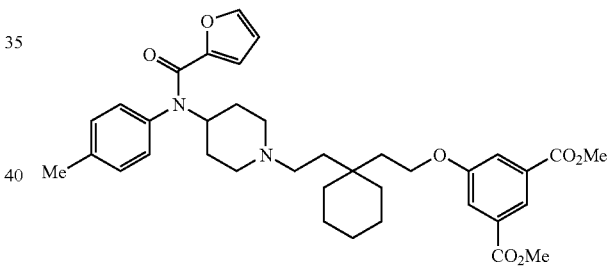

To a solution of dimethyl 5-[2-[1-[2-[4-(p-toluidino)piperidin-1-yl]ethyl]cyclohexyl]-ethoxy]isophthalate (synthesized in Example 27) (280 mg) dissolved in dichloromethane (5 mL) was added triethylamine (0.14 mL). After addition of 2-furoyl chloride (0.077 mL) under ice cooling, the temperature of solution was allowed to rise to room temperature. The solution was stirred for 15 hours. A 10% aqueous citric acid solution was added to the solution and it was extracted with chloroform. The organic layer was dried over anhydrous magnesium sulfate and filtered. The filtrate was then concentrated under reduced pressure. The resulting residue was purified by chromatography [NH silica gel, hexane-ethyl acetate (1:1)] to give the title compound (288 mg).

$^1$H-NMR (CDCl$_3$) δ: 1.35-1.56 (m, 14H), 1.79 (t, 2H, J=7.3 Hz), 1.87 (d, 2H, J=11.2 Hz), 2.12 (t, 2H, J=11.2 Hz), 2.33 (t, 2H, J=8.3 Hz), 2.39 (s, 3H), 2.99 (d, 2H, J=11.7 Hz), 3.94 (s, 6H), 4.03 (t, 2H, J=7.3 Hz), 4.78 (t, 1H, J=12.2 Hz), 5.35 (s, 1H), 6.13 (dd, 1H, J=1.9 Hz, 3.4 Hz), 7.01 (d, 2H, J=8.3 Hz), 7.17 (d, 2H, J=8.3 Hz), 7.35 (s, 1H), 7.70 (d, 2H, J=1.0 Hz), 8.26 (s, 1H); MS (ESI) m/z 631 (MH$^+$).

EXAMPLE 29

5-[2-[1-[2-[4-[N-(p-Tolyl)-2-furancarboxamido]piperidin-1-yl]ethyl]cyclohexyl]ethoxy]isophthalic acid

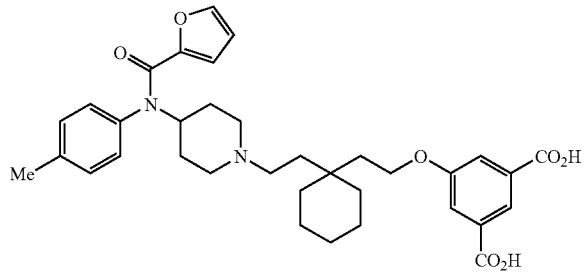

To a solution of dimethyl 5-[2-[1-[2-[4-[N-(p-tolyl)-2-furancarboxamido]piperidin-1-yl]ethyl]cyclohexyl]ethoxy]isophthalate (synthesized in Example 28) (255 mg) dissolved in methanol (5 mL) was added a 2N aqueous sodium hydroxide solution (2.0 mL). The solution was stirred at room temperature for 24 hours. The reaction solution was concentrated under reduced pressure. Water was then added to the solution, and it was neutralized with acetic acid (0.23 mL) and extracted with chloroform-ethanol (80:20). The organic layer was dried over anhydrous magnesium sulfate and filtered. The filtrate was then concentrated under reduced pressure to give the title compound (243 mg).

Hydrochloride $^1$H-NMR (DMSO-$d_6$) δ: 1.23-1.48 (m, 10H), 1.61-1.75 (m, 6H), 1.99-2.01 (brd, 2H, J=12.7 Hz), 2.36 (s, 3H), 2.91-2.98 (m, 2H), 3.04-3.19 (m, 3H), 4.72-4.83 (t like, 1H), 5.40 (s, 1H), 6.31 (d, 1H, J=2.0 Hz), 7.15 (d, 2H, J=7.8 Hz), 7.28 (d, 2H, J=8.3 Hz), 7.63-7.64 (d like, 3H), 8.06 (s, 1H); IR (KBr) cm$^{-1}$: 3426, 2928, 1713, 1621, 1596, 1469, 1469, 1403, 1298, 1231, 1192, 1119, 1041, 760; MS (ESI) m/z: 603 (MH$^+$).

EXAMPLE 30

1-[2-[1-[2-(tert-Butyldiphenylsiloxy)ethyl]cyclohexyl]ethoxy]-3,5-dihydroxymethylbenzene

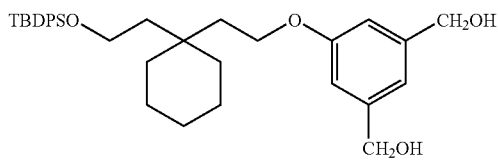

Lithium aluminum hydride (172 mg) was suspended in tetrahydrofuran (10 mL). To this was added a solution of dimethyl 5-[2-[1-[2-(tert-butyldiphenylsiloxy)ethyl]cyclohexyl]ethoxy]isophthalate (synthesized in Example 24) (1.30 g) in tetrahydrofuran (15 mL) dropwise at room temperature. The suspension was stirred for 3 hours. Water (0.16 mL) was added to the suspension and it was stirred for 10 minutes. A 15% aqueous sodium hydroxide solution (0.16 mL) was added to the suspension and it was stirred for 15 minutes. Diethyl ether was added to the mixture, followed by addition of water (0.48 mL). The solution was stirred for 30 minutes. The solution was dried over anhydrous magnesium sulfate, filtered and the filtrate was then concentrated under reduced pressure. The resulting residue was purified by chromatography [silica gel, ethyl acetate] to give the title compound (1.04 g).

$^1$H-NMR (CDCl$_3$) δ: 1.03 (s, 9H), 1.26-1.30 (m, 2H), 1.35-1.45 (m, 8H), 1.66 (t, 2H, J=7.3 Hz), 1.73-1.77 (t like, 2H), 3.74 (t, 2H, J=7.4 Hz), 3.93 (t, 2H, J=7.3 Hz), 4.12 (q, 2H, J=7.3 Hz), 4.65 (s, 4H), 6.78 (s, 2H), 6.92 (s, 1H), 7.34-7.40 (m, 6H), 7.66-7.71 (m, 4H).

EXAMPLE 31

2-[1-[2-(3,5-Diacetoxymethylphenyoxy)ethyl]cyclohexyl]ethanol

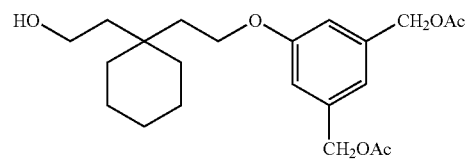

To a solution of 1-[2-[1-[2-(tert-butyldiphenylsiloxy)ethyl]cyclohexyl]ethoxy]-3,5-dihydroxymethylbenzene (synthesized in Example 30) (1.04 g) dissolved in pyridine (5.0 mL) was added acetic anhydride (5 mL) under ice cooling. The solution was stirred for 1 hour. After allowing the temperature to rise to room temperature, the solution was stirred for additional 1 hour. The reaction solution was concentrated under reduced pressure (by azeotropic distillation with toluene) to give 1-[2-[1-[2-(tert-butyldiphenylsiloxy)ethyl]cyclohexyl]ethoxy]-3,5-diacetoxymethylbenzene (1.13 g). This product was subjected to the subsequent step without further purification.

To a solution of 1-[2-[1-[2-(tert-butyldiphenylsiloxy)ethyl]cyclohexyl]ethoxy]-3,5-diacetoxymethylbenzene (1.13 g) dissolved in tetrahydrofuran (7 mL) was added a 1M tetrabutylammonium fluoride/tetrahydrofuran solution (2.8 mL) dropwise at room temperature. The solution was stirred for 15 hours. A 10% aqueous citric acid solution was added to the solution, and it was extracted with ethyl acetate. The organic layer was washed with saturated aqueous sodium bicarbonate solution and saturated aqueous sodium chloride solution. The organic layer was dried over anhydrous magnesium sulfate and filtered. The filtrate was then concentrated under reduced pressure. The resulting residue was purified by chromatography [silica gel, hexane:ethyl acetate (1:1)] to give the title compound (439 mg).

$^1$H-NMR (CDCl$_3$) δ: 1.35-1.54 (m, 11H), 1.68 (t, 2H, J=7.3 Hz), 1.83 (t, 2H, J=7.3 Hz), 2.12 (s, 6H), 3.75 (t, 2H, J=7.3 Hz), 4.04 (t, 2H, J=7.3 Hz), 5.07 (s, 4H), 6.85 (s, 2H), 6.92 (s, 1H).

EXAMPLE 32

1,3-Diacetoxymethyl-5-[2-[1-(formylmethyl)cyclohexyl]ethoxy]benzene

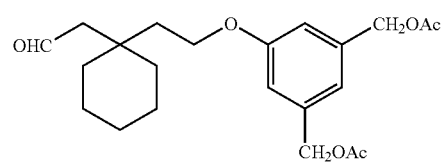

To a solution of 2-[1-[2-(3,5-diacetoxymethylphenyoxy)ethyl]cyclohexyl]ethanol (synthesized in Example 31) (430 mg) dissolved in dichloromethane (5 mL) were added diacetic acid iodobenzene (388 mg) and 2,2,6,6-tetramethyl-1-piperidinyloxy free radical (18.5 mg) successively at room temperature. The solution was stirred for 15 hours. Diethyl ether was added to the solution and it was washed in turn with a 10% aqueous sodium thiosulfate solution, 1N hydrochloric acid, saturated aqueous sodium bicarbonate solution and saturated aqueous sodium chloride solution. The organic layer was dried over anhydrous magnesium sulfate, and filtered. The filtrate was then concentrated under reduced pressure to give the title compound (479 mg). This product was subjected to the subsequent step without further purification.

EXAMPLE 33

1,3-Diacetoxymethyl-5-[2-[1-[2-[4-(p-toluidino) piperidin-1-yl]ethyl]cyclohexyl]ethoxy]benzene

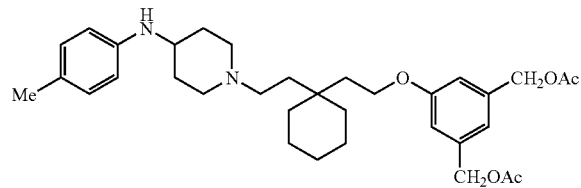

1,3-Diacetoxymethyl-5-[2-[1-(formylmethyl)cyclohexyl] ethoxy]benzene (synthesized in Example 32) (215 mg) and 4-(p-toluidino)piperidine (synthesized in Preparation Example 4-5) (127 mg) were dissolved in 1,2-dichloroethane (5 mL). To this was added acetic acid (0.04 mL) at room temperature. The solution was stirred for 45 minutes. Sodium triacetoxyborohydride (294 mg) was added to the solution at room temperature. The solution was stirred for 3 hours. saturated aqueous sodium bicarbonate solution was added to the solution and it was extracted with chloroform. The organic layer was dried over anhydrous magnesium sulfate, and filtered. The filtrate was then concentrated under reduced pressure. The resulting residue was purified by chromatography [silica gel, chloroform-methanol (10:1)] to give the title compound (334 mg). This product was subjected to the subsequent step without further purification.

$^1$H-NMR (CDCl$_3$) δ: 1.27-1.48 (m, 14H), 1.49-1.82 (m, 7H), 2.11 (s, 6H), 2.22 (s, 3H), 2.31-2.43 (m, 2H), 2.83-2.98 (m, 2H), 3.21-3.33 (m, 1H), 3.98-4.02 (m, 2H), 5.07 (s, 4H), 6.52 (d, 2H, J=8.3 Hz), 6.84 (s, 2H), 6.91 (s, 1H), 6.96 (d, 2H, J=7.8 Hz).

EXAMPLE 34

N-[1-[2-[1-[2-[3,5-Bis(hydroxymethyl)phenoxy] ethyl]cyclohexyl]ethyl]piperidin-4-yl]-N-(p-tolyl)-2-furancarboxamide

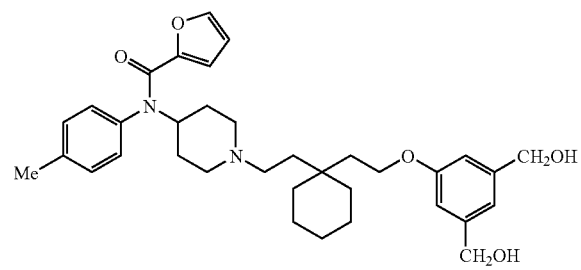

To a solution of 1,3-diacetoxymethyl-5-[2-[1-[2-[4-(p-toluidino)piperidin-1-yl]ethyl]cyclohexyl]ethoxy]benzene (synthesized in Example 33) (222 mg) dissolved in dichloromethane (4 mL) was added triethylamine (0.11 mL). 2-Furoyl chloride (0.06 mL) was added to the solution under ice cooling. The temperature was allowed to rise to room temperature, and the solution was stirred for 1 hour. The reaction solution was concentrated under reduced pressure. The resulting residue was purified by chromatography [silica gel, chloroform-methanol (10:1)] to give N-[1-[2-[1-[2-[3,5-bis(acetoxymethyl)phenoxy]ethyl]cyclohexyl]ethyl]piperidin-4-yl]-N-(p-tolyl)-2-furancarboxamide (276 mg). This product was subjected to the subsequent step without further purification.

To a solution of N-[1-[2-[1-[2-[3,5-bis(acetoxymethyl) phenoxy]ethyl]cyclohexyl]ethyl]piperidin-4-yl]-N-(p-tolyl)-2-furancarboxamide (276 mg) dissolved in methanol (4 mL) was added potassium carbonate (11 mg). The solution was stirred at room temperature for 2 hours. The reaction solution was concentrated under reduced pressure. Saturated aqueous sodium bicarbonate solution was added to the solution, and it was extracted with chloroform-ethanol (80:20). The organic layer was dried over anhydrous magnesium sulfate, and filtered. The filtrate was then concentrated under reduced pressure to give the title compound (228 mg).

Free Form $^1$H-NMR (CDCl$_3$) δ: 1.26-1.32 (m, 4H), 1.32-1.58 (m, 10H), 1.73-1.77 (m, 4H), 1.85 (brd, 2H, J=11.2 Hz), 2.12 (t, 2H, J=11.7 Hz), 2.28-2.41 (m, 2H), 2.39 (s, 3H), 2.97 (d, 2H, J=11.2 Hz), 3.99 (t, 2H, J=7.3 Hz), 4.63 (s, 4H), 4.71-4.77 (m, 1H), 5.38 (s, 1H), 6.13 (dd, 1H, J=1.9 Hz, 3.4 Hz), 6.82 (s, 2H), 6.89 (s, 1H), 7.01 (d, 2H, J=8.3 Hz), 7.18 (d, 1H, J=7.8 Hz), 7.34 (s, 1H).

Hydrochloride $^1$H-NMR (DMSO-d$_6$) δ: 1.26-1.50 (m, 10H), 1.55-1.72 (m, 6H), 2.01-2.04 (m, 2H), 2.39 (s, 3H), 2.95-3.03 (m, 2H), 3.10-3.18 (m, 2H), 3.54 (d, 2H, J=10.8 Hz), 3.97-4.01 (m, 2H), 4.45 (s, 4H), 4.77-4.83 (t like, 1H), 5.07-5.20 (m, 2H), 5.43 (s, 1H), 6.31 (d, 1H, J=1.4 Hz), 6.75 (s, 2H), 6.87 (s, 1H), 7.16 (d, 2H, J=7.8 Hz), 7.30 (d, 2H, J=8.3 Hz), 7.64 (s, 1H); IR (KBr) cm$^{-1}$ 3388, 2926, 1731, 1616, 1511, 1467, 1404, 1340, 1294, 1245, 1165, 1031, 954, 842, 766; MS (ESI) m/z 575 (MH$^+$).

EXAMPLE 35

Methyl 2-[2-[1-[2-(tert-butyldiphenylsiloxy)ethyl]cyclohexyl]ethoxy]benzoate

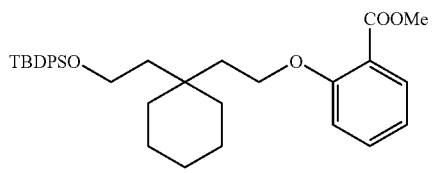

To a solution of methyl salicylate (456 mg) and potassium carbonate (498 mg) in N,N-dimethylformamide (10 mL) was added tert-butyl[2-[1-(2-iodoethyl)cyclohexyl]ethoxy] diphenylsilane (synthesized in Preparation Example 3A-3)

(1.7 g). The solution was heated at 80° C. with stirring for 24 hours. Water was added to the reaction solution and it was extracted with ether. The ether layer was washed with water and saturated aqueous sodium chloride solution. The ether layer was dried over anhydrous magnesium sulfate, and filtered. The filtrate was the concentrated under reduced pressure. The resulting residue was purified by chromatography [silica gel, hexane-ethyl acetate (10:1)] to give the title compound (547 mg).

$^1$H-NMR (CDCl$_3$) δ: 1.02 (s, 9H), 1.27-1.48 (m, 10H), 1.65 (t, 2H, J=7.3 Hz), 1.80 (t, 2H, J=7.6 Hz), 3.73 (t, 2H, J=7.3 Hz), 3.84 (s, 3H), 3.96 (t, 2H, J=7.6 Hz), 6.85-7.00 (m, 2H), 7.32-7.45 (m, 7H), 7.63-7.69 (m, 4H), 7.75 (dd, 1H, J=2.0 Hz, 7.8 Hz).

EXAMPLE 36

Methyl 2-[2-[1-(2-hydroxyethyl)cyclohexyl]ethoxy]benzoate

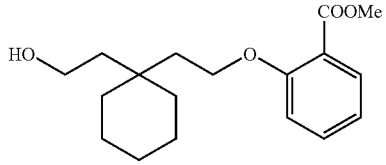

To a solution of methyl 2-[2-[1-[2-(tert-butyldiphenylsiloxy)ethyl]cyclohexyl]ethoxy]benzoate (synthesized in Example 35) (547 mg) in tetrahydrofuran (4 mL) was added a 1M tetrabutyl ammonium fluoride/tetrahydrofuran solution (1 mL) at room temperature. The solution was then stirred for 2 hours. The reaction solution was concentrated under reduced pressure. The resulting residue was purified by chromatography [silica gel, hexane-ethyl acetate (2:1)] to give the title compound (226 mg).

$^1$H-NMR (CDCl$_3$) δ: 1.28-1.52 (m, 10H), 1.75 (t, 2H, J=7.6 Hz), 1.90 (t, 2H, J=6.1 Hz), 2.30 (brs, 1H), 3.74 (t, 2H, J=7.6 Hz), 3.88 (s, 3H), 4.12 (t, 2H, J=6.1 Hz), 6.94-7.00 (m, 2H), 7.42-7.48 (m, 1H), 7.77 (dd, 1H, J=2.0 Hz, 7.8 Hz).

EXAMPLE 37

Methyl 2-[2-[1-(formylmethyl)cyclohexyl]ethoxy]benzoate

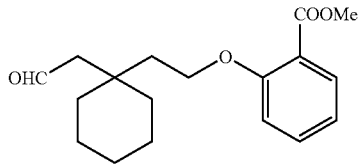

To a solution of methyl 2-[2-[1-(2-hydroxyethyl)cyclohexyl]ethoxy]benzoate (synthesized in Example 36) (226 mg) and 2,2,6,6-tetramethyl-1-piperidinyloxy free radical (23 mg) in dichloromethane (4 mL) was added diacetic acid iodobenzene (261 mg) at room temperature. The solution was stirred at room temperature for 48 hours. Silica gel was added to the reaction solution and it was concentrated under reduced pressure. The resulting residue was purified by chromatography [silica gel, hexane-ethyl acetate (5:1)] to give the title compound (118 mg).

1H-NMR (CDCl$_3$) δ: 1.40-1.60 (m, 10H), 2.05 (t, 2H, J=6.6 Hz), 2.51 (d, 2H, J=2.9 Hz), 3.86 (s, 3H), 4.15 (t, 2H, J=6.6 Hz), 6.95-7.00 (m, 2H), 7.42-7.48 (m, 1H), 7.75 (dd, 1H, J=1.4 Hz, 7.8 Hz), 9.90 (t, 1H, J=2.9 Hz).

EXAMPLE 38

Methyl 2-[2-[1-[2-[4-(p-toluidino)piperidin-1-yl]ethyl]cyclohexyl]-ethoxy]benzoate

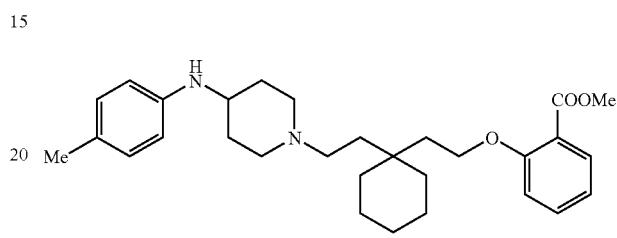

To a solution of methyl 2-[2-[1-(formylmethyl)cyclohexyl]ethoxy]benzoate (synthesized in Example 37) (118 mg), 4-(p-toluidino)piperidine ditrifluoroacetate (synthesized in Preparation example 4-5) (194 mg), 1,2-dichloroethane (2 mL) and triethylamine (94 mg) were added acetic acid (28 mg) and sodium triacetoxyborohydride (115 mg) at room temperature. After completion of addition, the solution was stirred at room temperature for 2 hours. The reaction solution was purified by chromatography [the upper layer: NH silica gel, and the lower layer: silica gel, chloroform-ethanol (20:1)] to give the title compound (205 mg).

EXAMPLE 39

Methyl 2-[2-[1-2-4-[N-(p-tolyl)-2-furancarboxamido]piperidin-1-yl]ethyl]cyclohexyl]ethoxy]benzoate

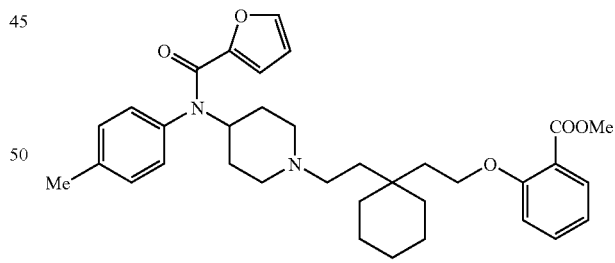

To a solution of methyl 2-[2-[1-[2-[4-(p-toluidino)piperidin-1-yl]ethyl]cyclohexyl]ethoxy]benzoate (synthesized in Example 38) (186 mg) and triethylamine (0.081 mL) in dichloromethane (2 mL) was added 2-furoyl chloride (0.046 mL) dropwise under ice cooling. After completion of the dropwise addition, the solution was stirred for 18 hours while the temperature was allowed to rise to room temperature. NH silica gel was added to the reaction solution and it was concentrated under reduced pressure. The resulting residue was purified by chromatography [NH silica gel, hexane-ethyl acetate (3:1)] to give the title compound (223 mg).

¹H-NMR (CDCl₃) δ: 1.30-1.58 (m, 14H), 1.80-1.90 (m, 4H), 2.05-2.14 (m, 2H), 2.25-2.32 (m, 2H), 2.39 (s, 3H), 2.94-3.00 (m, 2H), 3.87 (s, 3H), 4.00-4.06 (m, 2H), 4.72-4.82 (m, 1H), 5.33-5.37 (m, 1H), 6.13 (dd, 1H, J=1.5 Hz, 3.9 Hz), 6.91-7.05 (m, 4H), 7.15-7.20 (m, 2H), 7.33-7.35 (m, 1H), 7.39-7.45 (m, 1H), 7.76 (dd, 1H, J=2.0 Hz, 7.8 Hz)

EXAMPLE 40

2-[2-[1-[2-[4-[N-(p-Tolyl)-2-furancarboxamido]piperidin-1-yl]ethyl]cyclohexyl]ethoxy]benzoic acid

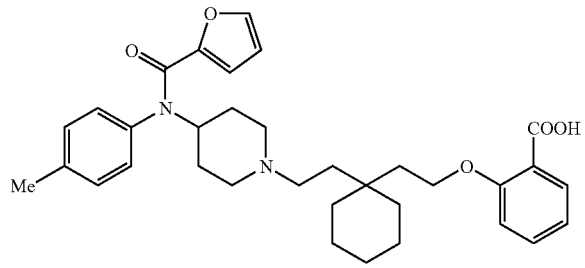

To a solution of methyl 2-[2-[1-[2-[4-[N-(p-tolyl)-2-furancarboxamido]piperidin-1-yl]ethyl]cyclohexyl]ethoxy]benzoate (synthesized in Example 39) (221 mg) in methanol (5 mL) was added a sodium hydroxide (77 mg) solution in water (3 mL) dropwise at room temperature. The solution was stirred for 18 hours. After neutralizing the reaction solution with 2N hydrochloric acid, silica gel was added to the solution. The solution was concentrated under reduced pressure. The resulting residue was purified by chromatography [silica gel, chloroform-methanol (10:1)] to give the title compound (172 mg).

Hydrochloride

¹H-NMR (CDCl₃) δ: 1.30-1.52 (m, 10H), 1.83-1.90 (m, 2H), 1.93-2.10 (m, 6H), 2.17-2.30 (m, 2H), 2.42 (s, 3H), 3.00-3.12 (m, 2H), 3.53-3.62 (m, 2H), 4.25-4.32 (m, 2H), 4.98-5.08 (m, 1H), 5.32-5.36 (m, 1H), 6.16-6.18 (m, 1H), 7.01-7.08 (m, 3H), 7.14-7.19 (m, 1H), 7.23-7.29 (m, 4H), 7.39-7.41 (m, 1H), 7.42-7.54 (m, 1H), 7.95-8.00 (m, 1H), 11.81 (brs, 1H).

EXAMPLE 41

N-[1-[2-[1-[2-(2-Methyl-2H-tetrazol-5-yl)ethyl]cyclohexyl]ethyl]piperidin-4-yl]-N-(5-methylpyridin-2-yl)-2-furancarboxamide

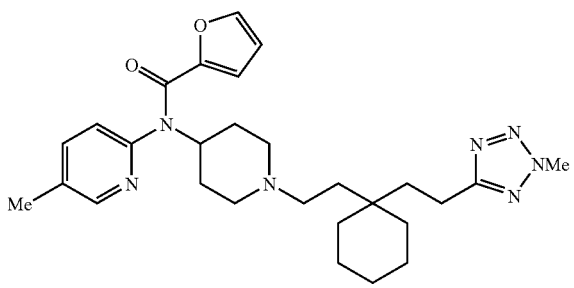

N-[1-[2-[1-[2-(1-Methyl-1H-tetrazol-5-yl)]ethyl]cyclohexyl]ethyl]piperidin-4-yl]-N-(5-methylpyridin-2-yl)-2-furancarboxamide

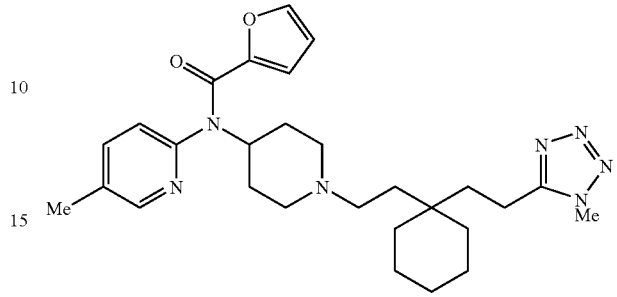

N-[1-[2-[1-(2-Tetrazolyethyl)cyclohexyl]ethyl]piperidin-4-yl]-N-(5-methylpyridin-2-yl)-2-furancarboxamide (synthesized in Example 4D-7) (228 mg) was dissolved in methanol (0.065 mL) and benzene (3.25 mL). To this was added trimethylsilyldiazomethane (0.30 mL) under ice cooling. After allowing the temperature to rise to room temperature, the solution was stirred for 19 hours. Trimethylsilyldiazomethane (0.60 mL) was further added to the solution at room temperature and it was stirred for 75 hours. Trimethylsilyldiazomethane (1.12 mL) was further added and the solution was stirred for 24 hours. The reaction solution was concentrated under reduced pressure. The resulting residue was purified by chromatography [NH silica gel, hexane-ethyl acetate (1:1) to ethyl acetate] to give the title compound, N-[1-[2-[1-[2-(2-methyl-2H-tetrazol-5-yl)ethyl]cyclohexyl]ethyl]piperidin-4-yl]-N-(5-methylpyridin-2-yl)-2-furancarboxamide, as a low polarity fraction (151 mg) and also to give the title compound, N-[1-[2-[1-[2-(1-methyl-1H-tetrazol-5-yl)ethyl]cyclohexyl]-ethyl]piperidin-4-yl]-N-(5-methylpyridin-2-yl)-2-furancarboxamide, as a high polarity fraction (55 mg).

N-[1-[2-[1-[2-(2-Methyl-2H-tetrazol-5-yl)ethyl]cyclohexyl]ethyl]piperidin-4-yl]-N-(5-methylpyridin-2-yl)-2-furancarboxamide ¹H-NMR (CDCl₃) δ: 1.26-1.51 (m, 14H), 1.70-1.73 (m, 2H), 1.95 (d, 2H, J=11.7 Hz), 2.10 (t, 2H, J=11.2 Hz), 2.29 (m, 2H), 2.38 (s, 3H), 2.74-2.79 (m, 2H), 2.99 (d, 2H, J=11.7 Hz), 4.29 (s, 3H), 4.74 (t like, 1H), 5.93 (d, 1H, J=3.4 Hz), 6.19 (dd, 1H, J=2.0 Hz, 3.4 Hz), 6.99 (d, 1H, J=8.3 Hz), 7.22 (d, 1H, J=1.0 Hz) 7.50 (dd, 1H, J=1.9 Hz, 8.8 Hz), 8.37 (d, 1H, J=1.9 Hz).

N-[1-[2-[1-[2-(1-Methyl-1H-tetrazol-5-yl)ethyl]cyclohexyl]-ethyl]piperidin-4-yl]-N-(5-methylpyridin-2-yl)-2-furancarboxamide ¹H-NMR (CDCl₃) δ: 1.26-1.52 (m, 14H), 1.75-1.78 (m, 2H), 1.95 (d, 2H, J=12.2 Hz), 2.10 (t, 2H, J=11.2 Hz), 2.29 (m, 2H), 2.39 (s, 3H), 2.70-2.74 (m, 2H), 2.99 (d, 2H, J=11.2 Hz), 3.98 (s, 3H), 4.72 (t like, 1H), 5.94 (d, 1H, J=3.4 Hz), 6.19 (dd, 1H, J=2.0 Hz, 3.4 Hz), 6.98 (d, 1H, J=8.3 Hz), 7.22 (d, 1H, J=1.0 Hz), 7.51 (dd, 1H, J=2.0 Hz, 8.3 Hz), 8.37 (d, 1H, J=2.4 Hz).

EXAMPLE 42

N-[1-[2-[1-(1,1-Dimethylcarbamoylmethyl)cyclohexyl]ethyl]piperidin-4-yl]-N-(5-methylpyridin-2-yl)-2-furancarboxamide

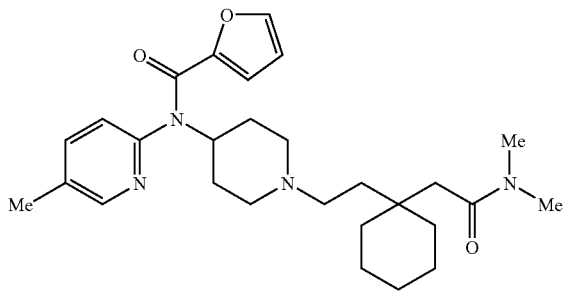

To a solution of [1-[2-[4-[N-(5-methylpyridin-2-yl)-2-furancarboxamido]piperidin-1-yl]ethyl]cyclohexyl]acetic acid (synthesized in Example 3A-3) (300 mg) in dichloromethane (4 mL) was added N,N-dimethylformamide (1 drop) dropwise and then oxalyl chloride (0.087 mL) under ice cooling. The solution was stirred under ice cooling for 2 hours. A 2 mL aliquot of the reaction solution was taken and it was added to a 50% aqueous dimethylamine solution (2 mL) dropwise. The solution was stirred for 18 hours while the temperature was allowed to rise to room temperature. NH Silica gel was then added to the reaction solution and it was concentrated under reduced pressure. The resulting residue was purified by silica gel column chromatography [NH silica gel, hexane-ethyl acetate (1:1)] to give the title compound (90 mg).

Hydrochloride $^1$H-NMR (CDCl$_3$) δ: 1.25-1.56 (m, 10H), 2.03-2.12 (m, 2H), 2.23 (s, 2H), 2.25-2.46 (m, 4H), 2.57 (s, 3H), 2.85-3.15 (m, 10H), 3.52-3.60 (m, 2H), 4.95-5.05 (m, 1H), 6.34 (dd, 1H, J=1.9 Hz, 3.4 Hz), 6.85 (d, 1H, J=3.4 Hz), 7.12-7.15 (m, 1H), 7.52-7.58 (m, 1H), 8.12-8.18 (m, 1H), 8.51-8.54 (m, 1H), 11.81 (brs, 1H).

EXAMPLE 43

N-[1-[2-[1-(2-Morpholin-4-yl-2-oxoethyl)cyclohexyl]ethyl]piperidin-4-yl]-N-(5-methylpyridin-2-yl)-2-furancarboxamide

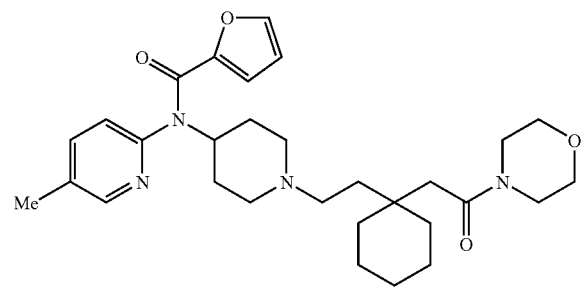

To a solution of [1-[2-[4-[N-(5-methylpyridin-2-yl)-2-furancarboxamido]piperidin-1-yl]ethyl]cyclohexyl]acetic acid (synthesized in Example 3A-3) (300 mg) in dichloromethane (4 mL) was added N,N-dimethylformamide (1 drop) dropwise and then oxalyl chloride (0.087 mL) under ice cooling. The solution was stirred under ice cooling for 2 hours. A 2 mL aliquot of the reaction solution was taken and it was added to a solution of morpholine (288 mg) in dichloromethane (4 mL) dropwise under ice cooling. The solution was stirred under ice cooling for 1.5 hours. NH silica gel was then added to the reaction solution and it was concentrated under reduced pressure. The residue was purified by chromatography [NH silica gel, hexane-ethyl acetate (1:1)] to give the title compound (60 mg).

Hydrochloride $^1$H-NMR (CDCl$_3$) δ: 1.20-1.60 (m, 10H), 2.03-2.11 (m, 2H), 2.23 (s, 2H), 2.25-2.42 (m, 4H), 2.53 (s, 3H), 3.05-3.20 (m, 4H), 3.21-3.30 (m, 4H), 3.50-3.75 (m, 4H), 4.00-4.05 (m, 2H), 4.92-5.08 (m, 1H), 6.30-6.34 (m, 1H), 6.52-6.56 (m, 1H), 7.20 (s, 1H), 7.45-7.55 (m, 1H), 7.98-8.05 (m, 1H), 8.51 (s, 1H), 11.59 (brs, 1H).

EXAMPLE 44

N-[1-[2-[1-[2-(1,2-Di-tert-butoxycarbonylguanidino)ethyl]-cyclohexyl]ethyl]piperidin-4-yl]-N-(5-methylpyridin-2-yl)-2-furancarboxamide

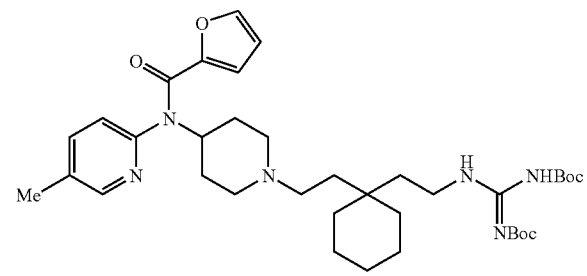

To a solution of N-[1-[2-[1-(2-aminoethyl)cyclohexyl]ethyl]piperidin-4-yl]-N-(5-methylpyridin-2-yl)-2-furancarboxamide (synthesized in Example 3F-5) (104 mg) and 1,3-bis(tert-butoxycarbonyl)-2-methyl-2-thiopseudourea (85 mg) in N,N-dimethylformamide (5 mL) were added N,N-diisopropylethylamine (0.12 g) and then mercury (II) chloride (113 mg) at room temperature. The solution was stirred at room temperature for 3 days. Dichloromethane was added to the solution and insolubles were filtered off with Celite. The solvent was distilled off under reduced pressure. The resulting residue was purified by chromatography [silica gel, dichloromethane-methanol-aqueous ammonia (97:3:0.2)] to give the title compound (0.1049 g).

$^1$H-NMR (DMSO-d$_6$) δ: 1.14-1.54 (m, 18H), 1.39 (s, 9H), 1.47 (s, 9H), 1.70-1.79 (m, 2H), 1.90-2.01 (m, 2H), 2.21-2.28 (m, 2H), 2.34 (s, 3H), 2.88-2.94 (m, 2H), 4.39-4.48 (m, 1H), 5.84 (d, 1H, J=3.4 Hz), 6.32 (dd, 1H, J=2.0 Hz, 3.4 Hz), 7.15 (d, 1H, J=7.9 Hz), 7.52 (d, 1H, J=2.0 Hz), 7.66 (dd, 1H, J=2.4 Hz, 7.9 Hz), 8.08-8.11 (m, 1H), 8.34 (d, 1H, J=2.4 Hz), 11.20-11.22 (m, 1H).

EXAMPLE 45

N-[1-[2-[1-(2-Guanidinoethyl)cyclohexyl]ethyl]piperidin-4-yl]-N-(5-methylpyridin-2-yl)-2-furancarboxamide

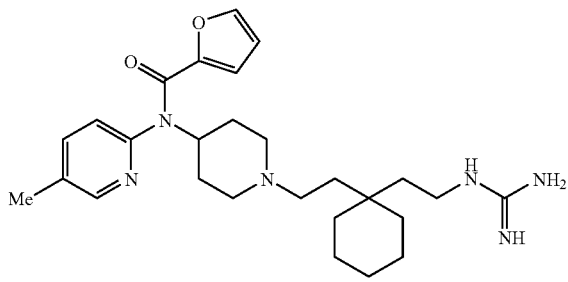

N-[1-[2-[1-[2-(1,2-Di-tert-butoxycarbonylguanidino)ethyl]cyclohexyl]ethyl]piperidin-4-yl]-N-(5-methylpyridin-2-yl)-2-furancarboxamide (synthesized in Example 44) (105 mg) was dissolved in a 4N hydrochloric acid/1,4-dioxane solution (12 mL) and methanol (5 mL). The solution was stirred at room temperature for 2 days. The solvent was distilled off under reduced pressure and the resulting residue was crystallized (from methanol-ethyl acetate) to give the title compound (69 mg).

Hydrochloride mp 156-160° C.; $^1$H-NMR (DMSO-d$_6$) δ: 1.18-1.51 (m, 12H), 1.58-1.69 (m, 2H), 1.83-1.96 (m, 2H), 1.97-2.08 (m, 2H), 2.37 (s, 3H), 2.90-3.03 (m, 2H), 3.04-3.20 (m, 4H), 3.49-3.59 (m, 2H), 4.70-4.80 (m, 1H), 5.89 (d, 1H, J=3.4 Hz), 6.35 (dd, 1H, J=1.5 Hz, 3.4 Hz), 7.24 (d, 1H, J=7.8 Hz), 7.56 (d, 1H, J=1.5 Hz), 7.57-7.65 (m, 1H), 7.73 (dd, 1H, J=2.0 Hz, 7.8 Hz), 8.39 (d, 1H, J=2.0 Hz); IR (KBr) cm$^{-1}$: 3365, 3178, 2927, 2855, 2714, 1651, 1469, 1403, 1386, 1340, 1321, 1191, 1032, 768, 754; MS (ESI) m/z: 481 (MH$^+$).

EXAMPLE 46

2-[2-[1-[2-[4-[N-(5-Methylpyridin-2-yl)-2-furancarboxamido]piperidin-1-yl]ethyl]cyclohexyl]acetylamino]benzoic acid

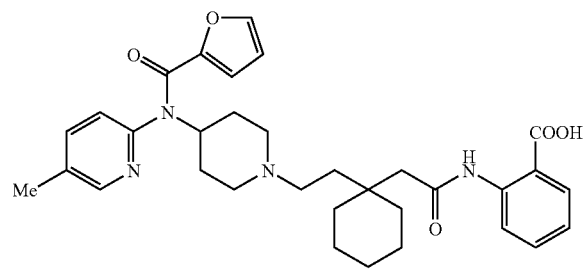

To a solution of [1-[2-[4-[N-(5-methylpyridin-2-yl)-2-furancarboxamido]piperidin-1-yl]ethyl]cyclohexyl]acetic acid (synthesized in Example 3A-3) (210 mg) in dichloromethane (2 mL) was added N,N-dimethylformamide (1 drop) dropwise and then oxalyl chloride (0.038 mL) under ice cooling. The solution was stirred under ice cooling for 2 hours. Methyl anthranylate (242 mg) was then added dropwise to the solution, and it was stirred for 18 hours while the temperature was allowed to rise to room temperature. NH Silica gel was added to the reaction solution and it was concentrated under reduced pressure. The resulting residue was purified by chromatography [silica gel, chloroform-ethanol (20:1)] to give methyl 2-[2-[1-[2-[4-[N-(5-methylpyridin-2-yl)-2-furancarboxamido]piperidin-1-yl]ethyl]cyclohexyl]acetylamino]benzoate (150 mg).

To a solution of this product in methanol (5 mL) was added a solution of sodium hydroxide (77 mg) in water (3 mL) dropwise at room temperature. The solution was stirred at room temperature for 18 hours. After neutralizing the solution with 2N hydrochloric acid, silica gel was added to the solution and it was concentrated under reduced pressure. The resulting residue was purified by chromatography [silica gel, chloroform-methanol (8:1)] to give the title compound (60 mg).

$^1$H-NMR (CDCl$_3$) δ: 1.30-1.60 (m, 10H), 1.80-1.90 (m, 2H), 2.00-2.20 (m, 4H), 2.23 (s, 3H), 2.30 (s, 2H), 2.74-2.86 (m, 2H), 3.08-3.18 (m, 2H), 3.50-3.60 (m, 2H), 4.82-4.92 (m, 1H), 5.87-5.90 (m, 1H), 6.18 (dd, 1H, J=1.5 Hz, 3.5 Hz), 6.91 (d, 1H, J=7.8 Hz), 6.98-7.04 (m, 1H), 7.21-7.23 (m, 1H), 7.34-7.41 (m, 2H), 7.88 (dd, 1H, J=1.5 Hz, 7.8 Hz), 8.16-8.19 (m, 1H), 8.57 (d, 1H, J=8.3 Hz), 12.71 (brs, 1H).

EXAMPLE 47

1,3-Diacetoxymethyl-5-[2-[1-[2-[4-(5-methylpyridin-2-ylamino)piperidin-1-yl]ethyl]cyclohexyl]ethoxy]benzene

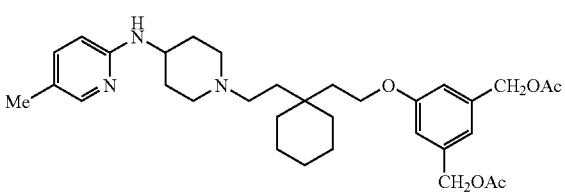

1,3-Diacetoxymethyl-5-[2-[1-(formylmethyl)cyclohexyl]ethoxy]benzene (synthesized in Example 32) (215 mg) and 2-(piperidin-4-ylamino)-5-methylpyridine (synthesized in Preparation Example 4-3) (126 mg) were dissolved in 1,2-dichloroethane (5 mL). To this was added acetic acid (0.04 mL) at room temperature. The solution was stirred for 45 minutes. Sodium triacetoxyborohydride (295 mg) was added to the solution at room temperature and it was stirred for 3 hours. Saturated aqueous sodium bicarbonate solution was added to the solution and it was extracted with chloroform. The organic layer was dried over anhydrous magnesium sulfate, and filtered. The filtrate was then concentrated under reduced pressure. The resulting residue was purified by chromatography [silica gel, chloroform-methanol (10:1)] to give the title compound (258 mg).

$^1$H-NMR (CDCl$_3$) δ: 1.26-1.54 (m, 10H), 1.57-1.61 (m, 4H), 1.80 (t, 2H, J=7.3 Hz), 2.05-2.10 (brd, 2H, J=7.3 Hz), 2.11 (s, 6H), 2.16 (s, 3H), 2.21-2.27 (m, 2H), 2.40 (t, 2H, J=7.8 Hz), 2.92-3.00 (m, 2H), 3.56-3.68 (m, 1H), 4.01 (t, 2H, J=7.3 Hz), 4.27 (brd, 1H, J=7.8 Hz), 5.07 (s, 4H), 6.30 (d, 1H, J=8.3 Hz), 6.84 (s, 2H), 6.91 (s, 1H), 7.23 (dd, 1H, J=2.5 Hz, 8.3 Hz), 7.88 (s, 1H).

EXAMPLE 48

N-[1-[2-[1-[2-[3,5-Bis(hydroxymethyl)phenoxy]ethyl]cyclohexyl]ethyl]piperidin-4-yl]-N-(5-methylpyridin-2-yl)-2-furancarboxamide

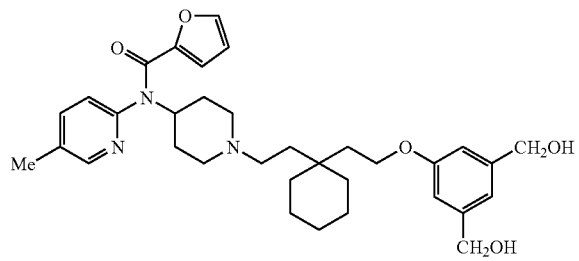

To a solution of 1,3-diacetoxymethyl-5-[2-[1-[2-[4-(5-methylpyridin-2-ylamino)piperidin-1-yl]ethyl]cyclohexyl]ethoxy]benzene (synthesized in Example 47) (249 mg) dissolved in 1,2-dichloroethane (4 mL) was added triethylamine (0.13 mL). 2-Furolyl chloride (0.065 mL) was added to the solution under ice cooling. The temperature was then allowed to rise to room temperature and the solution was stirred for 1 hour. The reaction solution was concentrated under reduced pressure. The resulting residue was purified by chromatography [silica gel, chloroform-methanol (10:1)] to give N-[1-[2-[1-[2-[3,5-bis(acetoxymethyl)phenoxy]ethyl]cyclohexyl]ethyl]piperidin-4-yl]-N-(5-methylpyridin-2-yl)-2-furancarboxamide (303 mg).

To a solution of this product in methanol (4 mL) was added potassium carbonate (12 mg). The solution was stirred at room temperature for 2 hours. The reaction solution was concentrated under reduced pressure. Saturated aqueous sodium bicarbonate solution was then added to the residue and it was extracted with chloroform-ethanol (80:20). The organic layer was dried over anhydrous magnesium sulfate, and filtered. The filtrate was then concentrated under reduced pressure to give the title compound (248 mg).

Free Form $^1$H-NMR (CDCl$_3$) δ: 1.25-1.51 (m, 14H), 1.56-1.64 (m, 2H), 1.73-1.77 (m, 2H), 1.92 (d, 2H, J=11.2 Hz), 2.07-2.12 (t like, 2H), 2.28-2.32 (m, 2H), 2.37 (s, 3H), 2.97 (d, 2H, J=11.2 Hz), 3.97-4.00 (t like, 2 Hz), 4.60 (s, 4H), 4.65-4.73 (m, 1H), 5.94 (d, 1H, J=3.4 Hz), 6.19 (dd, 1H, J=2.0 Hz, 3.4 Hz), 6.80 (s, 2H), 6.86 (s, 1H), 6.98 (d, 1H, J=7.8 Hz), 7.22 (s, 1H), 7.50 (dd, 1H, J=2.4 Hz, 7.8 Hz), 8.36 (s, 1H).

Hydrochloride $^1$H-NMR (DMSO-d$_6$) δ: 1.32-1.44 (m, 10H), 1.63-1.71 (m, 4H), 1.82-1.91 (m, 2H), 1.99-2.06 (m, 2H), 2.37 (s, 3H), 3.01-3.06 (m, 2H), 3.08-3.22 (m, 2H), 3.46-3.70 (m, 4H), 3.97-4.03 (m, 2H), 4.45 (s, 4H), 4.76 (t like, 1H), 5.87 (d, 1H, J=3.4 Hz), 6.35 (dd, 1H, J=2.0 Hz, 3.4 Hz), 6.75 (s, 2H), 6.83 (s, 1H), 7.24 (d, 1H, J=8.3 Hz), 7.56 (s, 1H), 7.73 (dd, 1H, J=2.4 Hz, 7.8 Hz), 8.40 (s, 1H), 9.50-9.60 (brm, 1H); IR (KBr) cm$^{-1}$ 3388, 2927, 1731, 1633, 1595, 1469, 1401, 1324, 1294, 1161, 1031, 754. MS (ESI) m/z 576 (MH$^+$).

EXAMPLE 49

N-[1-[2-[1-[5-Hydroxy-3,3-bis(hydroxymethyl)pentyl]cyclohexyl]ethyl]piperidin-4-yl]-N-(5-methylpyridin-2-yl)-2-furancarboxamide

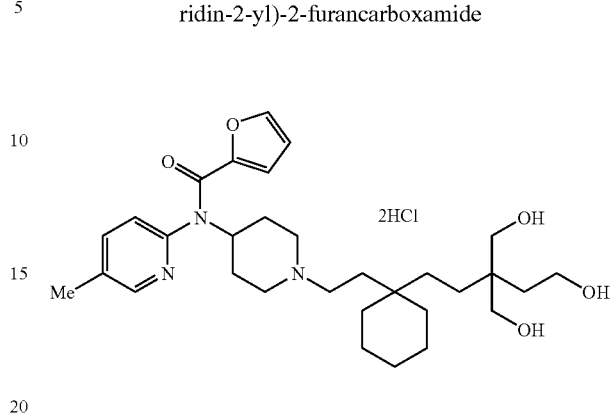

mp 122-125° C.; $^1$H-NMR (DMSO-d$_6$) δ: 1.04-1.15 (m, 4H), 1.15-1.23 (m, 4H), 1.34-1.39 (m, 8H), 1.55-1.59 (m, 2H), 1.83-1.92 (m, 2H), 2.02 (d, 2H, J=12.7 Hz), 2.37 (s, 3H), 2.92-3.02 (m, 2H), 3.01-3.11 (m, 2H), 3.19-3.25 (m, 4H), 3.44-3.49 (m, 4H), 4.75 (m, 1H), 5.90 (d, 1H, J=3.4 Hz), 6.35 (dd, 1H, J=1.9 Hz, 3.4 Hz), 7.24 (d, 1H, J=7.8 Hz), 7.56 (d, 1H, J=1.0 Hz), 7.74 (dd, 1H, J=1.5 Hz, 7.8 Hz), 8.39 (d, 1H, J=1.9 Hz), 9.54-9.71 (brs, 1H); IR (KBr) cm$^{-1}$: 3417, 2926, 1633, 1557, 1469, 1385, 1319, 1190, 1017. Anal. Calcd for C$_{31}$H$_{49}$Cl$_2$N$_3$O$_5$.1/2H$_2$O: C, 59.70; H, 8.08; N, 6.74. Found: C, 59.50; H, 8.33; N, 6.95.

EXAMPLE 50

N-[1-[2-[1-(4-Hydroxy-3-hydroxymethylbutyl)cyclohexyl]ethyl]piperidin-4-yl]-N-(5-methylpyridin-2-yl)-2-furancarboxamide

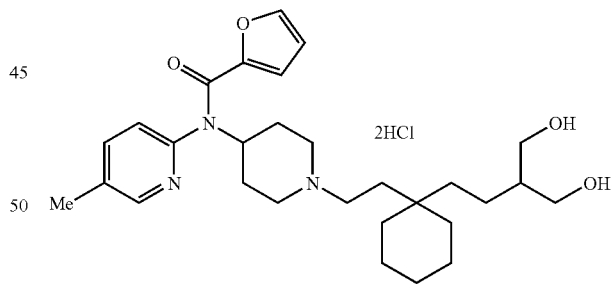

mp 115-117° C.; $^1$H-NMR (DMSO-d$_6$) δ: 1.15-1.24 (m, 8H), 1.24-1.39 (m, 8H), 1.51-1.66 (m, 2H), 1.85-1.94 (m, 2H), 2.00-2.03 (m, 2H), 2.37 (s, 3H), 2.84-2.95 (m, 2H), 3.05-3.13 (m, 2H), 3.34-3.42 (m, 4H), 3.49 (d, 2H, J=11.7 Hz), 4.75 (t-like, 1H), 5.89 (d, 1H, J=3.4 Hz), 6.36 (dd, 1H, J=1.5 Hz, 3.4 Hz), 7.24 (d, 1H, J=8.3 Hz), 7.56 (d, 1H, J=1.0 Hz), 7.74 (dd, 1H, J=1.4 Hz, 8.3 Hz), 8.40 (s, 1H), 9.83-9.94 (m, 1H); IR (KBr) cm$^{-1}$: 3417, 2927, 2645, 1651, 1633, 1557, 1470, 1385, 1320, 1190, 1032, 768. Anal. Calcd for C$_{29}$H$_{45}$Cl$_2$N$_3$O$_4$: C, 60.95; H, 7.95; N, 7.35. Found: C, 61.75; H, 8.56; N, 7.43.

EXAMPLE 51

2-[1-[2-[4-(p-Toluidino)piperidin-1-yl]ethyl]cyclohexyl]ethanol

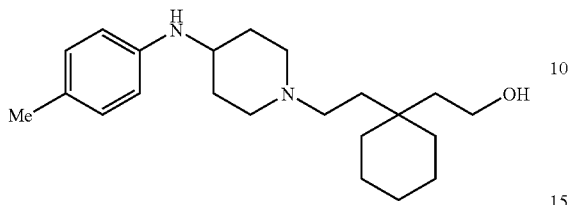

The title compound was synthesized from the compound obtained in Preparation Example 1F-1 and the compound obtained in Preparation Example 4-5 in the same manner as in Example 1F-1.

$^1$H-NMR (CDCl$_3$) δ: 1.26-1.32 (m, 4H), 1.32-1.52 (m, 10H), 1.53 (t, 2H, J=6.4 Hz), 1.58 (t, 2H, J=6.3 Hz), 2.03 (d, 2H, J=7.3 Hz), 2.13 (t, 2H, J=10.7 Hz), 2.23 (s, 3H), 2.32 (t, 2H, J=6.3 Hz), 2.91 (d, 2H, J=10.3 Hz), 3.28 (t, 1H, J=10.3 Hz), 3.68 (t, 2H, J=6.3 Hz), 6.51 (d, 2H, J=8.3 Hz), 6.96 (d, 2H, J=8.3 Hz); MS (ESI) m/z: 346 (MH$^+$).

EXAMPLE 52

2-[1-[2-[4-[N-(p-Tolyl)-2-furancarboxamido]piperidin-1-yl]ethyl]cyclohexyl]ethyl 2-furancarboxylate

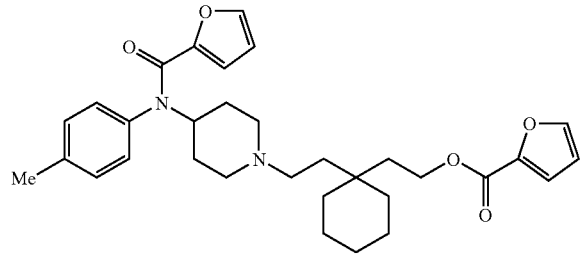

The title compound was synthesized from 2-[1-[2-[4-(p-toluidino)piperidin-1-yl]ethyl]cyclohexyl]ethanol (synthesized in Example 51) in the same manner as in Example 2-31.

Hydrochloride $^1$H-NMR (DMSO-d$_6$) δ: 1.23-1.42 (m, 11H), 1.60-1.66 (m, 6H), 2.02 (d, 2H, J=13.2 Hz), 2.37 (s, 3H), 2.96-2.99 (m, 2H), 3.08-3.16 (m, 2H), 3.50-3.53 (m, 2H), 4.27 (t, 2H, J=7.3 Hz), 4.76 (t, 1H, J=12.2 Hz), 5.49 (s, 1H), 6.32 (dd, 1H, J=1.4 Hz, 3.4 Hz), 6.67 (dd, 1H, J=2.0 Hz, 3.4 Hz), 7.15 (d, 2H, J=7.8 Hz), 7.26 (d, 1H, J=3.4 Hz), 7.29 (d, 2H, J=7.8 Hz), 7.63 (s, 1H), 7.94 (s, 1H), 9.40-9.60 (brs, 1H).

EXAMPLE 53

N-[1-[2-[1-(2-Hydroxyethyl)cyclohexyl]ethyl]piperidin-4-yl]-N-(p-tolyl)-2-furancarboxamide

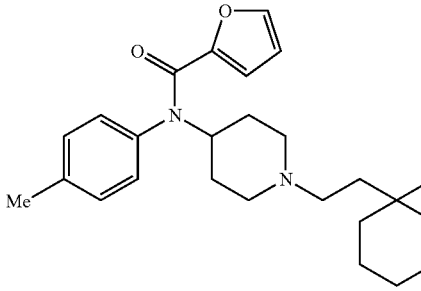

The title compound was synthesized from 2-furancarboxylic acid 2-[1-[2-[4-[N-(p-tolyl)-2-furancarboxamido]piperidin-1-yl]ethyl]cyclohexyl]ethyl ester (synthesized in Example 52) in the same manner as in Example 3C-4.

$^1$H-NMR (CDCl$_3$) δ: 1.24-1.29 (m, 4H), 1.30-1.48 (m, 9H), 1.51-1.55 (m, 4H), 1.85 (d, 2H, J=12.7 Hz), 2.11 (t, 2H, J=11.7 Hz), 2.26 (t, 2H, J=6.8 Hz), 2.39 (s, 3H), 2.98 (d, 2H, J=11.7 Hz), 3.60 (t, 2H, J=6.8 Hz), 4.75 (tt, 1H, J=3.9 Hz, 12.2 Hz), 5.35 (d, 1H, J=2.9 Hz), 6.13 (dd, 1H, J=2.0 Hz, 3.4 Hz), 7.00 (d, 2H, J=8.3 Hz), 7.18 (d, 2H, J=7.8 Hz), 7.34 (d, 1H, J=1.0 Hz); MS (ESI) m/z: 439 (MH$^+$).

EXAMPLE 54

N-[1-[2-[1-Carbamoylmethyl)cyclohexyl]ethyl]piperidin-4-yl]-N-(p-tolyl)-2-furancarboxamide

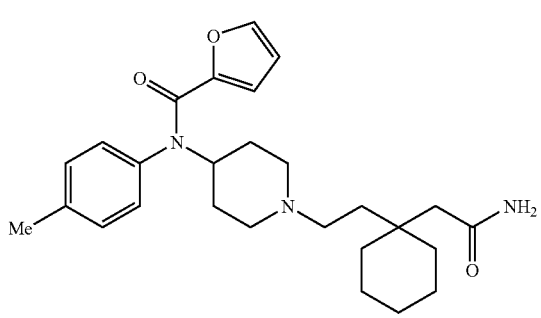

The title compound was synthesized from the compound synthesized in Example 3B-1 in the same manner as in Example 4D-1.

$^1$H-NMR (CDCl$_3$) δ: 1.23-1.28 (t-like, 2H), 1.31-1.53 (m, 10H), 1.56 (t, 2H, J=5.9 Hz), 1.88 (d, 2H, J=13.1 Hz), 2.12 (s, 2H), 2.17 (t, 2H, J=11.2 Hz), 2.33 (t, 2H, J=5.8 Hz), 2.42 (s, 3H), 3.00 (d, 2H, J=11.7 Hz), 4.77 (tt, 1H, J=3.9 Hz, 8.3 Hz), 5.01-5.07 (m, 1H), 5.35 (s, 3H), 6.14 (dd, 1H, J=1.5 Hz, 3.5 Hz), 6.99 (d, 2H, J=7.8 Hz), 7.20 (d, 2H, J=7.9 Hz), 7.35 (d, 1H, J=1.5 Hz), 7.67-7.75 (m, 1H); MS (ESI) m/z: 452 (MH$^+$).

EXAMPLE 55

N-[1-[2-[1-(Cyanomethyl)cyclohexyl]ethyl]piperidin-4-yl]-N-(p-tolyl)-2-furancarboxamide

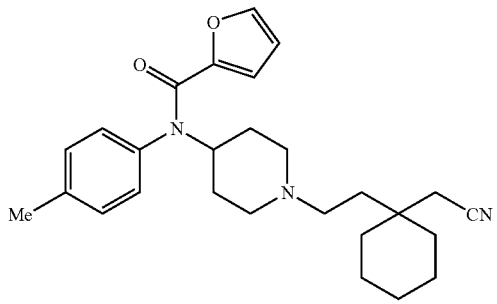

The title compound was synthesized from N-[1-[2-[1-(1-carbamoylmethyl)cyclohexyl]ethyl]piperidin-4-yl]-N-(p-tolyl)-2-furancarboxamide (synthesized in Example 54) in the same manner as in Example 4D-2.

$^1$H-NMR (CDCl$_3$) δ: 1.26-1.57 (m, 14H), 1.87 (d, 2H, J=12.2 Hz), 2.12 (t, 2H, J=10.7 Hz), 2.29 (t, 2H, J=7.8 Hz), 2.34 (s, 2H), 2.40 (s, 3H), 2.97 (d, 2H, J=11.7 Hz), 4.77 (tt, 1H, J=3.9 Hz, 12.2 Hz), 5.35 (s, 1H), 6.13 (dd, 1H, J=1.5 Hz, 3.5 Hz), 7.01 (d, 2H, J=8.3 Hz), 7.19 (d, 2H, J=7.8 Hz), 7.35 (d, 1H, J=1.4 Hz); MS (ESI) m/z: 434 (MH$^+$).

EXAMPLE 56

Methyl 4-[1-[2-[4-(p-toluidino)piperidin-1-yl]ethyl]cyclohexyl]-butyrate

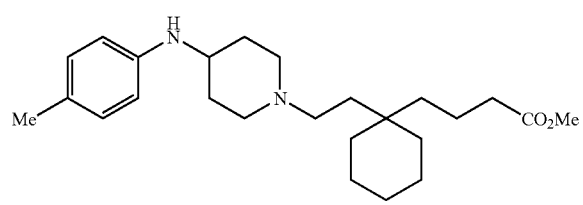

The title compound was synthesized from the compound obtained in Preparation Example 1F-3 and the compound obtained in Preparation Example 4-5 in the same manner as in Example 1F-1. This product was subjected to the subsequent step without further purification.

EXAMPLE 57

Methyl N-[1-[2-[4-(p-tolyl)-2-furancarboxamido]piperidin-1-yl]ethyl]cyclohexyl]butyrate

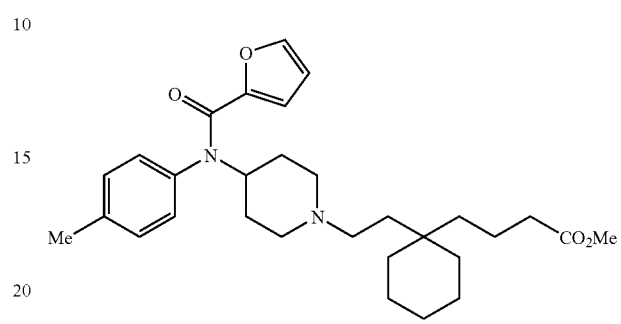

The title compound was synthesized from methyl 4-[1-[2-[4-(p-toluidino)piperidin-1-yl]ethyl]cyclohexyl]-butyrate (synthesized in Example 56) in the same manner as in Example 2-16.

$^1$H-NMR (CDCl$_3$) δ: 1.18-1.28 (m, 6H), 1.30-1.48 (m, 10H), 1.50-1.56 (m, 2H), 1.85 (d, 2H, J=12.7 Hz), 2.10 (t, 2H, J=11.7 Hz), 2.22-2.29 (m, 4H), 2.39 (s, 3H), 2.97 (d, 2H, J=11.7 Hz), 3.67 (s, 3H), 4.77 (t, 1H, J=11.8 Hz), 5.35 (m, 1H), 6.13 (dd, 1H, J=1.4 Hz, 3.4 Hz), 7.01 (d, 2H, J=8.3 Hz), 7.18 (d, 2H, J=7.9 Hz), 7.35 (s, 1H).

EXAMPLE 58

4-[1-[2-[4-[N-(p-tolyl)-2-furancarboxamido]piperidin-1-yl]-ethyl]cyclohexyl]butyric acid

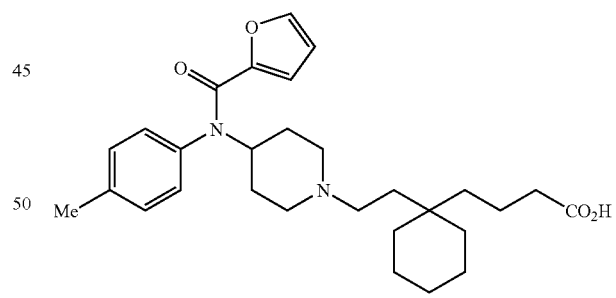

The title compound was synthesized from methyl 4-[1-[2-[4-[N-(p-tolyl)-2-furancarboxamido]piperidin-1-yl]-ethyl]cyclohexyl]butyrate (synthesized in Example 57) in the same manner as in Example 3C-1.

$^1$H-NMR (CDCl$_3$) δ: 1.15-1.26 (m, 6H), 1.26-1.44 (m, 8H), 1.45-1.49 (m, 2H), 1.66-1.75 (m, 2H), 1.88 (d, 2H, J=11.2 Hz), 1.98 (t, 2H, J=7.8 Hz), 2.34-2.46 (m, 5H), 2.50-2.54 (m, 2H), 3.34 (d, 2H, J=11.7 Hz), 4.83 (t, 1H, J=12.7 Hz), 5.36 (d, 1H, J=2.9 Hz), 6.14 (dd, 1H, J=1.5 Hz, 3.4 Hz), 6.99 (d, 2H, J=8.3 Hz), 7.19 (d, 2H, J=7.8 Hz), 7.36 (d, 1H, J=1.4 Hz).

EXAMPLE 59

Triethyl 3-[1-[2-[4-(p-toluidino)piperidin-1-yl]ethyl]cyclohexyl]-1,1,1-propanetricarboxylate

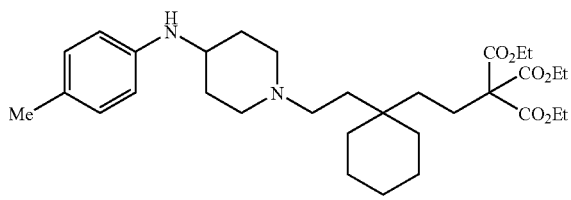

The title compound was synthesized from the compound obtained in Preparation Example 3A-6 and the compound obtained in Preparation Example 4-5 in the same manner as in Example 1D-5. This product was subjected to the subsequent step without further purification.

EXAMPLE 60

Triethyl 3-[1-[2-[4-[N-(p-tolyl)-2-furancarboxamido]piperidin-1-yl]-ethyl]cyclohexyl]-1,1,1-propanetricarboxylate

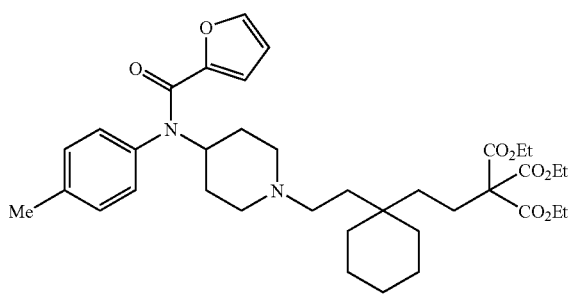

The title compound was synthesized from triethyl 3-[1-[2-[4-(p-tolyl)piperidin-1-yl]ethyl]cyclohexyl]-1,1,1-propanetricarboxylate (synthesized in Example 59) in the same manner as in Example 2-17.

$^1$H-NMR (CDCl$_3$) δ: 1.20-1.32 (m, 13H), 1.32-1.43 (m, 10H), 1.47-1.66 (m, 2H), 1.85 (d, 2H, J=10.8 Hz), 1.99-2.02 (m, 2H), 2.10 (t, 2H, J=10.7 Hz), 2.22-2.26 (m, 2H), 2.39 (s, 3H), 2.98 (d, 2H, J=11.8 Hz), 4.24 (q, 6H, J=7.3 Hz), 4.77 (t, 1H, J=3.4 Hz), 5.36 (s, 1H), 6.13 (dd, 1H, J=1.4 Hz, 3.4 Hz), 7.01 (d, 2H, J=8.3 Hz), 7.18 (d, 2H, J=7.9 Hz), 7.35 (s, 1H).

EXAMPLE 61

Ethyl cyclobutylideneacetate

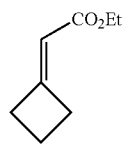

To an ice-cooled suspension of 60% sodium hydride (0.68 g) in N,N-dimethylformamide (20 mL) was added triethyl phosphonoacetate (3.4 mL) dropwise over 5 minutes. After stirring the suspension under ice cooling for 30 minutes, cyclobutanone (1.1 mL) was added dropwise over 5 minutes. The solution was stirred under ice cooling for additional 1 hour. The reaction solution was poured into saturated aqueous ammonium chloride solution, and it was extracted with ethyl acetate. The organic layer was washed with saturated aqueous sodium chloride solution, dried over anhydrous magnesium sulfate and filtered. The filtrate was concentrated under reduced pressure. The resulting residue was purified by chromatography [silica gel, hexane-ethyl acetate (20:1)] to give the title compound (1.27 g).

$^1$H-NMR (CDCl$_3$) δ: 1.27 (t, 3H, J=6.8 Hz), 2.04-2.13 (m, 2H), 2.82-2.85 (m, 2H), 3.10-3.15(m, 2H), 4.14 (q, 2H, J=6.8 Hz), 5.56-5.59 (m, 1H).

EXAMPLE 62

2-(Cyclobutylidene) ethyl acetate

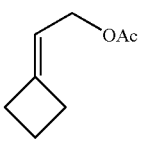

To an ice-cooled solution of ethyl cyclobutylideneacetate (1.27 g) in tetrahydrofuran (10 mL) was added a 1M diisobutylaluminum hydride/hexane solution (27 mL) dropwise over 10 minutes. After stirring the solution under ice cooling for 1 hour, 1N hydrochloric acid (30 mL) was added to the reaction solution. The temperature was allowed to rise to room temperature and the solution was stirred for additional 30 minutes. The reaction solution was extracted with dichloromethane. The organic layer was dried over anhydrous sodium sulfate and dried under reduced pressure. To the resulting residue were added pyridine (2 mL), acetic anhydride (2 mL) and N,N-dimethylaminopyridine (110 mg) successively. The solution was stirred at room temperature for 14 hours. The reaction solution was diluted with ethyl acetate and washed in turn with 3N-hydrochloric acid, saturated aqueous sodium bicarbonate solution and saturated aqueous sodium chloride solution. The organic layer was dried over anhydrous sodium sulfate and concentrated under reduced pressure. The resulting residue was purified by chromatography [silica gel, hexaneethyl acetate (50:1)] to give the title compound (0.98 g).

$^1$H-NMR (CDCl$_3$) δ:1.94-2.02 (m, 2H), 2.05 (s, 3H), 2.68-2.76 (m, 4H), 4.44 (d, 2H, J=7.3 Hz), 5.25-5.30 (m, 1H).

EXAMPLE 63

Methyl (1-vinylcyclobutyl)acetate

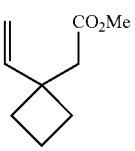

To an ice-cooled solution of diisopropylamine (1.07 mL) in THF (10 mL) was added 1.57 M n-butyllithium/hexane (4.47 mL) dropwise over 5 minutes. After stirring under ice cooling for additional 30 minutes, the reaction solution was cooled to −78° C. and a solution of 2-cyclobutyridene ethyl acetate (0.89 g) in tetrahydrofuran (0.8 mL) was added thereto dropwise over 5 minutes. After stirring the reaction solution at that temperature for 1 hour, chlorotrimethylsilane (0.97 mL) was added dropwise over 5 minutes. The reaction solution was stirred at room temperature for 1 hour, and then, heated under reflux for 4.5 hours. The reaction solution was ice-cooled, to which methanol (2 mL) and a 3N aqueous sodium hydroxide solution (5 ml) were added. The solution was stirred for 30 minutes. Then, conc. hydrochloric acid (2 mL) was added to the solution and it was stirred for additional 30 minutes. The organic layer was dried over anhydrous sodium sulfate and concentrated under reduced pressure. The resulting residue (1.77 g) was dissolved in N,N-dimethylformamide (10 mL), to which potassium carbonate (2.82 g) and methyl iodide (0.62 mL) were added. The solution was stirred at room temperature for 1 hour. The reaction solution was filtered with Celite and insolubles on Celite were washed with ethyl acetate. The filtrate was combined with the wash, and it washed in turn with 1N hydrochloric acid and saturated aqueous sodium chloride solution. The organic layer was dried over anhydrous sodium sulfate and concentrated under reduced pressure. The resulting residue was purified by chromatography [silica gel, hexane-ethyl acetate (20:1)] to give the title compound (0.67 g).

$^1$H-NMR (CDCl$_3$) δ: 2.01-2.13 (m, 6H), 2.55 (s, 2H), 3.63 (s, 3H), 5.03 (d, 1H, J=11.2 Hz), 5.04 (d, 1H, J=17.1 Hz), 5.99 (dd, 1H, J=10.7 Hz, 17.6 Hz).

EXAMPLE 64

7-Oxaspiro[3.5]nonan-6-one

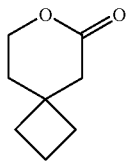

To an ice-cooled solution of methyl (1-vinylcyclobutyl) acetate (0.67 g) in tetrahydrofuran (3 mL) was added 0.5M9-borabicyclo[3.3.1]nonane/tetrahydrofuran (17.5 mL) dropwise over 10 minutes. The reaction solution was then allowed for its temperature to rise to room temperature and it was stirred for additional 9 hours. The reaction solution was again ice-cooled and ethanol (4 mL), a 6N aqueous sodium hydroxide solution (8 mL) and 30% hydrogen peroxide (8 mL) were successively added thereto. The reaction solution was then allowed for its temperature to rise to room temperature and it was stirred for additional 30 minutes. The reaction solution was again ice-cooled. After conc. hydrochloric acid (5 mL) was added to the solution, it was stirred for additional 30 minutes. The reaction solution was extracted with tert-butyl methyl ether. The organic layer was washed with saturated aqueous sodium chloride solution, dried over anhydrous sodium sulfate and concentrated under reduced pressure. The resulting residue was purified by chromatography [silica gel, hexane-ethyl acetate (9:1)] to give the title compound (0.31 g).

$^1$H-NMR (CDCl$_3$) δ: 1.88-1.98 (m, 8H), 2.61 (s, 2H), 4.33 (t, 2H, J=5.9 Hz).

EXAMPLE 65

7-Oxaspiro[3.5]nonan-6-ol

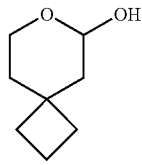

To a solution of 7-oxaspiro[3.5]nonan-6-one (0.67 g) in tetrahedrofuran (3 mL) cooled at −78° C. was added 1M diisobutylaluminum hydride/tetrahydrofuran (1.0 mL) dropwise over 5 minutes. The reaction solution was stirred at that temperature for 1.5 hours. Water (40 µL) was added to the reaction solution. After allowing the temperature to rise to room temperature, a 15% aqueous sodium hydroxide solution (40 µL) and water (120 µL) were successively added to the solution. After stirring the solution at room temperature for 10 minutes, diethyl ether (2 mL) and anhydrous magnesium sulfate (0.17 g) were added. The solution was stirred for additional 30 minutes. The reaction solution was then filtered with Celite. The filtrate was concentrated under reduced pressure to give the title compound (230 mg).

1HNMR (CDCl$_3$) δ: 1.32 (dd, 1H, J=7.8 Hz, 13.2 Hz), 1.42-1.46 (m, 2H), 1.63-1.79 (m, 7H), 3.34-3.40 (m, 1H), 3.75-3.81 (m, 1H), 4.62 (dd, 1H, J=2.4 Hz, 7.8 Hz).

EXAMPLE 66

2-[1-[2-[4-(p-Toluidino)piperidin-1-yl]ethyl]cyclobutyl]ethanol

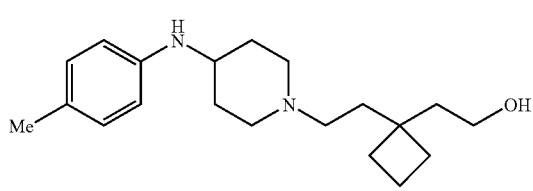

To a suspension of 4-(p-toluidino)piperidine trifluoroacetate (418 mg) (synthesized in Preparation Example 4-5) in tetrahydrofuran (3 mL) was added triethylamine (0.28 mL). The solution was stirred at room temperature for 5 minutes. Then, 7-oxaspiro[3.5]nonan-6-ol (104 mg) (synthesized in Example 65) in tetrahydrofuran (3 mL) was added to the solution and it was stirred at room temperature for additional 10 minutes. The reaction solution was ice-cooled and sodium triacetoxyborohydride (424 mg) was added thereto. The solution was then 4lowed for its temperature to rise to room temperature. The solution was stirred for additional 4.5 hours. A 3N aqueous sodium hydroxide solution (5 mL) was added to the reaction solution and it was extracted with tert-butyl methyl ether. The resulting residue was purified by chromatography [NH silica gel, hexane-ethyl acetate (7:3)] to give the title compound (175 mg).

$^1$H-NMR (CDCl$_3$) δ: 1.41-1.50 (m, 2H), 1.67-1.78 (m, 6H), 1.83-1.89 (m, 2H), 2.02-2.17 (m, 4H), 2.22 (s, 3H), 2.29 (t, 2H, J=5.9 Hz), 2.87-2.94 (m, 2H), 3.25-3.30 (m, 1H), 3.64 (t, 2H, J=5.9 Hz), 6.51 (d, 2H, J=8.3 Hz), 6.96 (d, 2H, J=8.3 Hz).

EXAMPLE 67

N-[1-[2-[1-(2-Hydroxyethyl)cyclobutyl]ethyl]piperidin-4-yl]-N-(p-tolyl)-2-furancarboxamide

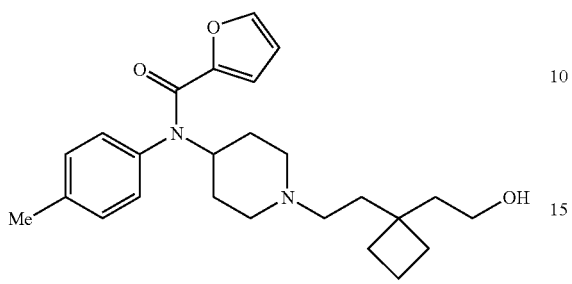

To a solution of 2-[1-[2-[4-(p-toluidino)piperidin-1-yl]ethyl]cyclobutyl]ethanol (synthesized in Example 66) (175 mg) in tetrahydrofuran (3 mL) was added triethylamine (0.46 mL) and 2-furoyl chloride (0.16 mL) sucessively. The solution was stirred at room temperature for 40 minutes. To the reaction solution were added methanol (4 mL) and a 3N aqueous potassium hydroxide solution (2 mL). The solution was stirred for additional 30 minutes. Saturated sodium chloride solution was added to the reaction solution and it was extracted with ethyl acetate. The organic layer was washed with saturated aqueous sodium chloride solution, dried over anhydrous sodium sulfate and concentrated under reduced pressure. The resulting residue was purified by chromatography [NH silica gel, hexane-ethyl acetate (1:1)] to give the title compound (159 mg).

$^1$H-NMR (CDCl$_3$) δ: 1.46-1.86 (m, 14H), 2.09-2.16 (m, 2H), 2.22-2.26 (m, 2H), 2.39 (s, 3H), 2.96-3.02 (m, 2H), 3.55 (t, 2H, J=6.8 Hz), 4.10 (brs, 1H), 4.71-4.78 (m, 1H), 5.37 (brs, 1H), 6.13 (dd, 1H, J=2.0 Hz, 3.5 Hz), 7.01 (d, 2H, J=8.3 Hz), 7.19 (d, 2H, J=8.3 Hz), 7.34 (brs, 1H).

EXAMPLE 68

Ethyl cyclooctylideneacetate

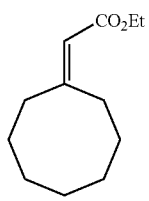

To an ice-cooled suspension of 60% sodium hydride (0.88 g) in tetrahydrofuran (40 mL) was added triethyl phosphonoacetate (4.8 mL) dropwise over 5 minutes. After stirring the suspension under ice cooling for 1 hour, cyclooctanone (2.52 g) was added. The suspension was stirred under ice cooling for additional 1 hour and then at room temperature for 87 hours. The reaction solution was poured into saturated aqueous ammonium chloride solution and it was extracted with ethyl acetate. The organic layer was washed with saturated aqueous sodium chloride solution, dried over anhydrous magnesium sulfate and concentrated under reduced pressure. The resulting residue was purified by chromatography [silica gel, hexane-isopropyl ether (97:3)] to give the title compound (2.67 g).

$^1$H-NMR (CDCl$_3$) δ: 1.27 (t, 3H, J=7.0 Hz), 1.40-1.56 (m, 6H), 1.71-1.84 (m, 4H), 2.29-2.33 (m, 2H), 2.73-2.77 (m, 2H), 4.13 (q, 2H, J=7.0 Hz), 5.72 (s, 1H).

EXAMPLE 69

2-(Cyclooctylidene)ethyl acetate

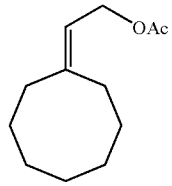

To an ice-cooled solution of ethyl cyclooctylideneacetate (4.82 g) in tetrahydrofuran (25 mL) was added 1M diisobutylaluminum hydride/hexane (73.8 mL) dropwise over 15 minutes. After stirring the reaction solution under ice cooling for 30 minutes, 2N hydrochloric acid (50 mL) was added. After allowing the solution for its temperature rise to room temperature, it was stirred for additional 30 minutes. The reaction solution was extracted with ethyl acetate. The organic layer was dried over anhydrous sodium sulfate and dried over under reduced pressure. To the resulting residue were added pyridine (22 mL), acetic anhydride (10.1 mL) and N,N-dimethylaminopyridine (0.26 g) sucessively. The solution was stirred at room temperature for 18 hours. The reaction solution was diluted with ethyl acetate, washed in turn with 2N hydrochloric acid, saturated aqueous sodium bicarbonate solution and saturated aqueous sodium chloride solution. The organic layer was dried over anhydrous sodium sulfate and concentrated under reduced pressure. The resulting residue was purified by chromatography [silica gel, hexane-ethyl acetate (97:3)] to give the title compound (3.41 g).

$^1$H-NMR (CDCl$_3$) δ: 1.45-1.56 (m, 6H), 1.58-1.70 (m, 4H), 2.06 (s, 3H), 2.18-2.23 (m, 2H), 2.23-2.28 (m, 2H), 4.60 (d, 2H, J=7.0 Hz), 5.37 (t, 1H, J=7.0 Hz).

EXAMPLE 70

Methyl (1-vinylcyclooctyl)acetate

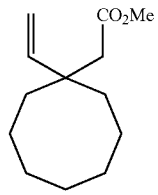

To an ice-cooled solution of diisopropylamine (1.68 mL) in tetrahydrofuran (10 mL) was added 1.57 M n-butyllithium/hexane (7.0 mL) dropwise over 10 minutes. After stirring the reaction solution under ice cooling for additional 30 minutes, it was cooled to −78° C. and a solution of 2-(cyclobutylidene)ethyl acetate (1.96 g) in tetrahydrofuran (2 mL) was added thereto dropwise over 10 minutes. After stirring the reaction solution at that temperature for 1 hour, chlorotrimethylsilane (1.52 mL) was added dropwise over 5 minutes. The reaction solution was stirred at room temperature for 1 hour, and then, heated under reflux for 4.5 hours. The reaction solution was ice-cooled and methanol (5 mL) and a 3N aqueous sodium hydroxide solution (8 ml) were added. The solution was stirred for 30 minutes. Then, conc. hydrochloric acid (4 mL) was added to the solution and it was stirred for additional 30 minutes. The reaction solution was extracted with chloroform. The organic layer was dried over anhydrous sodium sulfate and concentrated under reduced pressure. The resulting residue was dissolved in N,N-dimethylformamide (20 mL), to which potassium carbonate (8.29 g) and methyl iodide (1.87 mL) were added. The solution was stirred at room temperature for 3 hours. The reaction solution was filtered with Celite and insolubles on Celite were washed with ethyl acetate. The filtrate was combined with the wash and washed in turn with 2N hydrochloric acid and saturated aqueous sodium chloride solution. The organic layer was dried over anhydrous sodium sulfate and concentrated under reduced pressure. The resulting residue was purified by chromatography [silica gel, hexane-ethyl acetate (97:3)] to give the title compound (1.33 g).

$^1$H-NMR (CDCl$_3$) δ: 1.45-1.73 (m, 14H), 2.31 (s, 2H), 3.61 (s, 3H), 4.96 (d, 1H, J=17.5 Hz), 5.04 (d, 1H, J=10.5 Hz), 5.77 (dd, 1H, J=10.5 Hz, 17.5 Hz).

EXAMPLE 71

3-Oxaspiro[5.7]tridecan-2-one

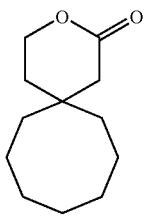

To an ice-cooled solution of methyl (1-vinylcyclooctyl) acetate (1.33 g) in tetrahydrofuran (6 mL) was added 0.5M 9-borabicyclo[3.3.1]nonane/tetrahydrofuran (25.3 mL) dropwise over 15 minutes. The reaction solution was then allowed for its temperature to rise to room temperature and it was stirred for additional 2 hours. The reaction solution was again ice-cooled, and ethanol (8 mL), a 6N aqueous sodium hydroxide solution (11 mL) and 30% hydrogen peroxide (11 mL) were successively to the solution. The reaction solution was allowed for its temperature to rise to room temperature and it was stirred for additional 75 minutes. The reaction solution was again ice-cooled. After addition of conc. hydrochloric acid (8 mL), the solution was stirred for additional 30 minutes. The reaction solution was extracted with ethyl acetate. The organic layer was washed with saturated aqueous sodium chloride solution, dried over anhydrous sodium sulfate and concentrated under reduced pressure. The resulting residue was purified by chromatography [silica gel, hexane-ethyl acetate (9:1)] to give the title compound (0.74 g).

$^1$H-NMR (CDCl$_3$) δ: 1.49-1.63 (m, 14H), 1.71 (t, 2H, J=6.0 Hz), 2.32 (s, 2H), 4.32 (t, 2H, J=6.0 Hz).

EXAMPLE 72

3-Oxaspiro[5.7]tridecan-2-ol

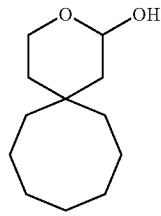

To a solution of 3-oxaspiro[5.7]tridecan-2-one (0.74 g) in tetrahydrofuran (9 mL) cooled at −78° C. was added 1M diisobutylaluminum hydride/tetrahydrofuran (4.9 mL) dropwise over 5 minutes. The reaction solution was then stirred at that temperature for 30 minutes. Water (0.18 mL) was added to the reaction solution. After allowing the temperature to rise to room temperature, a 15% aqueous sodium hydroxide solution (0.18 mL) and water (0.54 mL) were successively added to the solution. After stirring the reaction solution at room temperature for 10 minutes, diethyl ether (9 mL) and anhydrous magnesium sulfate (0.17 g) were added, and the solution was stirred for additional 15 minutes. The reaction solution was filtered with Celite. The filtrate was concentrated under reduced pressure. The resulting residue was purified by chromatography [silica gel, hexane-ethyl acetate (3:1 to 2:1 to 1:1)] to give the title compound (0.62 g).

$^1$H-NMR (CDCl$_3$) δ: 1.17 (dd, 1H, J=8.0 Hz, 13.0 Hz), 1.35-1.61 (m, 16H), 1.76 (d, 1H, J=13.0 Hz), 2.80 (brt, 1H, J=5.5 Hz), 3.66 (ddd, 1H, J=4.0 Hz, 9.5 Hz, 13.5 Hz), 3.89 (ddd, 1H, J=4.0 Hz, 4.0 Hz, 11.5 Hz), 4.93 (ddd, 1H, J=3.0 Hz, 5.5 Hz, 8.0 Hz).

EXAMPLE 73

2-[1-[2-[4-(p-Toluidino)piperidin-1-yl]ethyl]cyclooctyl]ethanol

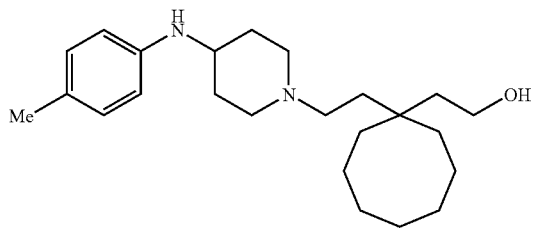

To a suspension of 4-(p-toluidino)piperidine ditrifluoroacetate (synthesized in Preparation Example 4-5) (1.31 g) in 1,2-dichloroethane (6 mL) was added triethylamine (0.96 mL). The suspension was stirred at room temperature for 5 minutes. Then, a solution of 3-oxaspiro[5.7]tridecan-2-ol (synthesized in Example 72) (0.62 g) in 1,2-dichloroethane (3 mL) was added to the suspension, and it was stirred at room temperature for additional 10 minutes. The reaction solution was ice-cooled and sodium triacetoxyborohydride (0.70 g) was added thereto. The reaction solution was then allowed for its temperature to rise to room temperature, and the solution was stirred for additional 4.5 hours. Saturated aqueous sodium bicarbonate solution was added to the reaction solution and it was extracted with ethyl acetate. The organic layer was dried over anhydrous sodium sulfate and concentrated under reduced pressure. The resulting residue was purified by chromatography [silica gel, methanol-chloroform (3:97 to 1:9)] to give the title compound (0.53 g).

$^1$H-NMR (CDCl$_3$) δ: 1.33-1.56 (m, 20H), 2.00-2.09 (m, 2H), 2.09-2.20 (m, 2H), 2.22 (s, 3H), 2.34 (t, 2H, J=6.0 Hz), 2.86-3.00 (m, 2H), 3.23-3.34 (m, 1H), 3.67 (t, 2H, J=6.0 Hz), 6.51 (d, 2H, J=8.0 Hz), 6.97 (d, 2H, J=8.0 Hz).

EXAMPLE 74

N-[1-[2-[1-(2-Hydroxyethyl)cyclooctyl]ethyl]piperidin-4-yl]-N-(p-tolyl)-2-furancarboxamide

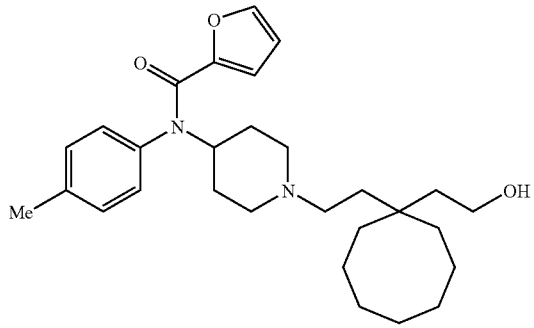

To a solution of 2-[1-[2-[4-(p-toluidino)piperidin-1-yl] ethyl]cyclooctyl]ethanol (synthesized in Example 73) (0.53 g) in tetrahydrofuran (7 mL) were added triethylamine (0.79 mL) and 2-furoyl chloride (0.35 mL) successively. The solution was stirred at room temperature for 1 hour. To the reaction solution was added methanol (7 mL) and a 3N aqueous potassium hydroxide solution (4.7 mL), and it was stirred at room temperature for 15 hours. Water was added to the reaction solution and it was extracted with ethyl acetate. The organic layer was washed with saturated aqueous sodium chloride solution, dried over anhydrous sodium sulfate and concentrated under reduced pressure. The resulting residue was purified by chromatography [silica gel, methanol-chloroform (5:95)] to give the title compound (0.55 g).

$^1$H-NMR (CDCl$_3$) δ: 1.30-1.55 (m, 20H), 1.81-1.89 (m, 2H), 2.07-2.16 (m, 2H), 2.23-2.29 (m, 2H), 2.40 (s, 3H), 2.94-3.02 (m, 2H), 3.59 (t, 2H, J=6.5 Hz), 4.76 (tt, 1H, J=4.0 Hz, 12.0 Hz), 5.32 (brs, 1H), 6.13 (dd, 1H, J=1.5 Hz, 3.0 Hz), 7.00 (d, 2H, J=8.0 Hz), 7.18 (d, 2H, J=8.0 Hz), 7.35 (brs, 1H).

EXAMPLE 75

Ethyl(tetrahydropyran-4-ylidene)acetate

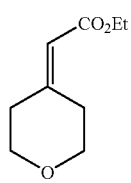

To an ice-cooled suspension of 60% sodium hydride (0.72 g) in N,N-dimethylformamide (30 mL) was added triethyl phosphonoacetate (3.6 mL) dropwise over 5 minutes. After stirring the suspension under ice cooling for 45 minutes, tetrahydro-4H-pyran-4-one (1.4 mL) was added to the suspension dropwise over 3 minutes. The suspension was stirred under ice cooling for additional 35 minutes. The reaction solution was poured into saturated aqueous ammonium chloride solution and it was extracted with ethyl acetate. The organic layer was washed with saturated aqueous sodium chloride solution, dried over anhydrous magnesium sulfate and concentrated under reduced pressure to give the title compound (3.31 g). This product was subjected to the subsequent step without further purification.

$^1$H-NMR (CDCl$_3$) δ: 1.28 (t, 3H, J=7.3 Hz), 2.32 (t, 3H, J=5.6 Hz), 3.01 (t, 2H, J=5.6 Hz), 3.73 (t, 2H, J=5.6 Hz), 3.77 (t, 2H, J=5.6 Hz), 4.15 (q, 2H, J=7.3 Hz), 5.68 (s, 1H).

EXAMPLE 76

2-(Tetrahydropyran-4-ylidene)ethyl acetate

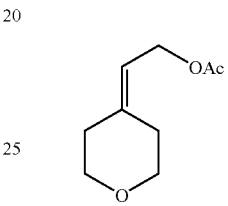

To an ice-cooled solution of ethyl (tetrahydropyran-4-ylidene) acetate (3.31 g) in tetrahydrofuran (20 mL) under ice cooling was added 1M diisobutylaluminum hydride/hexane (20 mL) dropwise over 25 minutes. After stirring the reaction solution under ice cooling for 1 hour, 1N hydrochloric acid (100 mL) was added thereto. The temperature was allowed to rise to room temperature, and the solution was stirred for additional 30 minutes. The reaction solution was extracted with ethyl acetate. The organic layer was dried over anhydrous sodium sulfate and dried under reduced pressure. To the resulting residue were added pyridine (3 mL), acetic anhydride (3 mL) and N,N-dimethylaminopyridine (0.18 g) successively. The solution was stirred at room temperature for 19 hours. The reaction solution was diluted with ethyl acetate, washed in turn with 1N hydrochloric acid, saturated aqueous sodium bicarbonate solution and saturated aqueous sodium chloride solution. The organic layer was dried over anhydrous sodium sulfate and concentrated under reduced pressure. The resulting residue was purified by chromatography [silica gel, hexane-ethyl acetate (20:1 to 7:3)] to give the title compound (2.50 g).

$^1$H-NMR (CDCl$_3$) δ: 2.06 (s, 3H), 2.22-2.27 (m, 2H), 2.34-2.37 (m, 2H), 3.66-3.72 (m, 4H), 4.59 (d, 2H, J=7.3 Hz), 5.38-5.42 (m, 1H).

EXAMPLE 77

Methyl (4-vinyltetrahydropyran-4-yl)acetate

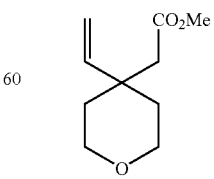

To an ice-cooled solution of diiospropylamine (1.00 mL) in tetrahydrofuran (10 mL) was added 1.57 M n-butyllithium/hexane (4.17 mL) dropwise over 5 minutes. After stirring the reaction solution under ice cooling for additional 30 minutes, it was cooled to −78° C., to which a solution of acetic acid 2-(tetrahydropyran-4-ylidene)ethyl (1.00 g) ester in tetrahydrofuran (1 mL) was added dropwise over 5 minutes. After stirring the reaction solution at that temperature for 80 minutes, chlorotrimethylsilane (0.90 mL) was added thereto dropwise over 5 minutes. The reaction solution was stirred at room temperature for 1 hour, and then, heated under reflux for 4.5 hours. The reaction solution was ice-cooled and methanol (3 mL) and a 3N aqueous sodium hydroxide solution (5 ml) were added thereto. The solution was stirred for 15 minutes. Then, conc. hydrochloric acid (2 mL) was added to the solution and the solution was stirred for additional 5 minutes. The reaction solution was extracted with chloroform. The organic layer was dried over anhydrous sodium sulfate and concentrated under reduced pressure. The resulting residue (1.27 g) was dissolved in N,N-dimethylformamide (10 mL), to which potassium carbonate (1.38 g) and methyl iodide (0.37 mL) were added. The reaction solution was stirred at room temperature for 1.5 hours. The reaction solution was poured into saturated aqueous ammonium chloride solution and it was extracted with ethyl acetate. The organic layer was washed with saturated aqueous sodium chloride solution, dried over anhydrous sodium sulfate and concentrated under reduced pressure. The resulting residue was purified by chromatography [silica gel, hexane-ethyl acetate (9:1 to 7:3)] to give the title compound (455 mg).

$^1$H-NMR (CDCl$_3$) δ: 1.68-1.80 (m, 4H), 2.39 (s, 2H), 3.58-3.64 (m, 2H), 3.63 (s, 3H), 3.71-3.76 (m, 2H), 5.05 (d, 1H, J=17.6 Hz), 5.23 (d, 1H, J=11.2 Hz), 5.79 (dd, 1H, J=11.2 Hz, 17.6 Hz).

EXAMPLE 78

3,9-Dioxaspiro[5.5]undecan-2-one

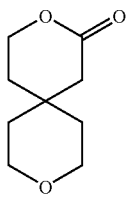

To an ice-cooled solution of methyl (4-vinyltetrahydropyran-4-yl) acetate (455 mg) in tetrahydofuran (3 mL) was added 0.5M 9-borabicyclo[3.3.1]-nonane/tetrahydrofuran (10.0 mL) dropwise over 10 minutes. The reaction solution was allowed for its temperature to rise to room temperature and it was stirred for additional 17 hours. The reaction solution was again ice-cooled and ethanol (2 mL), a 6N aqueous sodium hydroxide solution (4 mL) and 30% hydrogen peroxide (4 mL) were added thereto successively. The reaction solution was then allowed for its temperature to rise to room temperature and it was stirred for additional 30 minutes. The reaction solution was again ice-cooled. After addition of conc. hydrochloric acid (2.5 mL), the reaction solution was allowed for its temperature to rise to room temperature. The solution was stirred for additional 1 hour. The reaction solution was extracted with chloroform. The organic layer was washed with saturated aqueous sodium chloride solution, dried over anhydrous sodium sulfate and concentrated under reduced pressure. The resulting residue was purified by chromatography [silica gel, hexane-ethyl acetate (7:3 to 6:4)] to give the title compound (271 mg).

$^1$H-NMR (CDCl$_3$) δ: 1.57 (t, 4H, J=5.4 Hz), 1.82-1.86 (m, 2H), 2.48 (s, 3H), 3.64-3.74 (m, 4H), 4.34-4.37 (m, 2H).

EXAMPLE 79

3,9-Dioaxaspiro[5.5]undecan-2-ol

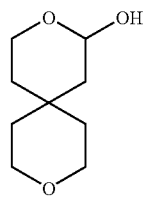

To a solution of 3,9-dioxaspiro[5.5]undecan-2-one (134 mg) in tetrahydrofuran (2 mL) cooled at −78° C. was added 1M diisobutylaluminum hydride/tetrahydrofuran (1.0 mL) dropwise over 5 minutes. The reaction solution was then stirred at that temperature for 1 hour. Water (40 μL) was added to the reaction solution. After allowing the solution for its temperature to rise to room temperature, a 15% aqueous sodium hydroxide solution (40 μL) and water (120 μL) were added successively. After stirring the solution at room temperature for 15 minutes, diethyl ether (2 mL) and anhydrous magnesium sulfate (0.17 g) were added thereto. The solution was stirred for additional 30 minutes. The reaction solution was filtered with Celite. The filtrate was concentrated under reduced pressure to give the title compound (136 mg). This product was subjected to the subsequent step without further purification.

$^1$H-NMR (CDCl$_3$) δ: 1.41 (dd, 1H, J=6.8 Hz, 13.2 Hz), 1.48-1.68 (m, 6H), 1.80 (dd, 1H, J=1.5 Hz, 13.2 Hz), 3.45 (brs, 1H), 3.61-3.73 (m, 5H), 3.93-3.99 (m, 1H), 5.01 (dd, 1H, J=2.4 Hz, 6.8 Hz).

EXAMPLE 80

2-[4-[2-[4-(p-Toluidino)piperidin-1-yl]ethyl]tetrahydropy-ran-4-yl]ethanol

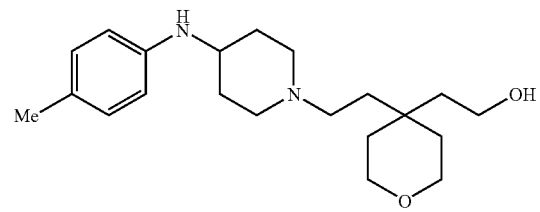

To a suspension of 4-(p-toluidino)piperidine trifluoroacetate (synthesized in Preparation Example 4-5) (656 mg) in tetrahydrofuran (5 mL) was added triethylamine (0.44 mL). The solution was stirred at room temperature for 25 minutes. Then, 3,9-dioxaspiro[5.5]undecan-2-ol (synthesized in Example 79) (135 mg) in tetrahydrofuran (3 mL) was added to the solution and it was stirred at room temperature for additional 5 minutes. The reaction solution was ice-cooled and sodium triacetoxyborohydride (333 mg) was added thereto. After allowing the reaction solution for its temperature rise to room temperature, it was stirred for additional 26 hours. To the reaction solution was added a 3N aqueous sodium hydroxide solution (10 mL) and it was extracted with ethyl acetate.

The organic layer was washed with saturated aqueous sodium chloride solution, dried over anhydrous sodium sulfate and concentrated under reduced pressure. The resulting residue was purified by chromatography [silica gel, chloroform-methanol (20:1)] to give the title compound (240 mg).

$^1$H-NMR (CDCl$_3$) δ: 1.41-1.53 (m, 6H), 1.67-1.70 (m, 4H), 2.05 (d, 2H, J=11.7 Hz), 2.11-2.17 (m, 2H), 2.22 (s, 3H), 2.34 (t, 2H, J=6.3 Hz), 2.91 (d, 2H, J=11.2 Hz), 3.25-3.31 (m, 1H), 3.61-3.71 (m, 6H), 6.50 (d, 2H, J=8.3 Hz), 6.96 (d, 2H, J=8.3 Hz).

EXAMPLE 81

N-[1-[2-[4-(2-Hydroxyethyl)tetrahydropyran-4-yl]ethyl]piperidin-4-yl]-N-(p-tolyl)-2-furancarboxamide

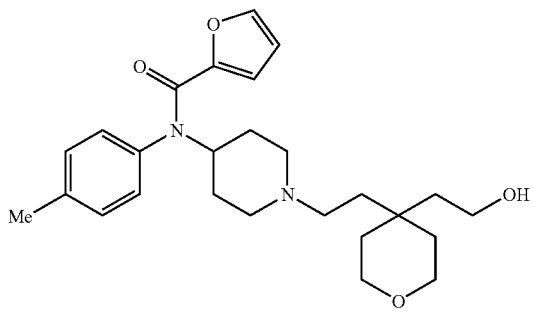

To a solution of 2-[4-[2-[4-(p-toluidino)piperidin-1-yl]ethyl]tetrahydropy-ran-4-yl]ethanol (synthesized in Example 80) (239 mg) in tetrahydrofuran (3 mL) was added triethylamine (0.29 mL) and 2-furoyl chloride (0.17 mL) sucessively. The reaction solution was stirred at room temperature for 30 minutes. To the reaction solution were added methanol (4 mL) and a 3N aqueous potassium hydroxide solution (2 mL). The reaction solution was stirred at room temperature for additional 15 minutes. Water was added to the reaction solution and it was extracted with ethyl acetate. The organic layer was washed with saturated aqueous sodium chloride solution, dried over anhydrous sodium sulfate and concentrated under reduced pressure. The resulting residue was purified by chromatography [silica gel, chloroform-methanol (30:1)] to give the title compound (210 mg).

$^1$H-NMR (CDCl$_3$) δ: 1.35-1.45 (m, 6H), 1.49 (dd, 2H, J=3.4 Hz, 12.2 Hz), 1.56 (t, 2H, J=6.8 Hz), 1.64 (t, 2H, J=6.8 Hz), 1.86 (brd, 2H, J=12.7 Hz), 2.14 (t, 2H, J=12.2 Hz), 2.29 (t, 2H, J=7.3 Hz), 2.40 (s, 3H), 2.98 (brd, 2H, J=11.7 Hz), 3.61-3.64 (m, 6H), 4.71-4.79 (m, 1H), 5.34 (brs, 1H), 6.13 (dd, 1H, J=1.5 Hz, 3.4 Hz), 7.00 (d, 2H, J=8.3 Hz), 7.19 (d, 2H, J=8.3 Hz), 7.34 (s, 1H).

EXAMPLE 82

Diethyl 1-benzylpiperidine-4,4-diacetate

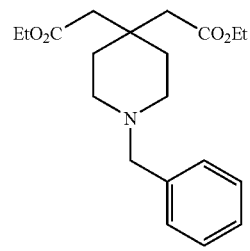

To ice-cooled 7M ammonia/methanol (28 mL) were added 1-benzyl-4-piperidone (9.27 mL) and ethyl cyanoacetate (10.6 mL) The solution was allowed to stand in a refrigerator (0° C.) for 5 days. The crystals thus separated out were recovered by filtration (9.14 g).

Water (8.81 mL) and conc. sulfuric acid (10.3 mL) were added to the resulting crystals (8.64 g). The mixture was heated in an oil bath at 100° C. for 2 days. After the temperature was allowed to rise to room temperature, ethanol (100 mL) was added to the mixture and it was concentrated by an evaporator to azeotropically distill water. This procedure was repeated four times. Ethanol (73 mL) was added to the product and the solution was heated under reflux for 24 hours. After ice cooling, sodium carbonate (20 g) was added to the solution and it was concentrated under reduced pressure. Ethyl acetate was added to the reaction solution and the solution was washed in turn with water and saturated aqueous sodium chloride solution. The organic layer was dried over anhydrous sodium sulfate and concentrated under reduced pressure. The resulting residue was purified by chromatography [silica gel, methanol-chloroform (3:97)] to give the title compound (6.25 g).

$^1$H-NMR (CDCl$_3$) δ: 1.24 (t, 6H, J=6.5 Hz), 1.68 (brt, 4H, J=5.5 Hz), 2.44 (brt, 4H, J=5.5 Hz), 2.56 (s, 4H), 3.50 (s, 2H), 4.11 (q, 4H, J=6.5 Hz), 7.21-7.32 (m, 5H).

EXAMPLE 83

1-Benzyl-4,4-bis(2-hydroxyethyl)piperidine

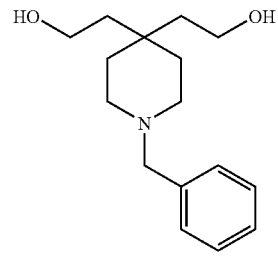

To an ice-cooled solution of lithium aluminum hydride (0.76 g) in tetrahydrofuran (120 mL) was added a solution of diethyl 1-benzylpiperidine-4,4-diacetate (3.47 g) in tetrahydrofuran (10 mL) dropwise. The ice bath was removed and the reaction solution was stirred at room temperature for 1 hour. The reaction solution was again ice-cooled, to which water (0.76 mL), a 15% aqueous sodium hydroxide solution (0.76 mL) and water (2.28 mL) were added successively. The substance thus separated out was filtered off with Celite. The filtrate was concentrated under reduced pressure to give the title compound (ca. 2.63 g). This product was subjected to the subsequent step without further purification.

$^1$H-NMR (CDCl$_3$) δ: 1.51 (brt, 4H, J=5.0 Hz), 1.68 (t, 4H, J=6.5 Hz), 2.42 (brt, 4H, J=5.0 Hz), 3.51 (s, 2H), 3.72 (t, 4H, J=6.5 Hz), 7.22-7.35 (m, 5H).

EXAMPLE 84

2-[1-Benzyl-[4-[2-(tert-butyldiphenylsiloxy)ethyl]piperidin-4-yl]ethanol

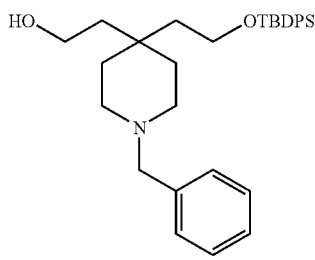

To a solution of 1-benzyl-4,4-bis(2-hydroxyethyl)piperidine (ca. 2.63 g) in dichloromethane (50 mL) were added triethylamine (1.81 mL) and tert-butyldiphenylchlorosilane (2.86 mL). The reaction solution was stirred at room temperature for 18 hours. Chloroform was added to the reaction solution, and the solution was washed with saturated aqueous sodium bicarbonate solution and saturated aqueous sodium chloride solution. The solution was dried over anhydrous magnesium sulfate and concentrated under reduced pressure. The resulting residue was purified by chromatography [silica gel, methanol-chloroform (3:97)] to give the title compound (2.61 g).

$^1$H-NMR (CDCl$_3$) δ: 1.04 (s, 9H), 1.43 (brt, 4H, J=5.5 Hz), 1.57 (t, 2H, J=7.5 Hz), 1.64 (t, 2H, J=7.0 Hz), 2.27-2.42 (m, 4H), 3.46 (s, 2H), 3.57 (t, 2H, J=7.5 Hz), 3.70 (t, 2H, J=7.0 Hz), 7.20-7.31 (m, 5H), 7.36-7.46 (m, 6H), 7.65-7.69 (m, 4H).

EXAMPLE 85

[1-Benzyl-4-[2-(tert-butyldiphenylsiloxy)ethyl]piperidin-4-yl]acetaldehyde

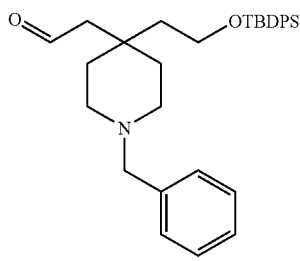

To a solution of oxalyl chloride (0.26 mL) in dichloromethane (3 mL) cooled at −78° C. was added a solution of dimethyl sulfoxide (0.43 mL) in dichloromethane (1 mL) dropwise over 10 minutes. The reaction solution was stirred at −78° C. for 30 minutes. To the reaction solution was added a solution of 2-[1-benzyl-[4-[2-(tert-butyldiphenylsiloxy)ethyl]piperidin-4-yl]ethanol (0.75 g) in dichloromethane (2 mL) dropwise over 10 minutes. The solution was stirred at −78° C. for 30 minutes. Triethylamine (2.1 mL) was added to the solution and it was stirred for 10 minutes. After allowing the temperature to rise to room temperature, the solution was stirred for 30 minutes. Dichloromethane was added to the solution and it was washed with saturated aqueous sodium bicarbonate solution, dried over anhydrous magnesium sulfate and concentrated under reduced pressure to give the title compound (0.75 g). This product was subjected to the subsequent step without further purification.

$^1$H-NMR (CDCl$_3$) δ: 1.03 (s, 9H), 1.54-1.61 (m, 6H), 1.79 (t, 2H, J=6.5 Hz), 2.34-2.44 (m, 4H), 3.47 (s, 2H), 3.75 (t, 2H, J=6.5 Hz), 7.22-7.33 (m, 5H), 7.36-7.46 (m, 6H), 7.63-7.67 (m, 4H), 9.78 (t, 1H, J=2.5 Hz).

EXAMPLE 86

1-[2-[1-Benzyl-4-[2-(tert-butyldiphenylsiloxy)ethyl]piperidin-4-yl]ethyl]-4-toluidinopiperidine

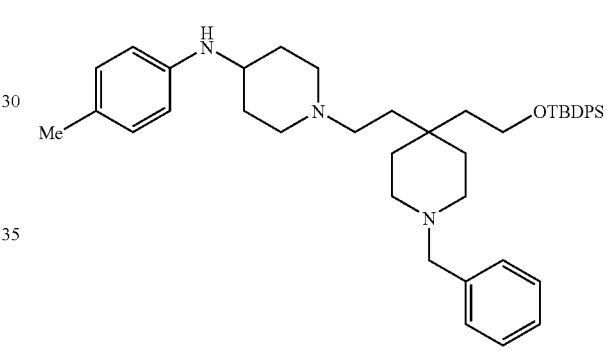

To a suspension of 4-(p-toluidino)piperidine ditrifluoroacetate (synthesized in Preparation Example 4-5) (0.63 g) in 1,2-dichloroethane (3 mL) was added triethylamine (0.42 mL). The suspension was stirred at room temperature for 25 minutes. Then, to the suspension was added [1-benzyl-4-[2-(tert-butyldiphenylsiloxy)ethyl]piperidin-4-yl]acetaldehyde (synthesized in Example 85) (0.75 g) in 1,2-dichloroethane (1.5 mL), and it was stirred at room temperature for additional 5 minutes. The reaction solution was ice-cooled, to which sodium triacetoxyborohydride (0.50 g) was added. After allowing the temperature to rise to room temperature, the solution was stirred for additional 15 hours. Saturated aqueous sodium bicarbonate solution was and it was extracted with ethyl acetate. The organic layer was washed with saturated aqueous sodium chloride solution, dried over anhydrous magnesium sulfate and concentrated under reduced pressure. The resulting residue was purified by chromatography [NH silica gel, ethyl acetate-chloroform (5:95)] to give the title compound (0.87 g).

$^1$H-NMR (CDCl$_3$) δ: 1.03 (s, 9H), 1.34-1.47 (m, 6H), 1.62 (t, 2H, J=7.0 Hz), 1.65-1.76 (m, 2H), 1.90-2.03 (m, 4H), 2.15-2.21 (m, 2H), 2.23 (s, 3H), 2.27-2.40 (m, 4H), 2.68-2.79 (m, 2H), 3.17-3.27 (m, 1H), 3.46 (s, 2H), 3.68 (t, 2H, J=7.0 Hz), 6.52 (d, 2H, J=8.0 Hz), 6.98 (d, 2H, J=8.0 Hz), 7.21-7.33 (m, 5H), 7.35-7.45 (m, 6H), 7.64-7.69 (m, 4H).

EXAMPLE 87

N-[1-[2-[1-Benzyl-4-[2-(tert-butyldiphenylsiloxy)ethyl]piperidin-4-yl]ethyl]piperidin-4-yl]-N-(p-tolyl)-2-furancarboxamide

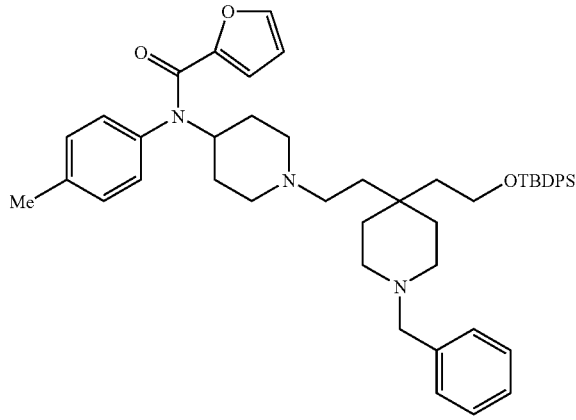

To a solution of 1-[2-[1-benzyl-4-[2-(tert-butyldiphenylsiloxy)ethyl]piperidin-4-yl]ethyl]-4-toluidinopiperidine (synthesized in Example 86) (0.87 g) in tetrahydrofuran (7 mL) was added triethylamine (0.35 mL) and 2-furoyl chloride (0.19 mL) successively. The reaction solution was stirred at room temperature for 1 hour. Saturated aqueous sodium bicarbonate solution was added to the solution and it was extracted with ethyl acetate. The organic layer was washed with saturated aqueous sodium chloride solution, dried over anhydrous magnesium sulfate and concentrated under reduced pressure. The resulting residue was purified by chromatography [silica gel, chloroform-methanol (95:5)] to give the title compound (0.73 g).

$^1$H-NMR (CDCl$_3$) δ: 1.02 (s, 9H), 1.27-1.51 (m, 6H), 1.58 (t, 2H, J=7.5 Hz), 1.63-1.74 (m, 2H), 1.75-1.83 (m, 2H), 1.88-1.97 (m, 2H), 2.08-2.15 (m, 2H), 2.26-2.36 (m, 4H), 2.39 (s, 3H), 2.77-2.84 (m, 2H), 3.45 (s, 2H), 3.64 (t, 2H, J=7.0 Hz), 4.73 (tt, 1H, J=4.0 Hz, 12.0 Hz), 5.35 (brs, 1H), 6.14 (dd, 1H, J=2.0 Hz, 3.5 Hz), 7.00 (d, 2H, J=8.0 Hz), 7.17 (d, 2H, J=8.0 Hz), 7.20-7.32 (m, 5H), 7.34-7.47 (m, 7H), 7.63-7.67 (m, 4H).

EXAMPLE 88

N-[1-[2-[1-Benzyl-4-(2-hydroxyethyl)piperidin-4-yl]ethyl]piperidin-4-yl]-N-(p-tolyl)-2-furancarboxamide

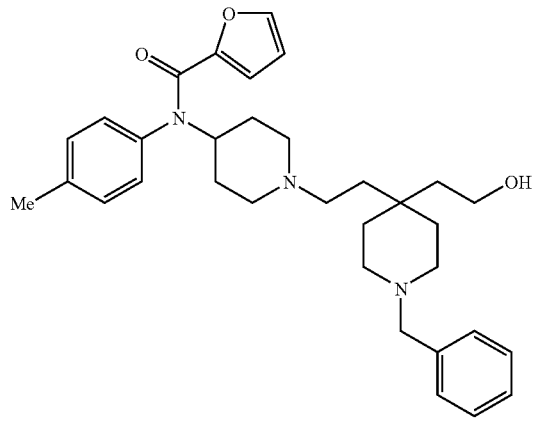

To a solution of N-[1-[2-[1-benzyl-4-[2-(tert-butyldiphenylsiloxy)ethyl]piperidin-4-yl]ethyl]piperidin-4-yl]-N-(p-tolyl)-2-furancarboxamide (synthesized in Example 87) (0.73 g) in tetrahydrofuran (3 mL) was added 1M tetra n-butylammonium fluoride/tetrahydrofuran (1.9 mL). The reaction solution was stirred at room temperature for 15 hours. Saturated aqueous sodium bicarbonate solution was added to the solution and it was extracted with ethyl acetate. The organic layer was washed with saturated aqueous sodium chloride solution, dried over anhydrous magnesium sulfate and concentrated under reduced pressure. The resulting residue was purified by chromatography [NH silica gel, chloroform-methanol (98:2) ] to give the title compound (0.32 g.)

$^1$H-NMR (CDCl$_3$) δ: 1.38-1.51 (m, 8H), 1.56 (t, 2H, J=6.5 Hz), 1.81-1.89 (m, 2H), 2.07-2.16 (m, 2H), 2.26 (t, 2H, J=7.0 Hz), 2.33-2.40 (m, 4H), 2.40 (s, 3H), 2.94-3.00 (m, 2H), 3.48 (s,2H), 3.60 (t, 2H, J=6.5 Hz), 4.75 (tt, 1H, J=4.0 Hz, 12.0 Hz), 5.32 (brs, 1H), 6.13 (dd, 1H, J=2.0 Hz, 3.0 Hz), 7.00 (d, 2H, J=8.0 Hz), 7.18 (d, 2H, J=8.0 Hz), 7.21-7.32 (m, 5H), 7.35 (d, 1H, J=1.0 Hz).

INDUSTRIAL APPLICABILITY

The novel 4-(2-furoyl)aminopiperidine derivatives obtained according to this invention posses opioid µ antagonistic activity and are effective for the treatment or prevention of side effects (which are caused by µ receptor agonists) selelcted from constipation, nausea and emesis or itching, or idiopathic constipation, postoperative ileus, paralyticilleus, irritable bowel syndrome or chronic itching.

The invention claimed is:

1. A compound represented by the general formula (I):

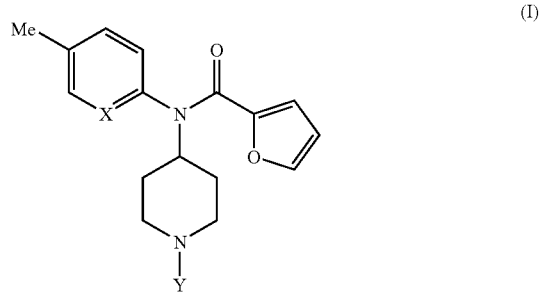

wherein
X is CH or N; and
Y is a group of the general formula (II):

or a group of the general formula (II-a):

or a group of the general formula (III):

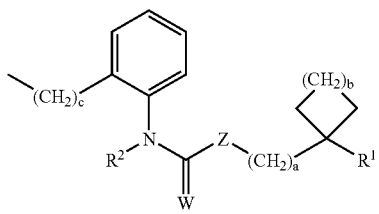

wherein
a, b and c are each an integer of 0-6;
Z is $CH_2$ or NH;
W is O or S;
T is O or N—$R^{15}$ wherein $R^{15}$ is H, a C1-C6 alkyl group, a benzyl group or a phenethyl group;
$R^1$ is H, a C1-C6 alkoxycarbonyl group, a benzyloxycarbonyl group, a carboxy group, a 2-phenyl-1,3-dioxan-5-yl group, a 2,2-dimethyl-1,3-dioxan-5-yl group,
or a group of the general formula (IV):

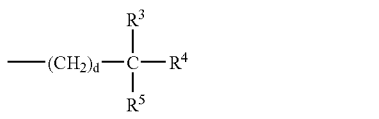

wherein
d is an integer of 0-6; and
$R^3$, $R^4$, and $R^5$ may be the same or different and are each independently H, —$(CH_2)_eR^6$ or —$(CH_2)_fCONR^7R^8$ wherein e and f are each an integer of 0-6; $R^6$ is a hydroxy group, a C1-C6 alkanoyloxy group, a benzoyloxy group, a 2-furoyloxy group, a C1-C6 alkoxy C1-C6 alkoxy group, a C1-C6 alkoxycarbonylphenoxy group, a carboxyphenoxy group, a dicarboxyphenoxy group, a di C1-C6 alkoxy-carbonylphenoxy group, a dihydroxy C1-C6 alkylphenoxy group, an amino group, a C1-C6 alkoxycarbonylamino group, a C1-C6 alkylsulfonamido group, benzenesulfonamido group, a p-toluenesulfonamido group, a p-halobenzene-sulfonamido group, a carboxy group, a C1-C6 alkoxycarbonyl group, a carbohydroxamic acid group, a carbohydroxamic acid C1-C6 alkyl ester group, a cyano group, a 1H-tetrazol-5-yl group, a 1-(C1-C6 alkyl)-1H-tetrazol-5-yl group, a 2-(C1-C6 alkyl)-2H-tetrazol-5-yl group, a $N^2$-hydroxycarbamidoyl group, a $N^1$-(C1-C6 alkoxycarbonyl)-$N^2$-hydroxycarbamidoyl group, a 2H-5-thioxo-1,2,4-oxadiazol-3-yl group, a 2H-5-oxo-1,2,4-oxadiazol-3-yl group, a guanidino group, a di C1-C6 alkoxycarbonyl-guanidino group or a morpholinocarbonyl group; and $R^7$ and $R^8$ may be the same or different and are each independently H, a C1-C6 alkyl group, a C1-C6 alkanoyloxy C1-C6 alkyl group, a hydroxy C1-C6 alkyl group, a bis(C1-C6 alkanoyloxy C1-C6 alkyl)methyl group, a bis(hydroxy C1-C6 alkyl) methyl group, a tris(C1-C6 alkanoyloxy C1-C6 alkyl) methyl group, a tris(hydroxy C1-C6 alkyl)-methyl group, a carboxy C1-C6 alkyl group, a C1-C6 alkoxycarbonyl C1-C6 alkyl group, a N,N-bis(C1-C6 alkanoyloxy C1-C6 alkyl)carbamoyl C1-C6 alkyl group, a N,N-bis(carboxy C1-C6 alkyl)carbamoyl C1-C6 alkyl group, a C1-C6 alkylsulfonyl group, a carboxyphenyl group or a pyrazinyl group; and
$R^2$ is H or a group of the above general formula (IV), or a pharmaceutically acceptable salt thereof.

2. The compound or a pharmaceutically acceptable salt according to claim 1, wherein in the general formula (I), X is CH or N; and Y is a group of the general formula (II) wherein a is an integer of 0-4, b is an integer of 2-5, $R^1$ is H, a methoxycarbonyl group, a carboxy group, a 2-phenyl-1,3-dioxan-5-yl group, a 2,2-dimethyl-1,3-dioxan-5-yl group, or a group of the general formula (IV) wherein d is an integer of 0-2, $R^3$, $R^4$, and $R^5$ may be the same or different and are each independently H or —$(CH_2)_eR^6$ wherein e is an integer of 0-3, and $R^6$ is a hydroxy group, an acetoxy group, a benzoyloxy group, a 2-furoyloxy group, a methoxymethoxy group, an amino group, a tert-butoxycarbamoyl group, a methanesulfonamido group, a carboxy group, a methoxycarbonyl group, an ethoxycarbonyl group, a carbohydroxamic acid group, a carbohydroxamic acid tert-butyl ester group, a cyano group, or a 1H-tetrazol-5-yl group.

3. The compound or a pharmaceutically acceptable salt thereof according to claim 1, wherein in the general formula (I), X is CH or N; and Y is a group of the general formula (II) wherein a is 2, b is 2-3, and $R^1$ is a group of the general formula (IV) wherein d is 0, $R^4$ and $R^5$ are H, and $R^3$ is —$(CH_2)_fCONR^7R^8$ wherein f is 0, $R^7$ and $R^8$ may be the same or different and are each independently H, a tris(acetoxymethyl)methyl group, a tris(hydroxymethyl)methyl group, an ethoxycarbonylmethyl group, a carboxymethyl group, a 2-ethoxycarbonylethyl group, a 2-carboxyethyl group, a 3-ethoxycarbonylpropyl group, a 3-carboxypropyl group, a N,N-bis(ethoxycarbonylmethyl)carbamoylmethyl group or a N,N-bis(carboxymethyl)carbamoylmethyl group.

4. The compound or a pharmaceutically acceptable salt thereof according to claim 1, wherein in the general formula (I), X is CH or N; and Y is a group of the general formula (III) wherein a is an integer of 0-2, b is 3, c is an integer of 1-3, Z is $CH_2$ or NH, W is O or S, $R^1$ is H, a methoxycarbonylmethyl group or a carboxymethyl group, and $R^2$ is H or a group of the general formula (IV) wherein d is an integer of 0-2, $R^4$ and $R^5$ are each independently H and $R^3$ is —$(CH_2)_eR^6$ wherein e is 0, and $R^6$ is a carboxy group or a C1-C6 alkanoyloxy group.

5. The compound or a pharmaceutically acceptable salt according to claim 2, wherein in the general formula (I), X is CH or N; and Y is a group of the general formula (II) wherein a is 2, b is 3, and $R^1$ is a carboxymethyl group, a 3,3-bis(hydroxymethyl)propyl group, a 5-hydroxy-3,3-bis(hydroxymethyl)pentyl group, an acetohydroxamic acid group or a 2-(1H-tetrazol-5-yl)ethyl group.

6. The compound or a pharmaceutically acceptable salt according to claim 2, wherein the compound is selected from [1-[2-[4-[N-(p-tolyl)-2-furancarboxamido]piperidin-1-yl] eth-yl]cyclohexyl]acetic acid, N-[1-[2-[1-(4-hydroxy-3-hydroxymethylbutyl)cyclohexyl]ethyl]piperidin-4-yl]-N-(5-methylpyridin-2-yl)-2-fu-rancarboxamide, N-[1-[2-[1-[5-hydroxy-3,3-bis(hydroxymethyl)pentyl]cyclohexyl]ethyl] piperidin-4-yl]-N-(5-methylpyridin-2-yl)-2-furancarboxamide, [1-[2-[4-[N-(p-tolyl)-2-furancarboxamido]piperidin-1-yl]ethyl]cyclohexyl] acetohydroxamic acid, or N-[1-[2-[1-(2-cyanoethyl) cyclohexyl]ethyl]piperidin-4-yl]-N-(p-tolyl)-2-furancarboxamide, [1-[2-[4-[N-(5-methylpyridin-2-yl)-2-furancarboxamido]piperidin-1-yl]ethyl]cyclohexyl]

acetohydroxamic acid, or N-[1-[2-[1-(2-tetrazolylethyl)cyclohexyl]ethyl]piperidin-4-yl]-N-(p-tolyl)-2-furancarboxamide.

7. A medicament comprising a compound of formula (I) or a pharmaceutically acceptable salt thereof and, if necessary, a pharmaceutically acceptable excipient compounded therewith;

wherein said compound of formula (I) is represented by the general formula:

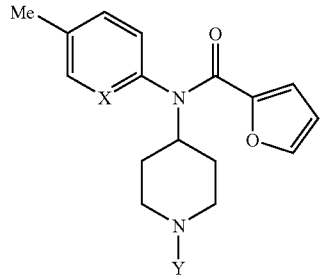

(I)

wherein
X is CH or N; and
Y is a group of the general formula (II):

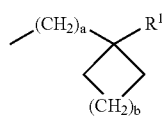

(II)

or a group of the general formula (II-a):

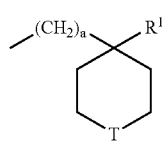

(II-a)

or a group of the general formula (III):

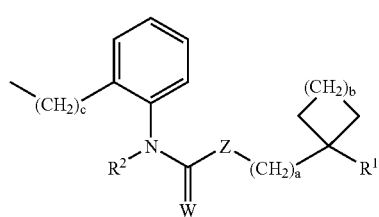

(III)

wherein
a, b and c are each an integer of 0-6;
Z is $CH_2$ or NH;
W is O or S;
T is O or N—$R^{15}$ wherein $R^{15}$ is H, a C1-C6 alkyl group, a benzyl group or a phenethyl group;

$R^1$ is H, a C1-C6 alkoxycarbonyl group, a benzyloxycarbonyl group, a carboxy group, a 2-phenyl-1,3-dioxan-5-yl group, a 2,2-dimethyl-1,3-dioxan-5-yl group, or a group of the general formula (IV):

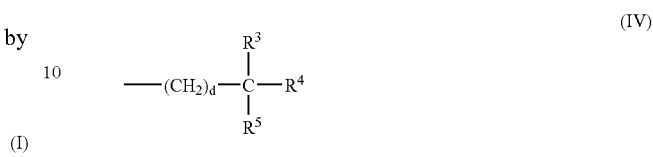

(IV)

wherein
d is an integer of 0-6; and
$R^3$, $R^4$, and $R^5$ may be the same or different and are each independently H, —$(CH_2)_eR^6$ or —$(CH_2)_fCONR^7R^8$ wherein e and f are each an integer of 0-6; $R^6$ is a hydroxy group, a C1-C6 alkanoyloxy group, a benzoyloxy group, a 2-furoyloxy group, a C1-C6 alkoxy C1-C6 alkoxy group, a C1-C6 alkoxycarbonylphenoxy group, a carboxyphenoxy group, a dicarboxyphenoxy group, a di C1-C6 alkoxy-carbonylphenoxy group, a dihydroxy C1-C6 alkylphenoxy group, an amino group, a C1-C6 alkoxycarbonylamino group, a C1-C6 alkylsulfonamido group, a benzenesulfonamido group, a p-toluenesulfonamido group, a p-halobenzene-sulfonamido group, a carboxy group, a C1-C6 alkoxycarbonyl group, a carbohydroxamic acid group, a carbohydroxamic acid C1-C6 alkyl ester group, a cyano group, a 1H-tetrazol-5-yl group, a 1-(C1-C6 alkyl)-1H-tetrazol-yl group, a 2-(C1-C6 alkyl)-2H-tetrazol-5-yl group, a $N^2$-hydroxycarbamidoyl group, a $N^1$-(C1-C6 alkoxy-carbonyl)-$N^2$-hydroxycarbamidoyl group, a 2H-5-thioxo-1,2,4-oxadiazol-3-yl group, a 2H-5-oxo-1,2,4-oxadiazol-3-yl group, a guanidino group, a di C1-C6 alkoxycarbonyl-guanidino group or a morpholinocarbonyl group; and $R^7$ and $R^8$ may be the same or different and are each independently H, a C1-C6 alkyl group, a C1-C6 alkanoyloxy C1-C6 alkyl group, a hydroxy C1-C6 alkyl group, a bis(C1-C6 alkanoyloxy C1-C6 alkyl)methyl group, a bis(hydroxy C1-C6 alkyl) methyl group, a tris(C1-C6 alkanoyloxy C1-C6 alkyl) methyl group, a tris(hydroxy C1-C6 alkyl)methyl group, a carboxy C1-C6 alkyl group, a C1-C6 alkoxycarbonyl C1-C6 alkyl group, a N,N-bis(C1-C6 alkanoyloxy C1-C6 alkyl)carbamoyl C1-C6 alkyl group, a N,N-bis(carboxy C1-C6 alkyl)carbamoyl C1-C6 alkyl group, a C1-C6 alkylsulfonyl group, a carboxyphenyl group or a pyrazinyl group; and $R^2$ is H or a group of the above general formula (IV), or a pharmaceutically acceptable salt thereof.

8. A medicament according to claim 7 wherein the medicament is an opioid μ receptor antgonist.

9. A medicament according to claim 7 wherein the medicament is an agent for the treatment of side effects which are caused by a μ receptor agonist and which are selected from constipation, nausea/emesis or itch, or for the treatment of idiopathic constipation, postoperative ileus, paralytic ileus, irritable bowel syndrome or chronic pruritus.

10. A compound of formula (I) or a pharmaceutically acceptable salt thereof which is provided with opioid μ receptor antagonistic activity;

wherein said compound of formula (I) is represented by the general formula:

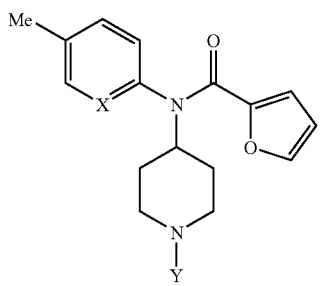

wherein
X is CH or N; and
Y is a group of the general formula (II):

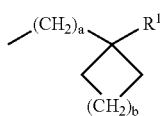

or a group of the general formula (II-a):

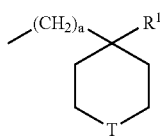

or a group of the general formula (III):

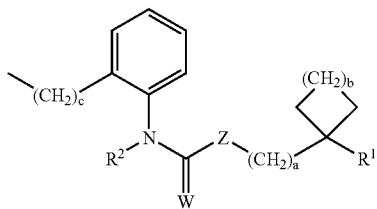

wherein
a, b and c are each an integer of 0-6;
Z is $CH_2$ or NH;
W is O or S;
T is O or $N-R^{15}$ wherein $R^{15}$ is H, a C1-C6 alkyl group, a benzyl group or a phenethyl group;

$R^1$ is H, a C1-C6 alkoxycarbonyl group, a benzyloxycarbonyl group, a carboxy group, a 2-phenyl-1,3-dioxan-5-yl group, a 2,2-dimethyl-1,3-dioxan-5-yl group,
or a group of the general formula (IV):

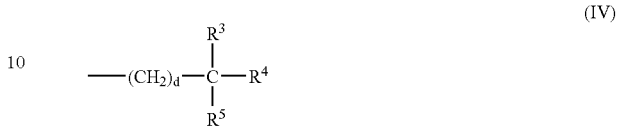

wherein
d is an integer of 0-6; and
$R^3$, $R^4$, and $R^5$ may be the same or different and are each independently H, $-(CH_2)_e R^6$ or $-(CH_2)_f CONR^7 R^8$ wherein e and f are each an integer of 0-6; $R^6$ is a hydroxy group, a C1-C6 alkanoyloxy group, a benzoyloxy group, a 2-furoyloxy group, a C1-C6 alkoxy C1-C6 alkoxy group, a C1-C6 alkoxycarbonylphenoxy group, a carboxyphenoxy group, a dicarboxyphenoxy group, a di C1-C6 alkoxy-carbonylphenoxy group, a dihydroxy C1-C6 alkylphenoxy group, an amino group, a C1-C6 alkoxycarbonylamino group, a C1-C6 alkylsulfonamido group, benzenesulfonamido group, a p-toluenesulfonamido group, a p-halobenzene-sulfonamido group, a carboxy group, a C1-C6 alkoxycarbonyl group, a carbohydroxamic acid group, a carbohydroxamic acid C1-C6 alkyl ester group, a cyano group, a 1H-tetrazol-5-yl group, a 1-(C1-C6 alkyl)-1H-tetrazol-5-yl group, a 2-(C1-C6 alkyl)-2H-tetrazol-5-yl group, a $N^2$-hydroxycarbamidoyl group, a $N^1$-(C1-C6 alkoxycarbonyl)-$N^2$-hydroxycarbamidoyl group, a 2H-5-thioxo-1,2,4-oxadiazol-3-yl group, a 2H-5-oxo-1,2,4-oxadiazol-3-yl group, a guanidino group, a di C1-C6 alkoxycarbonyl-guanidino group or a morpholinocarbonyl group; and $R^7$ and $R^8$ may be the same or different and are each independently H, a C1-C6 alkyl group, a C1-C6 alkanoyloxy C1-C6 alkyl group, a hydroxy C1-C6 alkyl group, a bis(C1-C6 alkanoyloxy C1-C6 alkyl)methyl group, a bis(hydroxy C1-C6 alkyl) methyl group, a tris(C1-C6 alkanoyloxy C1-C6 alkyl) methyl group, a tris(hydroxy C1-C6 alkyl)-methyl group, a carboxy C1-C6 alkyl group, a C1-C6 alkoxycarbonyl C1-C6 alkyl group, a N,N-bis(C1-C6 alkanoyloxy C1-C6 alkyl)carbamoyl C1-C6 alkyl group, a N,N-bis(carboxy C1-C6 alkyl)carbamoyl C1-C6 alkyl group, a C1-C6 alkylsulfonyl group, a carboxyphenyl group or a pyrazinyl group; and
$R^2$ is H or a group of the above general formula (IV), or a pharmaceutically acceptable salt thereof.

* * * * *